US012377104B1

(12) United States Patent
Taub et al.

(10) Patent No.: US 12,377,104 B1
(45) Date of Patent: Aug. 5, 2025

(54) METHODS FOR TREATING A FATTY LIVER DISEASE

(71) Applicant: Madrigal Pharmaceuticals, Inc., West Conshohocken, PA (US)

(72) Inventors: Rebecca Taub, Villanova, PA (US); Dominic Labriola, Belmar, NJ (US)

(73) Assignee: Madrigal Pharmaceuticals, Inc., West Conshohocken, PA (US)

( * ) Notice: Subject to any disclaimer, the term of this patent is extended or adjusted under 35 U.S.C. 154(b) by 0 days.

(21) Appl. No.: 19/045,070

(22) Filed: Feb. 4, 2025

Related U.S. Application Data

(60) Provisional application No. 63/550,201, filed on Feb. 6, 2024, provisional application No. 63/564,803, filed on Mar. 13, 2024, provisional application No. 63/655,870, filed on Jun. 4, 2024.

(51) Int. Cl.
*A61K 31/53* (2006.01)
*A61P 1/16* (2006.01)

(52) U.S. Cl.
CPC ............... *A61K 31/53* (2013.01); *A61P 1/16* (2018.01)

(58) Field of Classification Search
CPC .................................. A61K 31/53; A61P 1/16
See application file for complete search history.

(56) References Cited

U.S. PATENT DOCUMENTS

| | | | |
|---|---|---|---|
| 6,858,618 B2 | 2/2005 | Raza et al. | |
| 7,189,718 B2 | 3/2007 | Dunn et al. | |
| 7,452,882 B2 | 11/2008 | Haynes et al. | |
| 7,807,647 B2 | 10/2010 | Sheikhnejad et al. | |
| 7,807,674 B2 | 10/2010 | Haynes et al. | |
| 8,076,334 B2 | 12/2011 | Haynes et al. | |
| 8,858,502 B2 | 10/2014 | Baxter et al. | |
| 9,266,861 B2 | 2/2016 | Hester, II et al. | |
| 9,968,612 B2 | 5/2018 | Taub et al. | |
| 10,376,517 B2 | 8/2019 | Taub et al. | |
| 10,894,050 B2 | 1/2021 | Hester, II et al. | |
| 11,090,308 B2 | 8/2021 | Taub | |
| 11,564,926 B2 | 1/2023 | Hester, II et al. | |
| 11,806,353 B2 | 11/2023 | Taub | |
| 12,102,646 B2 * | 10/2024 | Lian | A61P 29/00 |
| 2009/0082310 A1 | 3/2009 | Haynes et al. | |
| 2015/0203473 A1 | 7/2015 | Hester, II et al. | |
| 2019/0381053 A1 | 12/2019 | Taub et al. | |
| 2020/0230146 A1 | 7/2020 | Taub | |
| 2021/0122740 A1 | 4/2021 | Mirmehrabi et al. | |
| 2021/0161904 A1 | 6/2021 | Hester, II et al. | |
| 2021/0330675 A1 | 10/2021 | Taub | |
| 2023/0210856 A1 | 7/2023 | Hester, II et al. | |
| 2024/0148742 A1 | 5/2024 | Hester, II et al. | |

FOREIGN PATENT DOCUMENTS

| | | |
|---|---|---|
| CN | 101014608 A | 8/2007 |
| CN | 101228135 A | 7/2008 |
| CN | 101801960 A | 8/2010 |
| EA | 200901651 A1 | 12/2010 |
| JP | S56-15272 A | 2/1981 |
| JP | 2009-501759 A | 1/2009 |
| JP | 2010-539209 A | 12/2010 |
| JP | 2015-532148 A | 11/2015 |
| RU | 2344128 C2 | 1/2009 |
| RU | 2379295 C2 | 1/2010 |
| TW | 200745052 A | 12/2007 |
| WO | 2005/009433 A1 | 2/2005 |
| WO | 2005/118824 A2 | 12/2005 |
| WO | 2006/050389 A2 | 5/2006 |
| WO | 2007/009913 A1 | 1/2007 |
| WO | 2008/149379 A2 | 12/2008 |
| WO | 2009/037172 A1 | 3/2009 |
| WO | 2014/043706 A1 | 3/2014 |
| WO | 2015/123256 A1 | 8/2015 |
| WO | 2018/075650 A1 | 4/2018 |
| WO | 2019/240938 A1 | 12/2019 |
| WO | 2020/010068 A1 | 1/2020 |
| WO | 2020/073974 A1 | 4/2020 |
| WO | 2020/123827 A1 | 6/2020 |

OTHER PUBLICATIONS

Office Action issued on Sep. 10, 2019, for Japanese Patent Application No. JP 2018-217045, 9 pages.
Ooshima, H., "Crystallization of Polymorphs and Pseudo-polymorphs and Its Control," Pharm Stage, 2007, 6(10):48-53.
Pinto, N. et al. "Clinically relevant genetic variations in drug metabolizing enzymes", Curr Drug Metab. Jun. 2011, 12(5):487-97.
Raunio, H. et al. "In Vitro Methods in the Prediction of Kinetics of Drugs: Focus on Drug Metabolism," ATLA, 2004, 32:425-430.
Refetoff, S., "The Syndromes of Resistance to Thyroid Hormone", Endocrine Reviews, Jun. 1993, 14(3):348-399.
Rodriguez-Spong B. et al., "General principles of pharmaceutical solid polymorphism: a supramolecular perspective", Adv Drug Deliv Rev., 2004, 56(3):241-274.

(Continued)

*Primary Examiner* — Kevin E Weddington

(74) *Attorney, Agent, or Firm* — Venable LLP

(57) ABSTRACT

The present disclosure provides a method of treating a fatty liver disease (e.g., non-alcoholic steatohepatitis (NASH)) in a human subject (e.g., an adult human subject) in need of such treatment (e.g., NASH/improving liver fibrosis) with 2-(3,5-dichloro-4-((5-isopropyl-6-oxo-1,6-dihydro-pyridazin-3-yl)oxy)phenyl)-3,5-dioxo-2,3,4,5-tetrahydro-1,2,4-triazine-6-carbonitrile (resmetirom) or a pharmaceutically acceptable salt thereof. The present disclosure also provides a method of improving liver fibrosis in a human subject (e.g., an adult human subject) in need of such treatment (e.g., NASH/improving liver fibrosis) with 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile (resmetirom) or a pharmaceutically acceptable salt thereof.

24 Claims, 43 Drawing Sheets

(56) References Cited

OTHER PUBLICATIONS

Serajuddin, A. T. M., "Solid dispersion of poorly water-soluble drugs: early promises, subsequent problems, and recent breakthroughs," J. Pharm. Sci., Oct. 1999, 88(10):1058-1066.
Shi, Y. et al., "Mutant-Selective Thyromimetics for the Chemical Rescue of Thyroid Hormone Receptor Mutants Associated with Resistance to Thyroid Hormone", Biochemistry, 2005, 44:4612-4626.
Stahl et al. "Handbook of Pharmaceutical Salts Properties, Selection, and Use" Verlag Helvetica Chemica Acta, Switzerland, Zurich, 2002, Cover pages and pp. 167-168, 170-173, and 216-217 (12 pages total).
Stahly, G. P. et al., "Diversity in Single- and Multiple-Component Crystals. The Search for and Prevalence of Polymorphs and Cocrystals". Crystal Growth & Design, 2007, 7(6):1007-1026.
Stahly, P., The Importance of Salt Selection and Polymorph Screening for the Drug Product, Pharmaceutics, 2006, 66(6), 435-439.
Sugimoto, I., Takahashi, Y. Solvates, Amorphous Solids and Pharmaceutical Preparations, Journal of the Society of Powder Technology, Japan, 1985, 22(2), pp. 85-97.
Takada, N. "API form screening and selection in drug discovery stage", Pharm Stage, 2007, 6(10):20-25.
Taub R et al, "Lipid Lowering in Healthy Volunteers Treated With Multiple Doses of Mgl-3196, a Liver-targeted Thyroid Hormone Receptor-Agonist", Atherosclerosis, Aug. 2013, 230(2):373-380.
"Test Procedures and Acceptance Criteria for New Drug Substances and New Drug Products", PMSB/ELD Notification, 2001, 568, 45 pages.
Wagner R. L. et al., "Hormone Selectivity in Thyroid Hormone Receptors", Molecular Endocrinology, 2001, 15(3):398-410.
Weiss R. E. et al., "Resistance to Thyroid Hormone (RTH) in the Absence of Abnormal Thyroid Hormone Receptor (TR) (nonTR-RTH)," Hot Thyroidology Sep. 9, 2009, 11 pages.
Yamada, M., "Resistance to thyroid hormone", Nihon Rinsho, Dec. 2006, 64(12):2237-42.
Yamano, M. "Approach to Crystal Polymorph in Process Research of New Drug", Journal of Synthetic Organic Chemistry, 2007, vol. 65, No. 9, p. 907-913.
Ye, H. F. et al., "A Subtype—Selective Thyromimetic Designed to Bind a Mutant Thyroid Hormone Receptor Implicated in Resistance to Thyroid Hormone", J Am Chem Soc, Feb. 21, 2001, 123(7):1521-2.
Yen, P. M., "Physiological and Molecular Basis of Thyroid Hormone Action", Physiological Reviews, 2001, 81(3):1097-1142.
Press Release, "Madrigal Pharmaceuticals Presents Preclinical Results Supporting the Therapeutic Potential of its Lead B-Selective Thyroid Hormone Receptor Agonist, MGL-3196, at AASLD Liver Meeting," Oct. 23, 2017.
Harrison et al., "MGL-3196, a selective thyroid hormone receptor-beta agonist significantly decreases hepatic fat in NASH patients at 12 weeks, the primary endpoint in a 36 week serial liver biopsy study," Journal of Hepatology, vol. 68, S38 (2018).
Harrison et al., "MGL-3196, a selective thyroid hormone receptor-beta agonist significantly decreases hepatic fat in NASH patients at 12 weeks, the primary endpoint in a 36 week serial liver biopsy study," The International Liver Congress, European Association for the Study of the Liver, Apr. 11-15, 2018.
Press Release, "Phase 2 Results for Madrigal's MGL-3196 in Non-Alcoholic Steatohepatitis (NASH) Presented during Presidential Plenary Clinical Session of The Liver Meeting® 2018," Nov. 12, 2018.
Harrison et al., "Resmetirom (MGL-3196) for the treatment of non-alcoholic steatohepatitis: a multicentre, randomised, double-blind, placebo-controlled, phase 2 trial," The Lancet, https://doi.org/10.1016/S0140-6736(19)32517-6 (2019).
Nasir et al., "Analysis of the Non-alcoholic Steatohepatitis (NASH) Drug Pipeline &Market: Sizing Up the First Wave," Pharmaceutical Online, Guest Column, Nov. 30, 2020.
Harrison et al., "Effects of Resmetirom on Noninvasive Endpoints in a 36-Week Phase 2 Active Treatment Extension Study in Patients With NASH," Hepatology Communications, vol. 5, pp. 573-588 (2021).
Harrison et al., "Reduction in Fibrosis and Steatohepatitis Imaging and Biomarkers in 52-Week Resmetirom Non-Alcoholic Steatohepatitis Trial," NAFLD Summit Poster, Sep. 16-17, 2021.
Qu et al., "Liver Fibrosis and MAFLD: From Molecular Aspects to Novel Pharmacological Strategies," Frontiers in Medicine, vol. 8, 761538 (2021).
Lucas et al., "Effect of Resmetirom, a Selective Thyroid Hormone Receptor Beta Agonist, on Hepatic Hypothyroidism in a 52-Week Non-Cirrhotic NASH Phase 3 Clinical Trial," Endocrine Practice, vol. 28, S154 (2022).
Tai et al., "Impact of Resmetirom-Mediated Reductions in Liver vol. and Steatosis Compared With Placebo on the Quantification of Fibrosis Using Second Harmonic Generation in a Serial Liver Biopsy Study," International Liver Conference Poster, Jun. 22-26, 2022.
Harrison et al., "Primary Data Analyses of MAESTRO-NAFLD-1:a 52-week Double-blind, Placebo-controlled Phase 3 Clinical Trial of Resmetirom in Patients With NAFLD," International Liver Conference Presentation, Jun. 21-24, 2023.
Harrison, "Nash Treatment: Review of Current and Future Therapies For Non-Alcoholic Steatohepatitis," Pan NASH, Aug. 25, 2022.
Harrison et al., "A 52-Week Phase 3 Clinical Trial of Resmetirom in 180 Patients With Well-Compensated NASH Cirrhosis," The Liver Meeting Digital Experience AASLD Presentation, Nov. 4-8, 2022.
Press Release, "Madrigal Announces Positive Topline Results from the Pivotal Phase 3 MAESTRO-NASH Clinical Trial of Resmetirom for the Treatment of NASH and Liver Fibrosis," Dec. 19, 2022.
Harrison et al., "Primary results from MAESTRO-NASH a pivotal phase 3 52-week serial liver biopsy study in 966 patients with NASH and fibrosis," The International Liver Congress Presentation, Jun. 21-24, 2023.
Harrison et al., "Resmetirom for nonalcoholic fatty liver disease: a randomized, double-blind, placebo-controlled phase 3 trial," Nature Medicine, vol. 29, pp. 2919-2928 (2023).
Press Release, "Madrigal Pharmaceuticals Presents New Data from the Phase 3 MAESTRO-NASH Trial Demonstrating Broad Treatment Effects of Resmetirom on Noninvasive Measures of Liver Health," Nov. 10, 2023.
Press Release, "Madrigal Pharmaceuticals Presents Phase 3 MAESTRO-NASH Data During the Opening General Session of the EASL Congress™," Jun. 22, 2023.
Press Release, "Madrigal Announces Additional Positive Results from the Pivotal Phase 3 MAESTRO-NASH Clinical Trial of Resmetirom for the Treatment of NASH with Liver Fibrosis," Jan. 6, 2023.
Press Release, "Madrigal Pharmaceuticals Presents Late-Breaking Phase 3 NASH Data and Multiple Oral Abstracts at EASL's International Liver Congress™," Jun. 25, 2022.
Press Release, "Positive Topline Phase 3 MAESTRO-NAFLD-1 Data Demonstrate Resmetirom was Safe, Well-Tolerated and Provided Statistically Significant Improvements in Key Measures of Liver and Cardiovascular Health," Jan. 31, 2022.
Press Release, "Positive Resmetirom Data from Completed Open-Label Portion of Phase 3 MAESTRO-NAFLD-1 Clinical Study Presented at American Association for the Study of Liver Diseases (AASLD) The Liver Meeting® Digital Experience 2021," Nov. 12, 2021.
Press Release, "Madrigal Pharmaceuticals Announces Presentation of Positive Clinical Data of Resmetirom from Open-Label Portion of Ongoing Phase 3 Clinical Trial MAESTRO-NAFLD-1 at The International Liver Congress™ 2021," Jun. 25, 2021.
Press Release, "Madrigal Pharmaceuticals Highlights Presentations at The Liver Meeting Digital Experience™, The American Association for the Study of Liver Diseases Meeting Nov. 13, 2020, Including NASH Expert Insights on the Ongoing Open Label Arm of Resmetirom 52-W," Nov. 13, 2020.

(56) References Cited

OTHER PUBLICATIONS

Press Release, "Madrigal's MGL-3196 Achieves Liver Biopsy Endpoints in Patients with Non-alcoholic Steatohepatitis (NASH) at 36 Weeks in Phase 2 Clinical Trial," May 31, 2018.

Press Release, "Madrigal's MGL-3196 Achieves Primary Endpoint in Patients with Biopsy-proven Non-alcoholic Steatohepatitis (NASH) in Phase 2 Clinical Trial," Dec. 6, 2017.

Swain, C.G. et al., "The Mechanism of Addition of Grignard Reagents to Ketones," J. Am. Chem. Soc., vol. 73, pp. 870-872 (1951).

Kelly, M.J. et al., "Discovery and Development of MGL-3196, a Liver-Directed Thyroid Hormone-β Agonist for the Treatment of Hypercholesterolemia/Dyslipidemia and Hypertriglyceridemia," 245th American Chemical Society National Meeting and Exposition (Apr. 10, 2013).

Abel, E. D. et al., "Divergent roles for thyroid hormone receptor β isoforms in the endocrine axis and auditory system", J. Clin. Invest, Aug. 1999, 104(3):291-300.

Adams, M. et al., "Genetic Analysis of 29 Kindreds with Generalized and Pituitary Resistance to Thyroid Hormone: Identification of Thirteen Novel Mutations in the Thyroid Hormone Receptor β Gene," J. Clin. Invest, 1994, 94:506-515.

Anonymous: "Madrigal's MGL-3196 Achieves Primary Endpoint in Patients With Heterozygous Familial Hypercholesterolemia (HeFH)", Drug Development & Delivery, Jan. 1, 2018, pp. 1-5.

Antonopoulos, S., et al., "Rosuvastatin as a novel treatment of non-alcoholic fatty liver disease in hyperlipidemic patients", Atherosclerosis, Jan. 1, 2006, 184(1):233-234.

Ashby, E. C. et al., "Mechanisms of Grignard reagent addition to ketones", Acc. Chem. Res., 1974, 7:272-280.

Ashizawa, K., "Physico-Chemical Studies on the Molecular Details of Drug Crystals", Pharm Tech Japan, Sep. 2002, 18(10):81-96.

Banker, G.S. and Rhodes, C.T., Modern Pharmaceutics, Fourth Edition, 2002, 172-174 (5 pages total).

Bavin, et al., "Polymorphism in Process Development." Chemistry & Industry, 1989, 527-529.

Beliard, S. et al. "Improvement in LDL-cholesterol levels of patients with familial hypercholesterolemia: can we do better? Analysis of results obtained during the past two decades in 1669 French subjects", Atherosclerosis, May 2014, 234(1):136-41.

Berge, S. M., et al., "Pharmaceutical salts", Journal of Pharmaceutical Sciences, Jan. 1977, 66(1):1-19.

Brittain, H.G., "Theory and Principles of Polymorphic Systems", Polymorphism in Pharmaceutical Solids, 2nd Ed., Drugs and the Pharmaceutical Sciences, 192(1):1-23 (H.G. Brittain ed., 2nd ed., 2009).

Byrn, S., et al., "Pharmaceutical solids: a strategic approach to regulatory considerations", Pharmaceutical Research, 1995, 12(7):945-954.

Caira, M. R., "Crystalline Polymorphism of Organic Compounds", Topics in Current Chemistry, Jan. 1, 1998, 198:163-208.

Charushin, V. et al. "Six-membered Rings with Three or more Heteroatoms, and their Fused Carbocyclic Derivatives: 1,2,4-Triazines and their Benzo Derivatives", 9.02, Comprehensive Heterocyclic Chemistry III, 2008, 102 pages.

ClinicalTrials.gov Identifier NCT03038022, "Study of MGL-3196 in Patients With Heterozygous Familial Hypercholesterolemia (HeFH)," Last Update Posted Jan. 25, 2018, 10 pages.

ClinicalTrials.gov Identifier NCT02912260, "Phase 2 Study of MGL-3196 in Patients With Non-Alcoholic Steatohepatitis (NASH)," Last Update Posted Dec. 19, 2017, 9 pages.

Database Cas Registry [Online], "6-(4-Amino-2,6-dichlorophenoxy)-4-(1-methylethyl)-3(2H)-pyridazinone", Chemical Abstracts Service, Columbus, OH, USA. STN entry date Feb. 12, 2007 (Feb. 12, 2007), Retrieved from STN, CAS RN: 920509-28-0, 51 pages.

Ding, E.L., et al., "Sex hormone-binding globulin and risk of type 2 diabetes in women and men," New England Journal of Medicine, Sep. 2009, 361 (12):1152-1163.

Gloss, B. et al. "Cardiac Ion Channel Expression and Contractile Function in Mice with Deletion of Thyroid Hormone Receptor α or β", Endocrinology, 2001, 142(2):544-55.

Goldfuss, B., "Organolithiums in Enantioselective Additions to π* and σ* Carbon-Oxygen Electrophiles", Synthesis, 2005, 14:2271-2280.

Hancock B.C. et al., "Molecular Mobility of Amorphous Pharmaceutical Solids Below Their Glass Transition Temperatures," Pharmaceutical Research, Jun. 1995, 12(6):799-806.

Hara, Y., et al. "Thyroid hormone resistance", Japanese Journal of Clinical Medicine, Syndrome by Region Series (1) Endocrine Syndrome (First volume), 1993, 254-257.

Harrison, S. et al. "MGL-3196, a selective thyroid hormone receptor-beta agonist, significantly decreases hepatic fat in NASH patients at 12 weeks, the primary endpoint in a 36 week serial liver biopsy study"; Madrigal Pharmaceuticals, Apr. 2018, 14 pages.

Harrison, S.A. et al., "Resmetirom (MGL-3196) for the treatment of non-alcoholic steatohepatitis: a multicenter, randomized, double-blind, placebo-controlled, phase 2 trial." Lancet, Nov. 30, 2019, 394(10213):2012-2014, 31 pages.

Hickey, D. M. B. et al., "Synthesis of Thyroid Hormone Analogues. Part 3. Iodonium Salt Approaches to Sk&F L-94901 ", J. Chem. Soc.: 3103-3111, 1988, Abstract, 1 page.

Hilfiker, R. et al. "Relevance of Solid-State Properties for Pharmaceutical Products", Polymorphism in the Pharmaceutical Industry, Wiley-VCH, Jan. 2006, 18 pages.

Hirayama, N., "Organic Compound Crystal Production Handbook—Principle and Know-How," Maruzen Co., Ltd., Jul. 25, 2008, 57-74.

Huber, B. R. et al., "Thyroid Hormone Receptor-B Mutations Conferring Hormone Resistance and Reduced Corepressor Release Exhibit Decreased Stability in the N-Terminal Ligand-Binding Domain", Molecular Endocrinology, 2003, 17(1):107-116.

Huber, B. R. et al. "Two Resistance to Thyroid Hormone Mutants with Impaired Hormone Binding", Molecular Endocrinology, Apr. 2003, 17(4):643-652.

ICH Harmonized Tripartite Guideline, "Specifications: Test Procedures and Acceptance Criteria for New Drug Substances and New Drug Products: Chemical Substances Q6A" dated Oct. 6, 1999, 35 pages.

Johansson, C. et al., "Evidence that decreased heart rate in thyroid hormone receptor-a1-deficient mice is an intrinsic defect", Am. J. Physiol., 1998, 275:R640-R646.

Joharapurkar, et al. "Selective thyromimetics using receptor and tissue selectivity approaches: prospects for dyslipidemia." J Med Chem., Jun. 28, 2012, 55(12):5649-75.

JP 56015272, Feb. 14, 1981; CA 94 208901, 1981. CAPLUS Abstract, 2 pages.

Kastelein J.J.P. et al., "LDL cholesterol, apolipoprotein B, lipoprotein(a), apolipoprotein CIII and triglyceride lowering by MGL-3196, a thyroid hormone beta selective agonist, in a 12 week study in HeFH patients", European Heart Journal, Aug. 1, 2018, 1105-1106.

Kawaguchi Y. et al. "Drug and crystal polymorphism", Journal of Human Environmental Engineering, 2002, vol. 4, p. 310-317.

Kelly M. J., et al., "Discovery of 2-[3,5-Dichloro-4-(5-isopropyl-6-oxo-1,6-dihydropyridazin-3-yloxy)phenyl]-3,5 dioxo-2,3,4,5-tetrahydro[1,2,4]triazine-6-carbonitrile (MGL-3196), a Highly Selective Thyroid Hormone Receptor β Agonist in Clinical Trials for the Treatment of Dyslipidemia," Journal of Medicinal Chemistry, 2014, 57, 10, 3912-3923.

Kumar, S. et al., "Pharmaceutical Solid Dispersion Technology: A Strategy to Improve Dissolution of Poorly Water-Soluble Drugs", Recent Patents on Drug Delivery & Formulation, May 2013, 7(2):111-121.

Lazar, M.A., "Thyroid Hormone Receptors: Multiple Forms, Multiple Possibilities", Endocrine Reviews, 1993, 14(2):184-193.

Liu, R. "Water-Insoluble Drug Formulation", Interpharm Press, Denver, Colorado, 2000, pp. 525, 557-561 (8 pages total).

Lu, C. et al., "Extranuclear signaling of mutated thyroid hormone receptors in promoting metastatic spread in thyroid carcinogenesis", Steroids, 2011, 76(9):885-91.

Mamas, M. et al. "The role of metabolites and metabolomics in clinically applicable biomarkers of disease," Arch Toxicol., 2011, 85:5-17.

(56) References Cited

OTHER PUBLICATIONS

Nigam, S. K. et al. "What do drug transporters really do?", Nat Rev Drug Discov. Jan. 2015, 14(1):29-44.

Nikolova, I. et al. "Anti-enteroviral activity of new MDL-860 analogues: Synthesis, in vitro/in vivo studies and QSAR analysis," Bioorganic Chemistry, Apr. 2019, 85:487-497.

Nikolova, I. et al. "Supplementary Data: Anti-enteroviral activity of new MDL-860 analogues: Synthesis, in vitro/in vivo studies and QSAR analysis," Bioorganic Chemistry, Apr. 2019, 85, 165 pages.

Nordestgaard, B. G. et al., "Familial hypercholesterolaemia is underdiagnosed and undertreated in the general population: guidance for clinicians to prevent coronary heart disease: Consensus Statement of the European Atherosclerosis Society", Eur Heart J. Dec. 2013;34(45):3478-90.

Office Action issued in Japanese Application No. 2020-572517, mailed on Jul. 11, 2023, 5 pages.

Office Action issued in Japanese Patent Application No. 2022-034154, mailed on May 9, 2023, 7 pages.

Office Action issued on Jun. 27, 2017, for Japanese Patent Application No. JP 2015-532148, 10 pages.

\* cited by examiner

FIG. 31

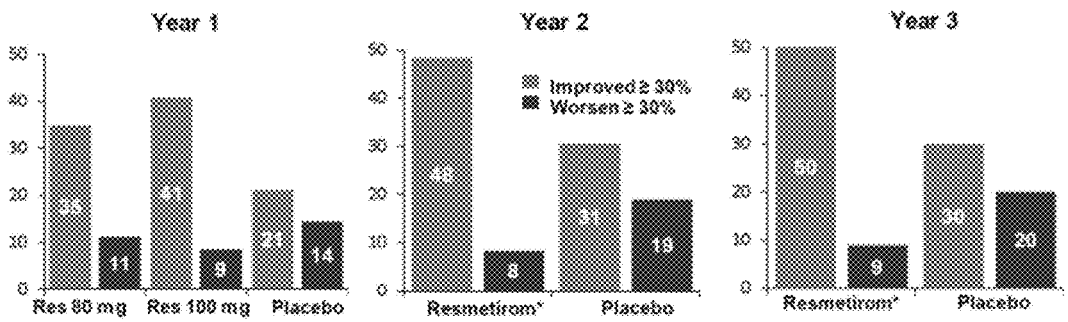

*All resmetirom treated patients (80 mg and 100 mg combined). VCTE, vibration-controlled transient elastography.

FIG. 32A

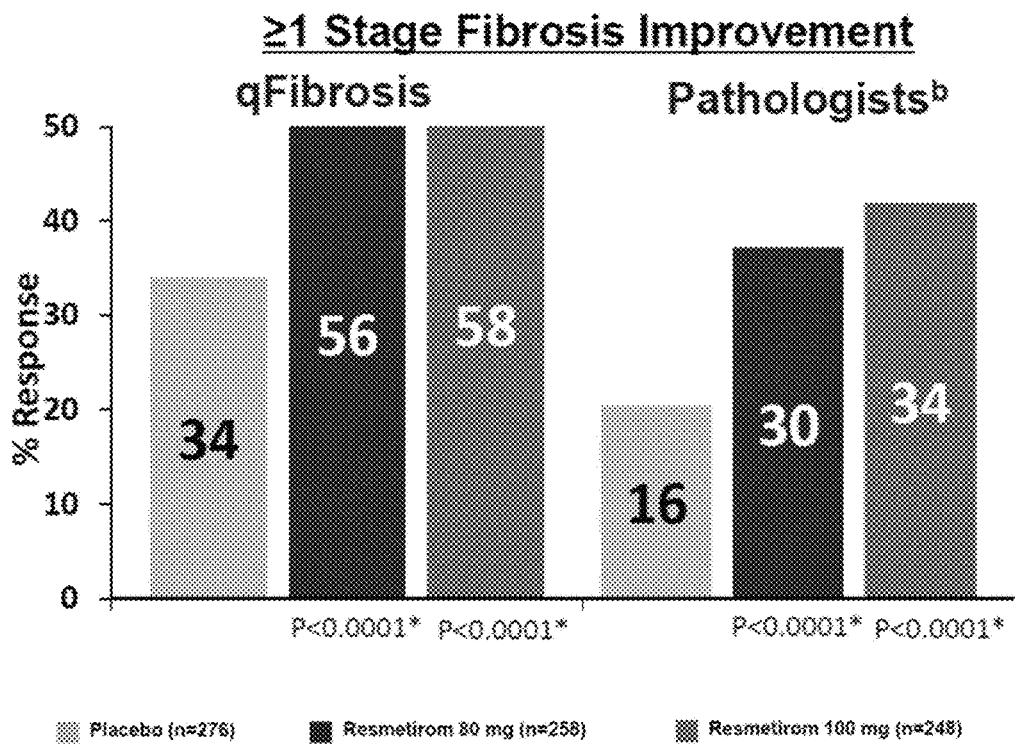

b Fibrosis improvement response: ≥1 stage improvement in fibrosis with no worsening of NAS
c Worsening was determined only in F1B/F2 patients by pathologists; worsening on qFibrosis is not directly linked to an ordinal fibrosis score
* All P values are nominal.

2 DOSAGE AND ADMINISTRATION

2.1 Recommended Dosage and Administration

The recommended dosage of REZDIFFRA is based on actual body weight. For patients weighing:
- <100 kg, the recommended dosage is 80 mg orally once daily.
- ≥100 kg, the recommended dosage is 100 mg orally once daily.

METHODS FOR TREATING A FATTY LIVER DISEASE

CROSS REFERENCE TO RELATED APPLICATIONS

This application claims the benefit of U.S. Provisional Application Nos. 63/550,201, filed Feb. 6, 2024, 63/564,803, filed Mar. 13, 2024, and 63/655,870, filed Jun. 4, 2024, the disclosures of all of which are incorporated herein by reference in their entireties.

TECHNICAL FIELD OF THE INVENTION

This disclosure is related to the area of treatment of a fatty liver disease, such as, for instance, non-alcoholic steatohepatitis (NASH) (e.g., noncirrhotic non-alcoholic steatohepatitis with moderate to advanced liver fibrosis consistent with stages F2 and F3 fibrosis. In particular, the disclosure relates to method for the efficacious treatment of a fatty liver disease (e.g., NASH) utilizing the thyroid hormone receptor-beta (THR-beta) agonist resmetirom or a pharmaceutically acceptable salt thereof. In addition, the disclosure is related to the area of treatment of stages F2 and F3 liver fibrosis associated with a fatty liver disease. In particular, the disclosure relates to a method for the efficacious treatment of stages F2 and F3 liver fibrosis associated with a fatty liver disease, with improvement of liver fibrosis by up to one or two stages, utilizing resmetirom or a pharmaceutically acceptable salt thereof.

BACKGROUND OF THE INVENTION

Thyroid hormones are critical for normal growth and development and for maintaining metabolic homeostasis. Circulating levels of thyroid hormones are tightly regulated by feedback mechanisms in the hypothalamus/pituitary/thyroid (HPT) axis. Thyroid dysfunction leading to hypothyroidism or hyperthyroidism clearly demonstrates that thyroid hormones exert profound effects on cardiac function, body weight, metabolism, metabolic rate, body temperature, cholesterol, bone, muscle, and behavior.

The development of thyroid hormone analogs which avoid the undesirable effects of hyperthyroidism and hypothyroidism while maintaining the beneficial effects of thyroid hormones would open new avenues of potential treatment for patients with metabolic disease such as obesity, hyperlipidemia, hypercholesterolemia, diabetes and other disorders and diseases such as liver steatosis and non-alcoholic steatohepatitis (NASH), atherosclerosis, cardiovascular diseases, hypothyroidism, thyroid cancer, thyroid diseases, resistance to thyroid hormone and related disorders and diseases.

Non-alcoholic steatohepatitis (NASH) is the most common chronic liver disease in the United States. NASH is a fatty inflammation of the liver and a major cause of fibrosis, cirrhosis and liver failure. The disease is progressive, starting as steatosis or nonalcoholic fatty liver disease (NAFLD), progressing to an inflamed fatty liver (NASH), and eventually leading to fibrosis and cirrhosis. The disease is generally asymptomatic until severe liver impairment occurs.

Human subjects with NASH may experience elevated liver volumes, which can be attributed to increased liver fat and fluid retention due to inflammatory processes in NASH. As NASH progresses to cirrhosis, liver fat decreases as the liver becomes increasingly fibrotic. Liver volume remains elevated in cirrhotic human subjects due to ongoing inflammation and venous congestion associated with portal hypertension. Reducing liver volume in noncirrhotic non-alcoholic steatohepatitis with moderate to advanced liver fibrosis consistent with stages F2 and F3 fibrosis human subjects is important for maintaining perfusion of the diseased liver and reversing disease progression to cirrhosis. Liver volume reduction in NASH and cirrhosis is associated with histopathologic improvement of the liver.

The prevalence of NAFLD in the U.S. population is about 20-23%, and may be as high as 33%, and the prevalence of NASH in the U.S. population is about 2-3%. Some NASH patients will progress to late-stage disease: approximately 15-50% of NASH patients progress to severe fibrosis, and approximately 7-16% progress to cirrhosis. The rate of liver-specific mortality in NASH cirrhotics is approximately 10% per decade.

Obesity is a common characteristic of both NASH and cirrhosis, due to insufficient weight loss through diet and lifestyle modifications, this patient population is often prescribed interventional surgical procedures (e.g., bariatric surgery). Liver volume reduction immediately prior to surgery is aggressively pursued to improve surgical access to the stomach.

SUMMARY

Resmetirom has previously been mentioned in connection with the treatment of a fatty liver disease, such as NASH. However, it has now been unexpectedly found that the 100 mg dose thereof leads to better outcomes than the 80 mg dose in human subjects that weigh at least 100 kg. The 80 mg dose is optimal for human subjects that weigh less than 100 kg to achieve better outcomes with discontinuation rates based upon adverse results in clinical trials similar to placebo. This weight-based dosing was recognized by the U.S. Food and Drug Administration (FDA) in the approval of REZDIFFRA™ (resmetirom), as reflected in the prescribing information (https://www.accessdata.fda.gov/drugsatfda_docs/label/2024/217785s0001bl.pdf, incorporated herein by reference in its entirety) and also shown in FIG. 46.

Disclosed herein is a method of treating or improving a fatty liver disease, such as, for example non-alcoholic steatohepatitis (NASH) (e.g., noncirrhotic non-alcoholic steatohepatitis with moderate to advanced liver fibrosis consistent with stages F2 and F3 fibrosis) in a human subject (e.g., an adult human subject) who may be in need of such treatment or improvement.

In particular, disclosed herein is a method of treating NASH. The method comprises: determining a weight of an adult human subject in need thereof; and based on determination of the weight of the adult human subject in need thereof, administering to the adult human subject in need thereof a solid oral dosage form comprising:
 (i) resmetirom or a pharmaceutically acceptable salt thereof at a dosage of 100 mg per day, if the adult human subject in need thereof is determined to weigh 100 kg or more; or
 (ii) resmetirom or the pharmaceutically acceptable salt thereof at a dosage of 80 mg per day, if the adult human subject in need thereof is determined to weigh less than 100 kg.

In some embodiments, the adult human subject in need thereof is determined to weigh 100 kg or more and is administered the solid oral dosage form comprising resmetirom or the pharmaceutically acceptable salt thereof at the dosage of 100 mg per day.

In some embodiments, the adult human subject in need thereof is determined to weigh less than 100 kg and is administered the solid oral dosage form comprising resmetirom or the pharmaceutically acceptable salt thereof at the dosage of 80 mg per day.

In some embodiments, the solid oral dosage form is a tablet.

In some embodiments, the solid oral dosage form comprises resmetirom.

Also disclosed herein is a method of treating or improving liver fibrosis associated with a fatty liver disease (e.g., NASH) in a human subject (e.g., an adult human subject) who may be in need of such treatment or improvement.

In particular, disclosed herein is a method of improving liver fibrosis. The method comprises: determining a weight of an adult human subject in need thereof; and based on determination of the weight of the adult human subject in need thereof, administering to the adult human subject in need thereof a solid oral dosage form comprising:
  (i) resmetirom or a pharmaceutically acceptable salt thereof at a dosage of 100 mg per day, if the adult human subject in need thereof is determined to weigh 100 kg or more; or
  (ii) resmetirom or the pharmaceutically acceptable salt thereof at a dosage of 80 mg per day, if the adult human subject in need thereof is determined to weigh less than 100 kg; and
  wherein the adult human subject in need thereof has nonalcoholic steatohepatitis (NASH) with moderate to advanced liver fibrosis consistent with stages F2 to F3.

In some embodiments, the adult human subject in need thereof is determined to weigh 100 kg or more and is administered the solid oral dosage form comprising resmetirom or the pharmaceutically acceptable salt thereof at the dosage of 100 mg per day.

In some embodiments, the adult human subject in need thereof is determined to weigh less than 100 kg and is administered the solid oral dosage form comprising resmetirom or the pharmaceutically acceptable salt thereof at the dosage of 80 mg per day.

In some embodiments, the method is of improving the liver fibrosis by at least one stage in the adult human subject in need thereof.

In some embodiments, the solid oral dosage form is a tablet.

In some embodiments, the solid oral dosage form comprises resmetirom.

In some embodiments, the adult human subject in need thereof has liver fibrosis characterized as fibrosis stage F3.

Also disclosed herein is a method of treating or improving liver fibrosis. The method comprises: determining a weight of an adult human subject in need thereof; and based on determination of the weight of the adult human subject in need thereof, administering to the adult human subject in need thereof a solid oral dosage form comprising:
  (i) resmetirom or a pharmaceutically acceptable salt thereof at a dosage of 100 mg per day, if the adult human subject in need thereof is determined to weigh 100 kg or more; or
  (ii) resmetirom or the pharmaceutically acceptable salt thereof at a dosage of 80 mg per day, if the adult human subject in need thereof is determined to weigh less than 100 kg; and
  wherein the adult human subject in need thereof has nonalcoholic steatohepatitis (NASH) with mild liver fibrosis consistent with stage F1.

Also disclosed herein is a method of treating or improving a fatty liver disease (e.g., NASH) in a human subject (e.g., an adult human subject) who may be in need of such treatment or improvement who may also be on a moderate CYP2C8 inhibitor regimen. In this instance, the human subject is administered resmetirom or a pharmaceutically acceptable salt thereof at a dosage that is reduced by 20 mg per day relative to what the same human subject would have otherwise been administered based on the determination of the weight. If the human subject was taking resmetirom or the pharmaceutically acceptable salt thereof prior to using a moderate CYP2C8 inhibitor, then the dose administered to the human subject as determined based on the weight of the human subject would be reduced by 20 mg per day to the reduced dosage, during the concomitant use of the moderate CYP2C8 inhibitor. If the human subject was not taking resmetirom or the pharmaceutically acceptable salt thereof prior to using a moderate CYP2C8 inhibitor, then the human subject would start with the reduced dosage and continue taking the reduced dosage, determined based on the weight of the human subject, during the concomitant use of the moderate CYP2C8 inhibitor.

In particular, disclosed herein is a method of treating NASH, which comprises: determining a weight of an adult human subject in need thereof; and based on determination of the weight of the adult human subject in need thereof, administering to the adult human subject in need thereof a solid oral dosage form comprising:
  (i) resmetirom or a pharmaceutically acceptable salt thereof at a reduced dosage of 80 mg per day, if the adult human subject in need thereof is determined to weigh 100 kg or more and the adult human subject in need thereof is using a moderate CYP2C8 inhibitor; or
  (ii) resmetirom or the pharmaceutically acceptable salt thereof at a reduced dosage of 60 mg per day, if the adult human subject in need thereof is determined to weigh less than 100 kg and the adult human subject in need thereof is using a moderate CYP2C8 inhibitor.

In some embodiments, the adult human subject in need thereof is determined to weigh 100 kg or more and is administered the solid oral dosage form comprising the resmetirom or the pharmaceutically acceptable salt thereof at the reduced dosage of 80 mg per day. In some embodiments, the adult human subject in need thereof used resmetirom or the pharmaceutically acceptable salt thereof at an oral dose of 100 mg per day before starting to use the moderate CYP2C8 inhibitor, and the oral dose of 100 mg per day is reduced to the reduced dosage of 80 mg per day.

In some embodiments, the adult human subject in need thereof is determined to weigh less than 100 kg and is administered the solid oral dosage form comprising the resmetirom or the pharmaceutically acceptable salt thereof at the reduced dosage of 60 mg per day. In some embodiments, the adult human subject in need thereof used resmetirom or the pharmaceutically acceptable salt thereof at an oral dose of 80 mg per day before starting to use the moderate CYP2C8 inhibitor, and the oral dose of 80 mg per day is reduced to the reduced dosage of 60 mg per day.

In some embodiments, the moderate CYP2C8 inhibitor is selected from the group consisting of rosiglitazone, trimethoprim, tamoxifen, irbesartan, quinine, efavirenz, rabeprazole, crisaborole, nabilone, bexarotene, ritonavir, nicardipine, loratadine, eltrombopag, diltiazem, enzalutamide, ketoconazole, fluvastatin, levothyroxine, oxybutynin, medroxyprogesterone acetate, spironolactone, amlodipine, saquinavir, abiraterone, genistein, lenvatinib, pioglitazone, clotrimazole, nilotinib, teriflunomide, topiroxostat, lovastatin, troglitazone, amitriptyline, pirtobrutinib, belinostat, bezafibrate, candesartan, cholecalciferol, cimetidine, colchicine, dabrafenib, deferasirox, diethylstilbestrol, enasidenib, erlotinib, ethinylestradiol, fenofibrate, gemfibrozil, idelalisib, isoniazid, ketoprofen, letermovir, lumacaftor, mefenamic acid, midostaurin, montelukast, nilutamide, opicapone, phenelzine, piroxicam, pyrimethamine, quercetin, raloxifene, repaglinide, rifampicin, rofecoxib, salmeterol, sorafenib, sulfaphenazole, tegaserod, terbinafine, terfenadine, thiazolidinediones, ticlopidine, trametinib, triazolam, troleandomycin, valproic acid, verapamil, vismodegib, clopidogrel, and zafirlukast.

In some embodiments, the moderate CYP2C8 inhibitor is clopidogrel, deferasirox, gemfibrozil, teriflunomide, trimethoprim, and/or pioglitazone.

In some embodiments, the method is of treating noncirrhotic nonalcoholic steatohepatitis with moderate to advanced liver fibrosis consistent with stages F2 to F3.

In some embodiments, the method is of treating noncirrhotic nonalcoholic steatohepatitis with mild liver fibrosis consistent with stage F1.

In some embodiments, the solid oral dosage form is a tablet.

Also disclosed herein is a method of treating or improving liver fibrosis associated with a fatty liver disease (e.g., NASH) in a human subject (e.g., an adult human subject) who may be in need of such treatment or improvement who may also be on a moderate CYP2C8 inhibitor regimen.

In particular, disclosed herein is a method of improving liver fibrosis, which comprises: determining a weight of an adult human subject in need thereof; and based on determination of the weight of the adult human subject in need thereof, administering to the adult human subject in need thereof a solid oral dosage form comprising:
(i) resmetirom or a pharmaceutically acceptable salt thereof at a reduced dosage of 80 mg per day, if the adult human subject in need thereof is determined to weigh 100 kg or more and the adult human subject in need thereof is using a moderate CYP2C8 inhibitor; or
(ii) resmetirom or the pharmaceutically acceptable salt thereof at a reduced dosage of 60 mg per day, if the adult human subject in need thereof is determined to weigh less than 100 kg and the adult human subject in need thereof is using a moderate CYP2C8 inhibitor; and
wherein the adult human subject in need thereof has liver fibrosis associated with nonalcoholic steatohepatitis (NASH).

In some embodiments, the adult human subject in need thereof is determined to weigh 100 kg or more and is administered the solid oral dosage form comprising resmetirom or a pharmaceutically acceptable salt thereof at the reduced dosage of 80 mg per day. In some embodiments, the adult human subject in need thereof used resmetirom or the pharmaceutically acceptable salt thereof at an oral dose of 100 mg per day before starting to use the moderate CYP2C8 inhibitor, and the oral dose of 100 mg per day is reduced to the reduced dosage of 80 mg per day.

In some embodiments, the adult human subject in need thereof is determined to weigh less than 100 kg and is administered the solid oral dosage form comprising resmetirom or the pharmaceutically acceptable salt thereof at the reduced dosage of 60 mg per day. In some embodiments, the adult human subject in need thereof used resmetirom or the pharmaceutically acceptable salt thereof at an oral dose of 80 mg per day before starting to use the moderate CYP2C8 inhibitor, and the oral dose of 80 mg per day is reduced to the reduced dosage of 60 mg per day.

In some embodiments, the adult human subject in need thereof has liver fibrosis characterized as fibrosis stage F1. In some embodiments, the method is of improving the liver fibrosis by one stage in the adult human subject in need thereof.

In some embodiments, the adult human subject in need thereof has liver fibrosis characterized as fibrosis stage F2. In some embodiments, the method is of improving the liver fibrosis by one or two stages in the adult human subject in need thereof.

In some embodiments, the adult human subject in need thereof has liver fibrosis characterized as fibrosis stage F3. In some embodiments, the method is of improving the liver fibrosis by one or two stages in the adult human subject in need thereof.

In some embodiments, the moderate CYP2C8 inhibitor is selected from the group consisting of rosiglitazone, trimethoprim, tamoxifen, irbesartan, quinine, efavirenz, rabeprazole, crisaborole, nabilone, bexarotene, ritonavir, nicardipine, loratadine, eltrombopag, diltiazem, enzalutamide, ketoconazole, fluvastatin, levothyroxine, oxybutynin, medroxyprogesterone acetate, spironolactone, amlodipine, saquinavir, abiraterone, genistein, lenvatinib, pioglitazone, clotrimazole, nilotinib, teriflunomide, topiroxostat, lovastatin, troglitazone, amitriptyline, pirtobrutinib, belinostat, bezafibrate, candesartan, cholecalciferol, cimetidine, colchicine, dabrafenib, deferasirox, diethylstilbestrol, enasidenib, erlotinib, ethinylestradiol, fenofibrate, gemfibrozil, idelalisib, isoniazid, ketoprofen, letermovir, lumacaftor, mefenamic acid, midostaurin, montelukast, nilutamide, opicapone, phenelzine, piroxicam, pyrimethamine, quercetin, raloxifene, repaglinide, rifampicin, rofecoxib, salmeterol, sorafenib, sulfaphenazole, tegaserod, terbinafine, terfenadine, thiazolidinediones, ticlopidine, trametinib, triazolam, troleandomycin, valproic acid, verapamil, vismodegib, clopidogrel, and zafirlukast.

In some embodiments, the moderate CYP2C8 inhibitor is clopidogrel, deferasirox, gemfibrozil, teriflunomide, trimethoprim, and/or pioglitazone.

In some embodiments, the solid oral dosage form is a tablet.

BRIEF DESCRIPTION OF THE DRAWINGS

The above and further features will be more clearly appreciated from the following detailed description when taken in conjunction with the accompanying drawings.

FIG. 31 is a graphical representation showing the VCTE responder analyses at years 1-3 in patients in the placebo, resmetirom 80 mg, and resmetirom 100 mg groups in the MAESTRO-NASH population in Example 2.

FIG. 32A is a graphical representation showing the percentage of patients in the placebo, resmetirom 80 mg, and resmetirom 100 mg groups that achieved ≥1 stage fibrosis improvement as determined by qFibrosis and pathologists in Example 2.

DETAILED DESCRIPTION

Figure 1:
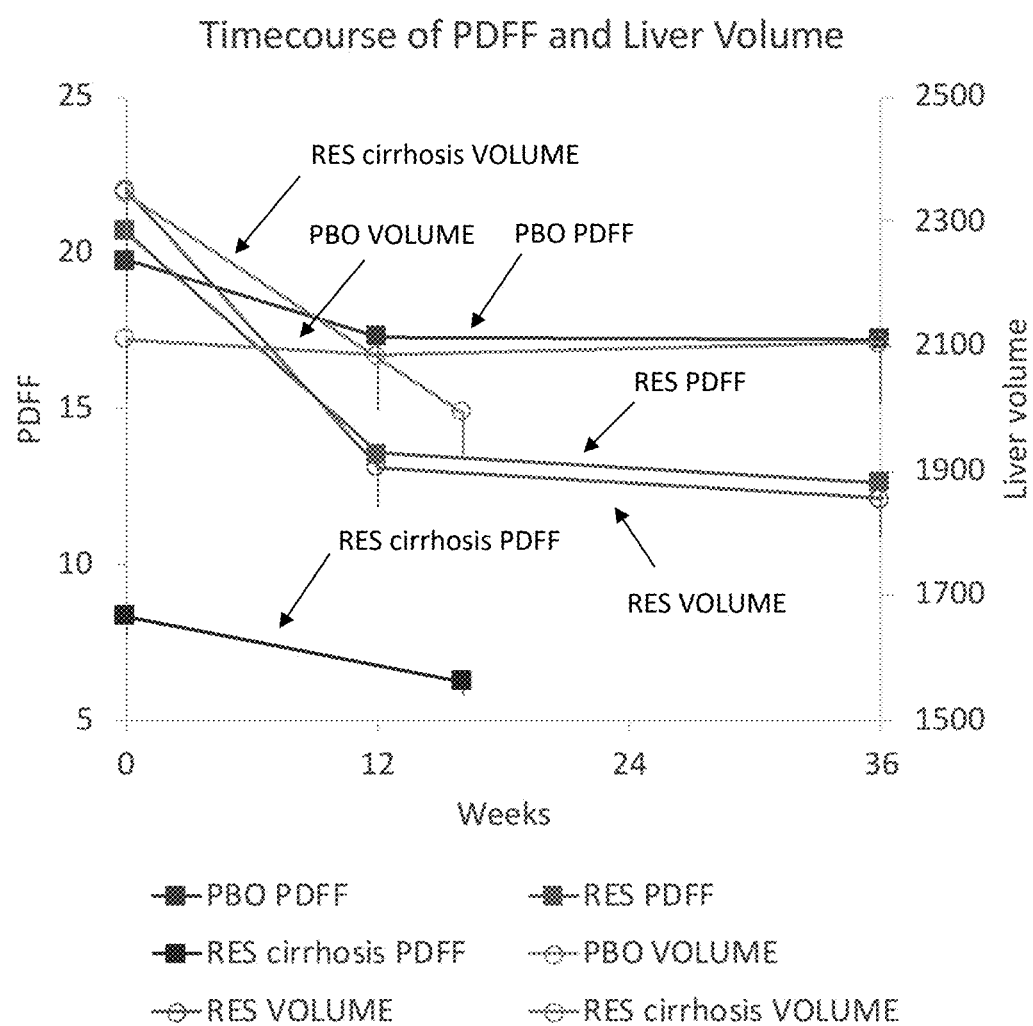
FIG. 1 is a graphical representation showing the correlation of liver volume reduction and proton density fat fraction (PDFF) reduction in placebo and resmetirom treated patients at 12 weeks in Example 1. "PBO" represents placebo patients and "RES" represents resmetirom-treated patients.

Unless otherwise defined, all technical and scientific terms used herein have the same meaning as commonly understood by one of ordinary skill in the art to which this disclosure belongs. The terminology used in the description is intended to describe particular embodiments only, and is not intended to limit the scope of the invention.

As used herein, the following terms have the meaning indicated, unless otherwise specifically noted in context. Unless otherwise defined herein, all technical terms used herein have the same meaning as commonly understood by one of ordinary skill in the art to which this disclosure belongs.

As used herein, the term "MRI-PDFF" describes proton-density-fat-fraction determined by a magnetic resonance imaging (MRI)-based determination. MRI-PDFF is an MRI-based diagnostic imaging biomarker of the liver. MRI-PDFF is a measure to assess liver fat content and is proposed to be used as non-invasive method used as a pre-screening strategy in an adult population having clinical signs or risk factors suggesting nonalcoholic fatty liver disease, e.g., noncirrhotic non-alcoholic steatohepatitis (NASH) with moderate to advanced liver fibrosis consistent with stages F2 and F3 fibrosis. MRI-PDFF is also used as a monitoring tool to demonstrate efficacy and reduction in NASH over time. MRI-PDFF is an accurate quantitative imaging biomarker with high repeatability and reproducibility and has provided results from test and validation datasets with MRI-PDFF compared to liver histology to show optimal MRI-PDFF cut-offs in order to reduce the number of unnecessary biopsies.

As used herein, the term "portal hypertension," refers to an increase in the pressure within the portal vein (the vein that carries blood from the digestive organs (large and small intestines, stomach, pancreas, spleen) to the liver). The increase in pressure is caused by a blockage in the blood flow through the liver.

As used herein, the term "cirrhosis," refers to a late stage of scarring (fibrosis) of the liver caused by many forms of liver diseases and conditions, such as hepatitis and chronic alcoholism. The liver fat of a cirrhosis human subject (e.g., as measured by MRI-PDFF) is no more than 5%.

As used herein, "administering" or "administered to" refers to prescribing a medicine to a human subject, directing others to administer a medicine to a human subject, directing a human subject to self-administer a medicine, and/or the act of physically ingesting the medicine. A medicine containing resmetirom (or a pharmaceutically acceptable salt of resmetirom) as its active pharmaceutical ingredient, can therefore be administered by a physician or other medical professional who writes prescriptions for a medicine(s) or otherwise directs a patient to self-administer a prescription, and/or by the human subject who ingests the medicine and/or by a human subject's caretaker who provides the medicine to a human subject.

As used herein, the term "preventing" or "prevent" describes reducing or eliminating the onset of the symptoms or complications of such disease, condition or disorder.

As used herein, the term "daily" means every day, where each day is defined by a 24 hour period. For the avoidance of doubt, the 24 hour period defining "daily" can bridge two calendar days, for example, Sunday-Monday; Monday-Tuesday; Tuesday-Wednesday; etc.

As used herein, the term "dose," "dosage" or "daily dosage" refers to the weight of an active ingredient (e.g., resmetirom).

As used herein, the term "reduced dosage" refers to a dose of resmetirom or the pharmaceutically acceptable salt thereof that is less than the dose that would otherwise be administered to the human subject based on the determination of the human subject's weight due to concomitant use of a moderate CYP2C8 inhibitor.

In some embodiments, the human subject who is administered resmetirom or the pharmaceutically acceptable salt thereof is concomitantly on a moderate CYP2C8 inhibitor regimen. Such a human subject is administered a reduced dosage of resmetirom or the pharmaceutically acceptable salt thereof per day compared to the daily dose that would otherwise be administered if this human subject were not on a moderate CYP2C8 inhibitor regimen.

In some embodiments, the human subject was already taking the moderate CYP2C8 inhibitor prior to being administered resmetirom or the pharmaceutically acceptable salt thereof.

As used herein, the term "pharmaceutically acceptable excipient" means an excipient that is useful in preparing a formulation that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

As used herein, the term "human subject" refers to a human subject who is an adolescent or an adult.

As used herein, an "adult human subject" refers to a human subject who is 18 years of age or older.

As used herein, an "adolescent human subject" refers to a human subject who is 12 years of age or older and younger than 18 years of age. A physician's prescription in connection with the treatment and/or improvement as disclosed herein to a human subject younger than 18 years old is considered to be off-label.

As used herein, the term "human subject in need thereof," refers to a human subject having a disease (to be treated) or having an increased risk of developing the disease (to be prevented). A human subject in need thereof can be one who has been previously diagnosed or identified as having a disease or disorder disclosed herein. A human subject in need thereof can also be one who has (e.g., is suffering from) a disease or disorder disclosed herein. Alternatively, a human subject in need thereof can be one who has an increased risk of developing such disease or disorder relative to the population at large (i.e., a human subject who is predisposed to developing such disorder relative to the population at large). A human subject in need thereof can have a refractory or resistant a disease or disorder disclosed herein (i.e., a disease or disorder disclosed herein that doesn't respond or hasn't yet responded to treatment). The human subject may be resistant at start of treatment or may become resistant during treatment. In some embodiments, the human subject in need thereof received and failed all known effective therapies for a disease or disorder disclosed herein. In some embodiments, the human subject in need thereof received at least one prior therapy.

As used herein, the term "salt" or "pharmaceutically acceptable salt" refers to a derivative of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc. Other examples of pharmaceutically acceptable salts include those derived from hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. Further examples of pharmaceutically acceptable salts include caffeine, urea, 2-picolinic acid, N-methyl-morpholine, piperazine, benzathine, and L-proline salts. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3. It is to be understood that all references to pharmaceutically acceptable salts include solvent addition forms (solvates) or crystal forms (polymorphs) or co-crystals as defined herein, of the same salt. Some pharmaceutically acceptable salts of resmetirom—and methods for preparing the same—are described in U.S. Patent Application Publication Nos. 2021/0122740 and 2023/0364099, both of which are incorporated herein by reference in their entireties.

As used herein, the term "treating" or "treat" describes the management and care of a patient for the purpose of combating a disease, condition, or disorder and includes the administration of a compound of the present disclosure to alleviate the symptoms or complications of a disease, condition or disorder, or to eliminate the disease, condition or disorder. That is, "treating" or "treatment" of a state, disorder, or condition therefore includes: (1) delaying the appearance of clinical symptoms of the state, disorder, or condition developing in a human that may be afflicted with the state, disorder, or condition but does not yet experience or display clinical or subclinical symptoms of the state, disorder, or condition, (2) inhibiting the state, disorder, or condition, i.e., arresting or reducing the development of the disease or a relapse thereof (in case of maintenance treatment) or at least one clinical or subclinical symptom thereof, or (3) relieving or attenuating the disease, i.e., causing regression of the state, disorder, or condition or at least one of its clinical or subclinical symptoms.

As used herein, a "solvate" refers to a crystalline form that includes a solvent (e.g., an organic solvent) chemically incorporated with the parent molecule in various fractional or integral molar ratios.

As used herein, a "hydrate" refers to a crystalline form that includes water chemically incorporated with the parent molecule in various fractional or integral molar ratios.

As used herein, a "co-crystal" refers to a crystalline material including at least two, different, molecules in the same crystalline lattice and associated by non-ionic and/or non-covalent bonds in a defined stoichiometric ratio. In some embodiments, the co-crystal includes two molecules which are in natural state. As used herein, this at least one other molecule is referred to as a "co-crystal former." For example, a co-crystal may be resmetirom with at least one co-crystal former in a defined stoichiometric ratio.

As used herein, an "amorphous form" refers to a non-crystalline material that lacks long-range order in its structure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Resmetirom is a compound having the chemical name 2-(3,5-dichloro-4-((5-isopropyl-6-oxo-1,6-dihydro-pyridazin-3-yl)oxy)phenyl)-3,5-dioxo-2,3,4,5-tetrahydro-1,2,4-triazine-6-carbonitrile. Resmetirom has the chemical structure depicted below:

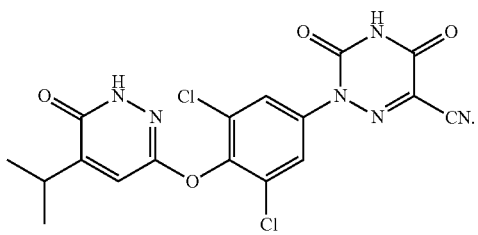 [SMILES: CC(C)c1cc(Oc2c(Cl)cc(-n3nc(C#N)c(=O)[nH]c3=O)cc2Cl)n[nH]c1=O]

It is to be understood that resmetirom or the pharmaceutically acceptable salt thereof can exist in crystalline or amorphous form. It is also to be understood that resmetirom or the pharmaceutically acceptable salt thereof can exist as a hydrate, solvate, or co-crystal. Various forms of resmetirom or the pharmaceutically acceptable salt thereof—and processes for preparing the same—are described in the following patents, applications, and/or publications, all of which are incorporated herein by reference in their entireties:

U.S. Pat. No. 9,266,861
U.S. Pat. No. 10,376,517
U.S. Patent Application Publication No. 2021/0122740
U.S. Patent Application Publication No. 2023/0416234
WO 2022/171200
WO 2025/011259
WO 2021/063367
CN 115124515A
IN 202241066042A
U.S. Patent Application Publication No. 2024/0423993
CN 118772117A
MSN Laboratories Private Limited, R&D Center, et al, "Solid-state forms of Resmetirom and processes for preparation thereof," found at https://www.tdcommons.org/cgi/viewcontent.cgi?article=8898&context=dpubs_series
U.S. Patent Application Publication No. 2022/0372021
U.S. Patent Application Publication No. 2023/0364099

It is to be understood that resmetirom or the pharmaceutically acceptable salt thereof may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Resmetirom is described, for example, in Examples 4 and 5 of U.S. Pat. No. 9,266,861 and PCT Pub. No. WO 2014/043706. One aspect of the present disclosure relates to methods of treatment or improvement as disclosed herein (e.g., of NASH and/or liver fibrosis) in which a solid dosage form administered to a human subject (e.g., an adult human subject) who may be in need of such treatment or improvement contains resmetirom or a pharmaceutically acceptable salt thereof, existing in a morphic form (e.g., an amorphous form, a crystalline form, a solvate, or a hydrate) or a mixture of morphic forms.

In some embodiments, the resmetirom exists in a crystalline form.

In some embodiments, the resmetirom exists in an amorphous form.

In some embodiments, the resmetirom is in the form of a solvate.

In some embodiments, the resmetirom is in the form of a hydrate.

In some embodiments, the resmetirom is in the form of a co-crystal along with a co-crystal former as part of the co-crystal.

All doses or dosages recited herein for resmetirom or the pharmaceutically acceptable salt thereof are based on the molecular weight of the compound itself, rather than the molecular weight of the pharmaceutically acceptable salt thereof, or the hydrate or solvate thereof, or the co-crystal thereof, or any excipients in the composition, unless otherwise stated. For example, administration of resmetirom or the pharmaceutically acceptable salt thereof at a dosage of 100 mg per day means administration of the equivalent of 100 mg of the compound itself per day, not 100 mg of the pharmaceutically acceptable salt thereof, or the hydrate or solvate thereof, or the co-crystal thereof, per day.

The present disclosure provides a method of treating or improving a fatty liver disease (e.g., NASH), the method comprising administering to the human subject (e.g., an adult human subject) who may be in need of such treatment or improvement resmetirom or a pharmaceutically acceptable salt thereof.

The present disclosure also provides a method of treating or improving liver fibrosis associated with a fatty liver disease (e.g., NASH), the method comprising administering to the human subject (e.g., an adult human subject) who may be in need of such treatment or improvement resmetirom or a pharmaceutically acceptable salt thereof.

The present disclosure also provides resmetirom or a pharmaceutically acceptable salt thereof for use for treating or improving a fatty liver disease (e.g., NASH) in a human subject (e.g., an adult human subject) who may be in need of such treatment or improvement.

The present disclosure also provides use resmetirom or a pharmaceutically acceptable salt thereof in the manufacture of a medicament for treating or improving a fatty liver disease (e.g., NASH) in a human subject (e.g., an adult human subject) who may be in need of such treatment or improvement.

In some aspects, the present disclosure provides a method of reducing liver volume in a human subject (e.g., an adult human subject) who may be in need of such a reduction and/or may be in need of treatment or improvement as disclosed herein (e.g., of NASH and/or liver fibrosis), the method comprising administering to this human subject resmetirom or a pharmaceutically acceptable salt thereof.

In some aspects, the present disclosure provides resmetirom or a pharmaceutically acceptable salt thereof for use for reducing liver volume in a human subject (e.g., an adult human subject) who may be in need of such a reduction and/or may be in need of treatment or improvement as disclosed herein (e.g., of NASH and/or liver fibrosis).

In some aspects, the present disclosure provides use of resmetirom or a pharmaceutically acceptable salt thereof in the manufacture of a medicament for reducing liver volume in a human subject (e.g., an adult human subject) who may be in need of such a reduction and/or the treatment or improvement as disclosed herein (e.g., of NASH and/or liver fibrosis).

In some aspects, the present disclosure provides resmetirom or a pharmaceutically acceptable salt thereof for use in treating or preventing NASH in a human subject (e.g., an adult human subject) who may be in need of such treatment or prevention.

In some aspects, the present disclosure provides resmetirom or a pharmaceutically acceptable salt thereof in the manufacture of a medicament for treating or preventing NASH in a human subject (e.g., an adult human subject) who may be in need of such treatment or prevention.

Specifically, the present disclosure provides a method of treating NASH. The method comprises: determining a weight of an adult human subject in need thereof; and based on determination of the weight of the adult human subject in need thereof, administering to the adult human subject in need thereof a solid oral dosage form comprising:
(i) resmetirom or a pharmaceutically acceptable salt thereof at a dosage of 100 mg per day, if the adult human subject in need thereof is determined to weigh 100 kg or more; or
(ii) resmetirom or the pharmaceutically acceptable salt thereof at a dosage of 80 mg per day, if the adult human subject in need thereof is determined to weigh less than 100 kg.

In some embodiments, the adult human subject in need thereof is determined to weigh 100 kg or more and is administered the solid oral dosage form comprising resmetirom or the pharmaceutically acceptable salt thereof at the dosage of 100 mg per day.

In some embodiments, the adult human subject in need thereof is determined to weigh less than 100 kg and is administered the solid oral dosage form comprising resmetirom or the pharmaceutically acceptable salt thereof at the dosage of 80 mg per day.

In some embodiments, the solid oral dosage form is a tablet.

In some embodiments, the solid oral dosage form comprises resmetirom.

Specifically, the present disclosure also provides a method of improving liver fibrosis. The method comprises: determining a weight of an adult human subject in need thereof; and based on determination of the weight of the adult human subject in need thereof, administering to the adult human subject in need thereof a solid oral dosage form comprising:
(i) resmetirom or a pharmaceutically acceptable salt thereof at a dosage of 100 mg per day, if the adult human subject in need thereof is determined to weigh 100 kg or more; or
(ii) resmetirom or the pharmaceutically acceptable salt thereof at a dosage of 80 mg per day, if the adult human subject in need thereof is determined to weigh less than 100 kg; and
wherein the adult human subject in need thereof has nonalcoholic steatohepatitis (NASH) with moderate to advanced liver fibrosis consistent with stages F2 to F3.

In some embodiments, the adult human subject in need thereof is determined to weigh 100 kg or more and is administered the solid oral dosage form comprising resmetirom or the pharmaceutically acceptable salt thereof at the dosage of 100 mg per day.

In some embodiments, the adult human subject in need thereof is determined to weigh less than 100 kg and is administered the solid oral dosage form comprising resmetirom or the pharmaceutically acceptable salt thereof at the dosage of 80 mg per day.

In some embodiments, the method is of improving the liver fibrosis by at least one stage in the adult human subject in need thereof.

In some embodiments, the solid oral dosage form is a tablet.

In some embodiments, the solid oral dosage form comprises resmetirom.

In some embodiments, the adult human subject in need thereof has liver fibrosis characterized as fibrosis stage F3.

In some embodiments, the adult human subject in need thereof has liver fibrosis characterized as fibrosis stage F2.

The present disclosure also provides a method of treating or improving a fatty liver disease (e.g., NASH). The method comprises: determining a weight of a human subject (e.g., an adult human subject); and based on determination of the weight of the human subject (e.g., an adult human subject), administering to the human subject (e.g., an adult human subject) a solid oral dosage form comprising:
(i) resmetirom or a pharmaceutically acceptable salt thereof at a dosage of 100 mg per day, if the human subject (e.g., an adult human subject) is determined to weigh 100 kg or more; or
(ii) resmetirom or a pharmaceutically acceptable salt thereof at a dosage of 80 mg per day, if the human subject is determined to weigh less than 100 kg.

The present disclosure also provides a method of improving a fatty liver disease (e.g., NASH). The method comprises: determining a weight of a human subject who may be in need of such improvement (e.g., an adult human subject); and based on determination of the weight of this human subject, administering to this human subject a solid oral dosage form comprising:
(i) resmetirom or a pharmaceutically acceptable salt thereof at a dosage of 100 mg per day, if this human subject is determined to weigh 100 kg or more; or
(ii) resmetirom or a pharmaceutically acceptable salt thereof at a dosage of 80 mg per day, if this human subject is determined to weigh less than 100 kg.

The present disclosure also provides a method of treating a fatty liver disease (e.g., NASH). The method comprises: determining a weight of a human subject in need of such treatment (e.g., an adult human subject); and based on determination of the weight of the human subject in need of such treatment (e.g., an adult human subject), administering to the human subject in need of such treatment (e.g., an adult human subject) a solid oral dosage form comprising:
(i) resmetirom or a pharmaceutically acceptable salt thereof at a dosage of 100 mg per day, if the human subject in need of such treatment (e.g., an adult human subject) is determined to weigh 100 kg or more; or
(ii) resmetirom or a pharmaceutically acceptable salt thereof at a dosage of 80 mg per day, if the human subject in need of such treatment (e.g., an adult human subject) is determined to weigh less than 100 kg.

The present disclosure also provides a method of treating or improving liver fibrosis associated with a fatty liver disease (e.g., NASH). The method comprises: determining a weight of a human subject (e.g., an adult human subject); and based on determination of the weight of the human subject (e.g., an adult human subject), administering to the human subject (e.g., an adult human subject) a solid oral dosage form comprising:
(i) resmetirom or a pharmaceutically acceptable salt thereof at a dosage of 100 mg per day, if the human subject (e.g., an adult human subject) is determined to weigh 100 kg or more; or
(ii) resmetirom or a pharmaceutically acceptable salt thereof at a dosage of 80 mg per day, if the human subject is determined to weigh less than 100 kg.

The present disclosure also provides a method of treating liver fibrosis associated with a fatty liver disease (e.g., NASH). The method comprises: determining a weight of a human subject (e.g., an adult human subject) who may be in need of such treatment; and based on determination of the weight of this human subject, administering to this human subject a solid oral dosage form comprising:
(i) resmetirom or a pharmaceutically acceptable salt thereof at a dosage of 100 mg per day, if this human subject is determined to weigh 100 kg or more; or
(ii) resmetirom or a pharmaceutically acceptable salt thereof at a dosage of 80 mg per day, if this human subject is determined to weigh less than 100 kg, and wherein this human subject has liver fibrosis associated with the fatty liver disease (e.g., NASH).

The present disclosure also provides a method of improving liver fibrosis associated with a fatty liver disease (e.g., NASH). The method comprises: determining a weight of a human subject (e.g., an adult human subject) in need of such improvement; and based on determination of the weight of the human subject (e.g., an adult human subject) in need of such improvement, administering to the human subject (e.g., an adult human subject) in need of such improvement a solid oral dosage form comprising:
(i) resmetirom or a pharmaceutically acceptable salt thereof at a dosage of 100 mg per day, if the human subject (e.g., an adult human subject) in need of such improvement is determined to weigh 100 kg or more; or
(ii) resmetirom or a pharmaceutically acceptable salt thereof at a dosage of 80 mg per day, if the human subject (e.g., an adult human subject) in need of such improvement is determined to weigh less than 100 kg, and wherein the human subject (e.g., an adult human subject) in need of such improvement has liver fibrosis associated with the fatty liver disease (e.g., NASH).

In some aspects, the human subject (e.g., an adult human subject) who may be in need of such treatment and/or improvement (e.g., of NASH and/or liver fibrosis) is determined to weigh 100 kg or more and is administered the solid oral dosage form comprising resmetirom or a pharmaceutically acceptable salt thereof at the dosage of 100 mg per day.

In some aspects, the human subject (e.g., an adult human subject) who may be in need of such treatment or improvement (e.g., of NASH and/or liver fibrosis) is determined to weigh less than 100 kg and is administered the solid oral dosage form comprising resmetirom or a pharmaceutically acceptable salt thereof at the dosage of 80 mg per day.

In some aspects, the fatty liver disease is NASH. In some aspects, the human subject (e.g., an adult human subject) who may be in need of such treatment or improvement (e.g., of NASH and/or liver fibrosis) may have noncirrhotic nonalcoholic steatohepatitis with moderate to advanced liver fibrosis consistent with stages F2 and F3 fibrosis. In some aspects, the human subject (e.g., an adult human subject) who may be in need of such treatment or improvement (e.g., of NASH and/or liver fibrosis) may have noncirrhotic nonalcoholic steatohepatitis with mild liver fibrosis consistent with stage F1.

In some aspects, the human subject (e.g., an adult human subject) who may be in need of such treatment or improvement (e.g., of NASH and/or liver fibrosis) is administered the solid oral dosage form comprising resmetirom or a pharmaceutically acceptable salt thereof.

In some aspects, the human subject (e.g., an adult human subject) who may be in need of such treatment or improvement (e.g., of NASH and/or liver fibrosis) has liver fibrosis characterized as fibrosis stage F2 or F3. In some aspects, the method is that of treating noncirrhotic nonalcoholic steatohepatitis with moderate to advanced liver fibrosis consistent with stages F2 to F3.

In some aspects, the method is of improving the liver fibrosis by one stage in the human subject (e.g., an adult human subject) who may be in need of such improvement. The human subject (e.g., an adult human subject) who may be in need of such improvement may have liver fibrosis characterized as fibrosis stage F2. The human subject (e.g., an adult human subject) who may be in need of such improvement may have liver fibrosis characterized as fibrosis stage F3.

In some aspects, the method is of improving the liver fibrosis by at least one stage (e.g., two stages) in the human subject (e.g., an adult human subject) who may be in need of such improvement. The human subject (e.g., an adult human subject) who may be in need of such improvement may have liver fibrosis characterized as fibrosis stage F2. The human subject (e.g., an adult human subject) who may be in need of such improvement may have liver fibrosis characterized as fibrosis stage F3.

In some embodiments, the human subject (e.g., an adult human subject) who may be in need of the treatment or improvement as disclosed herein (e.g., of NASH and/or liver fibrosis) has a body weight at or greater than 100 kilograms, and the solid oral dosage form comprising resmetirom or the pharmaceutically acceptable salt thereof is or has been administered to such a human subject at a dosage of 100 mg per day.

In some embodiments, the human subject (e.g., an adult human subject) who may be in need of the treatment or improvement as disclosed herein (e.g., of NASH and/or liver fibrosis) has a body weight less than 100 kilograms, and the solid oral dosage form comprising resmetirom or the pharmaceutically acceptable salt thereof is or has been administered to the human subject (e.g., an adult human subject) in need of such treatment (e.g., NASH/improving liver fibrosis) at a dosage of 80 mg per day.

In some embodiments, the human subject (e.g., an adult human subject) who may be in need of the treatment or improvement as disclosed herein (e.g., of NASH and/or liver fibrosis) has a body weight less than 100 kilograms, and the solid oral dosage form comprising resmetirom or the pharmaceutically acceptable salt thereof is or has been administered to the human subject (e.g., an adult human subject) in need of such treatment (e.g., NASH/improving liver fibrosis) at a dosage of 60 mg per day.

In some embodiments, the solid oral dosage form comprising resmetirom or the pharmaceutically acceptable salt thereof is administered to the human subject (e.g., an adult human subject) who may be in need of the treatment or improvement as disclosed herein (e.g., of NASH and/or liver fibrosis) with food. In other embodiments, the solid oral dosage form comprising resmetirom or the pharmaceutically acceptable salt thereof is administered to the human subject (e.g., an adult human subject) who may be in need of the treatment or improvement as disclosed herein (e.g., NASH and/or liver fibrosis) without food.

In some embodiments, the solid oral dosage form comprising resmetirom or the pharmaceutically acceptable salt thereof is taken daily.

In some embodiments, the solid oral dosage form comprising resmetirom or the pharmaceutically acceptable salt thereof is taken once or twice daily.

In some embodiments, the solid oral dosage form comprising resmetirom or the pharmaceutically acceptable salt thereof is taken once daily.

In some embodiments, the solid oral dosage form comprising resmetirom or the pharmaceutically acceptable salt thereof is or has been taken without any drug holiday.

In some embodiments, the solid oral dosage form comprising resmetirom or the pharmaceutically acceptable salt thereof is or has been taken with one or more drug holidays.

In some embodiments, the solid oral dosage form comprising resmetirom or the pharmaceutically acceptable salt thereof is or has been administered for one day, two days, three days, four days, five days, six days, one week, two weeks, three weeks, four weeks, five weeks, six weeks, seven weeks, eight weeks, nine weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or for any number of weeks therebetween.

In some embodiments, the solid oral dosage form comprising resmetirom or the pharmaceutically acceptable salt thereof is or has been administered for longer than 52 weeks.

In some embodiments, the human subject (e.g., an adult human subject) who may be in need of the treatment or improvement as disclosed herein (e.g., of NASH and/or liver fibrosis) administered a daily dose of resmetirom or the pharmaceutically acceptable salt thereof is not taking atorvastatin, pravastatin, rosuvastatin, or simvastatin. In some embodiments, the human subject (e.g., an adult human subject) who may be in need of the treatment or improvement as disclosed herein (e.g., of NASH and/or liver fibrosis) administered a daily dose of resmetirom or the pharmaceutically acceptable salt thereof is taking 20 mg or less rosuvastatin or simvastatin. In some embodiments, the human subject (e.g., an adult human subject) who may be in need of the treatment or improvement as disclosed herein (e.g., of NASH and/or liver fibrosis) administered a daily dose of resmetirom or the pharmaceutically acceptable salt thereof is taking 40 mg or less atorvastatin or pravastatin.

It was also found that concomitant use of resmetirom or the pharmaceutically acceptable salt thereof and a CYP2C8 inhibitor can increase resmetirom $C_{max}$ and AUC. As a result, the daily dose of resmetirom or the pharmaceutically acceptable salt thereof can be reduced to a reduced dosage and yet continue to provide the desired treatment or improvement of a fatty liver disease (e.g., NASH) and/or of fibrosis associated with the fatty liver disease (e.g., NASH) with such concomitant use.

Specifically, the reduction in the daily dose of resmetirom or the pharmaceutically acceptable salt thereof is 20 mg for a human subject (e.g., an adult human subject) who may be in need of the treatment or improvement of a liver disease (e.g., NASH) or of liver fibrosis associated with such a liver disease as described in this disclosure, who is on a moderate CYP2C8 inhibitor regimen. For instance, if such a human subject would otherwise be administered a dose of 100 mg of resmetirom per day based on the determination that the weight of this human subject is at least 100 kg, then the reduced dosage, due to the use of a moderate CYP2C8 inhibitor by this human subject, is 80 mg per day. If the human subject (e.g., an adult human subject) who may be in need of such treatment or improvement as disclosed herein (e.g., of NASH and/or liver fibrosis) would otherwise be administered a dose of 80 mg of resmetirom per day based on the determination that the weight of this human subject is less than 100 kg, then the reduced dosage, due to the use of a moderate CYP2C8 inhibitor by this human subject, is 60 mg per day.

If the human subject (e.g., an adult human subject) who may be in need of the treatment or improvement as disclosed herein (e.g., NASH and/or liver fibrosis) was taking a moderate CYP2C8 inhibitor prior to using resmetirom or the pharmaceutically acceptable salt thereof, then this human subject would start with the reduced dosage of 80 mg or 100 mg per day, depending on the weight determination. If the human subject (e.g., an adult human subject) who may be in need of the treatment or improvement as described herein (e.g., of NASH and/or liver fibrosis) was taking resmetirom or the pharmaceutically acceptable salt thereof at a dose of 100 mg per day or 80 mg per day, depending on the weight determination, but was not taking a moderate CYP2C8 inhibitor prior to using resmetirom or the pharmaceutically acceptable salt thereof, then the dose would be reduced from 100 mg per day or 80 mg per day to a reduced dosage of 80 mg or 60 mg per day, respectively, depending on the weight determination, once this human subject is concomitantly using a moderate CYP2C8 inhibitor. If the human subject (e.g., an adult human subject) who may be in need of the treatment or improvement as described herein (e.g., of NASH and/or liver fibrosis) was using neither resmetirom or the pharmaceutically acceptable salt thereof nor a moderate CYP2C8 inhibitor prior to their concomitant use, then this human subject would start taking resmetirom or the pharmaceutically acceptable salt thereof with the reduced dosage of 80 mg or 60 mg per day, depending on the weight determination, for this concomitant use.

Specifically, disclosed herein is a method of treating or improving a fatty liver disease (e.g., NASH or in particular noncirrhotic NASH), which method comprises: determining a weight of a human subject (e.g., an adult human subject) who may be in need of such treatment or improvement; and based on determination of the weight of the human subject (e.g., an adult human subject) who may be in need of such treatment or improvement, administering to this human subject (e.g., an adult human subject) who may be in need of such treatment or improvement a solid oral dosage form comprising:
  (i) resmetirom or a pharmaceutically acceptable salt thereof at a reduced dosage of 80 mg per day, if the human subject (e.g., an adult human subject) who may be in need of such treatment or improvement is determined to weigh 100 kg or more and the human subject (e.g., an adult human subject) who may be in need of such treatment or improvement is using a moderate CYP2C8 inhibitor; or
  (ii) resmetirom or the pharmaceutically acceptable salt thereof at a reduced dosage of 60 mg per day, if the human subject (e.g., an adult human subject) who may be in need of such treatment or improvement is determined to weigh less than 100 kg and the human subject (e.g., an adult human subject) who may be in need of such treatment or improvement is using a moderate CYP2C8 inhibitor.

Also disclosed herein is a method of treating or improving liver fibrosis, which method comprises: determining a weight of a human subject (e.g., an adult human subject) who may be in need of such treatment or improvement; and based on determination of the weight of the human subject (e.g., an adult human subject) who may be in need of such treatment or improvement, administering to the human subject (e.g., an adult human subject) who may be in need of such treatment or improvement a solid oral dosage form comprising:
(i) resmetirom or a pharmaceutically acceptable salt thereof at a reduced dosage of 80 mg per day, if the human subject (e.g., an adult human subject) who may be in need of such treatment or improvement is determined to weigh 100 kg or more and the human subject (e.g., an adult human subject) who may be in need of such treatment or improvement is using a moderate CYP2C8 inhibitor; or
(ii) resmetirom or the pharmaceutically acceptable salt thereof at a reduced dosage of 60 mg per day, if the human subject (e.g., an adult human subject) who may be in need of such treatment or improvement is determined to weigh less than 100 kg and the human subject (e.g., an adult human subject) who may be in need of such treatment or improvement is using a moderate CYP2C8 inhibitor,
wherein the human subject (e.g., an adult human subject) who may be in need of such treatment or improvement has liver fibrosis associated with nonalcoholic steatohepatitis (NASH).

In some aspects, the moderate CYP2C8 inhibitor is selected from the group consisting of rosiglitazone, trimethoprim, tamoxifen, irbesartan, quinine, efavirenz, rabeprazole, crisaborole, nabilone, bexarotene, ritonavir, nicardipine, loratadine, eltrombopag, diltiazem, enzalutamide, ketoconazole, fluvastatin, levothyroxine, oxybutynin, medroxyprogesterone acetate, spironolactone, amlodipine, saquinavir, abiraterone, genistein, lenvatinib, pioglitazone, clotrimazole, nilotinib, teriflunomide, topiroxostat, lovastatin, troglitazone, amitriptyline, pirtobrutinib, belinostat, bezafibrate, candesartan, cholecalciferol, cimetidine, colchicine, dabrafenib, deferasirox, diethylstilbestrol, enasidenib, erlotinib, ethinylestradiol, fenofibrate, idelalisib, isoniazid, ketoprofen, letermovir, lumacaftor, mefenamic acid, midostaurin, montelukast, nilutamide, opicapone, phenelzine, piroxicam, pyrimethamine, quercetin, raloxifene, repaglinide, rifampicin, rofecoxib, salmeterol, sorafenib, sulfaphenazole, tegaserod, terbinafine, terfenadine, thiazolidinediones, ticlopidine, trametinib, triazolam, troleandomycin, valproic acid, verapamil, vismodegib, clopidogrel, and zafirlukast.

In some aspects, the moderate CYP2C8 inhibitor is clopidogrel, deferasirox, teriflunomide, trimethoprim, and/or pioglitazone.

In some aspects, the fatty liver disease is NASH.

In some aspects, the human subject (e.g., an adult human subject) who may be in need of the treatment or improvement as disclosed herein (e.g., of NASH and/or liver fibrosis) who is on a moderate CYP2C8 inhibitor regimen is administered the resmetirom compound.

In some aspects, the human subject (e.g., an adult human subject) who may be in need of the treatment or improvement as disclosed herein (e.g., of NASH and/or liver fibrosis) was also previously on a moderate CYP2C8 inhibitor regimen.

In some embodiments, the reduced dosage of resmetirom or the pharmaceutically acceptable salt thereof is 80 mg per day.

In some embodiments, the reduced dosage of resmetirom or the pharmaceutically acceptable salt thereof is 60 mg per day.

In some embodiments, the method includes reducing the previously used oral dose of resmetirom or the pharmaceutically acceptable salt thereof to the reduced dosage.

In some embodiments, the human subject (e.g., an adult human subject) who may be in need of the treatment or improvement as disclosed herein (e.g., of NASH and/or liver fibrosis) used resmetirom or the pharmaceutically acceptable salt thereof at an oral dose of 100 mg per day before starting to use the moderate CYP2C8 inhibitor, and the oral dose of 100 mg per day is reduced to the reduced dosage of 80 mg per day.

In some embodiments, the human subject (e.g., an adult human subject) who may be in need of the treatment or improvement as disclosed herein (e.g., of NASH and/or liver fibrosis) used resmetirom or the pharmaceutically acceptable salt thereof at an oral dose of 80 mg per day before starting to use the moderate CYP2C8 inhibitor, and the oral dose of 80 mg per day is reduced to the reduced dosage of 60 mg per day.

In some embodiments, the human subject (e.g., an adult human subject) who may be in need of the treatment or improvement as disclosed herein (e.g., of NASH and/or liver fibrosis) uses the moderate CYP2C8 inhibitor concomitantly (e.g., together or on the same day) with the reduced dosage of the compound of resmetirom or the pharmaceutically acceptable salt thereof. In some embodiments, the moderate CYP2C8 inhibitor is used by the human subject (e.g., an adult human subject) who may be in need of the treatment or improvement as disclosed herein (e.g., of NASH and/or liver fibrosis) daily. In some embodiments, the moderate CYP2C8 inhibitor is used by the human subject (e.g., an adult human subject) who may be in need of the treatment or improvement as disclosed herein (e.g., of NASH and/or liver fibrosis) once daily.

In some embodiments, the human subject (e.g., an adult human subject) who may be in need of the treatment or improvement as disclosed herein (e.g., of NASH and/or liver fibrosis) administered a daily dose of resmetirom or the pharmaceutically acceptable salt thereof (e.g., a reduced dosage), is not using a strong CYP2C8 inhibitor (e.g., gemfibrozil).

In some embodiments, the human subject (e.g., an adult human subject) who may be in need of the treatment or improvement as disclosed herein (e.g., of NASH and/or liver fibrosis) administered a daily dose of resmetirom or the pharmaceutically acceptable salt thereof (e.g., a reduced dosage), is not using OATP1B1 (organic anion transporting polypeptide 1B1) or OATP1B3 (organic anion transporting polypeptide 1B3) inhibitors (e.g., cyclosporine).

In some embodiments, the concomitant use of the moderate CYP2C8 inhibitor is within 24 hours before the human subject (e.g., an adult human subject) who may be in need of the treatment or improvement as disclosed herein (e.g., of NASH and/or liver fibrosis) takes resmetirom or the pharmaceutically acceptable salt thereof.

In some embodiments, the concomitant use of the moderate CYP2C8 inhibitor is within 24 hours after the human subject (e.g., an adult human subject) who may be in need of the treatment or improvement as disclosed herein (e.g., of NASH and/or liver fibrosis) takes resmetirom or the pharmaceutically acceptable salt thereof.

In some embodiments, the concomitant use of the moderate CYP2C8 inhibitor by human subject (e.g., an adult human subject) who may be in need of the treatment or improvement as disclosed herein (e.g., of NASH and/or liver fibrosis) is conducted simultaneously with the administration of resmetirom or the pharmaceutically acceptable salt thereof.

The reduced dosage of resmetirom or the pharmaceutically acceptable salt thereof may be administered via a solid oral dosage form.

In some embodiments, the human subject (e.g., an adult human subject) who may be in need of such treatment or improvement as disclosed herein has a disease, disorder, or condition being NASH. It is understood that, in NASH, the fat accumulation may be associated with varying degrees of inflammation (hepatitis) and/or scarring (fibrosis) of the liver. In some embodiments, the fibrosis of the liver is a stage F2 fibrosis. In some embodiments, the fibrosis of the liver is a stage F3 fibrosis.

In some embodiments, the human subject (e.g., an adult human subject) who may be in need of the treatment or improvement as disclosed herein has a disease, disorder, or condition being liver inflammation.

In some embodiments, the human subject (e.g., an adult human subject) who may be in need of the treatment or improvement as disclosed herein has a disease, disorder, or condition being associated with an increased liver volume.

In some embodiments, the human subject (e.g., an adult human subject) who may be in need of the treatment or improvement as disclosed herein has a disease, disorder, or condition being portal hypertension.

In some embodiments, the human subject (e.g., an adult human subject) who may be in need of the treatment or improvement as disclosed herein has moderate hepatic impairment.

In some embodiments, the human subject (e.g., an adult human subject) who may be in need of the treatment or improvement as disclosed herein has autoimmune liver disease. In other embodiments, the human subject (e.g., an adult human subject) who may be in need of the treatment or improvement as disclosed herein does not have autoimmune liver disease.

In some embodiments, the human subject (e.g., an adult human subject) who may be in need of the treatment or improvement as disclosed herein has moderate to severe hepatic impairment (e.g., Child-Pugh Class B or C). In other embodiments, the human subject (e.g., an adult human subject) who may be in need of the treatment or improvement as disclosed herein does not have moderate to severe hepatic impairment.

In some embodiments, the human subject (e.g., an adult human subject) who may be in need of the treatment or improvement as disclosed herein (e.g., of NASH and/or liver fibrosis) has a liver volume being at least 5% greater, at least 10% greater, at least 20% greater, at least 30% greater, at least 40% greater, at least 50% greater, at least 60% greater, at least 70% greater, at least 80% greater, at least 90% greater, at least 100% greater, at least 150% greater, at least 200% greater, or any number therebetween, compared to the same human subject had this human subject not been affected by the disease, disorder, or condition (e.g., without NASH).

In some embodiments, the human subject (e.g., an adult human subject) who may be in need of the treatment or improvement as disclosed herein (e.g., of NASH and/or liver fibrosis) has a liver fat amount (e.g., as measured by proton density fat fraction (PDFF)) being at least 5% greater, at least 10% greater, at least 20% greater, at least 30% greater, at least 40% greater, at least 50% greater, at least 60% greater, at least 70% greater, at least 80% greater, at least 90% greater, at least 100% greater, at least 150% greater, at least 200% greater, or any number therebetween, compared to the same human subject had this human subject not been affected by the disease, disorder, or condition (e.g., without NASH).

In some embodiments, the human subject (e.g., an adult human subject) who may be in need of the treatment or improvement as disclosed herein (e.g., of NASH and/or liver fibrosis) has a liver fat amount (e.g., as measured by proton density fat fraction (PDFF)) being at most 200% greater, at most 150% greater, at most 100% greater, at most 90% greater, at most 80% greater, at most 70% greater, at most 60% greater, at most 50% greater, at most 40% greater, at most 30% greater, at most 20% greater, at most 10% greater, or at most 5% greater, or any number therebetween, compared to the same human subject had this human subject not been affected by the disease, disorder, or condition (e.g., without NASH).

In some embodiments, the human subject (e.g., an adult human subject) who may be in need of the treatment or improvement as disclosed herein (e.g., of NASH and/or liver fibrosis) has a liver fat amount (e.g., as measured by proton density fat fraction (PDFF)) being 50% or less, 40% or less, 30% or less, 25% or less, 20% or less, 15% or less, 10% or less, 5% or less, 4% or less, 3% or less, 2% or less, 1% or less, or any number therebetween.

In some embodiments, the human subject (e.g., an adult human subject) who may be in need of the treatment or improvement as disclosed herein (e.g., of NASH and/or liver fibrosis) has a liver fat amount (e.g., as measured by proton density fat fraction (PDFF)) being 5% or less.

In some embodiments, the human subject (e.g., an adult human subject) who may be in need of the treatment or improvement as disclosed herein (e.g., of NASH and/or liver fibrosis) has a liver fat amount (e.g., as measured by proton density fat fraction (PDFF)) greater than 5%, greater than 10%, greater than 15%, greater than 20%, greater than 25%, greater than 30%, greater than 40%, greater than 50%, greater than 60%, or any number therebetween.

In some embodiments, the human subject (e.g., an adult human subject) who may be in need of the treatment or improvement as disclosed herein (e.g., of NASH and/or liver fibrosis) has a liver fat amount (e.g., as measured by proton density fat fraction (PDFF)) being greater than 5%.

In some embodiments, the human subject (e.g., an adult human subject) who may be in need of the treatment or improvement as disclosed herein (e.g., of NASH and/or liver fibrosis) has a spleen volume being at least 5% greater, at least 10% greater, at least 20% greater, at least 30% greater, at least 40% greater, at least 50% greater, at least 60% greater, at least 70% greater, at least 80% greater, at least 90% greater, at least 100% greater, at least 150% greater, at least 200% greater, or any number therebetween, compared to the same human subject had this human subject not been affected by the disease, disorder, or condition (e.g., without portal hypertension).

In some embodiments, the human subject (e.g., an adult human subject) who may be in need of the treatment or improvement as disclosed herein (e.g., of NASH and/or liver fibrosis) administered a daily dose of resmetirom or the pharmaceutically acceptable salt thereof is not administered a strong CYP2C8 inhibitor (e.g., gemfibrozil).

In some embodiments, the human subject (e.g., an adult human subject) who may be in need of the treatment or improvement as disclosed herein (e.g., of NASH and/or liver fibrosis) administered a daily dose of resmetirom or the pharmaceutically acceptable salt thereof is not administered OATP1B1 or OATP1B3 inhibitors (e.g., cyclosporine).

In some embodiments, the human subject (e.g., an adult human subject) i who may be in need of the treatment or improvement as disclosed herein (e.g., of NASH and/or liver fibrosis) administered a daily dose of resmetirom or the pharmaceutically acceptable salt thereof is not administered atorvastatin, pravastatin, rosuvastatin, or simvastatin. In some embodiments, the human subject (e.g., an adult human subject) who may be in need of the treatment or improvement as disclosed herein (e.g., of NASH and/or liver fibrosis) administered a daily dose of resmetirom or the pharmaceutically acceptable salt thereof is taking 20 mg or less rosuvastatin or simvastatin. In some embodiments, the human subject (e.g., an adult human subject) who may be in need of the treatment or improvement as disclosed herein (e.g., of NASH and/or liver fibrosis) administered a reduced daily dose of resmetirom or the pharmaceutically acceptable salt thereof is taking 40 mg or less atorvastatin or pravastatin.

In some embodiments, the administration eliminates, or reduces the severity of, the disease, disorder, or condition.

In some embodiments, the administration reduces the liver volume by at least 5%, at least 10%, at least 15%, at least 20%, at least 25%, at least 30%, at least 35%, at least 40%, at least 45%, at least 50%, at least 55%, at least 60%, or any number therebetween (e.g., over a period of 12 weeks or 52 weeks).

In some embodiments, the administration reduces the liver volume by at least 5%, at least 10%, at least 15%, at least 20%, at least 25%, at least 30%, at least 35%, at least 40%, at least 45%, at least 50%, at least 55%, at least 60%, or any number therebetween, over a period of 12 weeks.

In some embodiments, the administration reduces the liver volume by at least 10% over a period of 12 weeks.

In some embodiments, the administration reduces the liver volume by at least 15% over a period of 12 weeks.

In some embodiments, the administration reduces the liver volume by at least 20% over a period of 12 weeks.

In some embodiments, the administration reduces the liver volume by at least 25% over a period of 12 weeks.

In some embodiments, the administration reduces the liver volume by at least 5%, at least 10%, at least 15%, at least 20%, at least 25%, at least 30%, at least 35%, at least 40%, at least 45%, at least 50%, at least 55%, at least 60%, or any number therebetween, over a period of 52 weeks.

In some embodiments, the administration reduces the liver volume by at least 10% over a period of 52 weeks.

In some embodiments, the administration reduces the liver volume by at least 15% over a period of 52 weeks.

In some embodiments, the administration reduces the liver volume by at least 20% over a period of 52 weeks.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver volume by at least 5%, at least 10%, at least 15%, at least 20%, at least 25%, at least 30%, at least 35%, at least 40%, at least 45%, at least 50%, at least 55%, at least 60%, or any number therebetween (e.g., over a period of 12 weeks or 52 weeks).

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver volume by at least 5%, at least 10%, at least 15%, at least 20%, at least 25%, at least 30%, at least 35%, at least 40%, at least 45%, at least 50%, at least 55%, at least 60%, or any number therebetween, over a period of 12 weeks.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver volume by at least 10% over a period of 12 weeks.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver volume by at least 15% over a period of 12 weeks.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver volume by at least 20% over a period of 12 weeks.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver volume by at least 25% over a period of 12 weeks.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver volume by at least 5%, at least 10%, at least 15%, at least 20%, at least 25%, at least 30%, at least 35%, at least 40%, at least 45%, at least 50%, at least 55%, at least 60%, or any number therebetween, over a period of 52 weeks.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver volume by at least 10% over a period of 52 weeks.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver volume by at least 15% over a period of 52 weeks.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver volume by at least 20% over a period of 52 weeks.

In some embodiments, the administration reduces the liver fat amount (e.g., as measured by MRI-PDFF) by 60% or less, 50% or less, 45% or less, 40% or less, 35% or less, 30% or less, 25% or less, 20% or less, 15% or less, 10% or less, 5% or less, or any number therebetween, as compared to the liver fat amount of the human subject (e.g., an adult human subject) who may be in need of the treatment or improvement as disclosed herein (e.g., of NASH and/or liver fibrosis) prior to the administration.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less, and the administration reduces the liver fat amount (e.g., as measured by MRI-PDFF) by 60% or less, 50% or less, 45% or less, 40% or less, 35% or less, 30% or less, 25% or less, 20% or less, 15% or less, 10% or less, 5% or less, or any number therebetween, as compared to the liver fat amount of the human subject (e.g., an adult human subject) who may be in need of the treatment or improvement as disclosed herein (e.g., of NASH and/or liver fibrosis) prior to the administration.

In some embodiments, the administration reduces the liver fat amount (e.g., as measured by MRI-PDFF) by 20% or less, 15% or less, 10% or less, 5% or less, 4% or less, 3% or less, 2% or less, 1% or less, or any number therebetween, as compared to the liver volume of the human subject (e.g., an adult human subject) who may be in need of the treatment or improvement as disclosed herein (e.g., of NASH and/or liver fibrosis) prior to the administration.

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less; the administration reduces the liver fat amount (e.g., as measured by MRI-PDFF) by 60% or less, 50% or less, 45% or less, 40% or less, 35% or less, 30% or less, 25% or less, 20% or less, 15% or less, 10% or less, 5% or less, or any number therebetween, as compared to the liver fat amount of the human subject (e.g., an adult human subject) who may be in need of the treatment or improvement as disclosed herein (e.g., of NASH and/or liver fibrosis) prior to the administration; and the administration reduces the liver volume by at least 5%, at least 10%, at least 15%, at least 20%, at least 25%, at least 30%, at least 35%, at least 40%, at least 45%, at least 50%, at least 55%, at least 60%, or any number therebetween (e.g., over a period of 12 weeks or 52 weeks).

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less; the administration reduces the liver fat amount (e.g., as measured by MRI-PDFF) by 40% or less, as compared to the liver fat amount of the human subject (e.g., an adult human subject) i who may be in need of the treatment or improvement as disclosed herein (e.g., of NASH and/or liver fibrosis) prior to the administration; and the administration reduces the liver volume by at least 10% (e.g., over a period of 12 weeks or 52 weeks).

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less; the administration reduces the liver fat amount (e.g., as measured by MRI-PDFF) by 35% or less, as compared to the liver fat amount of the human subject (e.g., an adult human subject) in n who may be in need of the treatment or improvement as disclosed herein (e.g., of NASH and/or liver fibrosis) prior to the administration; and the administration reduces the liver volume by at least 10% (e.g., over a period of 12 weeks or 52 weeks).

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less; the administration reduces the liver fat amount (e.g., as measured by MRI-PDFF) by 30% or less, as compared to the liver fat amount of the human subject (e.g., an adult human subject) who may be in need of the treatment or improvement as disclosed herein (e.g., of NASH and/or liver fibrosis) prior to the administration; and the administration reduces the liver volume by at least 10% (e.g., over a period of 12 weeks or 52 weeks).

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less; the administration reduces the liver fat amount (e.g., as measured by MRI-PDFF) by 40% or less, as compared to the liver fat amount of the human subject (e.g., an adult human subject) in who may be in need of the treatment or improvement as disclosed herein (e.g., of NASH and/or liver fibrosis) prior to the administration; and the administration reduces the liver volume by at least 15% (e.g., over a period of 12 weeks or 52 weeks).

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less; the administration reduces the liver fat amount (e.g., as measured by MRI-PDFF) by 35% or less, as compared to the liver fat amount of the human subject (e.g., an adult human subject) in who may be in need of the treatment or improvement as disclosed herein (e.g., of NASH and/or liver fibrosis) prior to the administration; and the administration reduces the liver volume by at least 15% (e.g., over a period of 12 weeks or 52 weeks).

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less; the administration reduces the liver fat amount (e.g., as measured by MRI-PDFF) by 30% or less, as compared to the liver fat amount of the human subject (e.g., an adult human subject) in who may be in need of the treatment or improvement as disclosed herein (e.g., of NASH and/or liver fibrosis) prior to the administration; and the administration reduces the liver volume by at least 15% (e.g., over a period of 12 weeks or 52 weeks).

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less; the administration reduces the liver fat amount (e.g., as measured by MRI-PDFF) by 40% or less, as compared to the liver fat amount of the human subject (e.g., an adult human subject) in who may be in need of the treatment or improvement as disclosed herein (e.g., of NASH and/or liver fibrosis) prior to the administration; and the administration reduces the liver volume by at least 20% (e.g., over a period of 12 weeks or 52 weeks).

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less; the administration reduces the liver fat amount (e.g., as measured by MRI-PDFF) by 35% or less, as compared to the liver fat amount of the human subject (e.g., an adult human subject) who may be in need of the treatment or improvement as disclosed herein (e.g., of NASH and/or liver fibrosis) prior to the administration; and the administration reduces the liver volume by at least 20% (e.g., over a period of 12 weeks or 52 weeks).

In some embodiments, prior to the administration the human subject (e.g., an adult human subject) who may be in need of the treatment or improvement as disclosed herein (e.g., of NASH and/or liver fibrosis) has a liver fat amount (e.g., as measured by MRI-PDFF) being 5% or less; the administration reduces the liver fat amount (e.g., as measured by MRI-PDFF) by 30% or less, as compared to the liver fat amount of the human subject (e.g., an adult human subject) who may be in need of the treatment or improvement as disclosed herein (e.g., of NASH and/or liver fibrosis) prior to the administration; and the administration reduces the liver volume by at least 20% (e.g., over a period of 12 weeks or 52 weeks).

In some embodiments, the liver volume reduction is dependent from the liver fat amount (e.g., the liver fat amount prior to the administration).

In some embodiments, the liver volume reduction is independent from the liver fat amount (e.g., the liver fat amount prior to the administration).

In some embodiments, the liver volume reduction is dependent from the liver fat amount reduction.

In some embodiments, the liver volume reduction is independent from the liver fat amount reduction.

In some embodiments, the liver volume reduction is greater than the liver fat amount reduction.

In some embodiments, the liver volume reduction is at least 5% greater, at least 10% greater, at least 20% greater, at least 30% greater, at least 40% greater, at least 50% greater, at least 60% greater, at least 70% greater, at least 80% greater, at least 90% greater, at least 100% greater, at least 150% greater, at least 200% greater, at least 300% greater, at least 400% greater, at least 500% greater, at least 600% greater, at least 700% greater, at least 800% greater, at least 900% greater, at least 1000%, or any number therebetween, as compared to the liver fat amount reduction.

In some embodiments, the administration eliminates, or reduces the severity of, liver inflammation.

In some embodiments, the administration eliminates, or reduces the severity of, portal hypertension.

In some embodiments, the administration reduces the blood pressure in the portal vein of the human subject (e.g., an adult human subject) who may be in need of the treatment or improvement as disclosed herein (e.g., of NASH and/or liver fibrosis).

In some embodiments, the administration reduces the blood pressure in the portal vein of the human subject (e.g., an adult human subject) who may be in need of the treatment or improvement as disclosed herein (e.g., of NASH and/or liver fibrosis) by at least 5%, at least 10%, at least 15%, at least 20%, at least 25%, at least 30%, at least 35%, at least 40%, at least 45%, at least 50%, at least 55%, at least 60%, or any number therebetween (e.g., over a period of 12 weeks or 52 weeks) as compared to before treatment.

In some embodiments, the administration reduces the spleen volume of the human subject (e.g., an adult human subject) who may be in need of the treatment or improvement as disclosed herein (e.g., of NASH and/or liver fibrosis).

In some embodiments, the administration reduces the spleen volume by at least 5%, at least 10%, at least 15%, at least 20%, at least 25%, at least 30%, at least 35%, at least 40%, at least 45%, at least 50%, at least 55%, at least 60%, or any number therebetween (e.g., over a period of 12 weeks or 52 weeks) as compared to before treatment.

In some embodiments, the administration reduces the spleen volume by at least 10% or at least 15% (e.g., over a period of 12 weeks or 52 weeks).

In some embodiments, the administration reduces the spleen volume by at least 10% or at least 15% over a period of 12 weeks.

In some embodiments, the administration reduces the spleen volume by at least 10% or at least 15% over a period of 52 weeks.

The pharmaceutical composition can be in a form suitable for oral use.

In some embodiments, the pharmaceutical composition is formulated in a solid oral dosage form. As used herein, the term "solid oral dosage form" refers to a dosage form that is taken by mouth in a solid form. The solid oral dosage form is designed to be swallowed and later dissolved in the gastrointestinal tract, allowing for systematic delivery of the medication to the human subject (e.g., an adult human subject) who may be in need of the treatment or improvement as disclosed herein (e.g., of NASH and/or liver fibrosis). The solid oral dosage form includes for example, a pill.

In some embodiments, the pharmaceutical composition is formulated in a pill. As used herein, the term "pill" includes for example, a capsule, a softgel, a sprinkle capsule, a tablet, a chewable tablet, or a caplet.

In some embodiments, the pharmaceutical composition is formulated in a tablet.

As used herein, the term "tablet" refers to a pill that is a solid formulation composed of medication and usually has no outer shell. Typically, the medication is in powder form where the medication and other inactive ingredients are compressed into a solid, smooth form. The tablet can be optionally coated.

The pharmaceutical compositions of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In some embodiments, the active compounds are prepared with pharmaceutically acceptable excipients that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable excipients.

Examples

The following Examples are provided by way of illustration and not by way of limitation.

Example 1

Liver Volume Reduction in Resmetirom-Treated Non-Cirrhotic and Cirrhotic NASH Patients Hepatomegaly may cause symptoms (e.g., pain) in NASH patients, and is thought to be driven primarily by high liver fat content. In a 36-week Phase 2 serial MRI-PDFF and liver biopsy study in adults with biopsy-confirmed NASH (NAS≥4, F1-F3) and hepatic fat fraction ≥10%, resmetirom treated patients, compared with placebo, showed statistically significant liver fat reduction that was associated with NASH resolution on liver biopsy. This study was to assess the relationship between liver triglycerides as measured by MRI-PDFF and liver volume (LV) in placebo and resmetirom-treated patients.

MRI-PDFF and liver volume (LV) were assessed in, (n=117), and a NASH-cirrhotic active resmetirom treatment arm of MAESTRO-NAFLD-1 (n=73), in patients who had at least baseline and one additional serial PDFF. LV was assessed using a validated artificial intelligence model for segmenting the liver on standard MR images.

LV at baseline was elevated in non-cirrhotic and cirrhotic NASH patients relative to literature values for healthy controls and was greater than predicted even after accounting for sex and body weight. PDFF correlated with LV at baseline in non-cirrhotic ($r2=0.19$, $p<0.001$) and more weakly in cirrhotic NASH ($r2=0.079$, $p=0.01$). Reduction in LV (CFB) correlated with reduction in PDFF in placebo ($r2=0.25$, $p=0.001$) and resmetirom ($r2=0.38$, $p<0.0001$) treated patients at 12 (and 36 (not shown)) weeks (see, e.g., FIG. 1). LV reduction was greater in resmetirom (−18.6% (1.1), −20.5%(1.2) compared to placebo (−0.4%(1.5), 0.1% (1.9) treated at 12 and 36 weeks, respectively ($p<0.0001$). A higher percentage of resmetirom (69.2%) than placebo (5.3%) patients had a ≥15% reduction in liver volume ($p<0.0001$) at Week 12, and similarly at Week 36. The relationship between LV reduction and PDFF reduction was proportionately weaker in placebo compared to resmetirom treated non-cirrhotic NASH patients. In cirrhotic NASH patients treated with resmetirom (see FIG. 1), LV reduction was much greater than expected based on the small reduction in PDFF, especially in patients with PDFF≤5% at baseline (LV mean ¾CFB, −16.3% versus PDFF, mean ¾CFB, −2.5% at week 16). Resmetirom treated patients who had NASH resolution and/or fibrosis reduction on biopsy at week 36 all had a PDFF reduction ≥30% and/or LV reduction of ≥15% at week 12.

Without wishing to be bound by theory, reduction in liver volume in resmetirom treated patients may be explained in part by reduction in liver triglycerides (measured by MRI-PDFF), but it also may be driven by other changes related to its mechanism of action. LV reduction may be associated with histopathologic improvement of NASH that may be further assessed by data from Phase 3 MAESTRO-NASH study, Biomarkers, Imaging and Safety in Resmetirom 52 Week Non-Cirrhotic NASH Phase 3 Clinical Trial, Completed Open-Label Arm of MAESTRO-NAFLD-1

MAESTRO-NASH NCT03900429 and MAESTRO-NAFLD-1 NCT04197479 are 52 week Phase 3 registrational double blind placebo controlled clinical trials to study the effect of resmetirom in more than 2,000 NASH patients. A goal of MAESTRO-NAFLD-1, a 1,200 patient "real life" NASH study is to identify non-invasive markers that correlate with patient response to resmetirom treatment. The 169 patient, 100 mg open label (OL) arm completed the 52 week study in July 2021.

Eligibility required at least 3 metabolic risk factors (Metabolic syndrome), fibroscan kilopascals (kPa) consistent with ≥F1 fibrosis stage, and MRI-PDFF≥8%. The primary and key secondary endpoints of MAESTRO-NAFLD-1 including safety, relative percent reduction of MRI-PDFF (week 16), LDL cholesterol (LDL-C) (week 24), apolipoprotein B and triglycerides, fibroscan and 52 week endpoints were analyzed in the OL arm.

Figure 2:
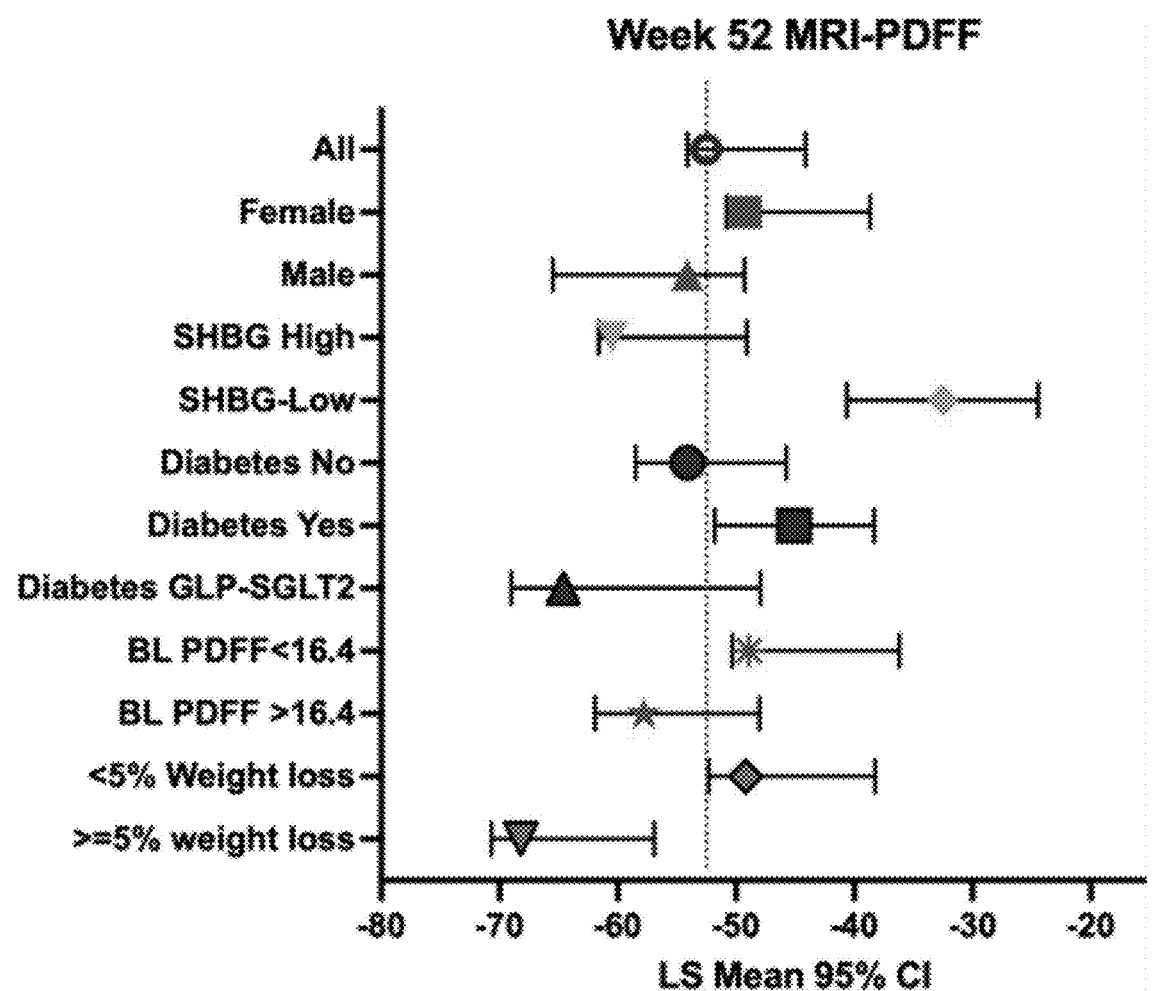
FIG. 2 is a graphical representation showing change in MRI-PDFF (Magnetic Resonance Imaging-PDFF) in several subgroups of patients treated with 100 mg resmetirom, once daily, for 52 weeks in Example 1. "High SHBG" corresponds with 2/3 study patients with the highest increase from baseline in sex hormone binding globulin (SHBG), a biomarker for resmetirom liver exposure.
Figure 3:
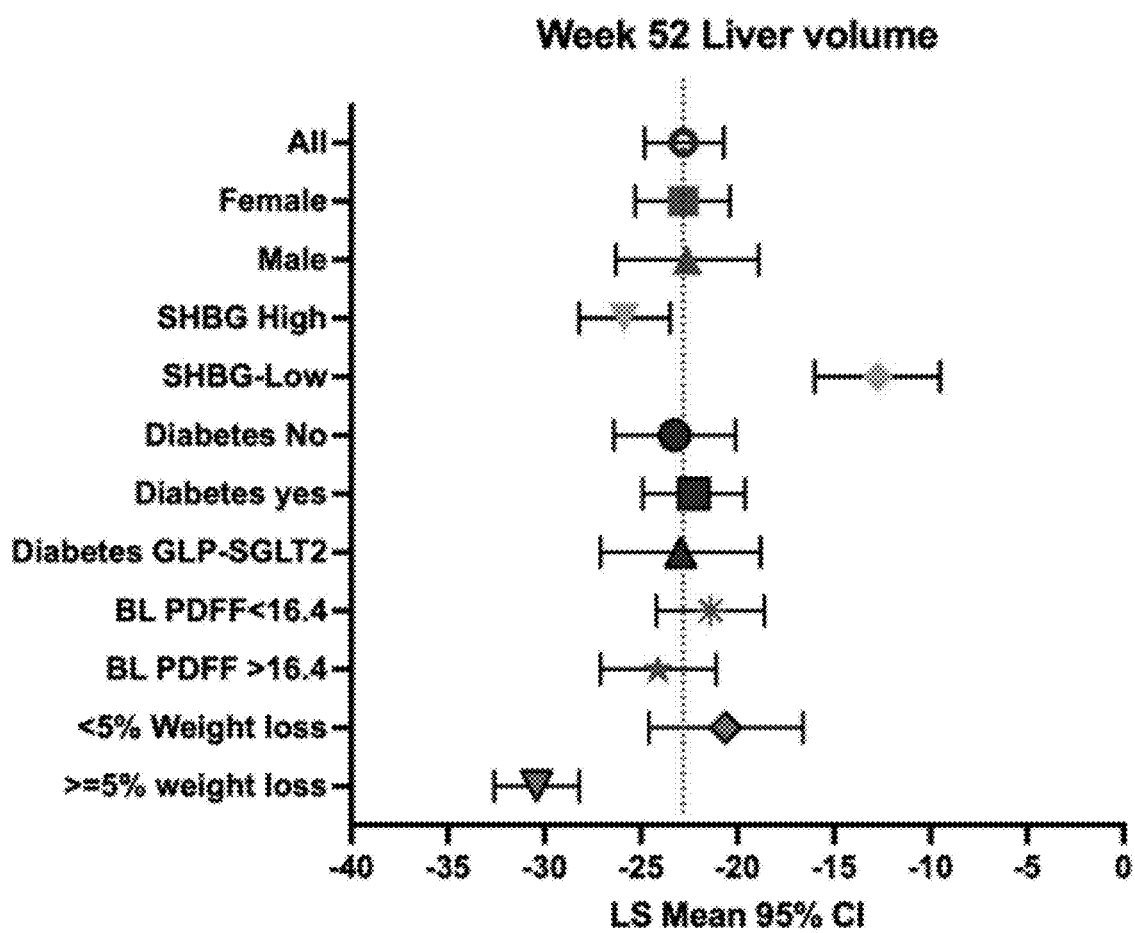
FIG. 3 is a graphical representation showing change in liver volume in several subgroups of patients treated with 100 mg resmetirom, once daily, for 52 weeks in Example 1. "High SHBG" corresponds with 2/3 study patients with the highest increase from baseline in SHBG, a biomarker for resmetirom liver exposure.

Mean age was 55.7 (11.5 Standard Deviation (SD)), female 69%, BMI 35.8 (6.0), diabetes 43%, hypertension 62%, dyslipidemia >70%, atherosclerotic cardiovascular disease (ASCVD) score 11.5%; fibroscan (kPa 7.7 (3.6)), and MRI-PDF 17% (7%). Statistically significant ($p<0.0001$) reduction of MRI-PDFF −53% (3.3% (Standard Error)) overall, and in several subgroups were observed at week 52 (see, e.g., FIG. 2). Liver volume (LV) was elevated at baseline (2202 cm3 (535)) by ~50% relative to normal controls and −15% after correction for BMI (Euro J of Radiol 106, 2018, 32-37). Resmetirom reduced LV −21% (1.0%), −23% (1.0%) respectively, at weeks 16 and 52 ($p<0.0001$), in all demographic groups (see, e.g., FIG. 3). LV reduction was 2-3 fold greater than predicted by % reduction in MRI-PDFF, a measure of liver fat content (Clin Gastroenterol Hepatol. 2015 13: 561-568); LY-corrected mean MRI-PDFF reduction was −63% (2.4%). Weight loss ≥5% occurred in −25% and was linked to resmetirom exposure (SHBG). At week 52, magnetic resonance elastography (MRE) (−0.34, p=0.03); fibroscan controlled attenuation parameter (CAP) (−39 (4.6)) and vibration-controlled transient elastography (VCTE) (−1.87; −20%) ($p<0.0001$) were reduced relative to baseline. LDL-C(−22% (1.9%), apolipoprotein-B (−24% (1.6%)), triglycerides (−24% (2.6) were statistically reduced ($p<0.0001$). Decreases from baseline in liver enzymes were ALT −20 International Unit (IU), aspartate aminotransferase (AST) −11 IU, gamma-glutamyl transferase (GGT) −25 IU ($p<0.0001$). Significant reductions in inflammatory and fibrosis biomarkers, reverse T3, enhanced liver fibrosis (ELF), and M30 (an apoptotic serum marker), and an increase in adiponectin were observed. No safety flags were identified; Blood pressure (systolic, diastolic) was reduced by −2 mmHg, (p=0.02); bone mineral density (DEXA) was unchanged at 52 weeks.

In this 52 week Phase 3 OL study, noninvasively identified NASH patients treated with 100 mg per day of resmetirom for up to 52 weeks demonstrated rapid and sustained reduction in (1) hepatic fat and liver volume; (2) fibrosis as assessed by biomarkers, MRE, and fibroscan; (3) LDL and atherogenic lipids; and (4) liver enzymes inflammatory biomarkers, providing support for the use of non-invasive tests to monitor individual NASH patient response to resmetirom treatment.

Biomarkers, Imaging and Safety in a Well-Compensated NASH Cirrhotic Cohort Treated with Resmetirom for 52 Weeks As mentioned above, MAESTRO-NAFLD-1 is a 52-week patient Phase 3 randomized double blind placebo controlled NASH clinical trial that was conducted to study safety and biomarker effects of resmetirom in NASH patients with F1-F4 fibrosis identified using non-invasive biomarkers and imaging (NCT04197479). The study included an open label active resmetirom treatment arm in well-compensated NASH cirrhotic patients.

Eligibility required at least 3 metabolic risk factors (metabolic syndrome), and NASH cirrhosis diagnosed on liver biopsy or according to accepted criteria. The primary and key secondary end points of the cirrhotic arm include safety, relative percent reduction of MRI-PDFF (week 16), LDL cholesterol (LDL-C) (week 24), Apolipoprotein B and triglycerides, and markers of fibrosis. Patients received 80-100 mg daily dose of resmetirom for 52 weeks.

105 well-compensated NASH cirrhotic patients were enrolled in the open label arm, 2/3 confirmed by liver biopsy. Demographics include mean age 62.7 (9.0 (SD)), female 64%, BMI 35.4 (7.4), diabetes 70%, hypertension 77%, dyslipidemia >70%, mean ASCVD score 16.1%, hypothyroid 32.4%, 51% on statins. MRE kPa, 5.7 (2.1); fibroscan kPa, 24.6 (14.9), CAP, 318 (59) and mean MRI-PDFF, 8.1% (5). Stage of cirrhosis was inversely correlated with baseline PDFF. At week 52 resmetirom lowered fibroscan CAP (−42 units (p <0.0001) and kPa (−7.6 kPa, p=0.02).

Figure 4:
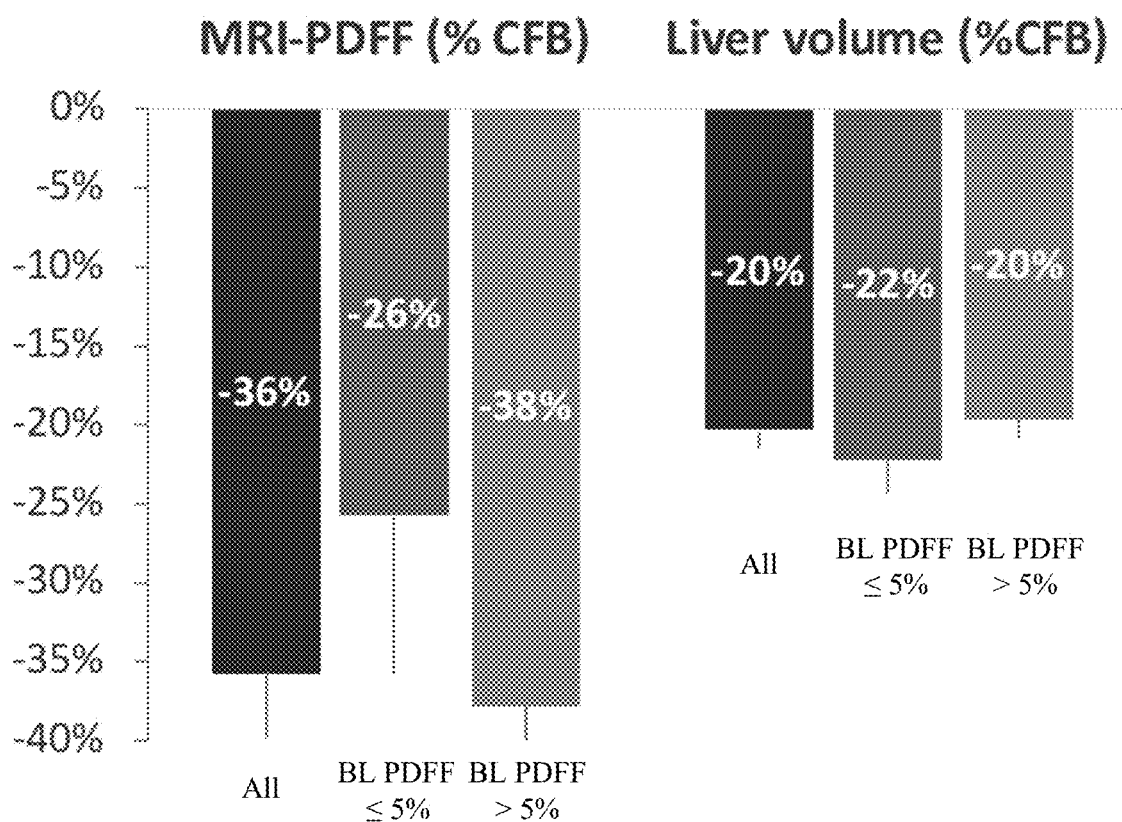
FIG. 4 is a graphical representation showing resmetirom-mediated changes to the MRI-PDFF and liver volume (LV) at week 52 in Example 1.
Figure 5:
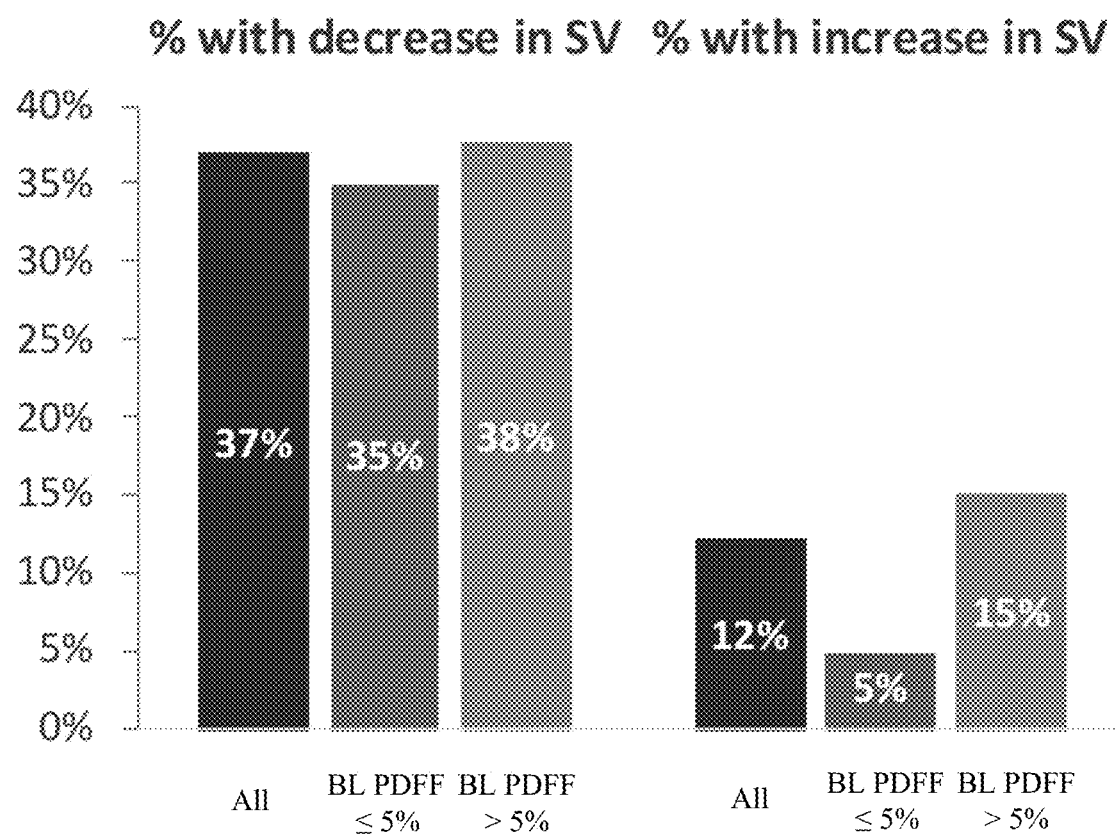
FIG. 5 is a graphical representation showing percentage of patients at week 52 with 10% reduction or 10% increase in spleen volume (SV) in Example 1.
Figure 6:
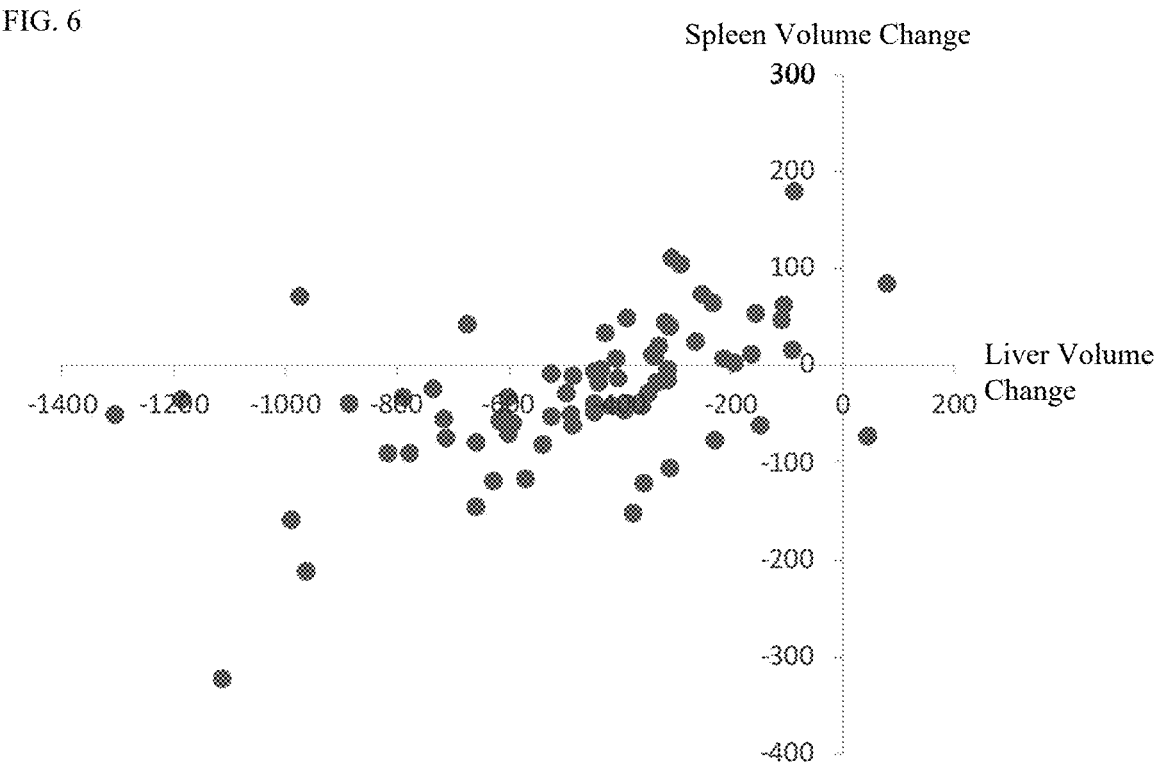
FIG. 6 is a graph showing the correlation between 52 week liver volume change and spleen volume change in patients who entered the study with baseline PDFF<8% in Example 1.

In patients with baseline PDFF>5% (5%=UL normal), resmetirom lowered PDFF by 37% (p<0.0057). Resmetirom lowered MRE by 0.68 kPa at week 52, and 34% had an MRE reduction of ≥15%. GGT, −27%, p=0.04 and alkaline phosphatase (ALP) −18%, p=0.04 were reduced. Liver volume (LV), which was elevated in NASH cirrhosis patients at baseline, was reduced −15.9% (7.7%) at week 16 (p<0.0001) independent of baseline PDFF. 73% of patients, independent of baseline cirrhosis severity, had >15% reduction in LV at week 52 (see, e.g., FIG. 4). Reduction in PDFF was related to LV reduction only in patients with baseline (BL) PDFF≥5%. Spleen volume (SV) changes were more variable than PDFF and LV reductions and were thus evaluated as a responder analysis (based on percentage of patients with ≥10% reduction or ≥10% increase in SV) (see, e.g., FIGS. 5 and 6). Exposure to resmetirom was strongly correlated with LV and SV changes.

LV reduction was correlated with reduction in MRE, MRI-PDFF, tissue inhibitor of metalloproteinase (TIMP), type III procollagen peptide (P3NP), and the SHBG responses to resmetirom (see, e.g., Table 1). Resmetirom reduced LDL-C(20%), triglycerides (21%), apolipoprotein B (ApoB) (20%), lipoprotein a (Lp(a)) (30%), independent of cirrhosis stage. Blood pressure (BP) was reduced by 4-5 mm. Resmetirom was safe and well-tolerated.

TABLE 1

| CFB in: | Pearson | | Spearman | |
| --- | --- | --- | --- | --- |
| | % CFB LV | CFB LV | CFB LV | P-value |
| TIMP | 0.500 | 0.350 | 0.369 | 0.007 |
| P3NP | 0.351 | 0.294 | 0.238 | 0.086 |
| MRI-PDFF (W 16) | 0.331 | 0.438 | 0.371 | 0.006 |
| MRE (W 16) | 0.327 | 0.273 | 0.347 | 0.014 |
| AST (W 52) | 0.197 | 0.254 | 0.191 | 0.170 |
| SHBG | −0.282 | −0.274 | −0.344 | 0.012 |

CFB, change from baseline; LV, liver volume; TIMP, tissue inhibitor metalloproteinase; P3NP, amino terminal procollagen peptide; W, week.

Resmetirom treatment of patients with NASH cirrhosis for up to 52 weeks was safe and effective at lowering markers of CV risk and NASH fibrosis.

Mechanism of Action

Resmetirom is a partial agonist of the THR-β. Resmetirom produced 83.8% of the maximum response compared to triiodothyronine (T3), with an $EC_{50}$ of 0.21 M in an in vitro functional assay for THR-β activation. The same functional assay for thyroid hormone receptor-alpha (THR-α) agonism showed 48.6% efficacy for resmetirom relative to T3, with an $EC_{50}$ of 3.74 M. THR-β is the major form of THR in the liver, and stimulation of THR-β in the liver reduces intrahepatic triglycerides, whereas actions of thyroid hormone outside the liver, including in heart and bone, are largely mediated through THR-α.

Pharmacodynamics

Liver Fat Content

Resmetirom decreased liver fat content as measured by magnetic resonance imaging-protein density fat fraction (MRI-PDFF) or FibroScan controlled attenuation parameter (CAP). Reductions in liver fat content by MRI-PDFF were observed at 16 (the first assessment) and 52 weeks of treatment. Reductions in liver fat content by CAP were observed at 52 weeks of treatment.

Lipids

Resmetirom reduced LDL-C, apolipoprotein B, triglycerides and total cholesterol. Reductions in LDL C, apolipoprotein B, triglycerides and total cholesterol were observed at the first assessment at 1 month of treatment. Similar decreases were observed at longer durations of treatment, including 24 and 52 weeks.

Pharmacokinetics

Following once daily doses, steady state was typically reached within 3 to 6 days of dosing. Resmetirom steady state exposure increased in a dose proportional manner between doses of 40 mg (0.5 times the lowest approved recommended dose) and 100 mg. Resmetirom exposure increased in a greater than dose proportional manner between doses of 100 mg and 200 mg (2 times the highest approved recommended dose). Resmetirom exposure increased 1.5- to 3-fold following once daily dosing; however, the MGL-3623 metabolite did not accumulate. The estimated resmetirom systemic exposure at steady state in NASH patients are summarized in Table 2. Resmetirom exposure was similar between NASH patients with F2 stage fibrosis and F3 stage fibrosis.

TABLE 2

Resmetirom Estimated Systemic Exposure at Steady State
in Patients with NASH with Fibrosis (F2 and F3)

| Parameter | Resmetirom 80 mg Once Daily Mean (CV %) | Resmetirom 100 mg Once Daily Mean (CV %) |
|---|---|---|
| $C_{max,ss}$ (ng/mL)[a] | 778 (41.5) | 971 (40.9) |
| $AUC_{tau,ss}$ (ng * h/mL)[a] | 5850 (60.5) | 7780 (65.5) |

[a]$AUC_{tau,ss}$ = area under the concentration-versus-time curve over one dosing interval at steady state; $C_{max,ss}$ = maximum concentration at steady state; CV = arithmetic coefficient of variation Absorption Resmetirom median time to maximum plasma concentration ($T_{max}$) was approximately 4 hours following multiple daily doses of resmetirom 80 mg or 100 mg.

Effect of Food: No clinically significant differences in resmetirom pharmacokinetics were observed following administration with a high-fat meal (approximately 150, 250, and 500-600 calories from protein, carbohydrate, and fat, respectively). Concomitant food administration resulted in a 33% decrease in $C_{max}$, an 11% decrease in AUC, and a delay in median $T_{max}$ by about 2 hours compared to under-fasted condition.

Distribution

Resmetirom apparent volume of distribution (Vd/F) at steady-state was 68 (227%) L. Resmetirom was greater than 99% protein-bound.

Elimination

Resmetirom median terminal plasma half-life (th) was 4.5 hours and the steady state apparent clearance (CL/F) was 17.5 (56.3%) L/h.

Metabolism: Resmetirom was metabolized by CYP2C8 and is not metabolized by other cytrochrome $P_{450}$ (CYP) enzymes in vitro. MGL-3623 is a major metabolite with a 28-times lower potency for THR-β than resmetirom. MGL-3623 represented 33% to 51% of resmetirom AUC at steady state following administration of 100 mg once daily.

Excretion

Following oral administration of a 100 mg radio-labeled dose of resmetirom, approximately 67% of the total radioactive dose was recovered in the feces, mostly as metabolites and 24% of the total radioactive dose was recovered in the urine. Unchanged labeled resmetirom was not detected in feces and accounted for 1% of the dose recovered in urine. A metabolite MGL-3623 accounted for 3.3% and 16% of the dose recovered in feces and urine, respectively. Oxalic acid metabolite was observed in plasma but not in urine.

Specific Populations

No clinically significant differences in the pharmacokinetics of resmetirom were observed based on age (18 to 83 years), sex, race (White, Black, or Asian), or ATP-binding cassette super-family G member 2 (ABCG2) genotype (breast cancer resistance protein (BCRP) p.Gln141Lys, p.Val12Met).

Population pharmacokinetics (PK) analyses indicated no clinically significant difference in the pharmacokinetics of resmetirom by mild to moderate renal impairment (eGFR 30 to 89 mL/min/1.73 m2, Modification of Diet in Renal Disease (MDRD)). The effect of severe renal impairment (estimated glomerular filtration rate (eGFR)<30 mL/min/1.73 m2, MDRD) on resmetirom pharmacokinetics is unknown.

Efficacy Studies

The efficacy of resmetirom was evaluated based on an efficacy analysis at Month 12 in Trial 1, a 54-month, randomized, double-blind, placebo-controlled trial. Enrolled patients had metabolic risk factors and a baseline or recent liver biopsy showing NASH with fibrosis stage 2 or 3 and a NAFLD Activity Score (NAS) of at least 4. Efficacy determination was based on the effect of resmetirom on resolution of steatohepatitis without worsening of fibrosis and one stage improvement in fibrosis without worsening of steatohepatitis, on post-baseline liver biopsies collected at 12 months.

The Month 12 analysis included 888 F2 and F3 (at eligibility) patients randomized 1:1:1 to receive placebo (n=294), resmetirom 80 mg once daily (n=298), or resmetirom 100 mg once daily (n=296), in addition to lifestyle counseling on nutrition and exercise. Patients were on stable doses of medications for diabetes, dyslipidemia, and hypertension.

Demographic and baseline characteristics were balanced between treatment and placebo groups. Overall, the median (Q1 to Q3) age of patients at baseline was 58 (51 to 65) years, 56% were female, 21% were Hispanic, 89% were White, 3% were Asian, and 2% were Black or African American. Median (Q1 to Q3) body mass index (BMI) was 35 (31 to 40) kg/m² and median (Q1 to Q3) body weight was 99 (85 to 114) kg. Baseline characteristics are presented in Table 3.

TABLE 3

Baseline Characteristics in Patiens with
Stage 2 to Stage 3 Fibrosis in Trial 1

| Characteristic | Overall N = 888 |
|---|---|
| Fibrosis stage, n (%) | |
| F2 | 328 (37) |
| F3 | 560 (63) |
| Type 2 Diabetes, n (%) | 608 (69) |
| Hypertension, n (%) | 700 (79) |
| Dyslipidemia, n (%) | 633 (71) |
| Satin use, n (%) | 434 (49) |
| Thyroxine use, n (%) | 124 (14) |
| Vibration-controlled Transient Elastography (VCTE) (kPa), Median (Q1, Q3)[a,b] | 11.8 (10, 15) |
| Controlled attenuation parameter (CAP) (Db/M), Median (Q1, Q3)[a] | 349 (320, 378) |
| Fibrosis Index Based on 4 Factors (FIB-4), Median (Q1, Q3)[a] | 1.3 (1, 1.8) |
| Enhanced Liver Fibrosis (ELF), Median (Q1, Q3)[a] | 9.7 (9.2, 10.4) |

[a]Less than 5% missingness 476 in these variables is omitted.
[b]kPa = kilopascal; Db/M = decibels per meter Table 4 presents the Month 12 histopathology results comparing resmetirom with placebo on 1) the percentage of patients with resolution of steatohepatitis and no worsening of liver fibrosis and 2) the percentage of patients with at least one stage improvement in liver fibrosis and no worsening of steatohepatitis. Two pathologists, Pathologist A and Pathologist B, independently read the liver biopsies for each patient. Both the 80 mg once daily and the 100 mg once daily dosages of resmetirom demonstrated statistically significant improvement on histopathology endpoints for NASH and fibrosis at Month 12 compared to placebo.

Examination of age, gender, diabetes status (Yes or No), and fibrosis stage (F2 or F3) subgroups did not identify differences in response to resmetirom among these subgroups. The majority of patients in the trial were white (89%); there were too few patients of other races to adequately assess differences in response by race.

TABLE 4

Efficacy Results at Month 12 in Adult Patients with Noncirrhotic NASH with Stage 2 or Stage 3 Fibrosis in Trial 1

|  | Placebo N = 294 | Resmetirom 80 mg Once Daily N = 298 | Resmetirom 100 mg Once Daily N = 296 |
|---|---|---|---|
| Resolution of steatohepatitis and no worsening of liver fibrosis |  |  |  |
| Response rate, Pathologist A (%) | 13 | 27 | 36 |
| Difference in response rate vs. placebo (95% CI) |  | 14 (8, 20) | 23 (16, 30) |
| Response rate, Pathologist B (%) | 9 | 26 | 24 |
| Difference in response rate vs. placebo (95% CI) |  | 17 (11, 23) | 15 (9, 21) |
| Improvement in liver fibrosis and no worsening of steatohepatitis |  |  |  |
| Response rate, Pathologist A (%) | 15 | 23 | 28 |
| Difference in response rate vs. placebo (95% CI) |  | 8 (2, 14) | 13 (7, 20) |
| Response rate, Pathologist B (%) | 13 | 23 | 24 |
| Difference in response rate vs. placebo (95% CI) |  | 11 (5, 17) | 11 (5, 17) |

CI: Confidence Interval

Liver fibrosis was evaluated on the NASH Clinical Research Network (CRN) fibrosis score as 0 to 4. Resolution of steatohepatitis was defined as a score of 0-1 for inflammation, 0 for ballooning, and any value for steatosis. No worsening of steatohepatitis was defined as no increase in NAS for ballooning, inflammation, or steatosis. The prespecified primary endpoints were resolution of NASH (ballooning score 0, inflammation score 0,1) with at least a 2-point reduction in NAS or at least a one stage improvement in fibrosis with no worsening of NAS. The effects on these prespecified endpoints were not different than the endpoints presented in Table 4.

Estimated using the Mantel-Haenszel method stratified by baseline type 2 diabetes status (presence or absence) and fibrosis stage (F2 or F3). 95% stratified Newcombe confidence intervals (CIs) are provided. Patients with missing liver biopsy at Month 12 were considered a non-responder.

On average, aminotgransferase (ALT) and aspartate aminotransferase (AST) appeared to be reduced from baseline in resmetirom groups as compared to the placebo group starting at Month 3 through Month 12.

Pharmacokinetics

Various body weight cutoffs for dosing were evaluated.

TABLE 5

Distribution of Resmetirom Average Concentration at Steady State ($C_{ave,ss}$) Across Quartiles for the 80 and 100 mg Doses

| $C_{ave,ss}$ (ng/mL) Range in Each Quartile | N | Percentage of $C_{ave,ss}$ in Each Quartile | |
|---|---|---|---|
|  |  | 80 mg | 100 mg |
| Placebo | 305 | 0% | 0% |
| Q1: [20-155) | 134 | 31% | 19% |
| Q2: [155-219) | 134 | 31% | 19% |
| Q3: [219-321) | 134 | 22% | 28% |
| Q4: [321-1326] | 134 | 17% | 34% |

Placebo; Q1 = first quartile; Q2 = second quartile; Q3 = third quartile; Q4 = fourth quartile

TABLE 6

Model-Predicted and Observed Probabilities of Response (NASH Resolution or Fibrosis Response) According to Resmetirom $C_{ave,ss}$

| $C_{ave,ss}$ (ng/mL) | N | Mean $C_{ave,ss}$ (ng/mL) | Estimated Probability (%) | Estimated 95% CI (%) | Observed Probability (%) | Observed 95% CI (%) |
|---|---|---|---|---|---|---|
| Placebo | 305 | 0 | 27.3 | (23.4-31.5) | 19.0 | (14.6-23.4) |
| Q1: [20-155) | 134 | 120 | 33.6 | (30.3-37.0) | 45.5 | (37.1-53.9) |
| Q2: [155-219) | 134 | 186 | 37.3 | (34.0-40.7) | 44.0 | (35.6-52.4) |
| Q3: [219-321) | 134 | 263 | 41.9 | (38.1-45.9) | 41.8 | (33.4-50.1) |
| Q4: [321-1326] | 134 | 495 | 56.2 | (48.9- 63.3) | 55.0 | (47.6-64.4) |

Placebo; Q1 = first quartile; Q2-second quartile; Q3 = third quartile; Q4 = fourth quartile Descriptive statistics of exposure parameters of resmetirom for the 80 and 100 mg doses by 10 kg body weight increments are presented in Table 7.

TABLE 7

Descriptive Statistics of Exposure Parameters of Resmetirom for the 80 and 100 mg Dose by 10 kg Body Weight Increments

| Assessment | Resmetirom 80 mg | | | | |
|---|---|---|---|---|---|
| | <80 kg (N = 56) | 80-<90 kg (N = 56) | 90-<100 kg (N = 59) | 100-<110 kg (N = 45) | ≥110 kg (N = 97) |
| $AUC_{tau,ss}$ (ng·h/mL) | | | | | |
| Mean (CV %) | 9230 (50.1%) | 6660 (53.2%) | 5790 (71.1%) | 4740 (52.0%) | 3750 (41.7%) |
| Median | 8180 | 5750 | 5030 | 4400 | 3550 |
| [Q05; Q95] | [3950; 18200] | [3400; 13400] | [2530; 10900] | [2860; 7440] | [1840; 6230] |
| Geometric Mean | 8080 | 6010 | 5060 | 4370 | 3470 |
| $C_{max,ss}$ (ng/mL) | | | | | |
| Mean (CV %) | 1210 (33.3%) | 869 (31.0%) | 789 (29.8%) | 654 (27.8%) | 520 (32.3%) |
| Median | 1140 | 870 | 795 | 644 | 504 |
| [Q05; Q95] | [664; 1890] | [428; 1270] | [358; 1140] | [381; 951] | [255; 821] |
| Geometric Mean | 1120 | 816 | 745 | 624 | 489 |
| $C_{ave,ss}$ (ng·h/mL) | | | | | |
| Mean (CV %) | 384 (50.1%) | 277 (53.2%) | 241 (71.1%) | 197 (52.0%) | 156 (41.7%) |
| Median | 341 | 240 | 210 | 183 | 148 |
| [Q05; Q95] | [165; 759] | [142; 560] | [105; 455] | [119; 310] | [76.5; 259] |
| Geometric Mean | 337 | 250 | 211 | 182 | 145 |
| $C_{min,ss}$ (ng/mL) | | | | | |
| Mean (CV %) | 72.8 (173.4%) | 55.9 (196.0%) | 52.0 (289.5%) | 37.3 (244.6%) | 26.0 (175.2%) |
| Median | 25.5 | 18.4 | 12.0 | 14.1 | 9.77 |
| [Q05; Q95] | [4.23; 336] | [3.36; 277] | [3.13; 270] | [2.93; 104] | [1.91; 107] |
| Geometric Mean | 26.7 | 20.7 | 14.2 | 13.2 | 11.5 |
| $t_{1/2\alpha}$ (h) | | | | | |
| Mean (CV %) | 1.27 (43.7%) | 1.34 (46.0%) | 1.21 (47.5%) | 1.26 (50.3%) | 1.30 (48.3%) |
| Median | 1.15 | 1.24 | 1.02 | 1.12 | 1.11 |
| [Q05; Q95] | [0.610; 2.24] | [0.599; 2.41] | [0.607; 2.48] | [0.567; 2.56] | [0.575; 2.51] |
| Geometric Mean | 1.13 | 1.21 | 1.10 | 1.12 | 1.16 |
| $t_{1/2\beta}$ (h) | | | | | |
| Mean (CV %) | 5.44 (51.6%) | 6.04 (95.1%) | 5.50 (81.5%) | 5.86 (88.7%) | 5.30 (50.5%) |
| Median | 4.53 | 4.41 | 4.29 | 4.50 | 4.45 |
| [Q05; Q95] | [3.68; 11.1] | [3.68; 13.4] | [3.69; 14.2] | [3.73; 15.8] | [3.63; 10.0] |
| Geometric Mean | 5.03 | 5.15 | 4.81 | 4.99 | 4.94 |
| Assessment | Resmetirom 100 mg | | | | |
| | <80 kg (N = 50) | 80-<90 kg (N = 48) | 90-<100 kg (N = 56) | 100-<110 kg (N = 45) | ≥110 kg (N = 105) |
| $AUC_{tau,ss}$ (ng·h/mL) | | | | | |
| Mean (CV %) | 10800 (72.6%) | 9660 (61.1%) | 9010 (54.3%) | 7430 (50.1%) | 4940 (65.7%) |
| Median | 9610 | 7550 | 7600 | 6250 | 3900 |

TABLE 7-continued

Descriptive Statistics of Exposure Parameters of Resmetirom
for the 80 and 100 mg Dose by 10 kg Body Weight Increments

| [Q05; Q95]<br>Geometric<br>Mean | [2440; 25600]<br>8680 | [5000; 23300]<br>8550 | [4050; 20500]<br>7990 | [3590; 14900]<br>6690 | [2330; 9890]<br>4330 |
|---|---|---|---|---|---|
| $C_{max,ss}$<br>(ng/mL) | | | | | |
| Mean (CV %) | 1310<br>(46.0%) | 1220<br>(28.3%) | 1010<br>(30.2%) | 958<br>(27.5%) | 642<br>(42.0%) |
| Median | 1370 | 1200 | 1060 | 966 | 647 |
| [Q05; Q95]<br>Geometric<br>Mean | [288; 2010]<br>1120 | [689; 1780]<br>1160 | [437; 1420]<br>954 | [499; 1370]<br>905 | [198; 1040]<br>575 |
| $C_{ave,ss}$<br>(ng · h/mL) | | | | | |
| Mean (CV %) | 451<br>(72.6%) | 402<br>(61.1%) | 375<br>(54.3%) | 310<br>(50.1%) | 206<br>(65.7%) |
| Median | 400 | 315 | 316 | 261 | 163 |
| [Q05; Q95]<br>Geometric<br>Mean | [102; 1070]<br>362 | [208; 970]<br>356 | [169; 856]<br>333 | [150; 622]<br>279 | [97.3; 412]<br>180 |
| $C_{min,ss}$ (ng/mL) | | | | | |
| Mean (CV %) | 119<br>(195.1%) | 100<br>(186.1%) | 113<br>(174.0%) | 65.4<br>(142.6%) | 43.4<br>(212.6%) |
| Median | 29.7 | 22.2 | 51.0 | 22.1 | 12.8 |
| [Q05; Q95]<br>Geometric<br>Mean | [4.32; 686]<br>31.4 | [5.57; 502]<br>32.0 | [4.23; 604]<br>41.7 | [4.06; 291]<br>26.5 | [3.40; 178]<br>16.2 |
| $t_{1/2\alpha}$ (h) | | | | | |
| Mean (CV %) | 1.47<br>(48.8%) | 1.30<br>(50.2%) | 1.54<br>(43.6%) | 1.30<br>(50.4%) | 1.38<br>(48.2%) |
| Median | 1.44 | 1.08 | 1.37 | 1.34 | 1.30 |
| [Q05; Q95]<br>Geometric<br>Mean | [0.570; 2.49]<br>1.26 | [0.601; 2.55]<br>1.16 | [0.655; 2.72]<br>1.39 | [0.517; 2.35]<br>1.14 | [0.655; 2.73]<br>1.24 |
| $t_{1/2\beta}$ (h) | | | | | |
| Mean (CV %) | 6.85<br>(124.6%) | 7.13<br>(124.0%) | 8.49<br>(144.6%) | 7.08<br>(145.9%) | 6.33<br>(92.7%) |
| Median | 4.41 | 4.43 | 5.29 | 4.65 | 4.50 |
| [Q05; Q95]<br>Geometric<br>Mean | [3.52; 15.8]<br>5.36 | [3.78; 15.1]<br>5.58 | [3.75; 27.3]<br>6.21 | [3.77; 11.6]<br>5.55 | [3.75; 17.0]<br>5.32 |

$AUC_{tau,ss}$ = area under the curve over the dosing interval at steady state; $C_{max,ss}$ = maximum concentration at steady state; $C_{ave,ss}$ = average concentration at steady state; $C_{min,ss}$ = minimum concentration at steady state; $t_{1/2\alpha}$ = distribution half-life; $t_{1/2\beta}$ = elimination half-life; CV = coefficient of variation; Q05 = $5^{th}$ quantile; Q95 = $95^{th}$ quantile The effect of body weight, as shown by increase in sex hormone binding globulin (SHBG), a measure of exposure, and response to resmetirom by dose in key efficacy measures, is presented in Table 8.

TABLE 8

Evaluation of Baseline Weight on Key Efficacy Outcomes with Resmetirom 80 mg and 100 mg

| | Resmetirom 80 mg | | | | | Resmetirom 100 mg | | | | |
|---|---|---|---|---|---|---|---|---|---|---|
| Assessment | <80 kg | 80-<90 kg | 90-<100 kg | 100-<110 kg | ≥110 kg | <80 kg | 80-<90 kg | 90-<100 kg | 100-<110 kg | ≥110 kg |
| ≥120% increase in SHBG at Week 52 | 39<br>(72.2) | 30<br>(56.6) | 28<br>(52.8) | 14<br>(34.1) | 21<br>(28.0) | 30<br>(68.2) | 27<br>(62.8) | 28<br>(63.6) | 27<br>(62.8) | 45<br>(50.6) |
| ≥30% reduction in MRI-PDFF at Week 52 Week 52 MITT(1) | 34<br>(73.9) | 28<br>(63.6) | 28<br>(62.2) | 23<br>(67.6) | 33<br>(51.6) | 24<br>(64.9) | 30<br>(76.9) | 24<br>(70.6) | 29<br>(70.7) | 53<br>(74.6) |
| Consensus Fibrosis Improvement Responder | 17<br>(28.3) | 20<br>(34.5) | 15<br>(25.4) | 8<br>(17.4) | 17<br>(17.2) | 16<br>(28.6) | 13<br>(26.5) | 12<br>(20.3) | 14<br>(27.5) | 27<br>(25.0) |
| Consensus NASH Resolution Responder Week 52 Paired Biopsies | 15<br>(25.0) | 17<br>(29.3) | 15<br>(25.4) | 13<br>(28.3) | 17<br>(17.2) | 14<br>(25.0) | 16<br>(32.7) | 13<br>(22.0) | 16<br>(31.4) | 30<br>(27.8) |
| Consensus Fibrosis Improvement Responder | 17<br>(34.7) | 20<br>(40.8) | 15<br>(30.6) | 8<br>(22.2) | 17<br>(22.7) | 16<br>(40.0) | 13<br>(31.7) | 12<br>(29.3) | 14<br>(35.0) | 27<br>(31.4) |
| Consensus NASH | 15 | 17 | 15 | 13 | 17 | 14 | 16 | 13 | 16 | 30 |

TABLE 8-continued

Evaluation of Baseline Weight on Key Efficacy Outcomes with Resmetirom 80 mg and 100 mg

| | Resmetirom 80 mg | | | | | Resmetirom 100 mg | | | | |
|---|---|---|---|---|---|---|---|---|---|---|
| Assessment | <80 kg | 80-<90 kg | 90-<100 kg | 100-<110 kg | ≥110 kg | <80 kg | 80-<90 kg | 90-<100 kg | 100-<110 kg | ≥110 kg |
| Resolution Responder | (30.6) | (34.7) | (30.6) | (36.1) | (22.7) | (35.0) | (39.0) | (31.7) | (40.0) | (34.9) |
| Discontinued Study | 6 | 6 | 6 | 3 | 19 | 12 | 4 | 15 | 9 | 18 |
| Prior to Week 52 | (10.0) | (10.3) | (10.2) | (6.5) | (19.2) | (21.4) | (8.2) | (25.4) | (17.6) | (16.7) |

Note:
(1) For NASH Resolution and Fibrosis Responder status, human subjects with composite clinical endpoints, missing responses and week 52 biopsies out of window were considered non-responders.

The pharmacokinetics of resmetirom were highly dependent on body weight and reflected in exposure response for liver biopsy and other study endpoints.

Example 2: A Phase 3, Randomized, Controlled Trial of Resmetirom in NASH with Liver Fibrosis A phase 3 trial was conducted involving adults with biopsy-confirmed NASH and a fibrosis stage of F1B, F2, or F3 (stages range from F0 [no fibrosis] to F4 [cirrhosis]). Patients were randomly assigned in a 1:1:1 ratio to receive once-daily resmetirom at a dose of 80 mg or 100 mg or placebo. The two primary end points at week 52 were NASH resolution (including a reduction in the nonalcoholic fatty liver disease [NAFLD]activity score by ≥2 points; scores range from 0 to 8, with higher scores indicating more severe disease) with no worsening of fibrosis, and an improvement (reduction) in fibrosis by at least one stage with no worsening of the NAFLD activity score.

Overall, 966 patients formed the primary analysis population (322 in the 80-mg resmetirom group, 323 in the 100-mg resmetirom group, and 321 in the placebo group). NASH resolution with no worsening of fibrosis was achieved in 25.9% of the patients in the 80-mg resmetirom group and 29.9% of those in the 100-mg resmetirom group, as compared with 9.7% of those in the placebo group (P<0.001 for both comparisons with placebo). Fibrosis improvement by at least one stage with no worsening of the NAFLD activity score was achieved in 24.2% of the patients in the 80-mg resmetirom group and 25.9% of those in the 100-mg resmetirom group, as compared with 14.2% of those in the placebo group (P<0.001 for both comparisons with placebo). The change in low-density lipoprotein cholesterol levels from baseline to week 24 was −13.6% in the 80-mg resmetirom group and −16.3% in the 100-mg resmetirom group, as compared with 0.1% in the placebo group (P<0.001 for both comparisons with placebo). Diarrhea and nausea were more frequent with resmetirom than with placebo. The incidence of serious adverse events was similar across trial groups: 10.9% in the 80-mg resmetirom group, 12.7% in the 100-mg resmetirom group, and 11.5% in the placebo group.

Both the 80-mg dose and the 100-mg dose of resmetirom were superior to placebo with respect to NASH resolution and improvement in liver fibrosis by at least one stage. (Funded by Madrigal Pharmaceuticals; MAESTRO-NASH ClinicalTrials.gov number, NCT03900429.).

Methods
Trial Design and Oversight

This phase 3, double-blind, randomized, placebo-controlled trial was conducted at 245 sites in 15 countries. The trial is ongoing and remains blinded to individual patient identification and trial-group assignments. The planned duration of the trial is 54 months; the two liver-biopsy primary end points were assessed at 52 weeks in the first 1050 patients who had undergone randomization, and the clinical-outcome primary end point is prespecified to be assessed at month 54. The planned duration of the trial is 54 months; the two liver-biopsy primary end points were assessed at 52 weeks in the first 1050 patients who had undergone randomization, and the clinical-outcome primary end point is prespecified to be assessed at month 54. The protocol was approved by the institutional review board and ethics committee at each participating site. The trial was and continues to be conducted in accordance with the principles of the Declaration of Helsinki, the International Council for Harmonisation Good Clinical Practice guidelines, and all relevant regulations. All the patients provided written informed consent.

Patients

Eligible patients were 18 years of age or older who had at least three of five metabolic risk factors, according to a modified version of the International Diabetes Foundation criteria for the metabolic syndrome, and who had undergone prescreening vibration-controlled transient elastography (VCTE; FibroScan) within the past 3 months that showed a controlled attenuation parameter (CAP) of 280 dB per meter or more and a liver-stiffness measurement of 8.5 kPa or more (alternatively, a liver biopsy that was performed within 6 months before randomization could be confirmed to be eligible as a baseline biopsy by the central pathologist of the trial). Additional key inclusion criteria were histologic evidence of NASH and an NAFLD activity score of 4 or more (on a scale of 0 to 8, with higher scores indicating more severe disease), with a score of 1 or more for each component (steatosis [on a scale from 0 to 3], lobular inflammation [on a scale from 0 to 3], and hepatocellular ballooning [on a scale from 0 to 2]). At least 50% of the total enrollment was required to have a fibrosis stage of F3. No more than 15% of the total enrollment could have a fibrosis stage of F1, primarily F1B (moderate fibrosis stage, pericentral area only), and no more than 3% of the total enrollment could have a fibrosis stage of F1A or F1C (only if the N-terminal type III collagen propeptide level was ≥14 ng per milliliter). Weight was required to be stable (<5% change in 3 months), and doses of glucagon-like peptide-1 agonists were required to be stable for at least 6 months before biopsy. Key exclusion criteria were alcohol consumption of more than 20 g per day for women and more than 30 g per day for men, a glycated hemoglobin level of more than 9.0% at screening, and causes of chronic liver disease other than noncirrhotic NASH. Full eligibility criteria are listed in the Supplementary Appendix.

Procedures

Figure 7:
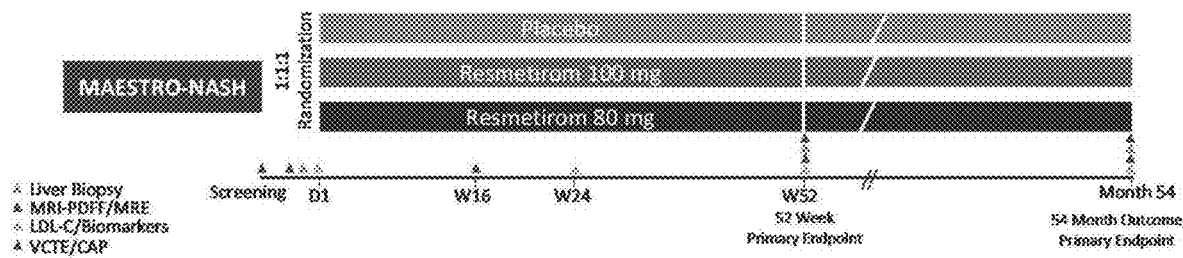
FIG. 7 is a graphical representation showing the study design in Example 2. CAP: controlled attenuation parameter; LDL-C: low-density lipoprotein cholesterol; MRE: magnetic resonance elastography; MRI-PDFF: magnetic resonance imaging-proton density fat fraction; VCTE: vibration-controlled transient elastography.

Patients were randomly assigned in a 1:1:1 ratio to receive resmetirom at a dose of 80 mg or 100 mg or placebo, administered orally once daily (FIG. 7). Randomization was performed with the use of an interactive Webresponse system. Patients were stratified according to status with respect to type 2 diabetes (presence or absence) and fibrosis stage (F1, F2, or F3). Throughout the trial, patients received nutrition and exercise counseling according to current recommendations. Patients were unaware of the trial-group assignments, as were site personnel, personnel of contract research organizations, and sponsor personnel who were conducting the trial, administering the investigational product, and performing clinical assessments. Selected persons were aware of the trial-group assignments to facilitate dispensation of resmetirom or placebo. All trial personnel were unaware of the results of postbaseline tests that could reveal the trial-group assignments, including levels of total and free thyroxine (T4), sex hormone-binding globulin, and lipids as well as magnetic resonance imaging proton density fat fraction (MRI-PDFF).

Screening biopsy results were used as baseline values for histologic variables, and a second biopsy was performed at week 52. Biopsy specimens on glass slides were assessed centrally by two independent expert pathologists (the second and third authors) to determine the NAFLD activity score and fibrosis stage (according to NASH Clinical Research Network criteria). For the primary analysis, all screening or baseline biopsy specimens and week 52 biopsy specimens on glass slides were reread independently by both pathologists in large unpaired groups of screening or baseline biopsy specimens (50 to 100 slides per group, spiked with biopsy specimens obtained from patients who had screening failure) or a separate matched set of week 52 biopsy specimens (50 to 100 slides per group). The pathologists were unaware of the trial-group assignments, patient characteristics, and each other's assessments. A consensus review was conducted as a supportive analysis wherein the two pathologists read blinded (to time of biopsy and identification code) digitized images for cases in which there was disagreement on the primary read with respect to response status for the two primary end points or a reduction in fibrosis by at least two stages. Only the NAFLD activity scores or fibrosis components that determined the response for which there was disagreement between the pathologists were reread. Details are provided in the Supplementary Appendix.

End Points

The two primary end points at week 52 were NASH resolution (achievement of a hepatocellular ballooning score of 0, a lobular inflammation score of 0 or 1, and a reduction in the NAFLD activity score by ≥2 points) with no worsening of fibrosis, and an improvement (reduction) in fibrosis by at least one stage with no worsening of the NAFLD activity score. The key secondary end point was the percent change from baseline in the low-density lipoprotein (LDL) cholesterol level at week 24. Safety end points included adverse events, biochemical assessments, and clinical assessments. Selected serious adverse events (including deaths, cardiovascular events, and potential drug-induced liver injury) were adjudicated by independent, external event-adjudication committees whose members were unaware of the trial-group assignments. A complete list of primary and secondary end points is provided in Table 13.

Statistical Analysis

Figure 8:
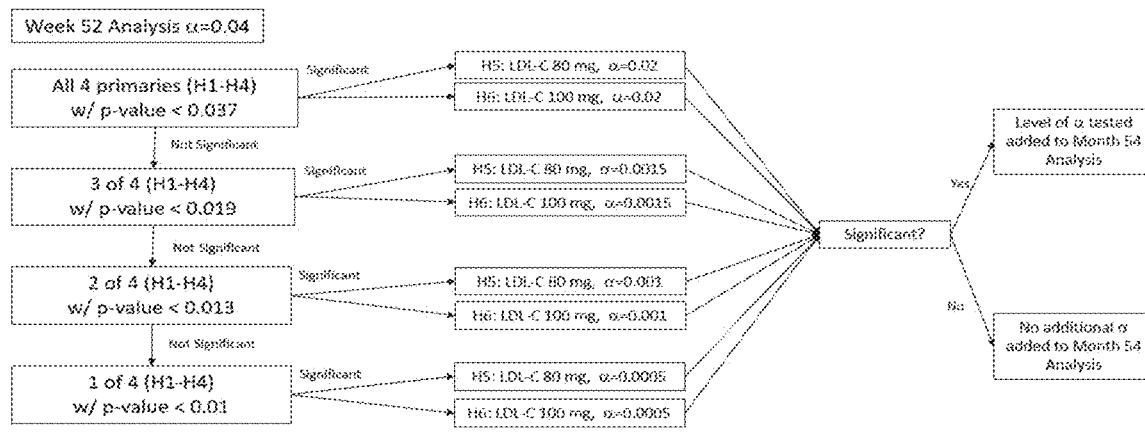
FIG. 8 is a schematic showing statistical testing process for primary and key secondary endpoints at week 52 in Example 2. LDL-C: low-density lipoprotein cholesterol.

On the basis of a sample size of at least 780 patients, the trial had more than 90% power to detect a difference between each dose of resmetirom and placebo with the use of a stratified Cochran-Mantel-Haenszel test, under the assumption that NASH resolution with no worsening of fibrosis would occur in 7.2% of the patients receiving placebo and 19.8% of those receiving resmetirom and that fibrosis improvement by at least one stage with no worsening of the NAFLD activity score would occur in 14% of the patients receiving placebo and 26% of those receiving resmetirom. No comparisons were planned between the two resmetirom dose groups. The trial recruited additional patients to further expand the safety profile of resmetirom, support more robust subgroup analyses, and allow for uncertainty in the assumed treatment effects relative to placebo. Multiplicity was controlled with the use of a weighted Bonferroni approach (alpha=0.04 at week 52 and alpha=0.01 at month 54) (FIG. 8). In addition, a two-stage gatekeeping procedure was used to control alpha at 0.04 for the week 52 family of end points. Recycling of alpha to the month 54 analysis, as appropriate, is planned.

TABLE 9

Demographic and Clinical Characteristics of the Patients at Baseline (Primary Population).*

| Characteristic | Resmetirom 80 mg (N = 322) | Resmetirom 100 mg (N = 323) | Placebo (N = 321) |
| --- | --- | --- | --- |
| Age - yr | 55.9 ± 11.5 | 57.0 ± 10.8 | 57.1 ± 10.5 |
| Male sex - no. (%)† | 140 (43.5) | 141 (43.7) | 143 (44.5) |
| Race or ethnic group - no. (%)† | | | |
| White | 291 (90.4) | 291 (90.1) | 281 (87.5) |
| Black | 5 (1.6) | 5 (1.5) | 9 (2.8) |
| Asian | 10 (3.1) | 9 (2.8) | 9 (2.8) |
| Other‡ | 12 (3.7) | 11 (3.4) | 18 (5.6) |
| Missing data | 4 (1.2) | 7 (2.2) | 4 (1.2) |
| Hispanic or Latino ethnic group - no. (%)† | 71 (22.0) | 81 (25.1) | 52 (16.2) |
| Body weight - kg | 100.1 ± 22.3 | 101.9 ± 22.9 | 100.2 ± 23.1 |
| Body-mass index | 35.5 ± 6.4 | 36.2 ± 7.4 | 35.3 ± 6.5 |
| Type 2 diabetes - no. (%) | 224 (69.6) | 213 (65.9) | 210 (65.4) |
| Hypertension - no. (%) | 243 (75.5) | 254 (78.6) | 257 (80.1) |
| Dyslipidemia - no. (%) | 229 (71.1) | 236 (73.1) | 224 (69.8) |
| Hypothyroidism - no. (%)§ | 39 (12.1) | 46 (14.2) | 45 (14.0) |

TABLE 9-continued

Demographic and Clinical Characteristics of the
Patients at Baseline (Primary Population).*

| Characteristic | Resmetirom 80 mg (N = 322) | Resmetirom 100 mg (N = 323) | Placebo (N = 321) |
|---|---|---|---|
| History of ASCVD - no. (%) | 20 (6.2) | 23 (7.1) | 14 (4.4) |
| Estimated 10-yr risk of ASCVD - %¶ | 14.7 ± 12.0 | 14.5 ± 12.1 | 15.4 ± 11.6 |
| FibroScan liver-stiffness measurement - kPa// | | | |
| Mean | 13.3 ± 6.8 | 13.6 ± 7.1 | 12.9 ± 5.5 |
| Median (IQR) | 11.5 (9.5-14.9) | 11.9 (9.5-15.9) | 11.7 (9.4-14.8) |
| FibroScan controlled attenuation parameter - dB/m** | 346.1 ± 37.2 | 349.4 ± 38.7 | 347.2 ± 37.0 |
| MRI-PDFF - %†† | 18.2 ± 6.8 | 17.2 ± 6.6 | 17.8 ± 6.8 |
| Liver stiffness on MRE - kPa | 3.5 ± 0.9 | 3.7 ± 1.1 | 3.5 ± 1.0 |
| Fibrosis-4 index score‡‡ | 1.4 ± 0.7 | 1.5 ± 0.7 | 1.4 ± 0.7 |
| LDL cholesterol level - mg/dl | 106.6 ± 37.4 | 103.0 ± 36.8 | 106.8 ± 41.1 |
| Alanine aminotransferase level - U/liter | 52.8 ± 27.3 | 56.3 ± 34.0 | 54.7 ± 34.8 |
| Aspartate aminotransferase level - U/liter | 38.2 ± 19.3 | 42.5 ± 25.2 | 40.7 ± 24.6 |
| γ-Glutamyltransferase level - U/liter | 84.3 ± 111.3 | 84.6 ± 99.0 | 75.7 ± 85.0 |
| Liver-biopsy findings - no. (%) | | | |
| NAFLD activity score ≥5§§ | 266 (82.6) | 288 (89.2) | 253 (78.8) |
| Fibrosis stage¶¶ | | | |
| F1B | 16 (5.0) | 15 (4.6) | 18 (5.6) |
| F2 | 107 (33.2) | 100 (31.0) | 112 (34.9) |
| F3 | 199 (61.8) | 208 (64.4) | 191 (59.5) |

*Plus-minus values are means ± SD. Percentages may not total 100 because of rounding.
ASCVD denotes atherosclerotic cardiovascular disease, IQR interquartile range, LDL low-density lipoprotein, and MRE magnetic resonance elastography.
†Data on sex, race, and ethnic group were reported by the patient.
‡"Other" includes American Indian or Alaska Native, Native Hawaiian or other Pacific Islander, and all other nonspecified race or ethnic group categories.
§Shown are patients who were receiving thyroxine-replacement therapy at screening.
¶The risk of cardiovascular events was derived from multiple risk factors, including age, sex, race, systolic blood pressure, diastolic blood pressure, total cholesterol, high-density lipoprotein cholesterol, LDL cholesterol, history of diabetes, smoking status, hypertension treatment, statin treatment, and aspirin therapy. Persons are preliminarily classified on the basis of estimated risk: a 10-year risk of ASCVD of less than 5% is low risk; 5 to 7.4% is borderline risk; 7.5 to 19.9% is intermediate risk; and 20% or more is high risk.
//Liver stiffness was measured by means of vibration-controlled transient elastography. Values of more than 8.5 are considered to be indicative of fibrosis of stage F2 or higher.
**Controlled attenuation parameter is a method for the noninvasive assessment of steatosis, which measures the increased attenuation of ultrasound waves when traveling through steatotic hepatic tissue, as compared with normal liver tissue. The maximum value is 360 dB per meter; for this trial, a reading of more than 280 dB per meter was considered to be high.
††Magnetic resonance imaging proton density fat fraction (MRI-PDFF) is a magnetic resonance imaging-derived noninvasive, quantitative biomarker to assess liver fat content. A reading of more than 5% is considered to be high.
‡‡The Fibrosis-4 index score is derived from platelet count, aspartate aminotransferase level, age, and alanine aminotransferase level. Scores of more than 2.67 are considered to be indicative of advanced fibrosis and an elevated risk of liver-related events.
§§The nonalcoholic fatty liver disease (NAFLD) activity score is assessed on a scale of 0 to 8, with higher scores indicating more severe disease; the components of this measure are steatosis (assessed on a scale of 0 to 3), lobular inflammation (assessed on a scale of 0 to 3), and hepatocellular ballooning (assessed on a scale of 0 to 2). NAFLD activity scores of 4 or more are considered to indicate at-risk nonalcoholic steatohepatitis (NASH).
¶¶Fibrosis stages range from F0 (no fibrosis) to F4 (cirrhosis). A stage of F1B indicates moderate fibrosis, pericentral area only. Five patients in each group who were scored as having F3 fibrosis at eligibility and who were rescored as having F4 fibrosis at baseline by one or both central pathologists were evaluated in the F3 group.

The primary statistical analysis model used the Cochran-Mantel-Haenszel test to determine response with respect to the biopsy end points. Patients with missing biopsies were considered to have not had a response. Disagreement was incorporated into a statistical Cochran-Mantel-Haenszel model that provided partial credit for cases in which pathologists disagreed on response status for any biopsy end point. Multiple sensitivity analyses were conducted, including multiple imputation and tipping-point analysis. Details of secondary, exploratory, and safety analyses were specified in the statistical analysis plan (available with the protocol). All reported P values are two-sided. For end points not included in the hierarchical plan to adjust for multiple testing, 95% confidence intervals are reported without P values; 95% confidence intervals should not be used in place of hypothesis tests.

Results

Patients

Figure 9:
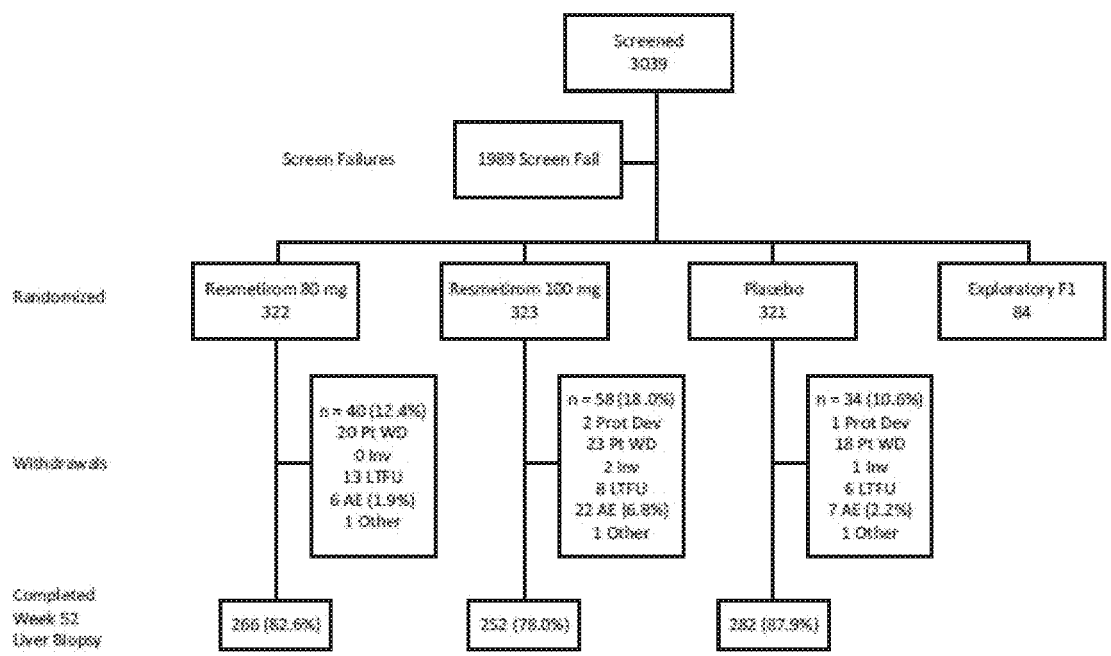
FIG. 9 is a schematic showing patient disposition in Example 2. AE: adverse event; LTFU: lost to follow up. The primary reasons for screen failure included biopsy, withdraw of consent, MRI-PDFF<8%, HbA1c>9. The exploratory F1 group included baseline F1A/F1C patients (n=84) that were considered only for exploratory efficacy and safety analyses. These patients received treatment but as prespecified in the statistical analysis plan, were not included in the primary analysis population.

From March 2019 through July 2021, a total of 1050 patients underwent randomization; 966 patients who had a fibrosis stage of F1B, F2, or F3 at baseline (primary population for safety and efficacy) were randomly assigned to receive 80 mg of resmetirom (322 patients), 100 mg of resmetirom (323 patients), or placebo (321 patients) (FIG. 9). A total of 84 patients who had a fibrosis stage of F1A or F1C at baseline were randomly assigned to receive 80 mg of resmetirom (30 patients), 100 mg of resmetirom (26 patients), or placebo (28 patients) (exploratory population for safety and efficacy) (Tables 19 and 20). A total of 11 of 966 patients had a delay in their week 52 biopsy for reasons related to coronavirus disease 2019 (Covid-19), were considered to have missing data completely at random, and were removed from the primary biopsy analysis population, a decision consistent with regulatory guidance regarding Covid-19. As such, the primary biopsy analysis population consisted of 955 patients: 316 in the 80-mg resmetirom group, 321 in the 100-mg resmetirom group, and 318 in the placebo group.

The demographic and clinical characteristics of the patients at baseline were similar across the trial groups (Table 9 and Table 14). Most patients were White (89.3%), with a high incidence of metabolic risk factors (hypertension, 78.1%; dyslipidemia, 71.3%; and type 2 diabetes, 67.0%). A total of 21.1% of the patients were Hispanic; only 2.0% of the patients were Black. (The representativeness of the trial population is described in Table 15.) The mean (±SD) age of the patients was 56.6±10.9 years, and the mean body-mass index (the weight in kilograms divided by the square of the height in meters) was 35.7±6.8. Baseline biopsies indicated that 83.5% of the patients had an NAFLD activity score of 5 or more; 5.1% had F1B fibrosis, 33.0% had F2 fibrosis, and 60.4% had F3 fibrosis. The use of medications at baseline was generally balanced across the trial groups. The demographic and clinical characteristics of the patients at baseline according to fibrosis stage are reported in Table 16. At the time of database lock for the week 52 end points, adherence to the trial regimen was high (92% with ≥80% adherence).

TABLE 10

| | Biopsy End Points* | | | | | | |
|---|---|---|---|---|---|---|---|
| Endpoint | Resmetirom 80 mg (N = 316) | Resmetirom 100 mg (N = 321) | Placebo (N = 318) | Difference between Resmetirom, 80 mg, and Placebo (95% CI)† percentage points | P-value | Difference between Resmetirom, 100 mg, and Placebo (95% CI)† percentage points | P-value |
| | percent with response | | | | | | |
| Primary endpoints | | | | | | | |
| NASH resolution with no worsening of fibrosis | 25.9 | 29.9 | 9.7 | 16.4 (11.0-21.8) | <0.001 | 20.7 (15.3-26.2) | <0.001 |
| Fibrosis improvement by ≥1 stage with no worsening of NAFLD activity score | 24.2 | 25.9 | 14.2 | 10.2 (4.8-15.7) | <0.001 | 11.8 (6.4-17.2) | <0.001 |
| Other endpoints | | | | | | | |
| ≥2-Point improvement in NAFLD activity score, including ≥1-point improvement in hepatocellular ballooning or lobular inflammation, with no worsening of fibrosis | 41.3 | 44.9 | 21.2 | 20.2 (13.8-26.5) | | 23.8 (17.4-30.2) | |
| ≥2-Point improvement in NAFLD activity score, including ≥1-point improvement in hepatocellular ballooning or lobular inflammation, with improvement in fibrosis | 18.8 | 21.2 | 8.5 | 10.5 (5.8-15.3) | | 13.0 (8.3-17.7) | |
| Improvement in each component of NAFLD activity score | 23.3 | 27.9 | 7.2 | 16.1 (11.1-21.0) | | 20.9 (15.8-25.9) | |
| Improvement in fibrosis by ≥2 stages | 8.3 | 10.1 | 2.8 | 5.6 (2.5-8.7) | | 7.4 (3.9-10.8) | |

TABLE 10-continued

Biopsy End Points*

| Endpoint | Resmetirom 80 mg (N = 316) percent with response | Resmetirom 100 mg (N = 321) percent with response | Placebo (N = 318) percent with response | Difference between Resmetirom, 80 mg, and Placebo (95% CI)† percentage points | P-value | Difference between Resmetirom, 100 mg, and Placebo (95% CI)† percentage points | P-value |
|---|---|---|---|---|---|---|---|
| Both NASH resolution and fibrosis improvement by ≥1 stage | 14.2 | 16.0 | 4.9 | 9.5 (5.4-13.6) | | 11.6 (7.5-15.8) | |

*Of the 966 patients in the primary population, 11 patients (6 in the 80-mg resmetirom group, 3 in the 100-mg resmetirom group, and 2 in the placebo group) had a delay in their week 52 biopsy for reasons related to coronavirus disease 2019 (Covid-19) and were not evaluated for the endpoints shown here. NASH resolution was defined as a hepatocellular ballooning score of 0, a lobular inflammation score of 0 or 1, and a reduction in the NAFLD activity score by at least 2 points.
†The widths of the confidence intervals have not been adjusted for multiplicity and may not be used for hypothesis testing.

TABLE 11

Key Secondary and Other Secondary Endpoints (Primary Population)*

| Measurement | Resmetirom, 80 mg (N = 322) least-squares mean percent change from baseline | Resmetirom, 100 mg, (N = 323) least-squares mean percent change from baseline | Placebo (N = 321) least-squares mean percent change from baseline | Difference between Resmetirom, 80 mg, and Placebo (95% CI)† percentage points | Difference between Resmetirom, 100 mg, and Placebo (95% CI)† percentage points |
|---|---|---|---|---|---|
| LDL cholesterol level at wk 24‡§ | −13.6 ± 1.7 | −16.3 ± 1.7 | 0.1 ± 1.7 | −13.7 (−17.5 to −10.0)¶ | −16.4 (−20.1 to −12.6)¶ |
| Apolipoprotein B level at wk 24§ | −16.8 ± 1.3 | −19.8 ± 1.3 | 0.39 ± 1.3 | −17.2 (−20.0 to −14.4) | −20.2 (−22.9 to −17.4) |
| Triglyceride level at wk 24§‖ | −22.7 ± 4.0 | −21.7 ± 4.3 | −2.6 ± 4.1 | −20.1 (−28.3 to −11.8) | −19.1 (−27.8 to −10.3) |
| Lipoprotein(a) level at wk 24§** | −30.4 ± 3.8 | −35.9 ± 4.0 | −0.84 ± 3.5 | −29.5 (−37.6 to −21.5) | −35.1 (−43.5 to −26.6) |
| MRI-PDFF at wk 52 | −35.4 ± 2.8 | −46.6 ± 2.8 | −8.7 ± 2.7 | −26.7 (−32.9 to −20.6) | −37.9 (−44.2 to −31.7) |
| Alanine aminotransferase level at wk 48†† | −26.6 ± 3.7 | −33.2 ± 3.9 | −6.9 ± 3.8 | −19.7 (−27.7 to −11.6) | −26.3 (−34.5 to −18.1) |
| Aspartate aminotransferase level at wk 48†† | −22.1 ± 3.9 | −28.3 ± 3.9 | −2.9 ± 3.8 | −19.3 (−27.2 to −11.3) | −25.4 (−33.5 to −17.4) |
| γ-Glutamyltransferase level at wk 48†† | −25.0 ± 5.5 | −31.9 ± 6.3 | 3.3 ± 5.2 | −28.3 (−37.3 to −19.3) | −35.2 (−45.5 to −25.0) |

*Multiple imputation analyses were used for lipids and liver enzymes. Details on the change from baseline in levels of lipids, lipoproteins, and lipid particles at weeks 24 and 52 are provided in Table 8.
†The widths of the confidence intervals have not been adjusted for multiplicity and may not be used for hypothesis testing.
‡The key secondary endpoint was the percent change from baseline in the LDL cholesterol level at week 24. LDL cholesterol was directly measured.
§Data were missing for one patient in the 80-mg resmetirom group.
¶P < 0.001.
‖Data are for patients with a baseline triglyceride level of more than 150 mg per deciliter.
**Data are for patients with a baseline lipoprotein(a) level of more than 10 nmol per liter.
††Data are for patients with a baseline alanine aminotransferase level of 30 U per liter or more.

Efficacy

Figures 10A, 10B, 10C:
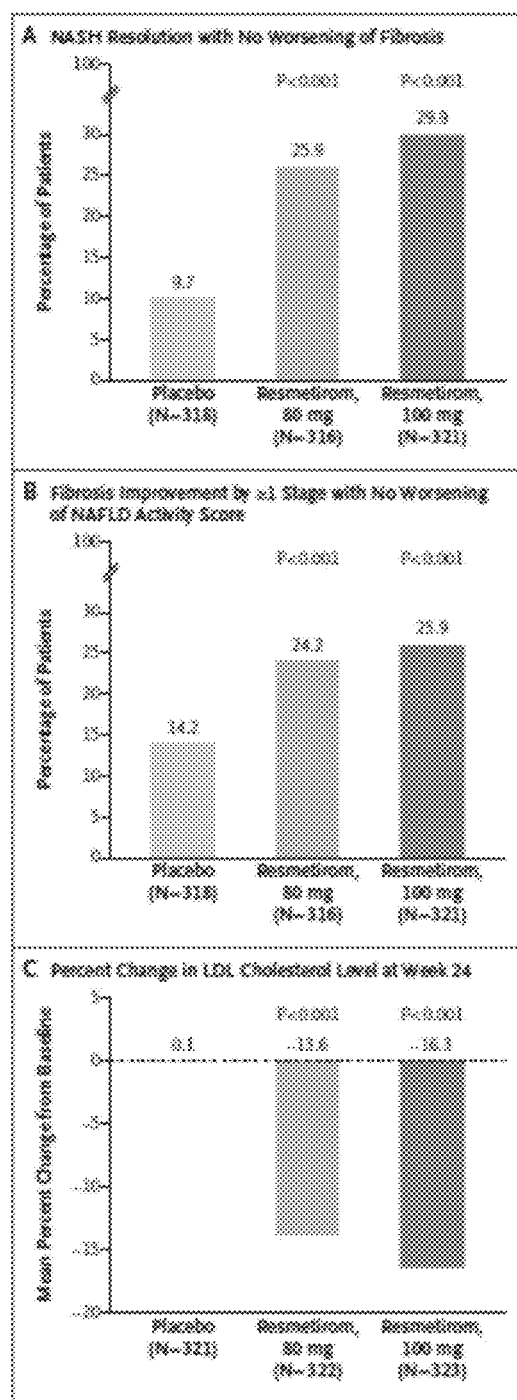
FIGS. 10A-10C show primary and Key Secondary End Points in Example 2. The two primary end points at week 52 were resolution of nonalcoholic steatohepatitis (NASH) with no worsening of fibrosis (Panel A, FIG. 10A), and an improvement (reduction) in fibrosis by at least one stage with no worsening of the nonalcoholic fatty liver disease (NAFLD) activity score (Panel B, FIG. 10B). The key secondary end point was the percent change from baseline in the low-density lipoprotein (LDL) cholesterol level at week 24 (Panel C, FIG. 10C). The NAFLD activity score is assessed on a scale of 0 to 8, with higher scores indicating more severe disease; the components of this measure are steatosis (assessed on a scale of 0 to 3), lobular inflammation (assessed on a scale of 0 to 3), and hepatocellular ballooning (assessed on a scale of 0 to 2). NASH resolution was defined as achievement of a hepatocellular ballooning score of 0, a lobular inflammation score of 0 or 1, and a reduction in the NAFLD activity score by at least 2 points. Fibrosis stages range from F0 (no fibrosis) to F4 (cirrhosis). A total of 11 patients had a delay in their week 52 biopsy due to coronavirus disease 2019-related closure of the biopsy site or related reasons and were removed from the primary analysis population for liver-biopsy analyses.

NASH resolution with no worsening of fibrosis was achieved in significantly more patients who received resmetirom than in those who received placebo (25.9% in the 80-mg group and 29.9% in the 100-mg group, vs. 9.7% in the placebo group; P<0.001 for both comparisons with placebo) (FIG. 10A and Table 10). An improvement in fibrosis by at least one stage with no worsening of the NAFLD activity score was also achieved in significantly more patients who received resmetirom than in those who received placebo (24.2% in the 80-mg group and 25.9% in the 100-mg group, vs. 14.2% in the placebo group; P<0.001 for both comparisons with placebo) (FIG. 10B and Table 10). A consensus read (sensitivity analysis) of digitized images of biopsy specimens for which there was disagreement between the pathologists as to whether there was a response with respect to either primary end point yielded results similar to those of the primary analysis (Table 17A). Similar results were obtained individually by each pathologist and in multiple sensitivity analyses (Tables 17B, 17C, and 18).

Figure 11A:
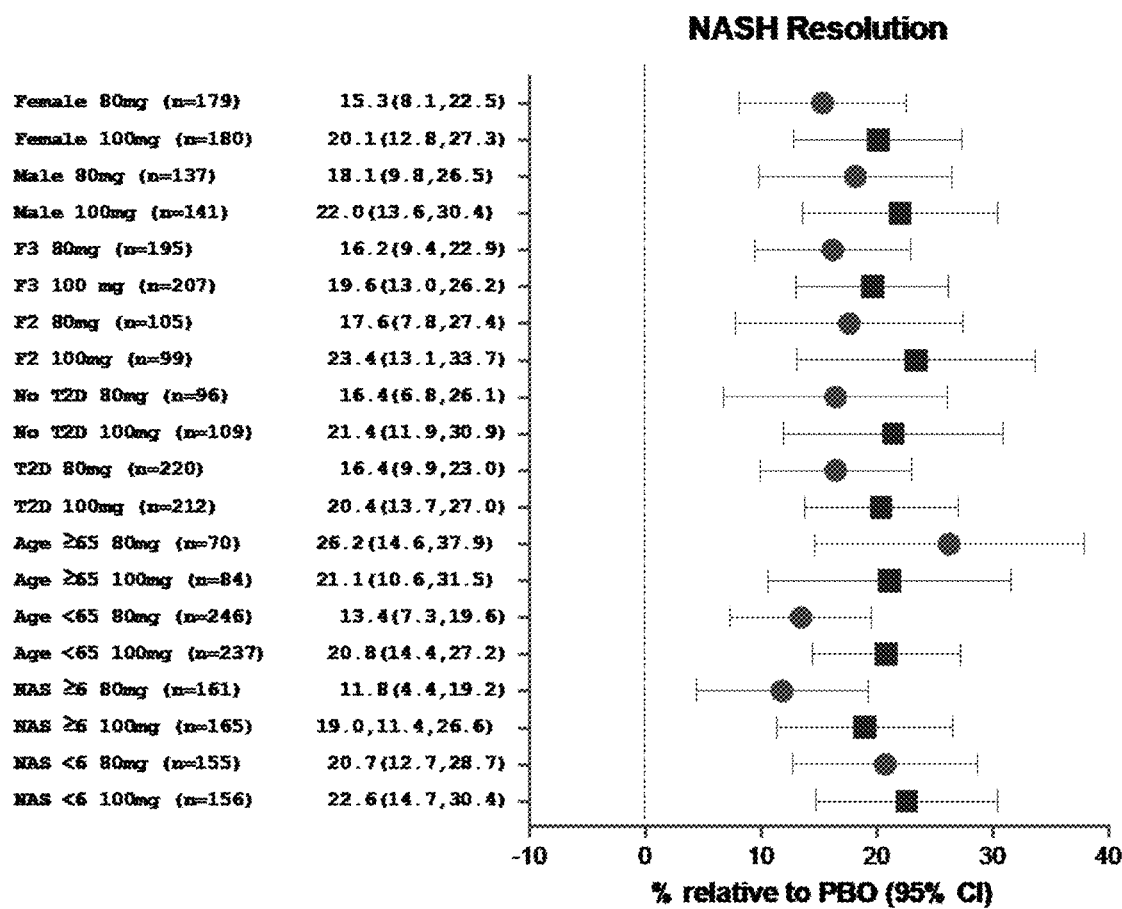
FIGS. 11A-11D are graphical representations showing subgroup analyses of the dual primary endpoints at Week 52 in Example 2: Resolution of nonalcoholic steatohepatitis (FIG. 11A and FIG. 11C) and improvement in fibrosis (FIG. 11B and FIG. 11D). Data are reported for the primary analysis population (n=955, after removal of the COVID impacted biopsies outside the Week 60 window). Eleven patients had a delay in their Week 52 biopsy due to COVID-19 biopsy site closure or related reasons and were removed from the analysis. Resolution of nonalcoholic steatohepatitis is defined as achievement of a ballooning score of 0, inflammation score of 0 or 1, and ≥2-point reduction in the nonalcoholic fatty liver disease activity score with no worsening of fibrosis. Fibrosis improvement is defined as achievement of ≥1-stage reduction in fibrosis with no worsening of the nonalcoholic fatty liver disease activity score. A 1-point improvement in fibrosis would be a change to F1A or F1C from F2 (a change of F2 to F1B is not considered a 1-point improvement). Forest plots include prespecified subgroups with minor modifications. Body weight subgroups based on ≤200, >200 pounds or BMI (Body Mass Index)≤35, >35 were not informative. PDFF reduction in resmetirom groups are compared to all placebo patients with any Week 52 PDFF; % SHBG CFB in resmetirom groups is compared to all placebo patients with a Week 52 SHBG. A posthoc subgroup of ≤100 kg, >100 kg is shown in Table 21 that also includes subgroups for ≥30% PDFF at Week 16, region (US-ExUS), weight gain ≥5% F2/F3, F1B. Subgroup analyses by statin use and NAFLD Activity Score (NAS) were post-hoc analyses. Confidence interval widths have not been adjusted for multiplicity and may not be used for hypothesis testing.
Figure 11B:
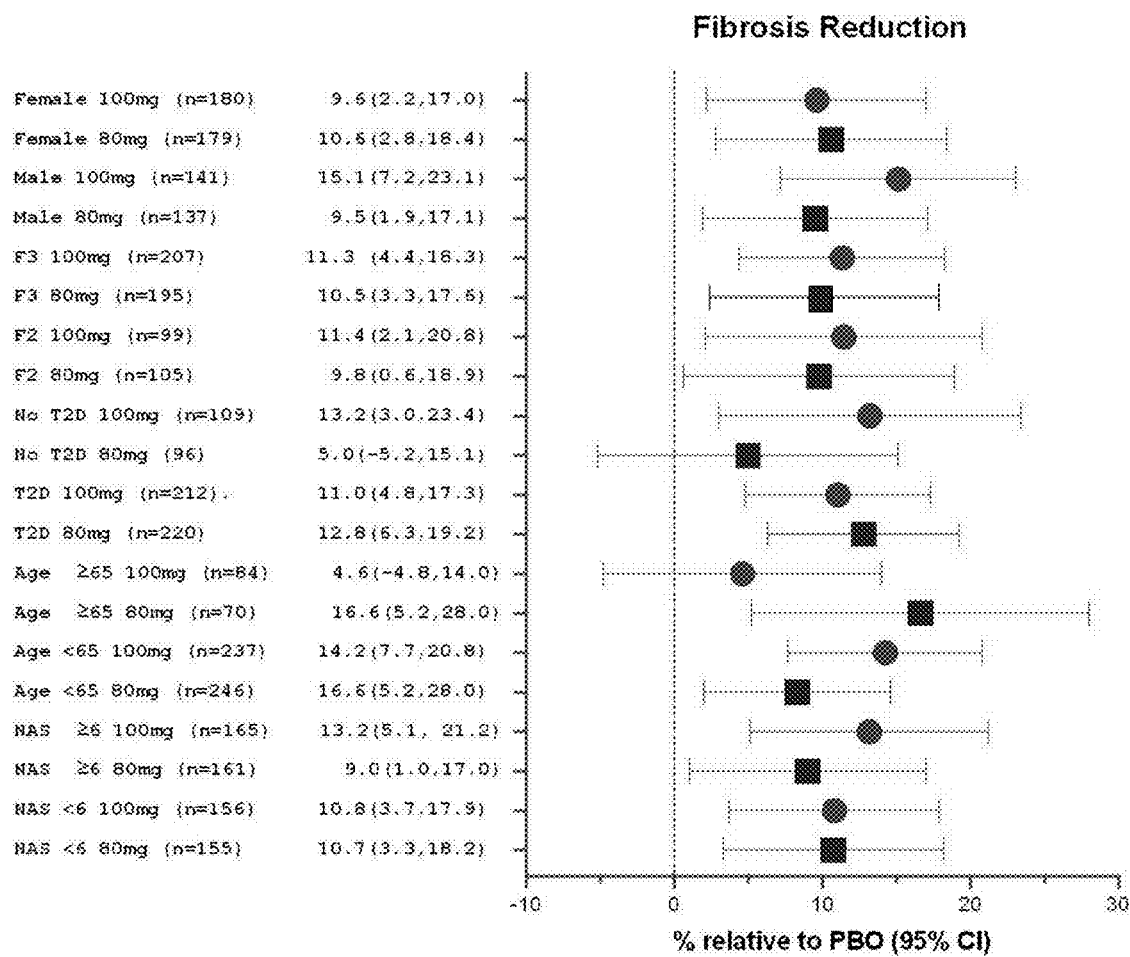
Figure 11C:
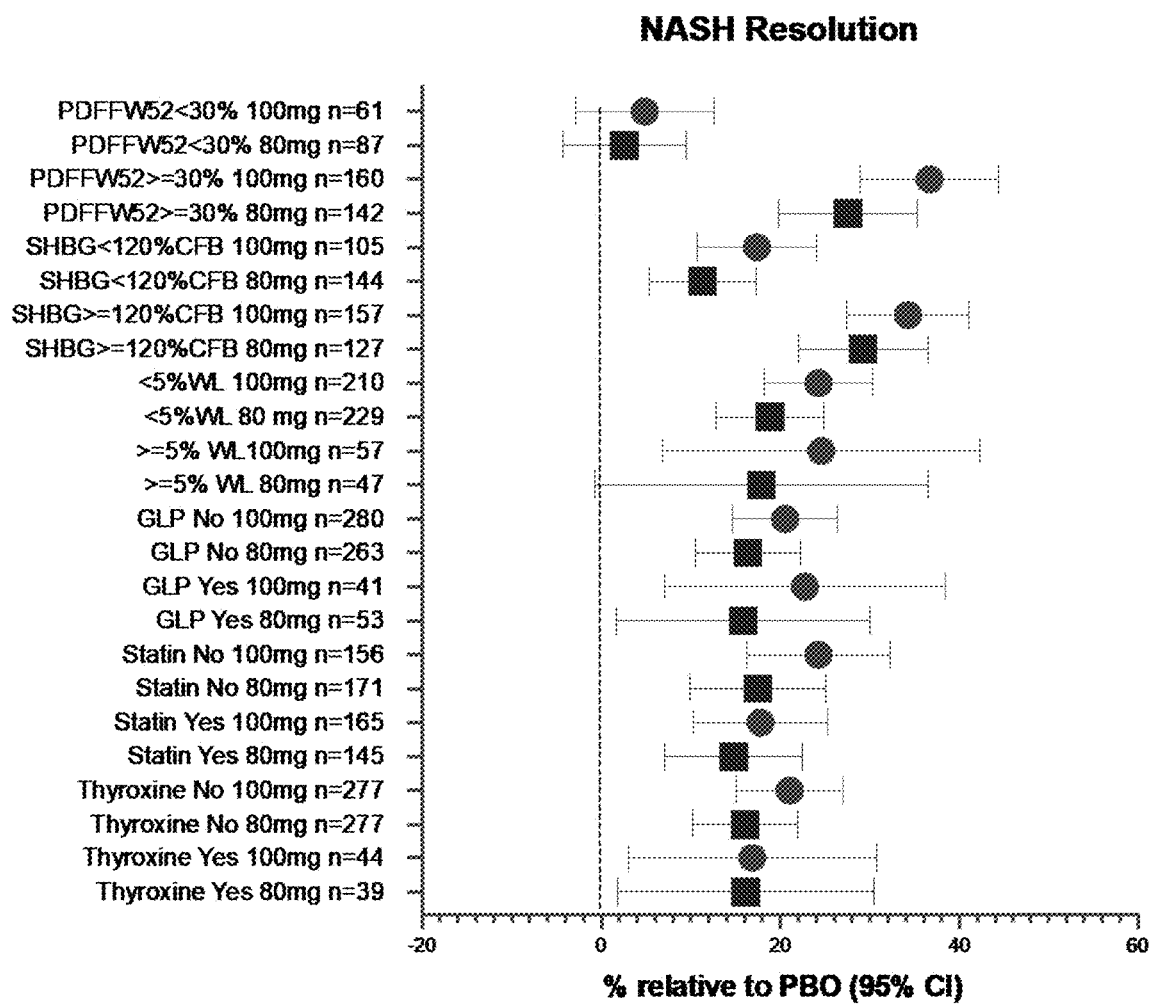
Figure 11D:
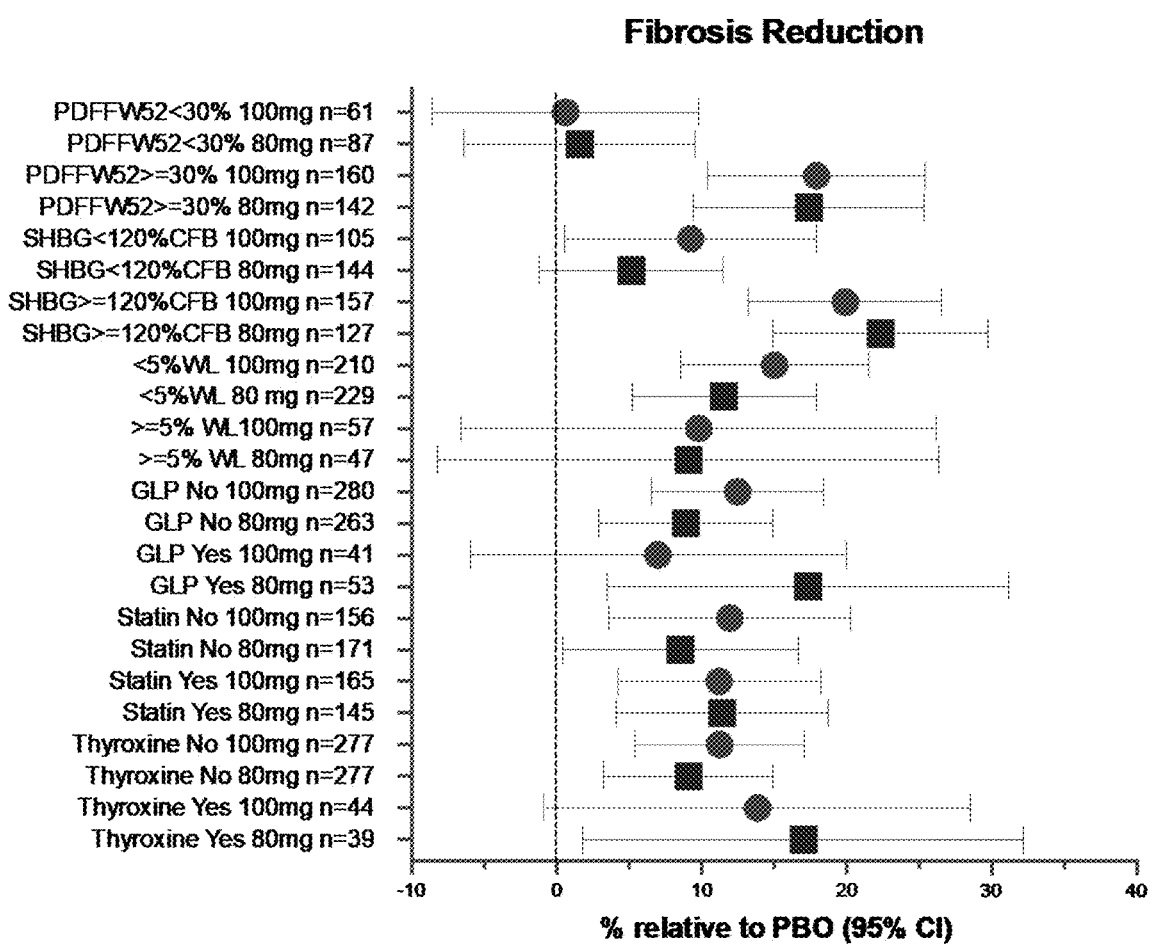
Figure 12:
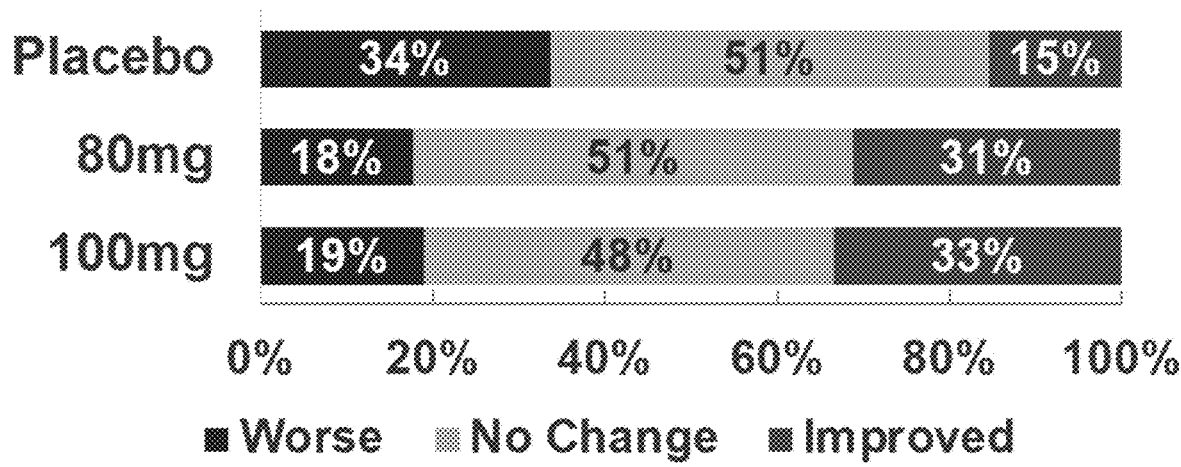
FIG. 12 is a graphical representation showing percentage of patients who were F1B or F2 at baseline with worse (progressed to >F3), stable (no change), or improved fibrosis stage at week 52 based on liver biopsy in Example 2. In patients with a baseline and eligible Week 52 biopsy (80 mg, 100 mg: resmetirom). The two pathologists' assessments were similar and were averaged to generate a single output.
Figure 13:
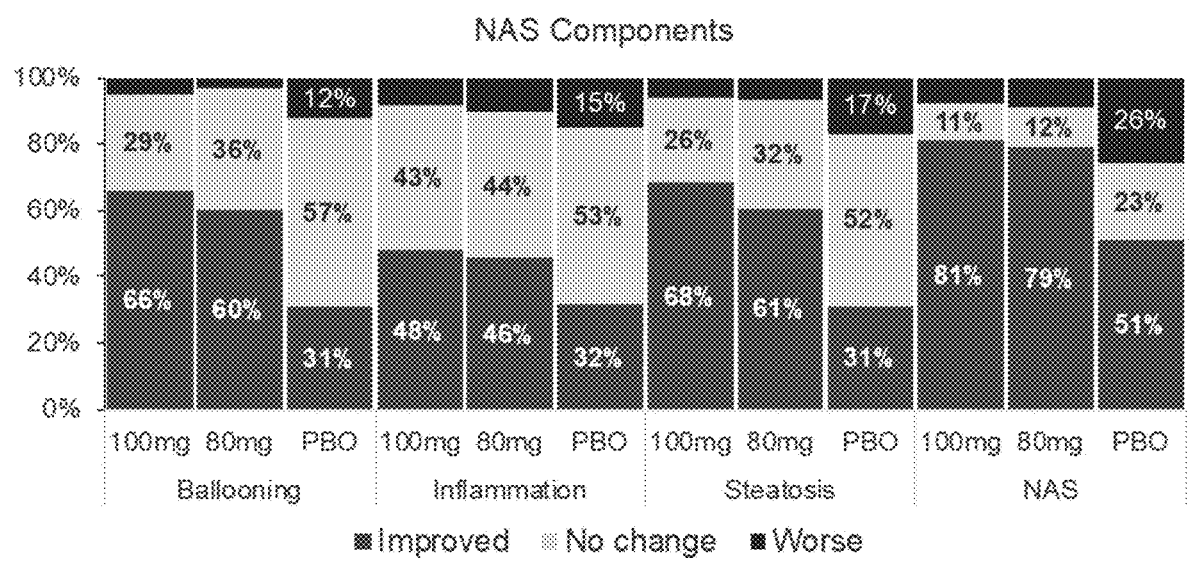
FIG. 13 is a graphical representation showing percent of patients with worsened, stable (no change), or improved individual components of the nonalcoholic fatty liver disease activity score (ballooning, inflammation, steatosis) in Example 2. In patients with a baseline and eligible Week 52 biopsy are shown. The two pathologists' assessments were similar and were averaged to generate a single output.

Subgroup analyses of the primary end points showed generally consistent results across the subgroups (defined according to baseline fibrosis stage, baseline NAFLD activity score, status with respect to type 2 diabetes, age, and sex), with more patients who received resmetirom having either NASH resolution or fibrosis improvement than those who received placebo (FIGS. 11A through 11D). The results of additional biopsy end points and sensitivity analyses were generally supportive of the results of the primary analyses of the two primary end points (FIGS. 12 and 13 and Tables 10, 21 and 22).

Figure 14:
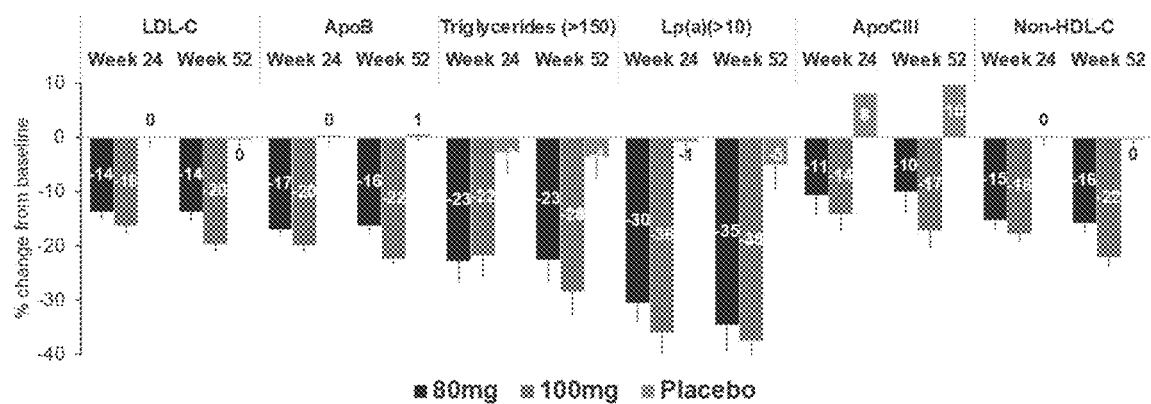
FIG. 14 is a graphical representation showing percent change from baseline in lipids and lipoproteins at weeks 24 and 52 in Example 2. ApoB: apolipoprotein B; ApoCIII: apolipoprotein CIII; LDL-C: low-density lipoprotein cholesterol; Lp(a): lipoprotein a; non-HDL-C: non-high-density lipoprotein cholesterol. (80 mg, 100 mg: resmetirom)

LDL cholesterol levels were reduced from baseline at week 24 among patients who received resmetirom (−13.6% in the 80-mg group and −16.3% in the 100-mg group) and not in those who received placebo (0.1%) (P<0.001 for both comparisons with placebo) (Table 11 and FIG. 10C); these effects seemed to be maintained at week 52 (Table 23 and FIG. 14). At week 24 and week 52, levels of triglycerides (in patients with baseline triglyceride levels of >150 mg per deciliter), non-high-density lipoprotein (HDL) cholesterol, apolipoprotein B, apolipoprotein C-III, and lipoprotein(a) appeared to decrease more from baseline in the resmetirom groups than in the placebo group. Levels of additional lipids and lipoproteins appeared to decrease more from baseline in the resmetirom groups than in the placebo group at week 52 (Table 24).

Figure 15A:
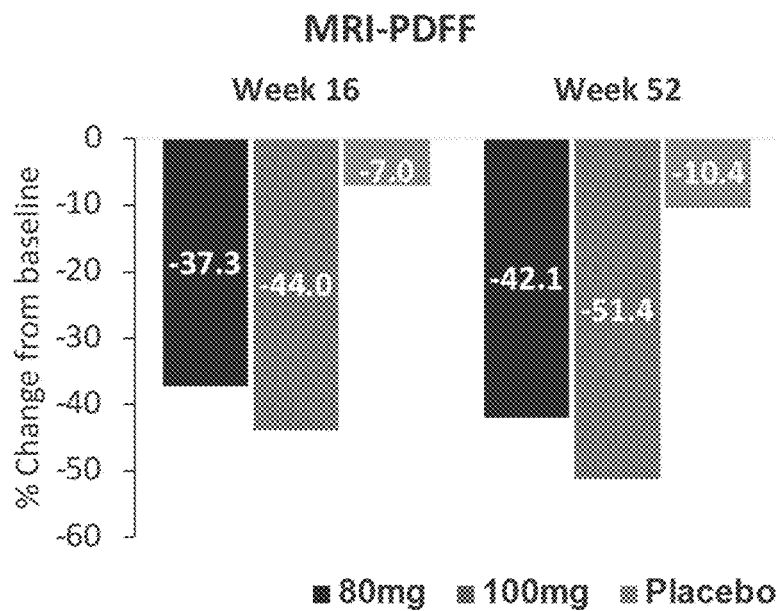
FIGS. 15A and 15B are graphical representations showing percent change from baseline in hepatic fat as measured by magnetic resonance imaging-proton density fat fraction at weeks 16 and 52 (FIG. 15A), and steatosis as measured by FibroScan controlled attenuation parameter at week 52 (FIG. 15B) in Example 2 (80 mg, 100 mg: resmetirom). Based on observed data, patients with a baseline and week 52 assessment.
Figure 15B:
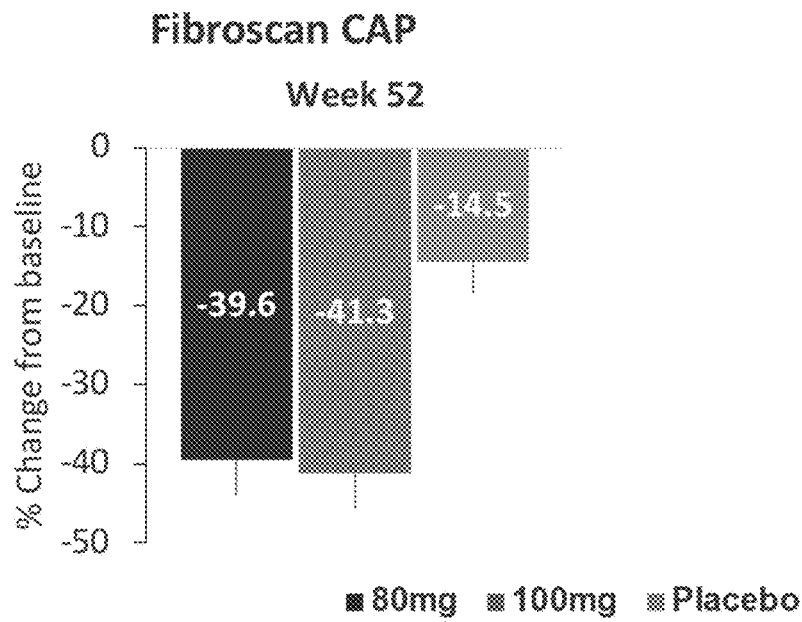
Figure 16:
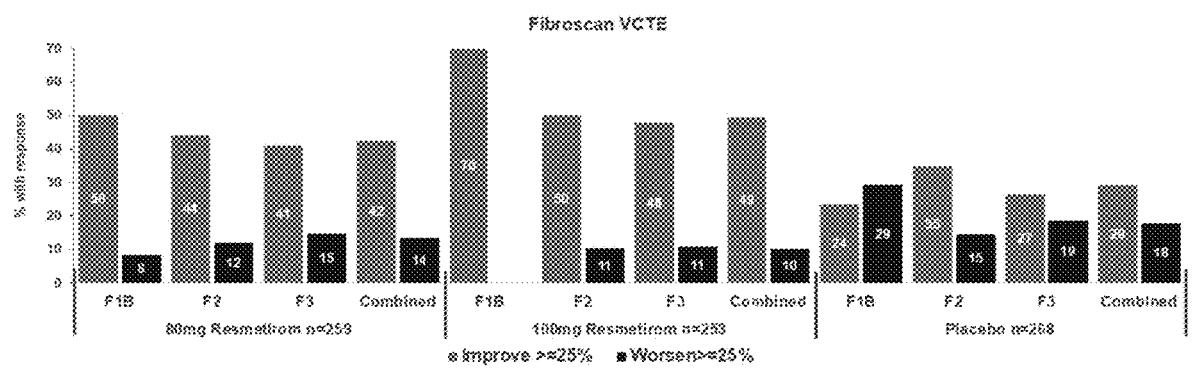
FIG. 16 is a graphical representation showing percentage of patients achieving a ≥25% reduction from baseline in liver stiffness as measured by FibroScan vibration-controlled transient elastography at week 52 in Example 2. Based on observed data, patients with a baseline and week 52 assessment.
Figure 17:
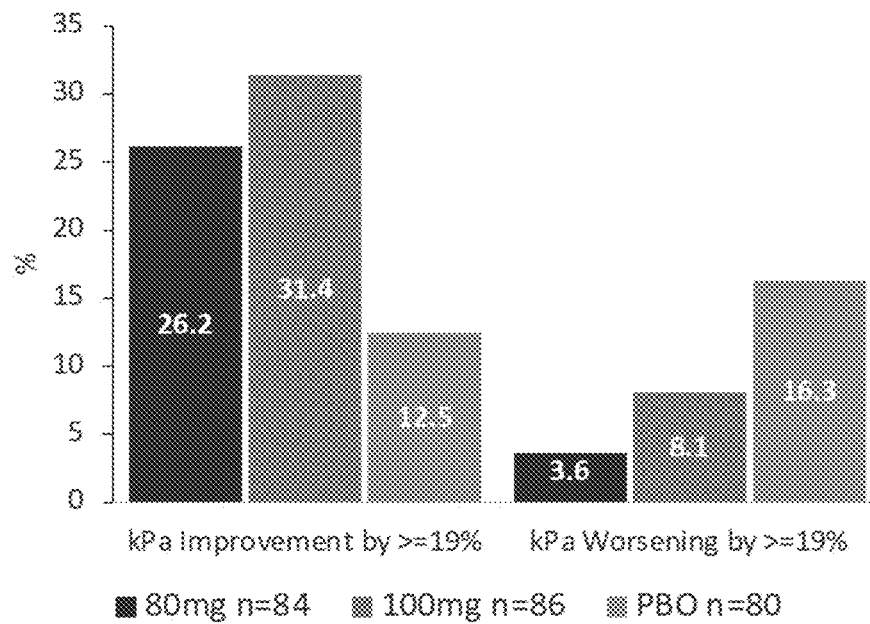
FIG. 17 is a graphical representation showing improvement or worsening from baseline in liver stiffness as measured by magnetic resonance elastography at week 52 in Example 2. (80 mg, 100 mg: resmetirom) Based on observed data, patients with a baseline and week 52 assessment.
Figure 18A:
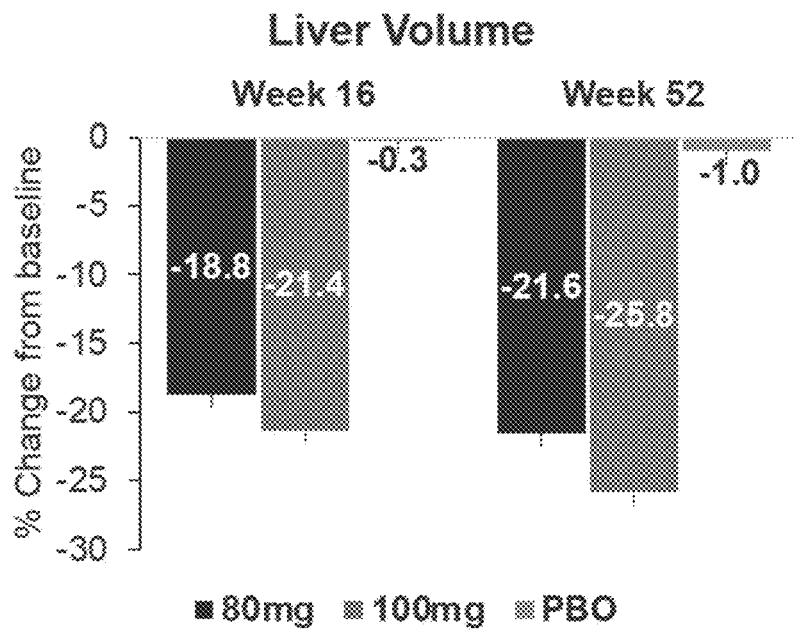
FIGS. 18A and 18B are graphical representations showing percent change from baseline in liver volume (FIG. 18A) and spleen volume (FIG. 18B) at weeks 16 and 52 in Example 2. (80 mg, 100 mg: resmetirom) Based on observed data, patients with a baseline and week 52 assessment.
Figure 18B:
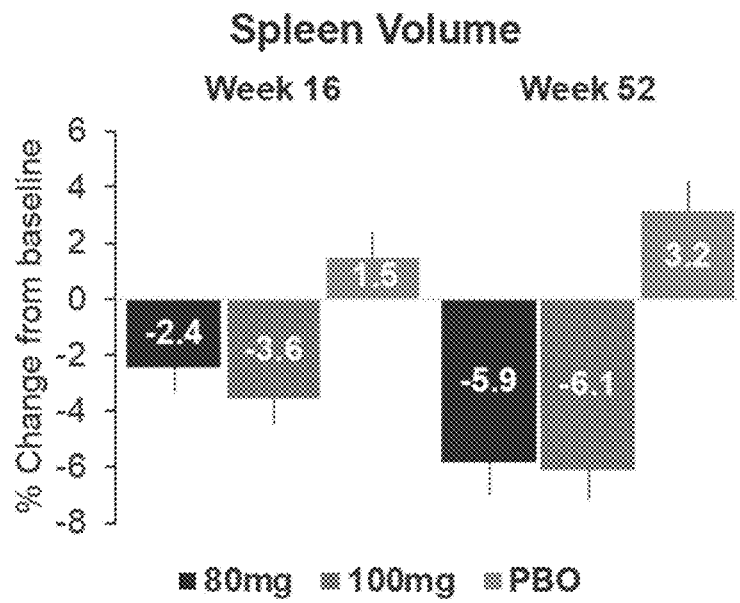

In addition, levels of liver enzymes—including alanine aminotransferase, aspartate aminotransferase, and 7-glutamyltransferase—seemed to decrease more in the resmetirom groups than in the placebo group (Table 11). Results of multiple noninvasive tests, including the MRI-PDFF at weeks 16 and 52 and Fibroscan CAP at week 52, suggested improvements associated with resmetirom treatment (Table 11 and FIGS. 15A and 15B). Liver stiffness (as assessed by VCTE or magnetic resonance elastography) appeared to decrease more from baseline with resmetirom treatment than with placebo (FIGS. 16 and 17). By week 16, both liver volume and spleen volume appeared to decrease more from baseline with resmetirom treatment; this effect was maintained at week 52 (FIGS. 18A and 18B).

Figure 19A:
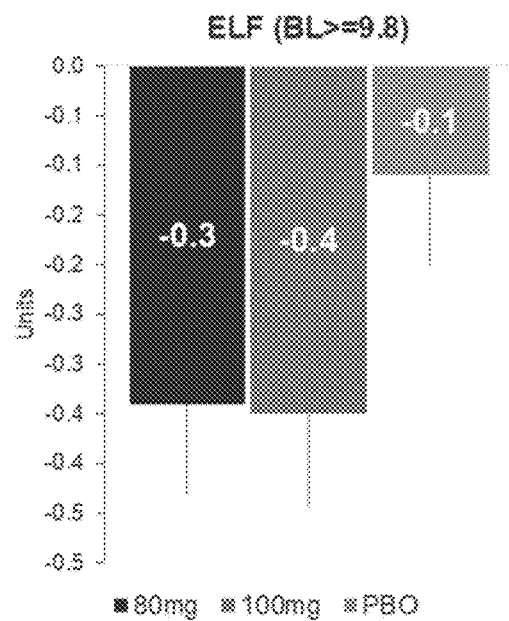
FIGS. 19A-19C are graphical representations showing change from baseline in the enhanced liver fibrosis score (FIG. 19A), TIMP-1 (FIG. 19B), and P3NP (FIG. 19C) in Example 2. (80 mg, 100 mg: resmetirom) Based on observed data.
Figure 19B:
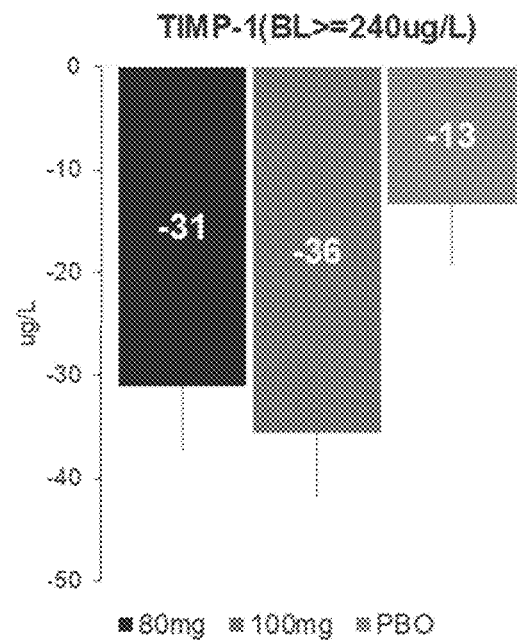
Figure 19C:
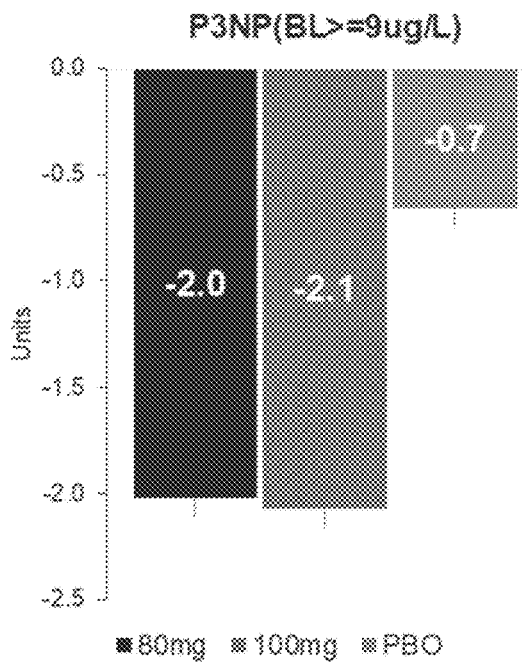

The Enhanced Liver Fibrosis test score and components of the score appeared to be improved by resmetirom treatment relative to placebo (FIGS. 19A-19C). In addition, there seemed to be improvements in levels of cytokeratin 18, adiponectin, and reverse triiodothyronine among patients who received resmetirom as compared with those who received placebo.

Safety

Figure 20:
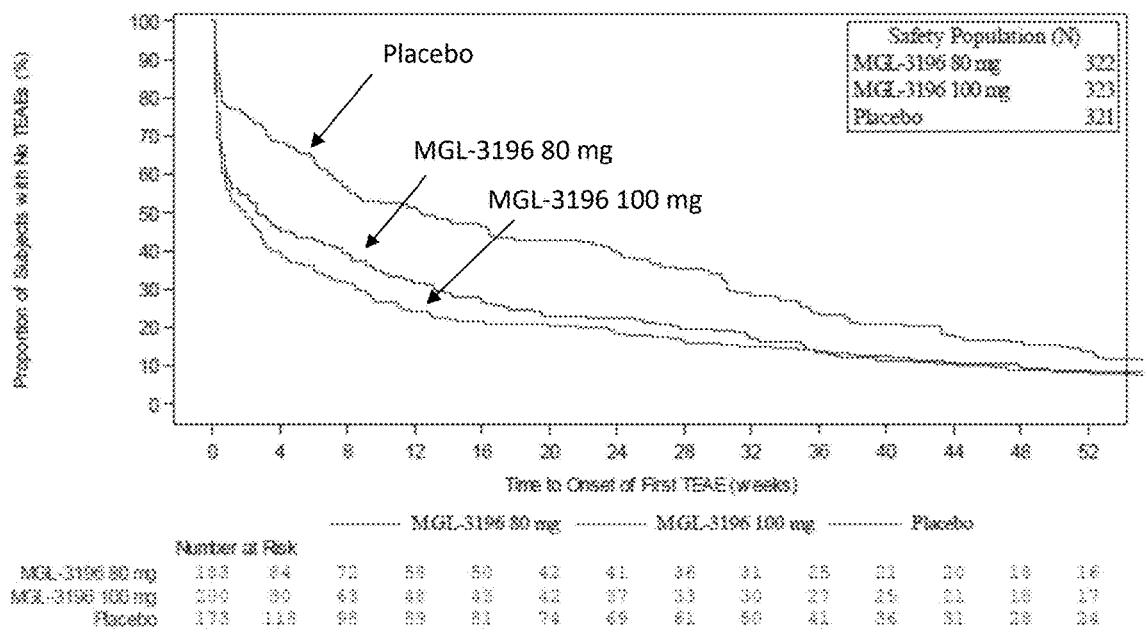
FIG. 20 is a graphical representation showing time to onset of first gastrointestinal adverse event in Example 2.
Figure 21:
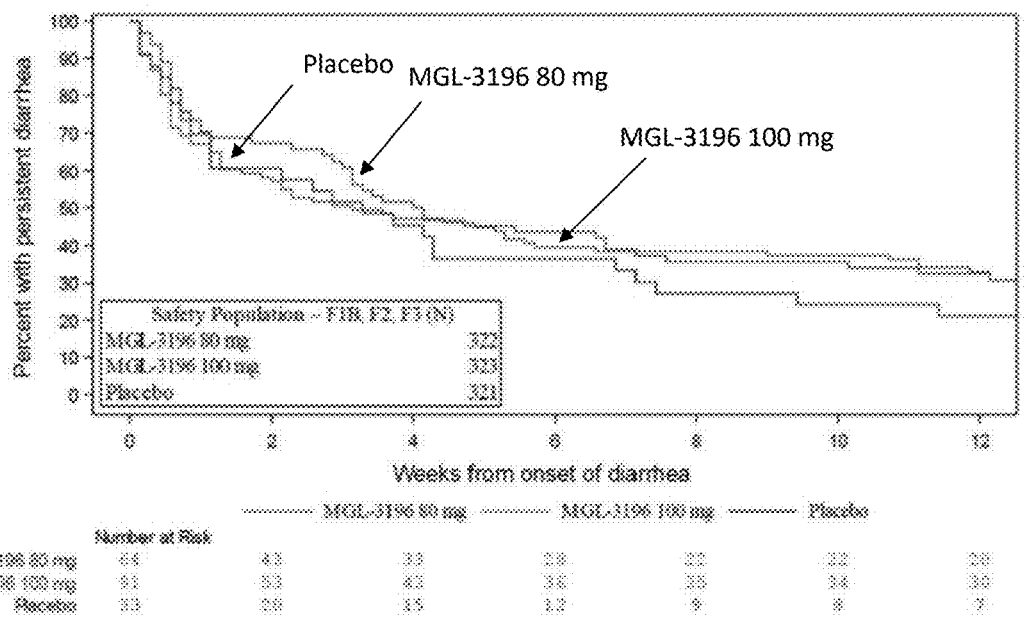
FIG. 21 is a graphical representation showing duration of diarrhea: duration of diarrhea reported in first 12 weeks of randomization in Example 2.

Overall, 91.6 to 91.9% of the patients who received resmetirom and 92.8% of those who received placebo reported an adverse event (Table 12). Most adverse events were mild or moderate in severity. The most frequent adverse events were gastrointestinal (diarrhea and nausea) (Table 25) and Covid-19. Diarrhea and nausea occurred more frequently in the resmetirom group than in the placebo group. The onset of diarrhea and nausea occurred at the initiation of resmetirom (FIG. 20). Approximately 50% of the cases of diarrhea were described as "worsening of preexisting diarrhea" or "intermittent/loose stool(s)"; no episodes of severe diarrhea were reported. The median duration of diarrhea was approximately 15 to 20 days, independent of resmetirom dose (FIG. 21).

TABLE 12

Safety Summary (Primary Population)

| Event | Resmetirom 80 mg (N = 322) | Resmetirom 100 mg (N = 323) | Placebo (N = 321) |
|---|---|---|---|
| | number of patients (percent) | | |
| ≥1 Adverse event | 296 (91.9) | 296 (91.6) | 298 (92.8) |
| Grade 1: mild | 73 (22.7) | 66 (20.4) | 77 (24.0) |
| Grade 2: moderate | 180 (55.9) | 183 (56.7) | 169 (52.6) |
| Grade 3 or higher: severe | 43 (13.4) | 47 (14.6) | 52 (16.2) |
| ≥1 Adverse event attributed to resmetirom or placebo* | 124 (38.5) | 134 (41.5) | 88 (27.4) |
| ≥1 Serious adverse event | 35 (10.9) | 41 (12.7) | 37 (11.5) |
| ≥1 Serious adverse event attributed to resmetirom or placebo* | 2 (0.6) | 0 | 1 (0.3) |
| Adverse event leading to trial discontinuation before wk 52† | 6 (1.9) | 22 (6.8) | 7 (2.2) |
| Adverse event leading to trial discontinuation during entire treatment period† | 9 (2.8) | 25 (7.7) | 11 (3.4) |
| Fatal adverse event | 1 (0.3) | 2 (0.6) | 1 (0.3) |
| Major adverse cardiovascular event‡ | 1 (0.3) | 1 (0.3) | 1 (0.3) |
| Other cardiovascular event‡ | 0 | 1 (0.3) | 3 (0.9) |
| Adverse events affecting >10% of patients in any group | | | |
| Diarrhea | 87 (27.0) | 108 (33.4) | 50 (15.6) |
| Covid-19 | 69 (21.4) | 54 (16.7) | 66 (20.6) |
| Nausea | 71 (22.0) | 61 (18.9) | 40 (12.5) |
| Arthralgia | 48 (14.9) | 35 (10.8) | 40 (12.5) |
| Back pain | 35 (10.9) | 27 (8.4) | 38 (11.8) |
| Urinary tract infection | 33 (10.2) | 27 (8.4) | 27 (8.4) |
| Fatigue | 33 (10.2) | 26 (8.0) | 28 (8.7) |
| Pruritus | 26 (8.1) | 37 (11.5) | 22 (6.9) |

*Shown are events that were considered by investigators to be related to resmetirom or placebo.
†Data are for events that emerged after the first dose of resmetirom or placebo and within 30 days after the last dose.
‡Major adverse cardiovascular events were defined as nonfatal stroke, nonfatal myocardial infarction, and death from cardiovascular causes. All cardiovascular events were adjudicated.

The incidence of serious adverse events was similar across the trial groups: 10.9% in the 80-mg resmetirom group, 12.7% in the 100-mg group, and 11.2% in the placebo group (Tables 12 and 26). Serious adverse events that were considered by investigators to be related to the trial regimen occurred in two patients in the 80-mg resmetirom group and one in the placebo group (Table 12). Cancer was reported in 1.2% of the patients in the 80-mg group, 3.4% of those in the 100-mg group, and 3.7% of those in the placebo group (Table 27). There was no incidence of drug-induced liver injury. At week 52, trial discontinuations due to adverse events were more common in the 100-mg resmetirom group than in the other two trial groups (6.8% in the 100-mg resmetirom group, 1.9% in the 80-mg resmetirom group, and 2.2% in the placebo groups). Thereafter, trial discontinuations were similar across the trial groups.

Resmetirom treatment had no effect on heart rate or body weight and was not associated with arrhythmias (Table 28). Blood pressure appeared slightly reduced among patients who received resmetirom. Levels of sex hormones were little changed from baseline (Table 29). Independent of thyroxine-replacement status, resmetirom treatment reduced levels of prohormone free T4 (FT4) by approximately 16 to 19%, with no effect on levels of thyrotropin or the active thyroid hormone, free triiodothyronine (FT3) (Table 30). There were no increases in fractures or substantial changes in bone mineral density T scores (Table 31). Diarrhea AEs and AE discontinuations were higher in the 100 mg resmetirom group; overall discontinuations at 100 mg were higher in the lower body weight groups (<100 kg). Discontinuations at 80 mg resmetirom were similar to placebo. Discontinuations related to the COVID pandemic (lost to follow up/patient decision) resulted in higher than expected discontinuation at week 52 in all treatment arms (placebo 11% discontinuation at week 52).

Discussion

Both the 80-mg dose and the 100-mg dose of resmetirom were superior to placebo with respect to the two primary histologic end points (NASH resolution with no worsening of fibrosis, and an improvement in fibrosis by ≥1 stage with no worsening of the NAFLD activity score) at week 52. These are consistent with the end points proposed by the FDA as reasonably likely to predict clinical benefit in a phase 3 trial involving adults with NASH and liver fibrosis. The primary analyses were supported by multiple sensitivity analyses. The effects that were observed with resmetirom treatment were consistent across key subgroups. Multiple noninvasive tests for NASH, steatosis, and fibrosis (including blood biomarkers and imaging) showed a similar direction of effects favoring resmetirom treatment, which supports the findings for the primary end points.

Among patients with NASH (the majority of whom have diabetes), cardiovascular risk and mortality are high. Levels of a broad range of atherogenic lipids and lipoproteins, including LDL cholesterol, non-HDL cholesterol, triglycerides, apolipoprotein B, and lipoprotein(a), appeared to be reduced by resmetirom relative to placebo, findings consistent with those of earlier studies. Although not yet shown for resmetirom, reductions in apolipoprotein B and LDL cholesterol levels of this magnitude have been associated with improvement in cardiovascular outcomes.

More patients in the 100-mg resmetirom group than in the other two trial groups discontinued the trial because of adverse events (6.8% in the 100-mg resmetirom group, 1.8% in the 80-mg resmetirom group, and 2.2% in the placebo group). Diarrhea and nausea occurred more frequently in the resmetirom groups than in the placebo group. The safety profile of resmetirom in the MAESTRO-NASH trial is consistent with that in previous phase 2 or 3 trials in which the most common adverse events were generally self-limited diarrhea and nausea at treatment initiation. The incidence of serious adverse events was similar in the three trial groups (10.9% to 12.7%).

Noninvasive testing to identify patients with NASH for treatment and to monitor treatment response will be important in clinical practice in which liver biopsy is infrequently used. The MAESTRO-NASH trial used a screening paradigm consistent with guidelines that identified a highrisk NASH population (metabolic risk factors, FibroScan thresholds, additional imaging, and biomarkers). In this trial, achievement of a 30% reduction in hepatic fat (MRI-PDFF) or a 120% increase in the sex hormone-binding globulin level appeared to be associated with biopsy responses (FIGS. 11C and 11D).

A current limitation in the data from the MAESTRO-NASH trial is the lack of clinical-outcomes data to correlate with histologic data. The safety of long-term use of resmetirom has not yet been assessed. The trial is planned to continue to 54 months in order to accrue and evaluate liver-related outcomes, including progression to cirrhosis.

Data for the first 1050 patients from the MAESTRO-NASH trial, together with data from completed resmetirom trials, support the potential for resmetirom to provide benefit to patients with NASH and liver fibrosis. Both the 80-mg dose and the 100-mg dose of resmetirom were shown to be efficacious with respect to the two primary histologic end points in patients with NASH and liver fibrosis.

Figure 22:
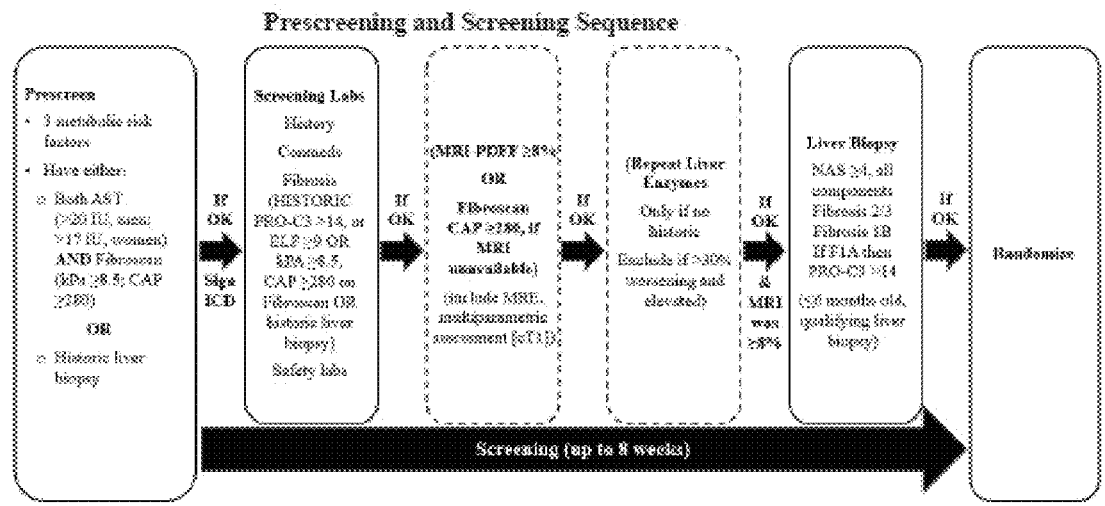
FIG. 22 is a schematic showing prescreening and screening sequence in Example 2.

Supplementary Appendix
Supplementary Methods
Patient Prescreening Criteria (FIG. 22)
Potential patients to be screened for this study should:
Not have any history of significant alcohol consumption (Exclusion Criterion #1)
Have at least 3 metabolic risk factors using a slightly modified version of the International Diabetes Foundation (IDF) criteria (Synopsis Table 2)
Have either
Both AST and fibroscan requirements
AST ≥17 IU (women) and AST ≥20 IU (men)
AND
A fibroscan within 3 months of planned screening shoring KpA≥8.5 CAP≥280. Fibroscan is a potential alternative to a historic eligible liver biopsy to meet inclusion 5 an dshould be obtained during the prescreening period if possible.
OR
Have a historic liver biopsy <2 years old demonstrating fibrosis stage 1B, 2 or 3 with NASH (NAS≥4, all components)
NOTE: Meets inclusion #5. Prior biopsy reflects documentation of NASH fibrosis and is not necessarily eligible as a baseline biopsy which must have been obtained 6 months prior to randomization with NAS and fibrosis score confirmed as eligible by the central pathology reader.

The IDF risk factors may be assessed by the investigator based on historic values and/or use of concomitant medications for dyslipidemia, hypertension, and diabetes.

Metabolic risk factors and the addition of an elevated serum AST value and fibroscan help ensure a higher degree of certainty that a patient will have biopsy-confirmed NASH, NAS≥4 with Stage 1A/1C (high-risk), 1B, 2, or 3 fibrosis with primary emphasis on identifying patients who will have Stage 2 or 3 fibrosis on liver biopsy.

A patient with a historical liver biopsy <2 years with confirmed NASH fibrosis as described above does not require an elevated AST or fibroscan with KpA≥8.5. In patients with historic liver biopsies, a baseline fibroscan KkpA obtained within 3 months of screening or during screening is still needed prior to randomization, but the fibroscan value does not determine eligibility. A baseline fibroscan in all randomized patients obtained during pre-screening or screening is used to compare with serial fibroscans during the study.

Inclusion and Exclusion Criteria

Inclusion Criteria

Only evaluate patients for study participation if they meet the Prescreening Criteria. Patients who do not initially meet eligibility criteria may be retested, based on Investigator judgment, to determine if they qualify to participate. Patients who meet all of the following criteria will be eligible to participate in the study:

Must be willing to participate in the study and provide written informed consent.

Male and female adults ≥18 years of age.

Female patients are eligible if they are of reproductive potential and have a negative serum pregnancy test (beta human chorionic gonadotropin), are not breast-feeding, and do not plan to become pregnant during the study and agree to use 2 highly effective birth control methods during the study OR if they are not of child bearing potential (i.e., surgically [bilateral oophorectomy, hysterectomy, or tubal ligation] or naturally sterile [>12 consecutive months without menses]). Highly effective birth control methods include condoms with spermicide, diaphragm with spermicide, hormonal and non-hormonal intrauterine device, hormonal contraception (estrogens stable ≥3 months), a vasectomized or sterile male partner, or sexual abstinence (defined as refraining from heterosexual intercourse), from Screening throughout the study and for at least 30 days after study drug administration. Reliance on abstinence from heterosexual intercourse is acceptable only if it is the human subject's habitual practice.

Male human subjects who are sexually active with a partner of child-bearing potential must either be sterile (vasectomy with history of a negative sperm count at least 90 days following the procedure); practice total abstinence from sexual intercourse as the preferred lifestyle (periodic abstinence is not acceptable); use a male condom with any sexual activity; or agree to use a birth control method considered to be appropriate by the Investigator (such as one of the methods identified above for female human subjects of childbearing potential) from the time of Screening until 30 days after the last dose of study drug administration. Male human subjects must agree not to donate sperm for a period of 30 days after the last dose of study drug administration.

Suspected or confirmed diagnosis of NASH fibrosis suggested by the historical data. Meet one of the following criteria that is consistent with NASH liver fibrosis:

Historical biochemical test for fibrosis: N-terminal type III collagen propeptide (PRO-C3) >14 ng/mL; or ELF≥9 (ELF is based on a historic value and is not obtained at screening; PRO-C3 is based on the historic PRO-C3 and not the screening PRO-C3.

Fibroscan with transient elastography ≥8.5 kPa; and controlled attenuation parameter ≥280 dB·m-1 (Fibroscan does not need to be repeated at screening if done at prescreening and/or a historical Fibroscan was done in the prior 3 months).

Historical liver biopsy obtained <2 years before expected randomization showing Stage 1B, 2 or 3 fibrosis with NASH (all 3 components) based on existing pathology review, with no significant change in body weight >5% or medication that might affect NAS or fibrosis stage.

NOTE: A biopsy that was >6 months before the time of anticipated randomization is not eligible for study entry; a biopsy done ≤6 months is potentially eligible for study entry as a baseline biopsy only after confirmation of eligibility based on Inclusion #7 by the central pathology reviewer. If a Fibroscan is not used to meet Inclusion #5 (as in the case of historic eligible PRO-C3/ELF or liver biopsy), a baseline Fibroscan should be obtained prior to randomization. If other criteria are used to meet inclusion #5 and the MRI-PDFF≥8% OR an eligible historical liver biopsy ≤6 months) has been confirmed by the central reader, and with confirmed no significant change in metabolic status since the time of that biopsy, the baseline Fibroscan can be KpA<8.5, CAP<280.

NOTE: Eligibility based on meeting Inclusion #5 should be determined based on historic medical and laboratory (PRO-C3/ELF, Fibroscan, liver biopsy) data and should be determined prior to informed consent and screening visit.

MRI-PDFF fat fraction ≥8% obtained during the screening period (Baseline MRI-PDFF). NOTE: To be eligible to perform the screening MRI-PDFF (Baseline MRI-PDFF) a patient must first meet Criterion #5. An eligible MRI-PDFF with fat fraction ≥8% must be obtained prior to performing the baseline liver biopsy (Criterion #7). Patients with contraindications to an MRI-PDFF (eg, metal prosthetics or uncontrolled claustrophobia) examination or screened at an investigative site where MRI-PDFF is not available are eligible for a liver biopsy if they have a Fibroscan with CAP≥280.

NOTE: An MRE and/or cT1 assessment will occur at sites with MRE equipment and/or multiparametric software. A historical MRI-PDFF≥8% is eligible as a baseline MRI-PDFF if obtained <8 weeks prior to randomization.

NOTE: In cases with an eligible historical biopsy (≤6 months) confirmed by central reader, and with confirmation that there were no significant change in metabolic status since the time of the biopsy, MRI-PDFF<8% may be eligible. These cases would require review by Sponsor for confirmation.

Biopsy-proven NASH baseline liver biopsy) based on a liver biopsy obtained 56 months before anticipated date of randomization (if the biopsy is deemed acceptable for interpretation by the central reader) with fibrosis stage 1A/1C, 1B, 2, or 3 on liver biopsy and NAS of ≥4 with a score of at least 1 in each of the following NAS components:

Steatosis (scored 0 to 3)

Ballooning degeneration (scored 0 to 2)

Lobular inflammation (scored 0 to 3)

Fibrosis stage 1A/IC patients must also have elevated PRO-C3 (>14 ng/mL) obtained at Screening to be eligible to participate. Numbers of eligible F1A/F1C, FIB and F2 patients are defined in Number of Patients and Target Population.

NOTE: A historical biopsy obtained ≤6 months prior to anticipated date of randomization may be eligible as a baseline biopsy if the patient has had: (1) no significant change in metabolic status (diabetes control, lipid metabolism, and/or >5% weight gain or loss); (2) no change in the use of any prohibited medication(s) listed as exclusionary within 12 weeks prior to the anticipated date of randomization (3) no change in the use of a NASH therapeutic (e.g., therapeutic with documented impact on liver biopsy or GLP-1 agonist) since the time of the biopsy.

The historical biopsy must be evaluated for eligibility by the central pathology reader and confirmed as eligible. The biopsy should be sent for review by the central reader after screening labs and medical history/conmeds confirm I/E requirements are met. In cases where the MRI-PDFF is <8% but based on the local interpretation of the historical biopsy (≤6 months) the investigator believes that the human subject would qualify then sending the biopsy for review by the central reader may be an option if discussed with the Sponsor.

NOTE: In cases with an eligible historical biopsy (≤6 months) confirmed by central reader, and with confirmed no significant change in metabolic status since the time of the biopsy, MRI-PDFF<8% may be eligible. These cases would require review by Sponsor for confirmation.

Estimated glomerular filtration rate (GFR)≥45 by the Modification of Diet in Renal Disease 6-variable formula (MDRD-6).

Exclusion Criteria

Patients who meet any of the following criteria will be excluded from participation in the study. Patients who do not initially meet eligibility criteria may be retested or rescreened, based on Investigator judgment, to determine if they qualify to participate.

History of significant alcohol consumption for a period of more than 3 consecutive months within 1 year prior to Screening.

NOTE: Significant alcohol consumption is defined as equal to or greater than approximately 2 alcoholic drinks per day for males, and approximately 1.5 alcoholic drinks per day for females. One alcoholic drink is equal to 12 ounces (355 mL) of 5% alcohol by volume (ABV) beer, 5 ounces (148 mL) of 12% ABV wine, or 1.5 ounces (44.4 mL) of 40% ABV distilled spirits.

Regular use of drugs historically associated with NAFLD, which include, but are not limited to the following: amiodarone, methotrexate, systemic oral glucocorticoids, tamoxifen, estrogens at doses greater than those used for hormone replacement or contraception, anabolic steroids except testosterone replacement, valproic acid, and known hepatotoxins for more than 4 weeks within the last 8 weeks prior to the initial Screening.

Thyroid diseases:
Active hyperthyroidism
NOTE: Patients with a history of hyperthyroidism are eligible to participate.
Untreated clinical hypothyroidism defined by thyroid stimulating hormone (TSH)>7 mIU/L with symptoms of hypothyroidism or >10 mIU/L without symptoms.
NOTE: TSH may be repeated once, and, if >10 mIU/L, even with normal FT4, patients may be stabilized on ≤75 pg thyroxine replacement therapy per day and rescreened for eligibility. Patients with TSH>7 and <10 with no symptoms of hypothyroidism are eligible, and TSH may be monitored normally. Subclinical hypothyroidism and patients on stable thyroxine (T4) therapy up to 75 µg per day are eligible to participate. NOTE: Patients enrolled in the 'Subsequent 900' population or patients who have completed the Week 52 visit in the study may be on 100 pg/day. Other thyroid replacement therapies equivalent to up to 100 µg thyroxine are allowed (e.g. Armour thyroid).
Patients who have had a thyroidectomy and are on replacement thyroxine doses ≥75 µg per day are allowed.

History of bariatric surgery or intestinal bypass surgery within the 5 years prior to randomization or planned during the conduct of the study.

Weight gain or loss ≥5% total body weight within 12 weeks prior to randomization. (NOTE: This includes the Screening period.)

Hemoglobin A1C (HbA1c) ≥9.0%.

NOTE: Patients with HbA1c>8.0% and ≤10.0% should have documented efforts to control HbA1C to ≤8. If no prior documentation of efforts to control HbA1c, patients with HbA1C >8% and ≤9.0% may be treated with new or higher doses of existing diabetic medication(s) and continue screening. If screening HbA1C was >9.0% and a new antidiabetic therapy was initiated, they may have a repeat HbA1C 4 weeks after initiating a new antidiabetic therapy. Patients must be on stable treatment for all diabetes medications, including any new doses or medications, for ≥30 days prior to randomization.

NOTE: Insulin doses may be altered by up to 10% during the screening period. For screening HbA1C>9% and previous attempts to control HbA1C (no new therapy), HbA1C may be repeated once.

Glucagon-like peptide 1 [GLP-1]agonist therapy (eg, exenatide, liraglutide, lixisenatide, albiglutide, dulaglutide, semaglutide and albiglutide) unless stable dose for 24 weeks prior to biopsy. (NOTE: GLP-1 therapeutics may not be initiated or doses increased during the first 52 weeks of the study. However, GLP-1 therapeutics may be initiated or increased after the Week 52 visit is completed.)

Use of high dose vitamin E (>400 IU/day) unless stable for ≥24 weeks prior to an eligible screening liver biopsy. Vitamin E can be discontinued but dose cannot be increased during the first 52 weeks of the study.

Presence of cirrhosis on liver biopsy defined as stage 4 fibrosis.

Diagnosis of hepatocellular carcinoma (HCC).

Model for End-Stage Liver Disease (MELD) score ≥12, as determined at Screening, due to liver disease.

NOTE: MELD of ≥12 on screening labs must be the result of liver disease to be exclusionary, NOT isolated lab abnormalities such as elevated creatinine due to chronic kidney disease, international normalized ratio (INR) abnormality secondary to anticoagulants or lab error, or bilirubin elevation due to Gilbert's Syndrome.

Hepatic decompensation or impairment defined as presence of any of the following: History of esophageal varices, ascites, or hepatic encephalopathy Serum albumin <3.5 g/dL, except as explained by non-hepatic causes INR>1.4 unless due to therapeutic anticoagulants or laboratory error; NOTE: INR may be repeated once to reassess eligibility.

Total bilirubin >1.5× upper limit of normal. NOTE: Patients with Gilbert's Syndrome are eligible with a total bilirubin above 1.5× upper limit of normal (ULN) if reticulocyte count is within normal limits (typically 0.5% to 2.5%), hemoglobin is within normal limits (typically 13.5 to 17.5 g/dL for men; 12.0 to 15.5 g/dL for women), and direct bilirubin is <20% of total bilirubin.

Chronic liver diseases:
Primary biliary cholangitis
Primary sclerosing cholangitis
Hepatitis B positive
Hepatitis C as defined by presence of hepatitis C virus (HCV) antibody (HCV Ab) and positive HCV RNA (tested for known cured HCV infection, or positive HCV Ab at Screening). NOTE: Patients who are HCV antibody positive and HCV RNA negative who have a history of clearly documented HCV infection (history of positive HCV RNA) are eligible to participate if prior treatment for HCV was given, and they have a documented sustained virologic response (SVR) of at least two years prior to the baseline liver biopsy.

History or evidence of current active autoimmune hepatitis History or evidence of Wilson's disease History or evidence of alpha-1-antitrypsin deficiency Evidence of genetic hemochromatosis (hereditary, primary)

Evidence of drug-induced liver disease, as defined on the basis of typical exposure and history Known bile duct obstruction Suspected or proven liver cancer.

Has an active autoimmune disease, including actively treated lupus, rheumatoid arthritis, inflammatory bowel disease, or autoimmune hepatitis, requiring systemic treatment within the past 12 weeks or a documented history of clinically severe autoimmune disease, including autoimmune liver disease, or a syndrome that requires systemic steroids or immunosuppressive agents. NOTE: Patients with vitiligo or resolved childhood asthma/atopy would be an exception to this rule. Patients that require intermittent use of bronchodilators, topical, inhaled, or intranasal corticosteroids or local steroid injections are not excluded from the study.

Serum ALT ≥250 U/L.

NOTE: Given the intrinsic variability in ALT and AST in NASH patients, investigators should use the following guide in an attempt to establish a relatively stable baseline for ALT and AST. Investigator discretion is allowed. Documented historical (3 weeks to ≤6 months prior to study entry) ALT and AST levels consistent with the Screening ALT and AST values may help establish a stable baseline. This consistency may be established based on the following:

If the historical and Screening ALT and AST values are both ≤1.5×ULN, there is no limit to the difference between the values.

Patients who do not have historical ALT and AST evaluations available will have their ALT and AST repeated during the Screening Period to help establish no worsening of >30% (both assessments during Screening period) with >2 weeks between assessments. If the historic ALT/AST are >1.5× elevated and Screening ALT and AST are markedly improved (>50% decreased or normalized) relative to historic, then a third ALT/AST determination will be made during Screening to help establish a stable Baseline.

If at least 1 of the values is >1.5×ULN and the second value is greater than the first value, the difference in the mean of ALT and AST values must be ≤30%. If the second value is greater than the first value by >30%, a third value assessed >2 weeks after the second value should be determined to help establish a lack of worsening trend in ALT/AST. If a worsening trend is confirmed (3 consecutive worsening values with difference from first value and second value >30% and difference between second and third value >30%), patient will be a screen failure, but may be rescreened if ALT and AST stabilize.

Statins and/or other lipid-lowering therapies unless dose(s) is stable for ≥30 days prior to anticipated randomization. Statins must be taken in the evening for at least 2 weeks prior to randomization, and permitted statins include rosuvastatin up to 20 mg/day, atorvastatin up to 40 mg/day, pravastatin up to 40 mg/day, simvastatin up to 20 mg/day, pitavastatin up to 2 mg/day and lovastatin up to 40 mg/day. Other stable dyslipidemia therapies not specifically listed as excluded or dose-restricted such as proprotein convertase subtilisin/kexin type 9 (PCSK9) inhibitors are allowed. Higher doses and other statins are excluded. Stable doses of bile acid sequestrants (eg, cholestyramine (Questran, Prevalite), colestipol (Colestid, Flavored Colestid), and colesevelam (Welchol)) are permitted only if taken at least 4 h after or at least 4 h before the dose of study drug.

Fenofibrate unless dose is stable for at least 6 weeks prior to anticipated randomization and unless taking fenofibrate for a history of and/or ongoing very high triglycerides (triglycerides >500 mg/dL).

NOTE: Patients already enrolled who are taking fenofibrate even if not for very high triglycerides may remain in the study, because there are no safety concerns in most patients taking fenofibrate (Section 8.6.1).

Pioglitazone >15 mg per day. Pioglitazone treatment must be stable for ≥24 weeks prior to the eligible liver biopsy.

Platelet count <140,000/mm$^3$. Patients with platelets <140,000 and ≥120,000/mm$^3$ are eligible if Fib-4<3.5.

Inability to safely obtain a liver biopsy.

History of biliary diversion.

Uncontrolled hypertension (either treated or untreated) defined as systolic blood pressure >170 mmHg or a diastolic blood pressure >100 mmHg at Screening.

New York Heart Association Class III or IV heart failure or known left ventricular ejection fraction <30%.

Uncontrolled cardiac arrhythmia.

Confirmed QT interval corrected using Fridericia's formula (QTcF)>450 sec for males and >470 msec for females at the Screening ECG assessment; At least 2/3 ECGs must show a prolongation and the average of the 3 ECGs must be prolonged to meet criteria for exclusion.

Prolonged QTcF may be repeated and confirmed following machine calibration if needed.

NOTE: Patients with bundle branch block or other conditions in which a QTcF cannot be calculated are allowed.

Myocardial infarction, unstable angina, percutaneous coronary intervention, coronary artery bypass graft, or stroke within 12 weeks prior to randomization.

Use of illicit intravenous drugs within 5 years prior to randomization or a urine drug screen result positive for amphetamines, barbiturates, benzodiazepines, cocaine, methadone, opiates, or phencyclidine at Screening, unless a prescribed drug accounts for the positive test.

Active, serious medical disease with a likely life expectancy <2 years.

Participation in an investigational new drug trial in the 60 days or 5 half-lives, whichever is longer, prior to randomization. Patients previously treated with NASH therapeutics in an investigational trial are allowed if follow up liver biopsy at the end of trial continued to show active NASH fibrosis meeting eligibility criteria, and they have been off the NASH therapeutic for at least 24 weeks prior to expected randomization. If a potential NASH therapeutic studied revealed no safety issues, and, in fact, was not a NASH therapeutic (no effect on liver biopsy compared to placebo) participation may occur 60 days or 5 half-lives, whichever is longer, after discontinuation of therapy.

History of major surgery (ie, surgery involving a risk to the life of the patient; specifically, an operation upon an organ within the cranium, chest, abdomen, or pelvic cavity) within 6 weeks prior to randomization.

History of cancer within the last 5 years (other than treated and believed to be cured basal or squamous cell carcinoma of the skin or resected carcinoma of the cervix).

Any other condition which, in the opinion of the Investigator, would impede compliance, hinder completion of the study, compromise the well-being of the patient, or interfere with the study outcomes.

Known immunocompromised status, including but not limited to individuals who have undergone organ transplantation, who are known to be positive for HIV, or who have recurrent or chronic systemic bacterial, fungal, viral, or protozoal infections.

Hypersensitivity to resmetirom or to any of the excipients or to placebo.

Compliance

We calculated compliance as the number of doses (pills) taken as a percentage of the number of days patients were identified as receiving IP. Compliance was defined in standard way, at least 80%. Overall compliance was high and no per protocol analysis was conducted.

Figure 23:
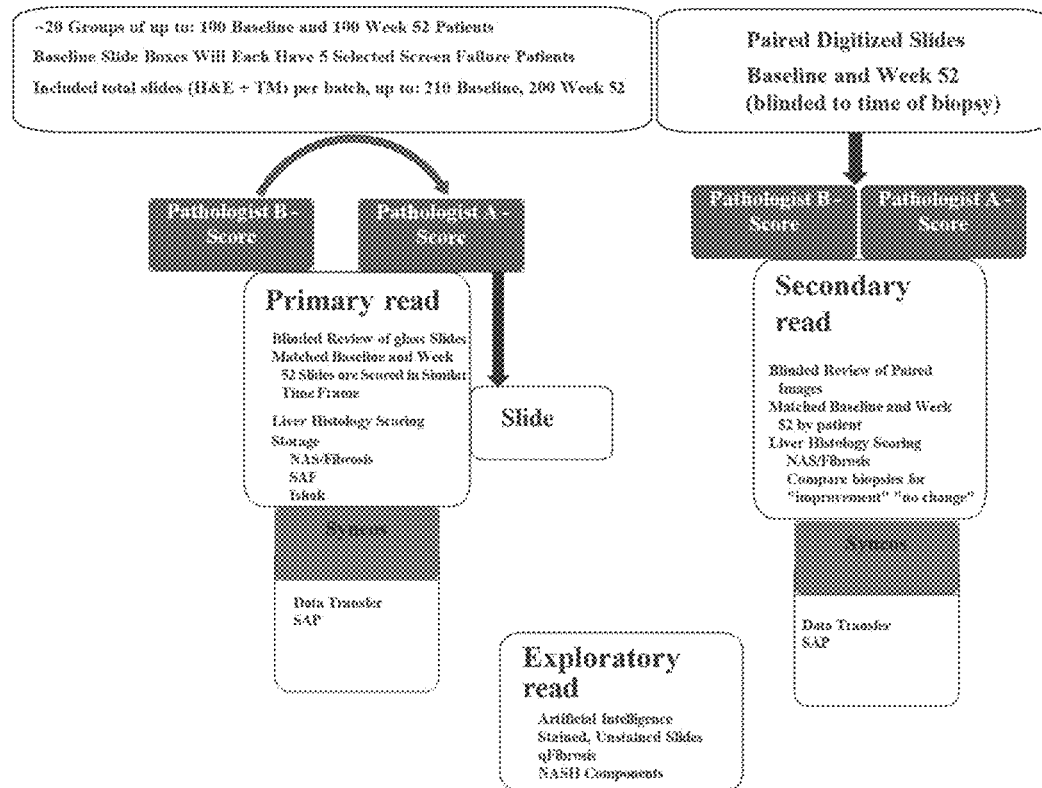
FIG. 23 is a schematic showing methodology for central pathologist evaluation of liver biopsies in Example 2.

Methodology for Central Pathologist Evaluation of Liver Biopsies (FIG. 23)

A liver biopsy review manual detailed the methodology for review of the liver biopsies. Briefly, glass slides were read by a central pathologist who was blinded to patient characteristics for eligibility at the time of screening based on the protocol definition of eligible biopsy. Approximately 4% of screening biopsies were considered technically inadequate. Biopsies were obtained using a 16-gauge needle when possible and average biopsy length was ~22 mm at baseline and Week 52 as determined by both pathologists. Biopsy adequacy was confirmed for each biopsy by both pathologists. Week 52 biopsies blinded to patient ID were read by the central pathologist at the time the biopsy was obtained to determine if the biopsy showed cirrhosis. If cirrhosis was detected, the result was reported to the Sponsor and clinical site. The glass slides were digitized and stored at the digitization facility. For the primary analysis, each pathologist read all baseline and Week 52 glass slides as up to 100 slide batches of baseline and 100 slide Week 52 slides from the same patient to assure that baseline and Week 52 slides from the same patient were evaluated in batches at roughly the same time. Slides were read in the 6 months prior to the last patient Week 52 biopsy from the primary analysis population (966 patients with F1B, F2, or F3 fibrosis at baseline).

A secondary read was conducted of digitized images (read as patient pairs, blinded to time of biopsy). As a supportive analysis, consensus reads were conducted of digitized biopsies on which there was disagreement between the pathologists on responder status for the primary endpoints or the 2-stage fibrosis reduction.

Intrareader agreement (weighted kappa) was assessed between screening eligibility read and primary read for Path A, and for both pathologists between glass and digital reads. Interreader agreement was assessed for baseline and Week 52, respectively, for each component; steatosis 0.50, 0.60; lobular inflammation 0.30, 0.37; ballooning 0.34, 0.53 and fibrosis, 0.49, 0.65 (7 fibrosis components). The weighted kappa statistic appeared to underestimate the degree of correlation between the two pathologists' scores, because Pathologist A consistently scored steatosis higher and Pathologist B consistently scored ballooning higher.

Baseline fibrosis stage was assigned the higher stage, when the two pathologists disagreed and scored FIB only when there was agreement between the two pathologists. Baseline F1a/F1c patients (n=84) were considered only for exploratory efficacy and safety analyses.

Patient's outcomes were classified and scored based on the following approach:
 (1,1): Both pathologist's scores indicated the patient was a Responder—score of 1
 (1,0): Path A's scores indicated patient was a responder; Path B's scores indicated a Non-Responder—score of 0.5
 (0,1): Path B3's scores indicated patient was a responder; Path A's scores indicated a Non-Responder—score of 0.5
 (0,0): Both pathologist's scores indicated the patient was a Non-Responder—score of 0. For each treatment, an average response rate was computed.

The primary analysis utilized a Cochran-Mantel-Haenszel (CM-1) test, stratified for type 2 diabetes status and baseline fibrosis stage. Estimates of risk difference and confidence interval were provided. Biopsies conducted at baseline and within 60 weeks of randomization and read as "adequate" on glass slides were considered valid. For patients without a Week 52 biopsy, response was imputed as "non-response"

Primary Liver Biopsy Analysis, Sensitivity Analyses Rationale and Methodology

The primary statistical analysis calculates within each pathologist the response rate using the Cochran-Mantel-Haenszel (CMH) model stratified for type 2 diabetes status and fibrosis stage. A single estimate of response difference from placebo is then obtained by averaging the difference obtained from each pathologist. The scoring of (1,1), (1,0), (0,1) and (0,0) provides higher weight to patients that are considered responders by both pathologists relative to when they disagree. The p-value was obtained from the CMH test using table scores to compare the active and placebo treatments. Patients with no valid biopsy within the Week 52 window that extended to Week 60 were considered non-responders for the Week 52 analysis, as were patients who experience a composite clinical endpoint (e.g., liver transplant, death) prior to their Week 52 biopsy.

Consensus Reads of Digitized Images of Glass Slides

Consensus reads of digitized images of glass slides by the two central pathologists were conducted in cases where the two pathologists scores disagreed as to whether there was a response for either NASH resolution (ballooning 0,1; 2-point NAS reduction and no worsening of fibrosis) OR ≥1 stage fibrosis reduction with no worsening of NAS (primary endpoints) OR a 2-stage reduction in fibrosis with no worsening of NAS. The study pathologists remained blinded to all clinical data, patient ID, and slide/image identity or time of biopsy. Study personnel remain blinded to patient level data and detailed group analyses. In total 387 total assessments took place requiring four Zoom meetings between the pathologists. The consensus meetings were conducted by an unblinded reviewer who showed the pathologists the initial scores on a spread sheet, and then the pathologists decided on the consensus score for the disagreed component.

Additional Sensitivity and Supportive Analyses of the Dual Primary Endpoints

Multiple additional sensitivity and supportive analyses were conducted on the dual primary endpoints.

Tipping Point Analyses: This analysis imputed missing placebo responses for NASH resolution (in increments from 0% to 100% placebo imputation) and fibrosis response (in increments from 0% up to 35% placebo imputation) at Week 52 as successful responses in order to determine how many missing responses (which were counted in the primary analysis labels as non-responders) could be imputed before losing statistical significance. Of note, the 100-mg treatment group continued to demonstrate significant improvement in NASH resolution (up to 100% missing placebo imputation) (nominal p=0.0246) and fibrosis response (up to 35% missing placebo imputation) (nominal p=0.0378) (Table 18).

Multiple Imputation Analysis: Multiple imputation analyses were conducted where data for patients with missing response at Week 52 were imputed under the missing at random assumption. Data for patients with missing response data at Week 52 were imputed under the missing at random assumption by running a simulation (100 times) which produces a correlated pair of binary 0/1 data for each patient that represents the patient's response status for each pathologist. The statistics were then calculated for each imputation using the same approach as for the primary endpoint. The normalized results from each dataset were combined using Rubin's rule. (Table 17).

General Estimating Equation (GEE) Model Analysis: A generalized estimation equation (GEE) analysis was performed as a sensitivity analysis. This approach treated the biopsy scores from the two pathologists as repeated measures (i.e. correlated binary outcomes) within a patient. Baseline diabetes status, fibrosis stage and interaction term between pathologist and treatment were also included in the model.

Sensitivity analyses were performed using a GEE model in which the odds ratios favored both the 100- and 80-mg resmetirom treatment groups compared with placebo for NASH resolution (Tables 17A and 17B).

Summary of Observed Cases Using In-window Week 52 Paired Liver Biopsies: Supportive analyses were performed on patients with in-window paired Week 52 biopsies. Missing Week 52 biopsies were not imputed.

Statistical Analysis of Change in LDL-C at Week 24

Within the study, we provided analyses based on an analysis of covariance (ANCOVA) model after having performed single imputation for LDL-C as described in the statistical analysis plan (SAP). The ANCOVA model estimated least-squares means using treatment and baseline LDL-C as covariate.

To this end, the Week 24 LDL-C assessment and assessments at any visit in which LDL-C is measured (Weeks 4, 12, 16, 20, 24, 28, 32, 36, 40, 44, 48, and 52) that has been impacted by kit shortage at the prior visit (unavailability of inpatient (IP) during the 4 weeks preceding the visit due to the COVID-19 pandemic as indicated on the electronic case report form (eCRF)), were considered missing and were imputed from an unaffected assessment at surrounding visits or using data from subjects unaffected by this intercurrent event as described in Section 11.2 of the SAP. In summary, single imputation utilizing adjacent and valid LDL-D measurements were imputed.

For missing lipid data that are still missing after the single imputation approach described, those missing lipid data were imputed using the non-missing lipid values (including the singly imputed data) based on missing at random (MAR)-based (MI). When applying the MAR-based Nil, data were imputed separately by randomized treatment group and baseline stratification factors.

TABLE 13

Complete List of Endpoints/Objectives for 52 Week Analyses

| Type of Endpoint | Endpoint | Reported | Rationale |
|---|---|---|---|
| Dual Primary (#1) | Proportion of NASH Resolution Responders as assessed by two pathologists at Week 52. | Included | N/A |
| Dual Primary (#2) | Proportion of Fibrosis Responders as assessed by two pathologists at Week 52. | Included | N/A |
| Key Secondary | Percent change from baseline in directly measured LDL-C at Week 24. | Included | N/A |
| Secondary | Proportion of patients meeting each of the criteria below at Week 52:<br>At least a 2-point improvement in NAS with at least 1-point improvement in ballooning or lobular inflammation with no worsening of fibrosis.<br>At least a 2-point improvement in NAS with at least 1-point improvement in ballooning or lobular inflammation and at least a 1-point improvement in fibrosis.<br>An improvement in each histologic NAS component (ballooning, inflammation, steatosis) by at least 1 point; or improvement by at least 1 point in both ballooning and inflammation with an MRI-PDFF response (≥30% relative fat reduction) at Week 16 or at Week 52 if no data available at Week 16.<br>The resolution of fibrosis (reduction to F0).<br>A 2-stage Fibrosis Responders (a ≥2-point reduction in fibrosis patients with no worsening of NAS) in patients with baseline fibrosis F2 or more severe.<br>A composite of NASH Resolution Responder and Fibrosis Responder.<br>No worsening of fibrosis is defined as no progression ≥1-stage (for patients with an F1B baseline stage, a change to F2 is not considered worsening). This analysis includes patients with paired biopsies (i.e., baseline and Week 52). | Included | N/A |
| Secondary | Change from baseline to week 52 in NAS component score for each of the NAS components (improvement, worsening, no change [change is defined by at least a 1-point change]), NAS (total of the 3 components), and individual | Included | N/A |

TABLE 13-continued

Complete List of Endpoints/Objectives for 52 Week Analyses

| Type of Endpoint | Endpoint | Reported | Rationale |
|---|---|---|---|
| | components, lobular inflammation, ballooning steatosis and fibrosis and the change from baseline in fibrosis (assuming a value of 1.8 for F1B). A change from F2 to F1B is not considered a decrease and from F1B to F2 is not considered an increase. Based on the paired liver biopsy population for each pathologist (based on glass slide [primary analysis]). For fibrosis, only the subset of patients with baseline F1B or F2 (combined) to be evaluated. | | |
| Secondary | Absolute change and percent change from baseline to Week 52 in MRI-PDFF in all patients with baseline and a Week 52 assessment. | Included | N/A |
| Secondary | Proportion of patients at Week 16 and Week 52 with ≥30% or ≥50% relative reduction from baseline in MRT-PDFF (analysis includes patients with paired data; that is a baseline assessment and an assessment at Week 16 and/or at baseline and at Week 52). | Included | N/A |
| Secondary | Absolute change and percent change from baseline to Week. 48 in liver parameters, including ALT, AST, and GGT, in patients with baseline ALT ≥30 TUL/ml. | Included | N/A |
| Secondary | Percent change from baseline at Week 24 and Week 52 in directly measured LDL-C, ApoB, triglycerides in patients with baseline triglycerides >150 mg/dL, ApoCIII, non-HDL-C, and Lp(a) in patients with baseline Lp(a) >10 nmol/L. | Included | N/A |
| Secondary | Absolute change from baseline in directly measured LDL-C in patients with baseline LDL-C ≥100 mg/dL, ApoB, ApoB in patients with baseline LDL-C ≥100 mg/dL, triglycerides in patients with baseline triglycerides >150 mg/dL, Lp(a) in patients with baseline Lp(a) >10 nmol/L. Note: Percent change from baseline in LDL-C at Week 24 is a key secondary endpoint. | Not included | % CFB only is included as the more relevant measurement |
| Secondary | Proportion of patients at Week 24 and Week. 52 with directly measured LDL-C >100 mg/dL at Baseline who achieve <100 mg/dL. | Not included | Endpoint not relevant to study objectives |
| Secondary | Proportion of patients at Week 24 and Week 52 with >70 mg/dL directly measured LDL-C at Baseline who achieve <70 mg/dL. | Not included | Endpoint not relevant to study objectives |
| Secondary | Percent change from baseline at Week 24 and Week 52 in HDL-C, ApoCIII, and lipoprotein particles. | Included | NA |
| Secondary | Absolute change and percent change from baseline to Week 52 in NASH inflammation and fibrosis biomarkers, including: adiponectin, reverse T3, CK-18, and ELF test with 3 direct components (ELF baseline ≥9.8; PTTTNP ≥9 µg/L; TTMP-1 ≥240 µg/L; HA ≥50 µg/L). | Included | NA |
| Secondary | Absolute change from baseline to Week 52 for NAFLD/NASH CLDQ, SF-LDQOL, and WPAI-NASH (QOL assessments). | Not included | This subanalysis will be presented separately |
| Secondary | Proportion of patients with baseline MRE as ≥2.9 kPa receiving serial (baseline and at least one of the following: Week 16, Week 52) MRE with ≥19% reduction from baseline and the proportion with ≥19% increase from baseline. F3, F1B, and F2 assessed separately. | Included | N/A |
| Secondary | Proportion of patients receiving serial (baseline and Week 52) FibroScan with ≥25% and ≥30% reduction from baseline in FibroScan VCTE over time. F3, F1B, and F2 assessed separately. | Included | N/A |
| Secondary | Absolute change from baseline at Week 52 in FibroScan CAP. | Included | N/A |
| Secondary | Percent change from baseline at Week 16 and Week 52 in liver volume in patients with baseline MRI-PDFF and at least one post baseline MRI-PDFF. | Included | N/A |
| Exploratory | Absolute change from baseline at Week 52 in other metabolic, liver, and cardiovascular assessments, including: Markers of insulin resistance and glucose homeostasis such as adiponectin, HOMA-IR, HbA1c, glucose, and insulin. Body weight, BMI. Systolic and diastolic blood pressure. Heart rate as determined by ECG. | Included | N/A |

TABLE 13-continued

Complete List of Endpoints/Objectives for 52 Week Analyses

| Type of Endpoint | Endpoint | Reported | Rationale |
|---|---|---|---|
| Exploratory | Agreement between:<br>The 2 pathologists in the assessment of NASH CRN scores (ballooning, inflammation, steatosis, fibrosis), NAS score, NASH Resolution Response, and Fibrosis Response.<br>The eligibility and Baseline liver biopsy assessments of NASH CRN scores (ballooning, inflammation, steatosis, fibrosis), NAS score, NASH Resolution Response, and Fibrosis Response for each pathologist. | Included | N/A |
| Exploratory | Proportion of patients at Week 52 defined as any improvement, no change, or any worsening in fibrosis stage. | Included | N/A |
| Exploratory | Change from baseline in fracture risk as assessed by T and Z scores at each of 3 sites: hip, femoral neck, and spine based on DEXA scan. | Included | |
| Exploratory | Adjudicated Events<br>MACE as adjudicated by an independent BAC in all patients. MACE includes cardiovascular mortality, myocardial infarction, cerebral vascular accident.<br>Events adjudicated as positive by an adjudication committee related to cardiovascular disease including a composite of 1) heart failure events, 2) hospitalization for unstable angina, and 3) urgent or emergent coronary revascularization.<br>Drug-induced liver injury (DILI) events adjudicated as positive by an adjudication committee | Included | |
| Exploratory | DILI events (adjudicated) | Included | |

TABLE 14

Additional Demographic and Baseline Characteristics (Primary Analysis Population)*

| | Resmetirom 80 mg (n = 322) | Resmetirom 100 mg (n = 323) | Placebo (n = 321) |
|---|---|---|---|
| HbA1c, % | 6.6 ± 1.1 | 6.6 ± 1.1 | 6.5 ± 1.0 |
| Total cholesterol, mg/dL | 179.6 ± 43.4 | 176.9 ± 46.0 | 180.0 ± 50.0 |
| HDL-C, mg/dL | 43.8 ± 12.6 | 44.0 ± 12.9 | 43.8 ± 13.3 |
| ApoB, mg/dL | 98.4 ± 27.8 | 95.9 ± 27.8 | 97.8 ± 32.0 |
| Lp(a), nmol/L | 44.7 ± 61.1 | 43.8 ± 60.8 | 42.2 ± 62.7 |
| Enhanced liver fibrosis score | 9.7 ± 0.89 | 9.8 ± 0.86 | 9.7 ± 0.86 |
| Triglycerides, mg/dL | 189.2 ± 112.5 | 188.7 ± 153.8 | 184.1 ± 125.8 |
| Alkaline phosphatase, U/L | 74.9 ± 27.1 | 73.9 ± 23.0 | 71.5 ± 23.7 |
| Bilirubin, mg/dL† | 0.63 ± 0.27 | 0.66 ± 0.32 | 0.66 ± 0.31 |
| Platelets, $10^9$/L† | 236.6 ± 67.9 | 230.6 ± 59.1 | 233.6 ± 60.4 |
| Albumin, g/dL† | 4.4 ± 0.32 | 4.3 ± 0.27 | 4.4 ± 0.29 |
| HOMA-IR | 11.9 ± 11.8 | 10.6 ± 8.3 | 11.0 ± 12.3 |
| GLP-1 RA, no. (%) | 54 (16.8) | 41 (12.7) | 42 (13.1) |
| SGLT2i, no. (%) | 55 (17.1) | 39 (12.1) | 36 (11.2) |
| Insulin, no. (%) | 40 (12.4) | 41 (12.7) | 37 (11.5) |
| Statin, no. (%) | 149 (46.3) | 166 (51.4) | 158 (49.2) |

*Plus-minus signs are mean ± SD.
†Safety population.
ApoB, apolipoprotein B; GLP-1 RA, glucagon-like peptide-1 receptor agonist; HbA1c, hemoglobin A1c; HDL-C, high-density lipoprotein cholesterol; HOMA-IR, homeostasis model assessment-estimated insulin resistance; Lp(a), lipoprotein (a); SD, standard deviation; SGLT2i, sodium/glucose cotransporter-2 inhibitor.

TABLE 15

Representativeness of Study Participants.

| Category | Details |
|---|---|
| Disease<br>Special considerations related to | Nonalcoholic steatohepatitis (NASH) |
| Age | NASH is prevalent in ages 45-65 |
| Gender and sex | NASH is common in both men and women |

TABLE 15-continued

Representativeness of Study Participants.

| Category | Details |
| --- | --- |
| Geography | NASH is common globally, with estimated 30% of US population has NAFLD |
| Race or ethnic group | NASH is highly prevalent in Hispanic and Latino communities and is less common in black patients |
| Other special considerations | NASH is more common in patients with multiple metabolic risk factors: Large waist or Body mass index (BMI) ≥30, Dyslipidemia (raised TGs >150 or receiving treatment for elevated lipids), Dyslipidemia (reduced HDL cholesterol); hypertension (BP >140/90 on two occasions or receiving BP lowering medications), Type 2 diabetes or evidence of insulin resistance derived by HOMA-IR. |
| Overall total representation in MAESTRO- NASH trial | This trial included participants of the expected age range and ≥3 metabolic comorbid conditions. The study was conducted globally, with the majority of patients from USA. Approximately 55% of participants were women. Representative of the USA population, approximately 20% of participants were Hispanic or Latino. |

TABLE 16

Demographic and Baseline Characteristics by Baseline Fibrosis Stage (Intent-to-Treat Population (n = 1050)*

|  | F1 (n = 84) | Primary (N = 966) | F1B (n = 49) | F2 (n = 319) | F3 (n = 598) |
| --- | --- | --- | --- | --- | --- |
| Age, years | 57.2 ± 13.3 | 56.6 ± 10.9 | 55.4 ± 12.8 | 55.0 ± 11.5 | 57.6 ± 10.3 |
| Sex, male, no. (%)† | 39 (46.4) | 424 (43.9) | 25 (51.0) | 134 (42.0) | 265 (44.3) |
| Body mass index, kg/m² | 35.5 ± 6.6 | 35.7 ± 6.8 | 36.2 ± 7.6 | 36.0 ± 6.7 | 35.4 ± 6.7 |
| Type 2 diabetes, no. (%) | 45 (53.6) | 647 (67.0) | 33 (67.3) | 189 (59.2) | 425 (71.1) |
| Hypertension, no. (%) | 62 (73.8) | 754 (78.1) | 39 (79.6) | 225 (70.5) | 490 (81.9) |
| Dyslipidemia, no. (%) | 57 (67.9) | 689 (71.3) | 37 (75.5) | 212 (66.5) | 440 (73.6) |
| Hypothyroidism, no. (%)‡ | 12 (14.3) | 130 (13.5) | 6 (12.2) | 48 (15.0) | 76 (12.7) |
| History of ASCVD, no. (%) | 3 (3.6) | 57 (5.9) | 6 (12.2) | 15 (4.7) | 36 (6.0) |
| FibroScan VCTE/LSM, kPa | 10.4 ± 3.5 | 13.3 ± 6.5 | 11.3 ± 4.8 | 11.6 ± 5.6 | 14.4 ± 6.8 |
| MRE, kPa | 2.7 ± 0.44 | 3.6 ± 1.0 | 3.0 ± 0.58 | 3.1 ± 0.71 | 3.9 ± 1.0 |
| FIB-4 | 1.2 ± 0.59 | 1.4 ± 0.70 | 1.2 ± 0.54 | 1.3 ± 0.64 | 1.5 ± 0.72 |
| Enhanced liver fibrosis score | 9.6 ± 0.93 | 9.8 ± 0.87 | 9.4 ± 0.78 | 9.5 ± 0.76 | 9.9 ± 0.88 |
| Statin, no. (%) | 33 (39.3) | 473 (49.0) | 32 (65.3) | 128 (40.1) | 313 (52.3) |

*Plus-minus signs are mean ± SD.
†Sex was self-reported by the patient.
‡Patients on thyroxine replacement therapy at screening.
Note:
"Primary" column denotes the primary analysis population and includes F1B (by consensus); F2 and F3 populations. The F1 population was scored as baseline F1A or F1C by both pathologists or F1A/F1B or F1C/F1B. The F1 population was an exploratory population and excluded from the primary analysis population because their NASH is not felt to be at risk for progression to advanced fibrosis.
ASCVD, atherosclerotic cardiovascular disease; FIB-4, fibrosis-4 index; LSM, liver stiffness measurement; MRE, magnetic resonance elastography; SD, standard deviation; VCTE, vibration-controlled transient elastography.

TABLE 17A

Sensitivity Analysis of Primary Endpoints: Consensus and Multiple Imputation

| | % Response Resmetirom 80 mg (n = 316) | % Response Resmetirom 100 mg (n = 321) | % Response Placebo (n = 318) | % Difference Resmetirom 80 mg from PBO (95% CI) | % Difference Resmetirom 100 mg from PBO (95% CI) |
|---|---|---|---|---|---|
| NASH resolution | | | | | |
| Consensus (sensitivity) | 24.4 | 27.7 | 7.9 | 16.8 (11.3, 22.4) | 20.7 (15.0, 26.3) |
| Multiple imputation (sensitivity) | 31.0 | 36.0 | 13.5 | 17.7 (11.3, 24.1) | 23.2 (16.8, 29.6) |
| Fibrosis improvement | | | | | |
| Consensus (sensitivity) | 24.4 | 25.5 | 12.3 | 12.2 (6.3, 18.2) | 13.4 (7.4, 19.3) |
| Multiple imputation (sensitivity) | 29.2 | 31.9 | 17.9 | 11.4 (5.1, 17.8) | 14.1 (7.9, 20.4) |

Data for patients with missing response data at Week 52 were imputed under the missing at random assumption by running a simulation (100 times) which produces a correlated pair of binary 0/1 data for each patient that represents the patient's response status for each pathologist. The statistics were then calculated for each imputation using the same approach as for the primary endpoint. The normalized results from each dataset were combined using Rubin's rule. Patients that were F3 at eligibility and re-evaluated as F4 at baseline by either pathologist are included in this analysis.
CI, confidence interval; NASH, nonalcoholic steatohepatitis; PBO, placebo. Unless otherwise stated "NASH resolution" means ballooning 0, 1 with at least a 2-pt reduction in NAS and no worsening of fibrosis; "Fibrosis improvement" means at least 1-stage reduction in fibrosis with no worsening of NAS. Confidence interval widths have not been adjusted for multiplicity and may not be used for hypothesis testing.

Data for patients with missing response data at Week 52 were imputed under the missing at random assumption by running a simulation (100 times) which produces a correlated pair of binary 0/1 data for each patient that represents the patient's response status for each pathologist. The statistics were then calculated for each imputation using the same approach as for the primary endpoint. The normalized results from each dataset were combined using Rubin's rule. Patients that were F3 at eligibility and re-evaluated as F4 at baseline by either pathologist are included in this analysis.

CI, confidence interval; NASH, nonalcoholic steatohepatitis; PBO, placebo. Unless otherwise stated "NASH resolution" means ballooning 0.1 with at least a 2-pt reduction in NAS and no worsening of fibrosis; "Fibrosis improvement" means at least 1-stage reduction in fibrosis with no worsening of NAS. Confidence interval widths have not been adjusted for multiplicity and may not be used for hypothesis testing.

TABLE 17B

Sensitivity Analysis of Primary Endpoint (NASH Resolution): Generalized Estimating Equation Model

| | Resmetirom 80 mg (n = 316) | Resmetirom 100 mg (n = 321) | Placebo (n = 318) |
|---|---|---|---|
| NASH resolution at Week 52, no. (%)* | | | |
| (1, 1) | 62 (19.6) | 62 (19.3) | 18 (5.7) |
| (1, 0) | 24 (7.6) | 55 (17.1) | 22 (6.9) |
| (0, 1) | 16 (5.1) | 13 (4.0) | 4 (1.3) |
| (0, 0) | 214 (67.7) | 191 (59.5) | 274 (86.2) |
| OR of resmetirom group to placebo† | 3.5 | 4.2 | |
| 95% CI of the OR | (2.3, 5.2) | (2.8, 6.2) | |
| Difference in percentage of responders, CMH, resmetirom group - placebo (SD)† | 17.5 (3.0) | 21.3 (3.0) | |
| 95% CT of the difference | (11.7, 23.3) | (15.4, 27.2) | |

*The ordered pair indicates (result according to pathologist A, result according to pathologist B). 1 indicates yes/responder; 0 indicates no/non-responder.
†The OR and difference in percentage of responders, 95% CTs, and p-values were obtained by fitting a GEE model with treatment arm, baseline type 2 diabetes status, baseline fibrosis stage, and pathologist by treatment interaction as factors, logit link function and a compound symmetric covariance structure, under the assumption that the scores from the two pathologists are repeated measurements for the same patient with some within-patient correlation structure.
Patients with no valid biopsy within the Week 52 window are considered non-responders for the Week 52 analysis, as are patients who experience a composite clinical endpoint (e.g., liver transplant, death) prior to their Week 52 biopsy.
Patients that were F3 at eligibility and re-evaluated as F4 at baseline by either pathologist are included in this analysis.
CI, confidence interval; GEE, generalized estimating equation; NASH, nonalcoholic steatohepatitis; OR, odds ratio; SD, standard deviation. Unless otherwise stated "NASH resolution" means ballooning 0, 1 with at least a 2-pt reduction in NAS and no worsening of fibrosis; "Fibrosis improvement" means at least 1 - stage reduction in fibrosis with no worsening of NAS. Confidence interval widths have not been adjusted for multiplicity and may not be used for hypothesis testing.

TABLE 17C

Sensitivity Analysis of Primary Endpoint (Fibrosis Improvement): Generalized Estimating Equation Model

|  | Resmetirom 80 mg (n = 316) | Resmetirom 100 mg (n = 321) | Placebo (n = 318) |
|---|---|---|---|
| Fibrosis improvement at Week 52, no. (%)* | | | |
| (1, 1) | 52 (16.5) | 51 (15.9) | 28 (8.8) |
| (1, 0) | 21 (6.6) | 34 (10.6) | 21 (6.6) |
| (0, 1) | 28 (8.9) | 30 (9.3) | 13 (4.1) |
| (0, 0) | 215 (68.0) | 206 (64.2) | 256 (80.5) |
| OR of resmetirom group to placebo† | 2.0 | 2.1 | |
| 95% CT of the OR | (1.4, 2.9) | (1.5, 3.0) | |
| Difference in percentage of responders, CMH, resmetirom group - placebo (SD)† | 9.7 (2.7) | 11.0 (2.7) | |
| 95% CT of the difference | (4.4, 15.0) | (5.7, 16.3) | |

*The ordered pair indicates (result according to pathologist A, result according to pathologist B). 1 indicates yes/responder; 0 indicates no/non-responder.

†The OR and difference in percentage of responders, 95% CTs, and p-values were obtained by fitting a GEE model with treatment arm, baseline type 2 diabetes status, baseline fibrosis stage, and pathologist by treatment interaction as factors, logit link function and a compound symmetric covariance structure, under the assumption that the scores from the two pathologists are repeated measurements for the same patient with some within-patient correlation structure.

Patients with no biopsy within the Week 52 window or experience a composite clinical endpoint (e.g., liver transplant, death) prior to their Week 52 biopsy are considered non-responders for the Week 52 analysis.

Patients that were F3 at eligibility and re-evaluated as F4 at baseline by either pathologist are included in this analysis.

CI, confidence interval; GEE, generalized estimating equation; OR, odds ratio; SD, standard deviation. Unless otherwise stated "NASH resolution" means ballooning 0,1 with at least a 2-pt reduction in NAS and no worsening of fibrosis; "Fibrosis improvement" means at least 1-stage reduction in fibrosis with no worsening of NAS. Confidence interval widths have not been adjusted for multiplicity and may not be used for hypothesis testing.

TABLE 18

Sensitivity Analysis of Primary Endpoints: Tipping Point

| | % Response Resmetirom 80 mg (n = 316) | % Response Resmetirom 100 mg (n = 321) | % Response Placebo (n = 318) | % Difference Resmetirom PBO 80 mg from (95% CI)† | p-value | % Difference Resmetirom PBO 100 mg from (95% CI)† | p-value |
|---|---|---|---|---|---|---|---|
| NASH resolution | | | | | | | |
| Placebo-0% imputed responders (Primary Analysis) | 25.9 | 29.9 | 9.7 | 16.4 (11.0, 21.8)* | <0.001 | 20.7 (15.3, 26.2)* | <0.001 |
| Placebo-30% imputed responders | 25.9 | 29.9 | 13.7 | 12.4 (6.5, 18.3) | <0.001 | 16.7 (10.9, 22.6) | <0.001 |
| Placebo-60% impute dresponders | 25.9 | 29.9 | 17.8 | 8.3 (2.2, 14.4) | 0.0154 | 12.7 (6.6, 18.8) | <0.001 |
| Placebo-67% imputed responders | 25.9 | 29.9 | 18.8 | 7.4 (1.2, 13.5) | 0.0377 | 11.7 (5.6, 17.9) | <0.001 |
| Placebo-90% imputed responders | 25.9 | 29.9 | 21.9 | 4.2 (−2.0, 10.4) | 0.3693 | 18.6 (2.4, 14.8) | 0.0130 |
| Placebo-100% imputed responders | 25.9 | 29.9 | 23.4 | 2.6 (−3.5, 8.8) | 0.4047 | 7.0 (0.9, 13.2) | 0.0246 |
| Fibrosis improvement | | | | | | | |
| Placebo-0% imputed responders (Primary Analysis) | 24.2 | 25.9 | 14.2 | 10.2 (4.8, 15.7)* | <0.001 | 11.8 (6.4, 17.2)* | <0.001 |
| Placebo-10% imputed responders | 24.2 | 25.9 | 15.6 | 8.8 (3.2, 14.4) | 0.0048 | 10.4 (4.8, 15.9) | <0.001 |
| Placebo-20% imputed responders | 24.2 | 25.9 | 16.8 | 7.5 (1.8, 13.3) | 0.0201 | 9.1 (3.4, 14.8) | 0.0038 |
| Placebo-25% imputed responders | 24.2 | 25.9 | 17.5 | 6.9 (1.1, 12.7) | 0.0398 | 8.5 (2.7, 14.2) | 0.0084 |

TABLE 18-continued

Sensitivity Analysis of Primary Endpoints: Tipping Point

|  | % Response Resmetirom 80 mg (n = 316) | % Response Resmetirom 100 mg (n = 321) | % Response Placebo (n = 318) | % Difference Resmetirom PBO 80 mg from (95% CI)† | p-value | % Difference Resmetirom PBO 100 mg from (95% CI)† | p-value |
|---|---|---|---|---|---|---|---|
| Placebo-30% imputed responders | 24.2 | 25.9 | 18.1 | 6.2 (0.3, 12.1) | 0.0762 | 7.8 (1.9, 13.6) | 0.0181 |
| Placebo-35% imputed responders | 24.2 | 25.9 | 18.9 | 5.5 (−0.5, 11.5) | 0.1410 | 7.1 (1.2, 13.0) | 0.0378 |

*Calculated using a stratified CMH approach. Patients with missing response at Week 52 are considered non-responders in both active and placebo groups.
†Active patients with missing response at Week 52 are considered non-responders. Placebo patients with missing response at Week 52 had their response imputed by running a simulation (100 times) which produces a correlated pair of binary 0/1 data that represents the patient's response for each pathologist. The statistics were then calculated for each imputation using the same approach as in preceding footnote. The normalized results from each dataset were combined using Rubin's rule.
Note:
Patients who experience a composite clinical endpoint (e.g., liver transplant, death) prior to their Week 52 biopsy. Patients that were F3 at eligibility and re-evaluated as F4 at baseline by either pathologist are included in this analysis. To account for multiplicity, 0.037 is considered to be the threshold for significance in this table. CI, confidence interval; NASH, nonalcoholic steatohepatitis; PBO, placebo. Unless otherwise stated "NASH resolution" means ballooning 0,1 with at least a 2-pt reduction in NAS and no worsening of fibrosis; "Fibrosis improvement" means at least 1-stage reduction in fibrosis with no worsening of NAS. Confidence interval widths have not been adjusted for multiplicity and may not be used for hypothesis testing.

TABLE 19

Baseline Characteristics, F1 Patients

|  | Resmetirom 80 mg (N = 30) | Resmetirom 100 mg (N = 26) | Placebo (N = 28) |
|---|---|---|---|
| Age, years | 55.4 ± 13.0 | 57.8 ± 13.0 | 58.5 ± 14.3 |
| Sex, male, no. (%) | 14 (46.7%) | 11 (42.3%) | 14 (50%) |
| White | 28 (93.3%) | 23 (88.5%) | 27 (96.4%) |
| Ethnicity, Hispanic or Latino, no. (%) | 8 (26.7%) | 8 (30.8%) | 2 (7.1%) |
| Body weight, kg | 165.5 ± 9.2 | 97.6 ± 17.0 | 99.8 ± 25.2 |
| Body mass index, kg/m$^2$ | 36.2 ± 6.9 | 35.5 ± 6.6 | 34.8 ± 6.4 |
| Type 2 diabetes, no. (%) | 13 (43.3%) | 16 (61.5%) | 16 (57.1%) |
| Hypertension, no. (%) | 23 (76.6%) | 18 (69.2%) | 21 (75.0%) |
| Dyslipidemia, no. (%) | 22 (73.3%) | 15 (57.7%) | 20 (71.4%) |
| Hypothyroidism, no. (%)§ | 3 (10%) | 3 (11.5%) | 6 (21.4%) |
| History of ASCVD, no. (%) | 0 | 1 (3.8%) | 2 (7.1%) |
| 10-year ASCVD risk score | 12.7 ± 15.9 | 14.7 ± 12.9 | 17.1 ± 13.0 |
| FibroScan VCTE/LSM, kPa | 9.8 ± 3.0 | 11.0 ± 7.1 | 12.9 ± 5.5 |
| Median (Q1, Q3) | 9.8 (8.8,11.7) | 10.0 (9.1, 11.1) | 9.7 (9.1, 10.9) |
| FibroScan CAP, dB/m | 364.4 ± 34.3 | 355.2 ± 40.4 | 340.2 ± 41.0 |
| MRI-PDFF, % fat fraction | 18.6 ± 7.2 | 24.2 ± 8.9 | 20.2 ± 6.8 |
| MRE, kPa | 2.7 ± 0.42 | 2.9 ± 0.30 | 2.6 ± 0.52 |
| FIB-4 | 1.2 ± 0.49 | 1.3 ± 0.74 | 1.2 ± 0.53 |
| LDL-C, mg/dL | 113.0 ± 48.1 | 113.3 ± 33.9 | 124.8 ± 48.8 |
| Alanine aminotransferase, U/L | 47.3 ± 28.4 | 58.1 ± 50.4 | 62.5 ± 48.2 |
| Aspartate aminotransferase, U/L | 30.4 ± 13.6 | 37.3 ± 20.2 | 38.0 ± 24.6 |
| Gamma-glutamyl transferase, U/L | 67.7 ± 54.8 | 68.3 ± 55.3 | 66.6 ± 65.7 |
| Screening NAS ≥5, no. (%) | 18 (60%) | 17 (65.4%) | 19 (67.9%) |

TABLE 20

Endpoints and Safety Data, F1 Patients

|  | Resmetirom 80 mg (N = 30) n (%) | Resmetirom 100 mg (N = 26) n (%) | Placebo (N = 28) n (%) |
|---|---|---|---|
| Biopsy endpoints |  |  |  |
| Nash resolution endpoint | 38.3 | 25.0 | 7.4 |
| relative to placebo | 31.9 (11.2, 52.5) | 17.6 (−0.9, 36.2) |  |
| Fibrosis improvement endpoint | 21.7 | 15.4 | 11.1 |
|  | 9.9 (−7.3, 27.0) | (−12.2, 21.1) |  |
| SAFETY |  |  |  |
| Any TEAE | 28 (93.3) | 21 (80.8) | 26 (92.9) |
| Any Serious TEAE | 6 (20.0) | 6 (23.1) | 4 (14.3) |

TABLE 20-continued

Endpoints and Safety Data, F1 Patients

|  | Resmetirom 80 mg (N = 30) n (%) | Resmetirom 100 mg (N = 26) n (%) | Placebo (N = 28) n (%) |
|---|---|---|---|
| Any TEAEs leading to Study Discontinuation | 4 (13.3) | 3 (11.5) | 1 (3.6) |
| Grade 1 | 6 (20.0) | 5 (19.2) | 6 (21.4) |
| Grade 2 | 16 (53.3) | 12 (46.2) | 17 (60.7) |
| Grade 3 | 5 (16.7) | 4 (15.4) | 3 (10.7) |
| AEs >5% | | | |
| Diarrhea | 8 (26.7) | 5 (19.2) | 7 (25.0) |
| Constipation | 4 (13.3) | 2 (7.7) | 3 (10.7) |
| Nausea | 5 (16.7) | 2 (7.7) | 2 (7.1) |
| Abdominal pain upper | 2 (6.7) | 1 (3.8) | 4 (14.3) |
| Vomiting | 1 (3.3) | 3 (11.5) | 2 (7.1) |
| Abdominal pain | 1 (3.3) | 2 (7.7) | 2 (7.1) |
| Arthralgia | 6 (20.0) | 2 (7.7) | 6 (21.4) |
| Back pain | 4 (13.3) | 3 (11.5) | 4 (14.3) |
| Osteopenia | 0 | 2 (7.7) | 3 (10.7) |
| COVID-19 | 6 (20.0) | 6 (23.1) | 3 (10.7) |
| Urinary tract infection | 2 (6.7) | 4 (15.4) | 1 (3.6) |
| Pruritus | 2 (6.7) | 4 (15.4) | 1 (3.6) |
| Fatigue | 3 (10.0) | 2 (7.7) | 2 (7.1) |
| Pyrexia | 2 (6.7) | 0 | 3 (10.7) |
| Headache | 4 (13.3) | 0 | 2 (7.1) |
| Dizziness | 2 (6.7) | 2 (7.7) | 1 (3.6) |
| Rash | 3 (10.0) | 2 (7.7) | 2 (7.1) |
| Type 2 diabetes mellitus | 1 (3.3) | 1 (3.8) | 5 (17.9) |
| Weight decreased | 1 (3.3) | 3 (11.5) | 1 (3.6) |
| Cough | 0 | 1 (3.8) | 4 (14.3) |
| Hypertension | 1 (3.3) | 0 | 4 (14.3) |

TABLE 21

Histologic Response in Patients with Eligible Biopsies at Baseline and Week 52

| | % Response Resmetirom 80 mg (N = 316) (N = 258) | % Response Resmetirom 100 mg (N = 321) (N = 248) | % Response Placebo (N = 318) (N = 276) | % Difference Resmetirom 80 mg from PBO (95% CI) | % Difference Resmetirom 100 mg from PBO (95% CI) |
|---|---|---|---|---|---|
| NASH resolution* (in window including a baseline and Week 52 biopsy) | | | | | |
| % Response | 31.8 | 38.7 | 11.2 | 20.9 (14.4, 27.2) | 28.6 (22.2, 35.0) |
| Fibrosis improvement* (in window including a baseline and Week 52 biopsy) | | | | | |
| % Response | 29.7 | 33.5 | 16.3 | 13.6 (7.3, 19.9) | 17.2 (10.9, 23.6) |
| NASH resolution* OR fibrosis improvement* (in-window including a baseline and Week 52 biopsy) | | | | | |
| % Response | 42.2 | 50.4 | 19.2 | 23.1 (15.4, 30.7) | 31.2 (23.4, 39.0) |

*NASH resolution or Fibrosis Improvement used the same definition as the primary endpoints (NASH resolution with ballooning 0, inflammation 0, 1, with at least a 2-point improvement in NAS and no worsening of fibrosis stage; At least 1 stage fibrosis improvement with no worsening of NAS). Confidence interval widths have not been adjusted for multiplicity and may not be used for hypothesis testing.

TABLE 22

Additional Subgroups, Primary Endpoints

Additional Prespecified Subgroups

| | Relative to Placebo Assessment (%) (CI) | | | |
|---|---|---|---|---|
| | Resmetirom 80 mg | | Resmetirom 100 mg | |
| | N | Result | N | Result |
| Nash Resolution | | | | |
| ≥5% Weight Gain from Baseline at Week 52 | 18 | 10.5 (−14.9, 36.0) | 19 | 14.5 (−8.5, 37.4) |
| <5% Weight Gain from Baseline at Week 52 | 258 | 19.5 (13.4, 25.7) | 248 | 26.9 (20.5, 33.2) |

TABLE 22-continued

Additional Subgroups, Primary Endpoints

Additional Prespecified Subgroups

| | Relative to Placebo Assessment (%) (CI) | | | |
|---|---|---|---|---|
| | Resmetirom 80 mg | | Resmetirom 100 mg | |
| | N | Result | N | Result |
| ≥30% PDFF Reduction at Week 16 | 135 | 20.0 (12.6, 27.4) | 157 | 26.2 (18.9, 33.5) |
| <30% PDFF Reduction at Week 16 | 90 | 13.8 (6.2, 21.3) | 60 | 17.3 (8.6, 26.1) |
| Region: US | 201 | 15.8 (9.0, 22.6) | 224 | 19.9 (13.2, 26.7) |
| Region: Non-US | 115 | 18.7 (9.4, 28.0) | 97 | 22.9 (13.7, 32.1) |
| F2/F3 | 300 | 16.7 (11.1, 22.3) | 306 | 20.9 (15.3, 26.5) |
| F1B | 16 | 11.3 (−11.3, 34.0) | 15 | 16.7 (−6.9, 40.2) |
| BMI <35 kg/m$^2$ | 164 | 22.4 (14.2, 30.6) | 162 | 21.0 (13.4, 28.7) |
| BMI ≥35 kg/m$^2$ | 152 | 9.8 (3.1, 16.6) | 159 | 20.0 (12.3, 27.7) |
| BW ≤200 pounds | 120 | 17.4 (7.8, 26.9) | 108 | 20.6 (11.0, 30.1) |
| BW >200 pounds | 196 | 16.2 (9.6, 22.7) | 212 | 21.1 (14.5, 27.8) |
| Fibrosis Improvement | | | | |
| ≥5% Weight Gain from Baseline at Week 52 | 18 | 0.9 (−22.6, 24.4) | 19 | 16.0 (−7.9, 39.9) |
| <5% Weight Gain from Baseline at Week 52 | 258 | 12.8 (6.5, 19.0) | 248 | 15.0 (8.8, 21.3) |
| ≥30% PDFF Reduction at Week 16 | 135 | 13.5 (5.5, 21.5) | 157 | 15.5 (8.0, 23.1) |
| <30% PDFF Reduction at Week 16 | 90 | 3.3 (−4.7, 11.4) | 60 | 2.7 (−6.8, 12.2) |
| Region: US | 201 | 7.8 (0.9, 14.6) | 224 | 10.4 (3.6, 17.1) |
| Region: Non-US | 115 | 14.6 (5.3, 23.9) | 97 | 14.4 (5.5, 23.4) |
| F2/F3 | 300 | 10.2 (4.6, 15.9) | 306 | 11.4 (5.8, 16.9) |
| F1B | 16 | 10.5 (−11.4, 32.4) | 15 | 19.6 (−2.6, 41.9) |
| BMI <35 kg/m$^2$ | 164 | 13.0 (5.2, 20.8) | 162 | 11.8 (4.2, 19.4) |
| BMT ≥35 kg/m$^2$ | 152 | 7.0 (−0.7, 14.7) | 159 | 11.1 (3.4, 18.9) |
| BW ≤200 pounds | 120 | 15.6 (6.1, 25.1) | 108 | 13.1 (3.9, 22.3) |
| BW >200 pounds | 196 | 7.0 (0.4, 13.7) | 213 | 10.8 (4.1, 17.6) |

Body Weight Impact on Biopsy Responses SHBG and MRI-PDFF by Dose (post hoc)
Assessment (%) (CI)

| | ≤100 kg | >100 kg | ≤100 kg | >100 kg |
|---|---|---|---|---|
| N | 178 | 174 | 167 | 156 |
| ≥120% Increase in SHBG at Week 52 | 60.9 (52.9, 68.5) | 29.6 (21.4, 38.8) | 64.2 (55.4, 72.3) | 55.0 (46.0, 63.8) |
| ≥30% Reduction in MRI-PDFF at Week 52 | 66.9 (58.3, 74.7) | 56.7 (46.3, 66.7) | 71.7 (62.4, 79.8) | 72.5 (63.1, 80.6) |
| | Week 52 Primary Population* | | | |
| Consensus Fibrosis Improvement1 | 29.2 (22.7, 36.5) | 17.4 (11.6, 24.6) | 25.1 (18.8, 32.4) | 25.6 (19.0, 33.2) |
| Consensus NASH Resolution1 | 26.4 (20.1, 33.5) | 20.8 (14.5, 28.4) | 26.9 (20.4, 34.4) | 28.2 (21.3, 36.0) |
| | Week 52 Paired Biopsies† | | | |
| N | 147 | 111 | 125 | 123 |
| Consensus Fibrosis Improvement | 35.4 (27.7, 43.7) | 22.5 (15.1, 31.4) | 33.6 (25.4, 42.6) | 32.5 (24.4, 41.6) |
| Consensus NASH Resolution | 32.0 (24.5, 40.2) | 27.0 (19.0, 36.3) | 36.0 (27.6, 45.1) | 35.8 (27.3, 44.9) |

CT = 95% Clopper-Pearson confidence interval;

BW = body weight

*For NASH Resolution and Fibrosis Responder status, missing responses and Week 52 biopsies out of window are considered non-responders.

†Patients with a baseline and valid Week 52 biopsy. PDFF reduction in resmetirom groups are compared to all placebo patients with any Week 16 PDFF.

1Unless otherwise stated "NASH resolution" means ballooning 0,1 with at least a 2-pt reduction in NAS and no worsening of fibrosis; "Fibrosis improvement" means at least 1-stage reduction in fibrosis with no worsening of NAS. Confidence interval widths have not been adjusted for multiplicity and may not be used for hypothesis testing.

TABLE 23

Change From Baseline in Lipids, Lipoproteins, and Lipid Particles at Weeks 24 and 52 (Primary Analysis Population)

|  | Least Squares Mean % CFB (Standard Error) Resmetirom 80 mg (n = 322) | Least Squares Mean % CFB (Standard Error) Resmetirom 100 mg (n = 323) | Least Squares Mean % CFB (Standard Error) Placebo (n = 321) | Least Squares Mean % CFB Difference Resmetirom 80 mg from PBO (95% CI) | Least Squares Mean % CFB Difference Resmetirom 100 mg from PBO (95% CI) |
|---|---|---|---|---|---|
| LDL-C, mg/dL (baseline LDL-C >100 mg/dL) | | | | | |
| Week 24 - no. | 148 | 133 | 150 | | |
| Baseline mean (SD) | 135.6 (26.5) | 134.4 (27.3) | 136.8 (34.0) | | |
| Week 24 (% CFB) | −21.3 (2.0) | −20.6 (2.0) | −5.9 (1.9) | −15.4 (−19.3, −11.6) | −14.7 (−18.6, −10.8) |
| Week 52 - no. | 147 | 125 | 144 | | |
| Baseline mean (SD) | 135.2 (26.0) | 133.3 (27.4) | 136.9 (34.2) | | |
| Week 52 (% CFB) | −25.3 (2.2) | −27.1 (2.3) | −9.6 (2.1) | −15.7 (−20.0, −11.4) | −17.5 (−22.0, −13.1) |
| ApoB, mg/dL (baseline LDL-C > 100 mg/dL) | | | | | |
| Week 24 - no. | 148 | 133 | 150 | | |
| Baseline mean (SD) | 117.9 (22.2) | 116.9 (24.0) | 118.3 (29.8) | | |
| Week 24 (% CFB) | −21.9 (1.7) | −22.1 (1.8) | −3.7 (1.6) | −18.1 (−21.4, −14.9) | −18.4 (−21.8, −15.0) |
| Week 52 - no. | 147 | 125 | 144 | | |
| Baseline mean (SD) | 117.4 (20.9) | 115.7 (24.1) | 118.1 (29.9) | | |
| Week 52 (% CFB) | −25.0 (2.0) | −26.6 (2.0) | −6.5 (1.9) | −18.5 (−22.4, −14.6) | −20.1 (−24.1, −16.1) |
| ApoCIII | | | | | |
| Week 24 - no. | 282 | 272 | 288 | | |
| Baseline mean (SD) | 10.9 (4.7) | 10.7 (5.3) | 10.5 (5.6) | | |
| Week 24 (% CFB) | −10.6 (3.6) | −14.1 (3.1) | 8.1 (3.1) | −18.7 (−27.1, −10.4) | −22.2 (−29.0, −15.4) |
| Week 52 - no. | 272 | 255 | 279 | | |
| Baseline mean (SD) | 10.9 (4.7) | 10.7 (5.5) | 10.3 (5.5) | | |
| Week 52 (% CFB) | −10.0 (3.8) | −17.1 (3.3) | 9.8 (3.3) | −19.8 (−28.4, −11.1) | −26.9 (−34.1, −19.6) |
| Non-HDL-C | | | | | |
| Week 24 - no. | 285 | 280 | 294 | | |
| Baseline mean (SD) | 135.6 (43.2) | 131.8 (44.7) | 135.7 (50.6) | | |
| Week 24 (% CFB) | −15.2 (1.5) | −17.7 (1.6) | 0.16 (1.5) | −15.4 (−18.8, −12.0) | −17.9 (−21.2, −14.5) |
| Week 52 - no. | 276 | 262 | 284 | | |
| Baseline mean (SD) | 136.1 (43.1) | 132.4 (46.7) | 135.2 (50.6) | | |
| Week 52 (% CFB) | −15.7 (1.7) | −22.1 (1.7) | −0.40 (1.6) | −15.3 (−19.0, −11.7) | −21.7 (−25.2, −18.1) |
| HDL-C | | | | | |
| Week 24 - no. | 285 | 280 | 294 | | |
| Baseline mean (SD) | 43.9 (12.5) | 43.5 (12.8) | 43.8 (13.5) | | |
| Week 24 (% CFB) | 2.7 (1.5) | 2.9 (1.5) | 1.7 (1.5) | 0.98 (−2.3, 4.2) | 1.2 (−2.1, 4.5) |
| Week 52 - no. | 276 | 262 | 284 | | |
| Baseline mean (SD) | 44.1 (12.5) | 43.6 (12.7) | 44.1 (13.3) | | |
| Week 52 (% CFB) | 4.7 (1.4) | 4.6 (1.5) | 2.7 (1.4) | 2.1 (−0.99, 5.1) | 2.0 (−1.2, 5.1) |
| HDL particles, umol/L | | | | | |
| Week 52 - no. | 266 | 252 | 275 | | |
| Baseline mean (SD) | 30.5 (6.5) | 31.0 (6.0) | 30.8 (6.2) | | |
| Week 52 (% CFB) | 5.2 (1.3) | 2.3 (1.3) | 1.6 (1.2) | 3.6 (0.80, 6.3) | 0.69 (−2.1, 3.5) |
| HDL particle size, nm | | | | | |
| Week 52 - no. | 266 | 252 | 275 | | |
| Baseline mean (SD) | 8.9 (0.46) | 9.0 (0.46) | 9.0 (0.45) | | |
| Week 52 (% CFB) | 0.90 (0.28) | 0.40 (0.28) | 0.30 (0.27) | 0.60 (−0.01, 1.2) | 0.10 (−0.51, 0.71) |
| LDL particles, nmol/L | | | | | |
| Week 52 - no. | 266 | 252 | 275 | | |
| Baseline mean (SD) | 1322.9 (438.5) | 1273.5 (440.1) | 1282.5 (476.1) | | |
| Week 52 (% CFB) | −16.8 (1.7) | −20.0 (1.7) | −0.69 (1.6) | −16.1 (−19.8, −12.4) | −19.4 (−23.1, −15.6) |
| LDL particle size, nm | | | | | |
| Week 52 - no. | 260 | 251 | 273 | | |
| Baseline mean (SD) | 20.4 (0.59) | 20.3 (0.59) | 20.4 (0.60) | | |
| Week 52 (% CFB) | −0.32 (0.17) | −0.35 (0.17) | 0.04 (0.16) | −0.36 (−0.73, 0.01) | −0.39 (−0.76, −0.02) |
| Large HDL particles, umol/L | | | | | |
| Week 52 - no. | 265 | 251 | 275 | | |
| Baseline mean (SD) | 5.5 (2.9) | 5.5 (2.9) | 5.8 (2.9) | | |
| Week 52 (% CFB) | 12.3 (5.5) | 4.5 (5.6) | 12.2 (5.3) | 0.06 (−11.9, 12.0) | −7.7 (−19.8, 4.4) |
| Large LDL particles, nmol/L | | | | | |
| Week 52 - no. | 234 | 213 | 239 | | |
| Baseline mean (SD) | 366.8 (263.0) | 330.2 (265.6) | 355.7 (257.3) | | |
| Week 52 (% CFB) | 47.8 (25.3) | 55.6 (26.0) | 86.4 (24.3) | −38.6 (−93.6, 16.3) | −30.8 (−87.0, 25.4) |

TABLE 23-continued

Change From Baseline in Lipids, Lipoproteins, and Lipid Particles at Weeks 24 and 52 (Primary Analysis Population)

|  | Least Squares Mean % CFB (Standard Error) Resmetirom 80 mg (n = 322) | Least Squares Mean % CFB (Standard Error) Resmetirom 100 mg (n = 323) | Least Squares Mean % CFB (Standard Error) Placebo (n = 321) | Least Squares Mean % CFB Difference Resmetirom 80 mg from PBO (95% CI) | Least Squares Mean % CFB Difference Resmetirom 100 mg from PBO (95% CI) |
|---|---|---|---|---|---|
| Large VLDL and chylomicron particles, nmol/L | | | | | |
| Week 52 - no. | 266 | 252 | 275 | | |
| Baseline mean (SD) | 8.2 (5.8) | 8.2 (8.9) | 8.3 (8.7) | | |
| Week 52 (% CFB) | −5.7 (4.9) | −9.1 (5.0) | 11.2 (4.7) | −16.8 (−27.5, −6.2) | −20.2 (−31.1, −9.4) |
| Medium HDL particles, umol/L | | | | | |
| Week 52 - no. | 260 | 245 | 271 | | |
| Baseline mean (SD) | 5.5 (4.1) | 5.7 (4.6) | 5.1 (4.1) | | |
| Week 52 (% CFB) | 88.2 (28.0) | 130.2 (28.7) | 65.1 (27.1) | 23.1 (−38.2, 84.4) | 65.2 (2.9, 127.5) |
| Medium VLDL particles, nmol/L | | | | | |
| Week 52 - no. | 253 | 240 | 260 | | |
| Baseline mean (SD) | 25.0 (25.2) | 23.2 (25.6) | 23.1 (27.6) | | |
| Week 52 (% CFB) | −18.7 (52.0) | −27.4 (53.5) | 115.8 (50.6) | −134.5 (−249.6, −19.5) | −143.2 (−259.8, −26.7) |
| Small LDL particles, nmol/L | | | | | |
| Week 52 - no. | 266 | 252 | 275 | | |
| Baseline mean (SD) | 880.7 (336.3) | 882.0 (360.3) | 850.0 (356.9) | | |
| Week 52 (% CFB) | −3.3 (9.2) | 6.6 (9.5) | 21.7 (8.9) | −25.0 (−45.2, −4.7) | −15.0 (−35.5, 5.5) |
| Small VLDL particles, nmol/L | | | | | |
| Week 52 - no. | 260 | 250 | 270 | | |
| Baseline mean (SD) | 25.8 (15.0) | 27.1 (17.0) | 27.4 (15.3) | | |
| Week 52 (% CFB) | 62.9 (38.2) | 26.3 (39.0) | 41.6 (36.9) | 21.3 (−62.8, 105.4) | −15.3 (−100.2, 69.5) |
| VLDL and chylomicron particles, nmol/L | | | | | |
| Week 52 - no. | 266 | 252 | 275 | | |
| Baseline mean (SD) | 57.2 (32.4) | 57.1 (38.8) | 57.1 (38.2) | | |
| Week 52 (% CFB) | −11.2 (4.3) | −20.2 (4.4) | 8.2 (4.1) | −19.4 (−28.8, −10.0) | −28.4 (−37.9, −18.9) |
| VLDL particle size, nm | | | | | |
| Week 52 - no. | 266 | 252 | 274 | | |
| Baseline mean (SD) | 55.5 (6.5) | 55.3 (6.9) | 54.7 (7.3) | | |
| Week 52 (% CFB) | 1.9 (0.92) | 3.4 (0.94) | 2.0 (0.89) | −0.05 (−2.1, 2.0) | 1.4 (−0.65, 3.4) |
| VLDL and chylomicron triglycerides, mg/dl | | | | | |
| Week 52 - no. | 266 | 252 | 275 | | |
| Baseline mean (SD) | 114.1 (68.6) | 113.5 (92.1) | 113.6 (91.7) | | |
| Week 52 (% CFB) | −14.7 (3.1) | −17.9 (3.1) | 4.9 (3.0) | −19.6 (−26.3, −12.9) | −22.8 (−29.6, −16.0) |

ApoB, apolipoprotein B; ApoCIII, apolipoprotein CIII; CFB, change from baseline; CI, confidence interval; HDL, high-density lipoprotein; LDL, low-density lipoprotein; LS, least squares; PBO, placebo; RLP, remnant-like protein; SD, standard deviation; SE, standard error; VLDL, very low-density lipoprotein. Confidence interval widths have not been adjusted for multiplicity and may not be used for hypothesis testing.

TABLE 24

Additional Secondary Endpoints (Primary Analysis population)

|  | Least Squares Mean % CFB (Standard Error) Resmetirom 80 mg (n = 321) | Least Squares Mean % CFB (Standard Error) Resmetirom 100 mg (n = 323) | Least Squares Mean % CFB (Standard Error) Placebo (n = 321) | Least Squares Mean % CFB Difference Resmetirom 80 mg from PBO (95% CI) | Least Squares Mean % CFB Difference Resmetirom 100 mg from PBO (95% CI) |
|---|---|---|---|---|---|
| LDL-C (mg/dL) | | | | | |
| Week 24* - no. | 285 | 280 | 294 | | |
| Baseline mean (SD) | 106.6 (37.8) | 102.9 (37.6) | 106.2 (41.4) | | |
| Week 24 (% CFB) | −13.6 (1.7) | −16.3 (1.7) | 0.11 (1.7) | −13.7 (−17.5, −10.0) | −16.4 (−20.1, −12.6) |
| p value | | | | <0.001 | <0.001 |
| Week 52 - no. | 276 | 262 | 284 | | |
| Baseline mean (SD) | 106.9 (37.9) | 102.9 (36.8) | 106.1 (41.7) | | |
| Week 52 (% CFB) | 13.7 (1.8) | −19.5 (1.8) | −0.4 (1.7) | −13.3 (−17.3, −9.3) | −19.0 (−23.0, −15.1) |

TABLE 24-continued

Additional Secondary Endpoints (Primary Analysis population)

| | Least Squares Mean % CFB (Standard Error) Resmetirom 80 mg (n = 321) | Least Squares Mean % CFB (Standard Error) Resmetirom 100 mg (n = 323) | Least Squares Mean % CFB (Standard Error) Placebo (n = 321) | Least Squares Mean % CFB Difference Resmetirom 80 mg from PBO (95% CI) | Least Squares Mean % CFB Difference Resmetirom 100 mg from PBO (95% CI) |
|---|---|---|---|---|---|
| ApoB (U/L) | | | | | |
| Week 24 - no. | 285 | 280 | 294 | | |
| Baseline mean (SD) | 98.4 (28.1) | 95.9 (28.3) | 97.5 (32.1) | | |
| Week 24 (% CFB) | −16.8 (1.3) | 19.8 (1.3) | 0.39 (1.3) | −17.2 (−20.0, −14.4) | −20.2 (−22.9, −17.4) |
| Week 52 - no. | 276 | 262 | 284 | | |
| Baseline mean (SD) | 98.5 (27.6) | 95.6 (27.8) | 97.1 (32.1) | | |
| Week 52 (% CFB) | 16.2 (1.5) | 22.3 (1.5) | 0.59 (1.4) | −16.8 (−20.0, −13.7) | −22.9 (−26.0, −19.7) |
| Triglycerides (mg/dL) (baseline triglycerides >150 mg/dL) | | | | | |
| Week 24 - no. | 170 | 146 | 144 | | |
| Baseline mean (SD) | 237.9 (120.7) | 244.7 (132.8) | 261.5 (146.0) | | |
| Week 24 (% CFB) | 22.7 (4.0) | −21.7 (4.3) | −2.6 (4.1) | −20.1 (−28.3, −11.8) | −19.1 (−27.8, −10.3) |
| Week 52 - no. | 165 | 134 | 140 | | |
| Baseline mean (SD) | 241.0 (122.4) | 252.1 (160.2) | 256.5 (145.7) | | |
| Week 52 (% CFB) | −22.5 (4.2) | −28.4 (4.4) | −3.5 (4.2) | −19.0 (−27.9, −10.1) | −24.9 (−34.1, −15.7 |
| Lp(a) (nmol/L) (baseline Lp(a) >10 nmol/L) | | | | | |
| Week 24 - no. | 200 | 187 | 200 | | |
| Baseline mean (SD) | 62.0 (67.5) | 58.7 (64.6) | 57.9 (70.2) | | |
| Week 24 (% CFB) | 30.4 (3.8) | −35.9 (4.0) | −0.84 | 29.5 −37.6, −(21.5) | 35.1 (−43.5, −26.6) |
| Week 52 - no. | 193 | 172 | 194 | | |
| Baseline mean (SD) | 64.5 (68.4) | 57.6 (62.7) | 57.7 (70.0) | | |
| Week 52 (% CFB) | −34.0 (4.9) | −37.5 (5.6) | −5.0 (4.6) | −29.5 (−39.4, −19.6) | −32.4 (−43.1, −21.8) |
| MRI-PDFF, % fat fraction | | | | | |
| Week 16 - no. | 228 | 218 | 224 | | |
| Baseline mean (SD) | 18.2 (6.8) | 17.2 (6.5) | 17.9 (6.6) | | |
| Week 16 (% CFB) | −37.8 (2.2) | 42.1 (2.2) | 6.4 (2.2) | −31.4 (−36.3, −26.4) | −35.7 (−40.7, −30.7) |
| Week 52 - no. | 233 | 222 | 230 | | |
| Baseline mean (SD) | 18.2 (6.8) | 17.2 (6.7) | 17.9 (6.6) | | |
| Week 52 (% CFB) | −35.4 (2.8) | 46.6 (2.8) | −8.7 (2.7) | −26.7 (−32.9, −20.6) | −37.9 (−44.2, −31.7) |
| ALT (U/L)* | | | | | |
| Baseline - no. | 265 | 264 | 244 | | |
| Baseline mean (SD) | 59.1 (25.4) | 65.4 (33.5) | 63.1 (26.7) | | |
| Week 48 (CFB) | −20.4 (2.2) | 24.8 (2.3) | 8.5 (2.3) | | |
| Week 48 (% CFB) | −26.6 (3.7) | −33.2 (3.9) | −6.9 (3.8) | −19.7 (−27.7, −11.6) | −26.3 (−34.5, −18.1) |
| AST (U/L) | | | | | |
| Baseline - no. | 265 | 264 | 244 | | |
| Baseline mean (SD) | 41.5 (18.6) | 48.5 (26.0) | 44.9 (20.8) | | |
| Week 48 (CFB) | −13.9 (1.7) | 15.8 (1.7) | 6.0 (1.7) | | |
| Week 48 (% CFB) | −22.1 (3.9) | 28.3 (3.9) | −2.9 (3.8) | −19.3 (−27.2, −11.3) | −25.4 (−33.5, −17.4) |
| GGT (U/L) | | | | | |
| Baseline - no. | 265 | 264 | 244 | | |
| Baseline mean (SD) | 87.3 (122.2) | 92.4 (109.4) | 80.1 (87.2) | | |
| Week 48 (CFB) | −31.3 (3.9) | 32.7 (4.0) | 7.3 (3.9) | | |
| Week 48 (% CFB) | −25.0 (5.5) | 31.9 (6.3) | 3.3 (5.2) | −28.3 (−37.3, −19.3) | −35.2 (−45.5, −25.0) |
| FibroScan CAP, dB/m | | | | | |
| Week 52 - no. | 256 | 252 | 267 | | |
| Baseline mean (SD) | 346.7 (37.4) | 348.4 (40.3) | 347.0 (36.9) | | |
| Week 52 (CFB) | −39.6 (4.3) | −41.3 (4.4) | −14.5 (4.1) | −25.2 (−34.5, −15.9) | −26.9 (−36.2, −17.5) |

TABLE 24-continued

Additional Secondary Endpoints (Primary Analysis population)

| | Least Squares Mean % CFB (Standard Error) Resmetirom 80 mg (n = 321) | Least Squares Mean % CFB (Standard Error) Resmetirom 100 mg (n = 323) | Least Squares Mean % CFB (Standard Error) Placebo (n = 321) | Least Squares Mean % CFB Difference Resmetirom 80 mg from PBO (95% CI) | Least Squares Mean % CFB Difference Resmetirom 100 mg from PBO (95% CI) |
|---|---|---|---|---|---|
| FibroScan VCTE/LSM, kPa | | | | | |
| F1B - no. | 12 | 10 | 17 | | |
| Baseline mean (SD) | 11.1 (5.5) | 12.5 (5.7) | 10.9 (4.4) | | |
| Week 52 (CFB) | −3.7 (1.0) | −3.7 (1.3) | −0.62 (0.87) | −3.1 (−5.8, −0.33) | −3.1 (−6.1, −0.02) |
| Responder Analysis - no. | 12 | 10 | 17 | | |
| Improving >25% - no. (%) | 6 (50.0) | 7 (70.0) | 4 (23.5) | 3.7 (0.70, 19.1) | 10.0 (1.3, 75.3) |
| Improving ≥30% - no. (%) | 5 (41.7) | 6 (60.0) | 4 (23.5) | 2.7 (0.50, 14.0) | 4.5 (0.78, 25.5) |
| Worsening ≥25% - no. (%) | 1 (8.3) | 0 | 5 (29.4) | 0.17 (0.02, 2.0) | 0 |
| Worsening ≥30% - no. (%) | 1 (8.3) | 0 | 5 (29.4) | 0.17 (0.02, 2.0) | 0 |
| F2 - no. | 84 | 76 | 89 | | |
| Baseline mean (SD) | 11.6 (5.5) | 10.9 (3.3) | 10.7 (3.3) | | |
| Week 52 (CFB) | −2.3 (0.44) | −2.4 (0.46) | 1.3 (0.43) | 1.1 (−2.3, 0.12) | −1.2 (−2.4, 0.04) |
| Responder Analysis - no. | 84 | 76 | 89 | | |
| Improving ≥25% - no. (%) | 37 (44.0) | 38 (50.0) | 31 (34.8) | 1.5 (0.80, 2.7) | 1.9 (1.0, 3.6) |
| Improving ≥30% - no. (%) | 28 (33.3) | 31 (40.8) | 23 (25.8) | 1.4 (0.75, 2.8) | 2.0 (1.0, 3.8) |
| Worsening ≥25% - no. (%) | 10 (11.9) | 8 (10.5) | 13 (14.6) | 0.80 (0.33, 1.9) | 0.68 (0.26, 1.8) |
| Worsening ≥30% - no. (%) | 7 (8.3) | 5 (6.6) | 12 (13.5) | 0.57 (0.21, 1.5) | 0.47 (0.16, 1.4) |
| F3 - no. | 163 | 167 | 162 | | |
| Baseline mean (SD) | 14.2 (6.2) | 14.7 (8.4) | 13.8 (5.1) | | |
| Week 52 (CFB) | 2.0 (0.41) | −3.2 (0.41) | 1.1 (0.41) | −0.86 (−2.0, 0.25) | −2.1 (−3.2, −1.0) |
| Responder Analysis - no. | 163 | 167 | 162 | | |
| Improving ≥25% - n (%) | 67 (41.1) | 80 (47.9) | 43 (26.5) | 2.0 (1.2, 3.1) | 2.5 (1.6, 4.0) |
| Improving ≥30% - n (%) | 56 (34.4) | 65 (38.9) | 29 (17.9) | 2.5 (1.5, 4.2) | 2.9 (1.7, 4.7) |
| Worsening ≥25% - n (%) | 24 (14.7) | 18 (10.8) | 30 (18.5) | 0.77 (0.43, 1.4) | 0.53 (0.28, 1.0) |
| Worsening ≥30% - n (%) | 21 (12.9) | 17 (10.2) | 21 (13.0) | 1.0 (0.53, 1.9) | 0.76 (0.39, 1.5) |
| MRE, kPa | | | | | |
| F1B - no. | 7 | 10 | 11 | | |
| Baseline mean (SD) | 3.1 (0.53) | 2.8 (0.44) | 3.2 (0.71) | | |
| Week 52 (% CFB) | −5.7 (7.2) | 2.4 (6.2) | 7.5 (5.5) | −13.2 (−31.3, 4.8) | −5.1 (−21.9, 11.8) |
| Responder Analysis - no. | 5 | 5 | 6 | | |
| ≥19% increase from BL - no. (%) | 0 | 1 (20.0) | 2 (33.3) | | 0.50 (0.03, 9.0) |
| ≥19% reduction from BL - no. (%) | 1 (20.0) | 0 | 0 | NA | — |
| F2 - no. | 47 | 42 | 61 | | |
| (0.71) | | | | | |
| Baseline mean (SD) | 3.0 (0.69) | 3.0 (0.71) | 3.0 (0.61) | | |
| Week 52 (% CFB) | −1.9 (3.1) | 1.1 (3.2) | 2.1 (2.7) | 4.0 (−12.0, 4.0) | 0.99 (−9.2, 7.3) |
| Responder Analysis - no. | 20 | 22 | 33 | | |
| ≥19% increase from BL - no. (%) | 0 | 0 | 2 (6.1) | 0 | 0 |
| ≥19% reduction from BL - no. (%) | 7 (35.0) | 5 (22.7) | 8 (24.2) | 1.6 (0.45, 5.6) | 0.89 (0.25, 3.2) |
| F3 - no. | 94 | 96 | 91 | | |
| Baseline mean (SD) | 3.8 (0.92) | 4.0 (1.1) | 3.9 (1.1) | | |
| Week 52 (% CFB) | −8.9 (1.9) | 5.2 (1.9) | −0.38 (1.9) | −8.6 (−13.7, −3.4) | −4.8 (−10.0, 0.30) |
| Responder Analysis - no. | 84 | 86 | 80 | | |
| ≥19% increase from BL - no. (%) | 3 (3.6) | 7 (8.1) | 13 (16.3) | 0.19 (0.05, 0.70) | 0.46 (0.17, 1.2) |
| ≥19% reduction from BL - no. (%) | 22 (26.2) | 27 (31.4) | 10 (12.5) | 2.5 (1.1, 5.5) | 3.2 (1.4, 7.2) |
| Enhanced liver fibrosis score (baseline enhanced liver fibrosis score ≥9.8) | | | | | |
| no. | 122 | 123 | 122 | | |
| Baseline mean (SD) | 10.5 (0.59) | 10.5 (0.53) | 10.5 (0.59) | | |
| Week 52 (CFB) | 0.34 (0.092) | −0.35 (0.094) | −0.11 (0.091) | −0.22 (−0.40, −0.05) | −0.24 (−0.41, −0.07) |
| PIIINP, ng/mL (baseline PIIINP ≥9 ng/mL) | | | | | |
| no. | 193 | 200 | 200 | | |
| Baseline mean (SD) | 14.0 (4.4) | 13.6 (4.4) | 13.4 (3.9) | | |
| Week 52 (% CFB) | −10.7 (2.8) | 10.3 (2.7) | −0.99 (2.6) | −9.7 (−15.5, −3.8) | −9.3 (−15.1, −3.5) |
| Week 52 (CFB) | 2.0 (0.38) | −2.1 (0.37) | −0.66 (0.36) | −1.4 (−2.2, −0.56) | −1.4 (−2.2, −0.61) |

TABLE 24-continued

Additional Secondary Endpoints (Primary Analysis population)

| | Least Squares Mean % CFB (Standard Error) Resmetirom 80 mg (n = 321) | Least Squares Mean % CFB (Standard Error) Resmetirom 100 mg (n = 323) | Least Squares Mean % CFB (Standard Error) Placebo (n = 321) | Least Squares Mean % CFB Difference Resmetirom 80 mg from PBO (95% CI) | Least Squares Mean % CFB Difference Resmetirom 100 mg from PBO (95% CI) |
|---|---|---|---|---|---|
| TIMP-I, ng/ml (baseline TIMP-I ≥240 ng/ml) | | | | | |
| no. | 174 | 172 | 183 | | |
| Baseline mean (SD) | 304.0 (64.7) | 309.3 (73.4) | 303.7 (64.0) | | |
| Week 52 (% CFB) | −9.3 (2.0) | −10.1 (2.0) | −3.6 (1.9) | −5.7 (−9.6, −1.8) | −6.5 (−10.4, −2.6) |
| Week 52 (CFB) | −31.0 (6.2) | 35.7 (6.2) | −13.3 (6.0) | −17.7 (−30.1, −5.3) | −22.3 (−34.8, −9.9) |
| Hyaluronic acid, ug/L (baseline hyaluronic acid ≥50 ng/ml) | | | | | |
| no. | 156 | 152 | 155 | | |
| Baseline mean (SD) | 114.9 (99.2) | 122.9 (88.4) | 125.3 (111.0) | | |
| Week 52 (% CFB) | 17.2 (7.8) | 11.8 (8.1) | 24.8 (7.8) | −7.6 (−23.1, 7.8) | −13.0 (−28.5, 2.5) |
| Week 52 (CFB) | 1.1 (9.7) | −2.9 (10.1) | 0.55 (9.7) | 0.58 (−18.7, 19.9) | −3.5 (−22.9, 16.0) |
| CK-18, U/L | | | | | |
| no. | 279 | 264 | 277 | | |
| Baseline mean (SD) | 834.8 (476.3) | 849.2 (520.3) | 857.9 (519.0) | | |
| Week 52 (CFB) | −278.2 (29.2) | 309.5 (29.8) | −143.9 (28.5) | −134.3 (−198.1, −70.5) | −165.7 (−230.3, −101.0) |
| Adiponectin, ug/mL | | | | | |
| no. | 277 | 266 | 279 | | |
| Baseline mean (SD) | 4.1 (2.6) | 4.2 (2.5) | 3.9 (2.3) | | |
| Week 52 (CFB) | 0.86 (0.19) | 1.1 (0.19) | −0.10 (0.18) | 0.97 (0.56, 1.4) | 1.3 (0.83, 1.7) |
| rT3, ng/dL | | | | | |
| no. | 278 | 269 | 282 | | |
| Baseline mean (SD) | 18.5 (5.4) | 19.2 (6.2) | 18.4 (5.6) | | |
| Week 52 (CFB) | 4.6 (0.31) | 5.1 (0.32) | 0.17 (0.30) | −4.7 (−5.4, −4.1) | 5.2 (−5.9, −4.6) |
| Liver volume | | | | | |
| Week 16 - no. | 229 | 217 | 226 | | |
| Baseline mean (SD) | 2447.0 (615.7) | 2376.0 (642.8) | 2404.5 (666.0) | | |
| Week 16 (% CFB) | −18.8 (0.90) | 21.4 (0.91) | −0.29 (0.87) | 18.5 (−20.5, −16.5) | −21.1 (−23.1, −19.1) |
| Week 52 - no. | 235 | 225 | 235 | | |
| Baseline mean (SD) | 2410.1 (598.9) | 2368.8 (645.5) | 2406.6 (683.9) | | |
| Week 52 (% CFB) | −21.6 (1.1) | 25.8 (1.1) | −1.0 (1.0) | −20.5 (−22.9, −18.2) | 24.8 (−27.2, −22.4) |
| Spleen volume | | | | | |
| Week 16 - no. | 229 | 217 | 226 | | |
| Baseline mean (SD) | 373.4 (170.6) | 357.2 (164.9) | 361.8 (193.5) | | |
| Week 16 (% CFB) | −2.4 (0.95) | 3.6 (0.96) | 1.5 (0.92) | −3.9 (−6.0, −1.8) | −5.0 (−7.2, −2.9) |
| Week 52 - no. | 235 | 225 | 235 | | |
| Baseline mean (SD) | 364.0 (168.3) | 355.8 (163.8) | 360.2 (189.8) | | |
| Week 52 (% CFB) | −5.9 (1.1) | −6.1 (1.1) | 3.2 (1.1) | −9.0 (−11.5, −6.5) | −9.3 (−11.8, −6.7) |

*Key secondary endpoint.
multiply imputed values. Direct LDL-C was measured.
CI, confidence interval;
NAS, nonalcoholic fatty liver disease activity score;
NASH, nonalcoholic steatohepatitis;
PBO, placebo.
BL, baseline;
CAP, controlled attenuation parameter;
CFB, change from baseline;

TABLE 24-continued

Additional Secondary Endpoints (Primary Analysis population)

| | Least Squares Mean % CFB (Standard Error) Resmetirom 80 mg (n = 321) | Least Squares Mean % CFB (Standard Error) Resmetirom 100 mg (n = 323) | Least Squares Mean % CFB (Standard Error) Placebo (n = 321) | Least Squares Mean % CFB Difference Resmetirom 80 mg from PBO (95% CI) | Least Squares Mean % CFB Difference Resmetirom 100 mg from PBO (95% CI) |
|---|---|---|---|---|---|

CI, confidence interval;
CK-18, cytokeratin 18;
FIB-4, fibrosis-4 index;
LS, least squares;
LSM, liver stiffness measurement;
MRE, magnetic resonance elastography;
MRI-PDFF, magnetic resonance imaging-proton density fat fraction;
OR, odds ratio;
rT3, reverse triiodothyronine;
VCTE, vibration-controlled transient elastography;
SD, standard deviation;
SE, standard error.
Confidence interval widths have not been adjusted for multiplicity and may not be used for hypothesis testing.

TABLE 25

Adverse Events Reported in ≥5% of Patients (Safety Population)

| Preferred Term, no. (%) | Resmetirom 80 mg (n = 322) | Resmetirom 100 mg (n = 323) | Placebo (n = 321) |
|---|---|---|---|
| Abdominal pain upper | 23 (7.1) | 27 (8.4) | 29 (9.0) |
| Headache | 30 (9.3) | 25 (7.7) | 27 (8.4) |
| Vomiting | 28 (8.7) | 35 (10.8) | 17 (5.3) |
| Type 2 diabetes | 24 (7.5) | 26 (8.0) | 25 (7.8) |
| Abdominal pain | 23 (7.1) | 29 (9.0) | 18 (5.6) |
| Constipation | 21 (6.5) | 28 (8.7) | 17 (5.3) |
| Muscle spasms | 14 (4.3) | 22 (6.8) | 22 (6.9) |
| Hypertension | 16 (5.0) | 13 (4.0) | 25 (7.8) |
| Dizziness | 20 (6.2) | 19 (5.9) | 11 (3.4) |
| Nasopharyngitis | 14 (4.3) | 20 (6.2) | 14 (4.4) |
| Pain in extremity | 12 (3.7) | 12 (3.7) | 23 (7.2) |
| Upper respiratory tract infection | 23 (7.1) | 8 (2.5) | 17 (5.3) |
| Rash | 12 (3.7) | 21 (6.5) | 12 (3.7) |
| Cough | 14 (4.3) | 18 (5.6) | 12 (3.7) |
| Abdominal distension | 14 (4.3) | 13 (4.0) | 17 (5.3) |
| Procedural pain | 16 (5.0) | 9 (2.8) | 19 (5.9) |
| Gastrooesophageal reflux disease | 16 (5.0) | 7 (2.2) | 8 (2.5) |
| Decreased appetite | 5 (1.6) | 16 (5.0) | 4 (1.2) |
| Sinusitis | 10 (3.1) | 13 (4.0) | 17 (5.3) |

TABLE 26

Serious Adverse Events

| System Organ Class* | Resmetirom 80 mg (N = 322) n (%) | Resmetirom 100 mg (N = 323) n (%) | Placebo (N = 321) n (%) |
|---|---|---|---|
| Patients with at least one TE-SAEs | 35 (10.9) | 41 (12.7) | 37 (11.5) |
| Infections and infestations | 12 (3.7) | 5 (1.5) | 13 (4.0) |
| COVID-19 | 1 (0.3) | 1 (0.3) | 2 (0.6) |
| COVID-19 pneumonia | 2 (0.6) | 0 | 3 (0.9) |
| Gastrointestinal disorders | 3 (0.9) | 7 (2.2) | 7 (2.2) |
| Acute Gallstone-related disorders# | 3 (0.9) | 3 (0.9) | 1 (0.3) |
| Injury, poisoning and procedural complications | 3 (0.9) | 8 (2.5) | 4 (1.2) |
| Post procedural haemorrhage | 1 (0.3) | 1 (0.3) | 2 (0.6) |
| Cardiac disorders | 3 (0.9) | 3 (0.9) | 7 (2.2) |
| Respiratory, thoracic and mediastinal disorders | 3 (0.9) | 4 (1.2) | 16 (1.9) |
| Musculoskeletal and connective tissue disorders | 7 (2.2) | 1 (0.3) | 4 (1.2) |
| Nervous system disorders | 3 (0.9) | 2 (0.6) | 6 (1.9) |
| General disorders and administration site conditions | 2 (0.6) | 5 (1.5) | 3 (0.9) |

*Included SAEs where category was not unblinding

Includes a combination of acute cholecystitis, gallstone related pancreatitis, or choledo-lithiasis. Individual SAEs that were unblinding for treatment of individual patients are not shown because MAESTRO-NASH is a blinded ongoing 54-month outcome study.

TABLE 27

Malignancies

| | Resmetirom 80 mg (N = 322) n (%) | Resmetirom 100 mg (N = 323) n (%) | Placebo (N = 321) n (%) |
|---|---|---|---|
| Patients with any malignancy | 4 (1.2) | 11 (3.4) | 12 (3.7) |
| Basal cell carcinoma | 2 (0.6) | 3 (0.9) | 2 (0.6) |
| Breast carcinoma | 1 (0.3) | 2 (0.6) | 1 (0.3) |
| Malignant melanoma | 0 | 1 (0.3) | 1 (0.3) |
| Skin cancer (squamous cell) | 1 (0.3) | 1 (0.3) | 3 (0.9) |

*Malignancies that were unblinding for treatment of individual patients are not shown because MAESTRO-NASH is a blinded ongoing 54-month outcome study.

TABLE 28

Change From Baseline in Metabolic Factors at Week 52
(Primary Analysis Population)

| | Least Squares Mean % CFB (Standard Error) Resmetirom 80 mg (n = 322) | Least Squares Mean % CFB (Standard Error) Resmetirom 100 mg (n = 323) | Least Squares Mean % CFB (Standard Error) Placebo (n = 321) | Least Squares Mean % CFB Difference Resmetirom 80 mg from PBO (95% CI) | Least Squares Mean % CFB Difference Resmetirom 100 mg from PBO (95% CI) |
|---|---|---|---|---|---|
| Body weight, kg | | | | | |
| no. | 281 | 265 | 286 | | |
| Baseline mean (SD) | 98.6 (21.9) | 102.1 (22.6) | 99.5 (22.4) | | |
| Week 52 (% CFB) | −1.2 (0.37) | −1.8 (0.38) | 0.87 (0.36) | 0.35 (−1.2, 0.45) | −0.88 (−1.7, −0.07) |
| SBP, mmHg | | | | | |
| no. | 281 | 265 | 286 | | |
| Baseline mean (SD) | 129.7 (13.6) | 129.8 (15.1) | 130.2 (14.4) | | |
| Week 52 (% CFB) | −1.9 (0.70) | 2.1 (0.71) | 0.74 (0.67) | 2.7 (−4.2, −1.2) | 2.9 (−4.4, −1.4) |
| DBP, mmHg | | | | | |
| no. | 281 | 265 | 286 | | |
| Baseline mean (SD) | 79.4 (8.8) | 79.1 (9.7) | 80.8 (9.5) | | |
| Week 52 (% CFB) | −1.6 (0.71) | −2.0 (0.72) | −0.17 (0.69) | −1.5 (−3.0, 0.08) | −1.9 (−3.4, −0.32) |
| Heart rate, beats/min (based on electrocardiogram) | | | | | |
| no. | 278 | 267 | 280 | | |
| Baseline mean (SD) | 70.4 (10.7) | 69.0 (10.4) | 69.7 (10.9) | | |
| Week 52 (% CFB) | −1.7 (0.83) | 2.6 (0.84) | −0.19 (0.81) | −1.5 (−3.3, 0.28) | −2.4 (−4.2, −0.57) |
| Glucose (mg/dL) | | | | | |
| no. | 277 | 261 | 285 | | |
| Baseline mean (SD) | 131.7 (40.8) | 129.4 (35.0) | 128.4 (38.8) | | |
| Week 52 (% CFB) | 0.72 (1.8) | −3.4 (1.9) | 2.2 (1.7) | 2.9 (−6.8, 1.0) | 5.6 (−9.5, −1.6) |
| Insulin (mIU/L) | | | | | |
| no. | 277 | 261 | 285 | | |
| Baseline mean (SD) | 34.5 (24.5) | 31.5 (20.1) | 33.2 (30.6) | | |
| Week 52 (% CFB) | 2.8 (5.0) | 3.3 (5.1) | 5.1 (4.8) | 2.3 (−13.0, 8.4) | 1.8 (−12.6, 9.1) |
| HOMA-IR | | | | | |
| no. | 276 | 261 | 285 | | |
| Baseline mean (SD) | 11.8 (11.1) | 10.3 (8.0) | 11.0 (12.7) | | |
| Week 52 (% CFB) | 9.1 (7.1) | 3.4 (7.2) | 14.4 (6.8) | −5.3 (−20.5, 9.9) | 11.0 (−26.4, 4.4) |
| HbA1c (%) | | | | | |
| no. | 277 | 262 | 285 | | |
| Baseline mean (SD) | 6.6 (1.1) | 6.6 (1.1) | 6.5 (1.0) | | |
| Week 52 (% CFB) | 1.7 (0.88) | 1.5 (0.89) | 1.5 (0.85) | 0.19 (−1.7, 2.1) | 0.05 (−1.9, 1.9) |

CFB, change from baseline;
CI, confidence interval;
ECG, electrocardiogram;
PBO, placebo;
SD, standard deviation;
SE, standard error.
Confidence interval widths have not been adjusted for multiplicity and may not be used for hypothesis testing.

TABLE 29

Change From Baseline in Sex Hormones at Week 52 (Safety Population)

| | Least Squares Mean % CFB or CFB (Standard Error) Resmetirom 80 mg (n = 322) | Least Squares Mean % CFB or CFB (Standard Error) Resmetirom 100 mg (n = 323) | Least Squares Mean % CFB or CFB (Standard Error) Placebo (n = 321) | Least Squares Mean Difference Resmetirom 80 mg from PBO (95% CI) | Mean Difference Least Squares Resmetirom 100 mg from PBO (95% CI) |
|---|---|---|---|---|---|
| Estradiol, ng/L (female) | | | | | |
| no. | 160 | 147 | 155 | | |
| Baseline mean (SD) | 28.6 (37.0) | 32.1 (56.3) | 32.8 (65.9) | | |
| Week 52 CFB (Standard Error) | 17.7 (8.0) | 30.6 (8.3) | 1.8 (8.0) | 15.9 (−1.3, 33.1) | 28.8 (11.3, 46.3) |
| Estradiol, ng/L (male) | | | | | |
| no. | 118 | 118 | 128 | | |
| Baseline mean (SD) | 28.0 (11.6) | 27.6 (10.9) | 29.3 (12.1) | | |
| Week 52 CFB (Standard Error) | 8.9 (1.3) | 11.0 (1.3) | −0.15 (1.2) | 9.0 (6.3, 11.8) | 11.2 (8.4, 13.9) |
| FSH, mIU/mL (female) | | | | | |
| no. | 160 | 148 | 155 | | |
| Baseline mean (SD) | 39.2 (25.7) | 39.3 (22.6) | 39.8 (23.2) | | |
| Week 52 CFB (Standard Error) | −0.54 (0.89) | 0.63 (0.92) | −1.3 (0.89) | 0.79 (−1.1, 2.7) | 2.0 (0.02, 3.9) |
| FSH, mIU/mL (male) | | | | | |
| no. | 118 | 119 | 128 | | |
| Baseline mean (SD) | 8.1 (7.7) | 7.8 (9.7) | 7.2 (6.5) | | |
| Week 52 CFB (Standard Error) | 1.1 (0.24) | 1.7 (0.24) | 0.01 (0.22) | 1.1 (0.57, 1.6) | 1.7 (1.1, 2.2) |
| LH, mIU/mL (female) | | | | | |
| no. | 160 | 148 | 155 | | |
| Baseline mean (SD) | 23.5 (14.1) | 24.2 (13.2) | 23.3 (12.0) | | |
| Week 52 CFB (Standard Error) | −0.93 (0.69) | 0.80 (0.72) | 0.60 (0.70) | −0.33 (−1.8, 1.2) | 1.4 (−0.11, 2.9) |
| LH, mIU/mL (male) | | | | | |
| no. | 118 | 119 | 128 | | |
| Baseline mean (SD) | 6.3 (4.1) | 6.0 (4.6) | 6.1 (4.0) | | |
| Week 52 CFB (Standard Error) | 1.7 (0.30) | 1.9 (0.30) | −0.10 (0.28) | 1.8 (1.1, 2.4) | 2.0 (1.4, 2.7) |
| Testosterone, ug/L (female) | | | | | |
| no. | 160 | 147 | 156 | | |
| Baseline mean (SD) | 0.2 (0.17) | 0.2 (0.16) | 0.1 (0.24) | | |
| Week 52 CFB (Standard Error) | 0.15 (0.019) | 0.19 (0.020) | 0 (0.019) | 0.15 (0.10, 0.19) | 0.19 (0.14, 0.23) |
| Testosterone, ug/L (male) | | | | | |
| no. | 118 | 118 | 128 | | |
| Baseline mean (SD) | 3.5 (1.6) | 3.7 (2.0) | 3.3 (1.5) | | |
| Week 52 CFB (Standard Error) | 2.6 (0.26) | 3.5 (0.25) | 0.44 (0.24) | 2.2 (1.6, 2.8) | 3.0 (2.5, 3.6) |
| Free testosterone, nmol/L (female) | | | | | |
| no. | 121 | 110 | 106 | | |
| Baseline mean (SD) | 0 (0.01) | 0 (0.01) | 0 (0.01) | | |
| Week 52 CFB (Standard Error) | 0 (0.001) | 0 (0.001) | 0 (0.001) | 0 | 0 |
| Free testosterone, nmol/L (male) | | | | | |
| no. | 116 | 108 | 127 | | |
| Baseline mean (SD) | 0.2 (0.09) | 0.2 (0.11) | 0.2 (0.07) | | |
| Week 52 CFB (Standard Error) | 0.04 (0.009) | 0.03 (0.009) | 0.02 (0.008) | 0.02 (0, 0.04) | 0.01 (−0.01, 0.03) |
| SHBG, nmol/L | | | | | |
| no. | 275 | 262 | 283 | | |
| Baseline mean (SD) | 48.8 (56.7) | 45.6 (37.9) | 47.2 (43.7) | | |
| Week 52 % CFB (Standard Error) | 157.5 (10.2) | 217.4 (10.3) | 9.0 (9.8) | 148.5 (126.6, 170.4) | 208.4 (186.3, 230.5) |
| Week 52 CFB (Standard Error) | 60.2 (4.0) | 80.7 (4.1) | 1.3 (3.9) | 58.9 (50.3, 67.5) | 79.4 (70.7, 88.1) |

TABLE 29-continued

Change From Baseline in Sex Hormones at Week 52 (Safety Population)

| | Least Squares Mean % CFB or CFB (Standard Error) Resmetirom 80 mg (n = 322) | Least Squares Mean % CFB or CFB (Standard Error) Resmetirom 100 mg (n = 323) | Least Squares Mean % CFB or CFB (Standard Error) Placebo (n = 321) | Least Squares Mean Difference Resmetirom 80 mg from PBO (95% CI) | Mean Difference Least Squares Resmetirom 100 mg from PBO (95% CI) |
|---|---|---|---|---|---|
| SHBG, nmol/L (female) | | | | | |
| no. | 159 | 145 | 155 | | |
| Baseline mean (SD) | 58.2 (71.7) | 48.9 (44.5) | 55.7 (54.6) | | |
| Week 52 % CFB (Standard Error) | 193.0 (15.3) | 251.8 (16.0) | 15.6 (15.5) | 177.4 (144.3, 210.5) | 236.2 (202.3, 270.0) |
| Week 52 CFB (Standard Error) | 74.1 (6.0) | 94.0 (6.3) | 0.82 (6.1) | 73.3 (60.3, 86.2) | 93.2 (79.9, 106.5) |
| SHBG, nmol/L (male) | | | | | |
| no. | 116 | 117 | 128 | | |
| Baseline mean (SD) | 36.0 (17.2) | 41.4 (27.1) | 37.0 (20.8) | | |
| Week 52 % CFB (Standard Error) | 108.0 (11.2) | 174.0 (10.9) | 0.74 (10.1) | 107.3 (83.4, 131.2) | 173.3 (149.4, 197.2) |
| Week 52 CFB (Standard Error) | 41.9 (4.2) | 60.8 (4.1) | 1.5 (3.8) | 40.4 (31.4, 49.4) | 59.3 (50.3, 68.3) |

CFB, change from baseline;
CI, confidence interval;
FSH, follicle-stimulating hormone;
LH, luteinizing hormone;
LS, least squares;
SD, standard deviation;
SE, standard error;
SHBG, sex hormone binding globulin.
Confidence interval widths have not been adjusted for multiplicity and may not be used for hypothesis testing.

TABLE 30

Change From Baseline in Thyroid Hormones at Week 52 (Safety Population)

| | Least Squares Mean % CFB or CFB (Standard Error) Resmetirom 80 mg (n = 322) | Least Squares Mean % CFB or CFB (Standard Error) Resmetirom 100 mg (n = 323) | Least Squares Mean % CFB or CFB (Standard Error) Placebo (n = 321) | Least Squares Mean Difference Resmetirom 80 mg from PBO (95% CI) | Least Squares Mean Difference Resmetirom 100 mg from PBO (95% CI) |
|---|---|---|---|---|---|
| FT3, ng/L | | | | | |
| no. | 279 | 265 | 286 | | |
| Baseline mean (SD) | 3.0 (0.41) | 3.0 (0.48) | 3.0 (0.41) | | |
| Week 52 CFB (Standard Error) | −0.01 (0.030) | 0.08 (0.031) | 0.03 (0.029) | 0.02 (−0.05, 0.08) | −0.05 (−0.12, 0.01) |
| FT3, ng/L (not on thyroxine) | | | | | |
| no. | 248 | 229 | 245 | | |
| Baseline mean (SD) | 3.0 (0.40) | 3.0 (0.42) | 3.1 (0.39) | | |
| Week 52 CFB (Standard Error) | −0.01 (0.032) | −0.08 (0.033) | −0.02 (0.031) | 0.01 (−0.06, 0.08) | −0.06 (−0.13, 0.01) |
| FT3, ng/L (thyroxine-treated) | | | | | |
| no. | 31 | 36 | 41 | | |
| Baseline mean (SD) | 2.7 (0.38) | 2.8 (0.72) | 2.8 (0.41) | | |
| Week 52 CFB (Standard Error) | 0.04 (0.089) | −0.03 (0.081) | −0.02 (0.079) | 0.05 (0.13, 0.23) | 0.01 (−0.19, 0.17) |
| FT4, ng/dL | | | | | |
| no. | 279 | 265 | 286 | | |
| Baseline mean (SD) | 1.1 (0.19) | 1.1 (0.21) | 1.1 (0.17) | | |

TABLE 30-continued

Change From Baseline in Thyroid Hormones at Week 52 (Safety Population)

| | Least Squares Mean % CFB or CFB (Standard Error) Resmetirom 80 mg (n = 322) | Least Squares Mean % CFB or CFB (Standard Error) Resmetirom 100 mg (n = 323) | Least Squares Mean % CFB or CFB (Standard Error) Placebo (n = 321) | Least Squares Mean Difference Resmetirom 80 mg from PBO (95% CI) | Least Squares Mean Difference Resmetirom 100 mg from PBO (95% CI) |
|---|---|---|---|---|---|
| Week 52 % CFB (Standard Error) | 13.9 (0.96) | −18.1 (0.97) | 2.6 (0.92) | −16.6 (−18.6, −14.5) | 20.7 (−22.8, −18.6) |
| Week 52 CFB (Standard Error) | −0.17 (0.011) | −0.22 (0.011) | 0.02 (0.010) | −0.19 (−0.21, −0.16) | −0.24 (−0.26, −0.21) |
| FT4, ng/dL (not on thyroxine) | | | | | |
| no. | 248 | 229 | 245 | | |
| Baseline mean (SD) | 1.1 (0.18) | 1.1 (0.18) | 1.1 (0.16) | | |
| Week 52 % CFB (Standard Error) | −13.8 (0.97) | −17.6 (1.0) | 2.5 (0.95) | −16.3 (−18.4, −14.2 | 20.0 (−22.2, −17.9) |
| Week 52 CFB (Standard Error) | 0.16 (0.011) | −0.21 (0.011) | 0.02 (0.010) | −0.18 (−0.20, −0.16) | −0.23 (−0.25, −0.20) |
| FT4, ng/dL (thyroxine-treated) | | | | | |
| no. | 31 | 36 | 41 | | |
| Baseline mean (SD) | 1.3 (0.23) | 1.2 (0.31) | 1.2 (0.21) | | |
| Week 52 % CFB (Standard Error) | −14.0 (3.6) | 20.6 (3.3) | 3.8 (3.1) | −17.9 (−25.2, −10.5 | −24.4 (−31.6, −17.3) |
| Week 52 CFB (Standard Error) | 0.18 (0.041) | −0.26 (0.037) | 0.02 (0.036) | −0.21 (−0.29, −0.12) | 0.29 (−0.37, −0.21) |
| rT3, ng/dL | | | | | |
| no. | 1278 | 269 | 282 | | |
| Baseline mean (SD) | 18.5 (5.4) | 19.2 (6.2) | 18.4 (5.6) | | |
| Week 52 CFB (Standard Error) | −4.6 (0.31) | 5.1 (0.32) | 0.17 (0.30) | −4.73 (−5.4, −4.1) | −5.2 (−5.9, −4.6) |
| rT3, ng/dL (not on thyroxine) | | | | | |
| no. | 2247 | 232 | 244 | | |
| Baseline mean (SD) | 18.3 (5.3) | 18.7 (5.7) | 18.3 (5.6) | | |
| Week 52 CFB (Standard Error) | −4.5 (0.33) | 4.9 (0.34) | 0.19 (0.33) | −4.5 (−5.4, −3.9) | −5.1 (−5.9, −4.8) |
| rT3, ng/dL (thyroxine-treated) | | | | | |
| no. | 31 | 37 | 38 | | |
| Baseline mean (SD) | 20.7 (6.1) | 22.2 (8.1) | 19.1 (5.6) | | |
| Week 52 CFB (Standard Error) | −5.1 (0.94) | −6.3 (0.85) | −0.01 (0.84) | 5.1 (−7.1, −3.1) | −6.3 (−8.2, −4.4) |
| FT3/rT3 | | | | | |
| no. | 278 | 269 | 282 | | |
| Baseline mean (SD) | 0.18 (0.058) | 0.17 (0.054) | 0.18 (0.058) | | |
| Week 52 CFB (Standard Error) | 0.06 (0.004) | 0.06 (0.004) | 0 (0.004) | 0.06 (0.05, 0.07) | 0.07 (0.06, 0.08) |
| FT3/rT3 (not on thyroxine) | | | | | |
| no. | 247 | 232 | 244 | | |
| Baseline mean (SD) | 0.18 (0.057) | 0.18 (0.051) | 0.18 (0.057) | | |
| Week 52 CFB (Standard Error) | 0.06 (0.005) | 0.06 (0.005) | 0 (0.005) | 0.06 (0.05, 0.07) | 0.07 (0.06, 0.08) |
| FT3/rT3 (thyroxine-treated) | | | | | |
| no. | 31 | 37 | 38 | | |
| Baseline mean (SD) | 0.14 (0.051) | 0.14 (0.058) | 0.16 (0.065) | | |
| Week 52 CFB (Standard Error) | 0.05 (0.011) | 0.06 (0.010) | −0.01 (0.010) | 0.06 (0.04, 0.09) | 0.06 (0.04, 0.09) |
| TSH, mIU/L | | | | | |
| no. | 279 | 265 | 286 | | |
| Baseline mean (SD) | 2.0 (1.1) | 2.1 (1.2) | 2.0 (1.1) | | |
| Week 52 CFB (Standard Error) | −0.28 (0.059) | −0.20 (0.060) | −0.10 (0.057) | −0.18 (−0.31, −0.05) | 0.10 (−0.23, 0.03) |
| TSH, mIU/L (not on thyroxine) | | | | | |
| no. | 248 | 229 | 245 | | |
| Baseline mean (SD) | 2.0 (1.0) | 2.0 (1.1) | 1.9 (0.98) | | |

TABLE 30-continued

Change From Baseline in Thyroid Hormones at Week 52 (Safety Population)

| | Least Squares Mean % CFB or CFB (Standard Error) Resmetirom 80 mg (n = 322) | Least Squares Mean % CFB or CFB (Standard Error) Resmetirom 100 mg (n = 323) | Least Squares Mean % CFB or CFB (Standard Error) Placebo (n = 321) | Least Squares Mean Difference Resmetirom 80 mg from PBO (95% CI) | Least Squares Mean Difference Resmetirom 100 mg from PBO (95% CI) |
|---|---|---|---|---|---|
| Week 52 CFB (Standard Error) | −0.23 (0.056) | −0.20 (0.058) | −0.08 (0.055) | −0.15 (−0.27, −0.03) | −0.12 (−0.24, 0) |
| TSH, mIU/L (thyroxine-treated) | | | | | |
| no. | 31 | 36 | 41 | | |
| Baseline mean (SD) | 2.0 (1.9) | 2.6 (1.5) | 2.2 (1.8) | | |
| Week 52 CFB (Standard Error) | −0.63 (0.27) | −0.13 (0.25) | −0.22 (0.24) | −0.41 (−0.97, 0.15) | 0.09 (−0.46, 0.63) |
| TBG, mg/L | | | | | |
| no. | 269 | 261 | 283 | | |
| Baseline mean (SD) | 24.4 (7.3) | 24.5 (8.1) | 24.3 (8.1) | | |
| Week 52 CFB (Standard Error) | −0.32 (0.45) | −0.60 (0.45) | 1.6 (0.43) | −1.9 (−2.8, −0.91) | −2.2 (−3.1, −1.2) |
| TBG, mg/L (not on thyroxine) | | | | | |
| no. | 238 | 225 | 244 | | |
| Baseline mean (SD) | 24.4 (7.5) | 24.1 (7.7) | 23.8 (7.7) | | |
| Week 52 CFB (Standard Error) | 0.19 (0.47) | 0.21 (0.49) | 1.6 (0.45) | −1.8 (−2.8, −0.74) | 1.8 (−2.8, −0.74) |
| TBG, mg/L (thyroxine-treated) | | | | | |
| no. | 31 | 36 | 39 | | |
| Baseline mean (SD) | 24.9 (5.8) | 26.6 (9.8) | 27.5 (9.7) | | |
| Week 52 CFB (Standard Error) | 1.1 (1.4) | 3.1 (1.3) | 1.5 (1.3) | −2.6 (−5.5, 0.43) | 4.6 (−7.5, −1.8) |

CFB, change from baseline;
CI, confidence interval;
LS, least squares;
rT3, reverse triiodothyronine;
SE, standard error;
FT3, free triiodothyronine;
FT4, free thyroxine;
TBG, thyroxine binding globulin;
TSH, thyroid-stimulating hormone.
Confidence interval widths have not been adjusted for multiplicity and may not be used for hypothesis testing.

TABLE 31

Shift Table of Bone Mineral Density T Score Risk Category

| | Baseline | | | | | | | | |
|---|---|---|---|---|---|---|---|---|---|
| | Resmetirom 80 mg (N = 78) | | | Resmetirom 100 mg (N = 61) | | | Placebo (N = 82) | | |
| Week 52 | Normal N (%) | Low Density N (%) | Possible Osteoporosis N (%) | Normal N (%) | Low Density N (%) | Possible Osteoporosis N (%) | Normal N (%) | Low Density N (%) | Possible Osteoporosis N (%) |
| Femoral Neck | | | | | | | | | |
| Normal | 40 (51.3) | 2 (2.6) | 0 | 32 (52.5) | 3 (4.9) | 0 | 41 (50.0) | 2 (2.4) | 0 |
| Low Density | 6 (7.7) | 25 (32.1) | 0 | 2 (3.3) | 21 (34.4) | 0 | 4 (4.9) | 31 (37.8) | 0 |
| Possible Osteoporosis | 0 | 1 (1.3) | 1 (1.3) | 0 | 1 (1.6) | 0 | 0 | 0 | 0 |
| Hip | | | | | | | | | |
| Normal | 67 (85.9) | 1 (1.3) | 0 | 47 (77.0) | 0 | 0 | 64 (78.0) | 1 (1.2) | 0 |
| Low Density | 1 (1.3) | 6 (7.7) | 0 | 2 (3.3) | 10 (16.4) | 0 | 2 (2.4) | 11 (13.4) | 0 |
| Possible Osteoporosis | 0 | 0 | 0 | 0 | 0 | 0 | 0 | 0 | 0 |

TABLE 31-continued

Shift Table of Bone Mineral Density T Score Risk Category

| | Baseline | | | | | | | | |
|---|---|---|---|---|---|---|---|---|---|
| | Resmetirom 80 mg (N = 78) | | | Resmetirom 100 mg (N = 61) | | | Placebo (N = 82) | | |
| Week 52 | Normal N (%) | Low Density N (%) | Possible Osteoporosis N (%) | Normal N (%) | Low Density N (%) | Possible Osteoporosis N (%) | Normal N (%) | Low Density N (%) | Possible Osteoporosis N (%) |
| | Spine | | | | | | | | |
| Normal | 54 (69.2) | 2 (2.6) | | 45 (73.8) | 2 (3.3) | 0 | 52 (63.4) | 2 (2.4) | 0 |
| Low Density | 2 (2.6) | 14 (17.9) | 0 | 1 (1.6) | 8 (13.1) | 0 | 14 (4.9) | 18 (22.0) | 0 |
| Possible Osteoporosis | 0 | 1 (1.3) | 1 (1.3) | 0 | 1 (1.6) | 3 (4.9) | 0 | 0 | 2 (2.4) |

Note:
Category Criteria: Normal = T Score ≥-1.0; Low Density = T Score ≥-2.5 and <-1.0; Possible Osteoporosis = T Score <-2.5
Observed Data (Primary Analysis Population, Subgroup: Female Human Subjects Not Taking Thyroxine at Baseline, Estradiol <30 ng/L at Baseline, and Weight Loss <5% at Week 52; Spine Adjusted Total; L1-L4
Note:
Column headers are baseline status and row headers are status at the post-baseline visit.

Related Assessments
Assessment of Resmetirom Efficacy (80 mg Vs. 100 mg) Stratified by Baseline Body Mass Index and Weight in Patients from the MAESTRO-NASH Trial Resmetirom was approved in March 2024 in the United States for the treatment of adults with noncirrhotic nonalcoholic steatohepatitis (NASH) with moderate to advanced liver fibrosis (consistent with stages F2 to F3 fibrosis). At Week 52, both primary endpoints were met at both clinical doses.

Figures 45, 46:
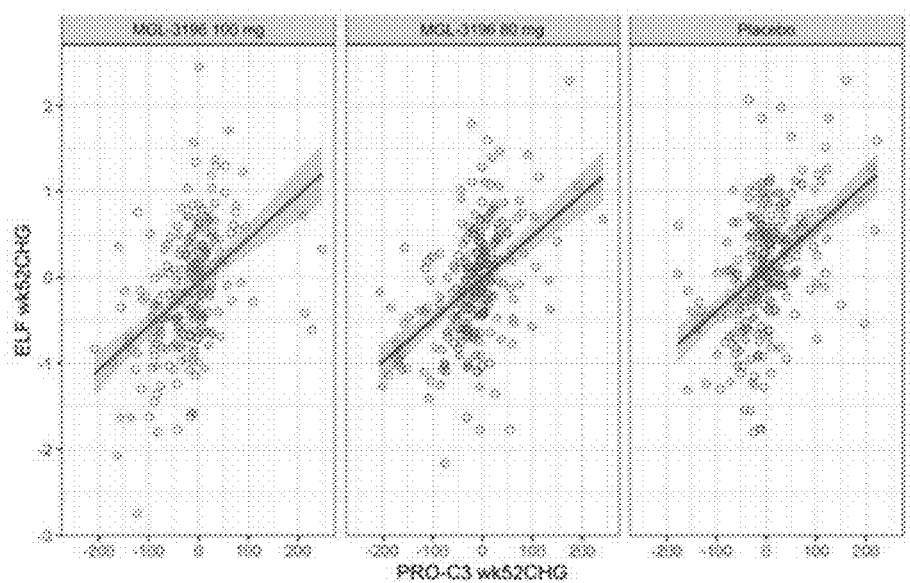
FIG. 45 is a graphical representation showing the ELF change vs. the PRO-C3 change at Week 52 in patients in the placebo, resmetirom 80 mg, and resmetirom 100 mg groups in Example 2.
FIG. 46 is a reproduction of an excerpt of the prescribing information of REZDIFFRA™ (resmetirom).

The recommended dosage of resmetirom is based on actual body weight (see FIG. 46). For patients weighing <100 kg, the recommended dosage is 80 mg orally once daily. For patients weighing ≥100 kg, the recommended dosage is 100 mg orally once daily. In the MAESTRO-NASH study, randomization to 80 mg and 100 mg doses was equal across all body weights. Analyses were conducted to provide additional evidence of a relationship between resmetirom dose, baseline body weight and body mass index (BMI), and safety/efficacy readouts. The baseline body mass index mean (SD) for the resmetirom 80 mg, resmetirom 100 mg, and placebo groups were 35.5 kg/m² (6.4), 36.2 kg/m² (7.4), and 35.3 kg/m² (6.5), respectively. The baseline body weight for each group was 100.1 kg (22.3), 101.9 kg (22.9), and 100.2 kg (23.1), respectively.

Figure 24A:
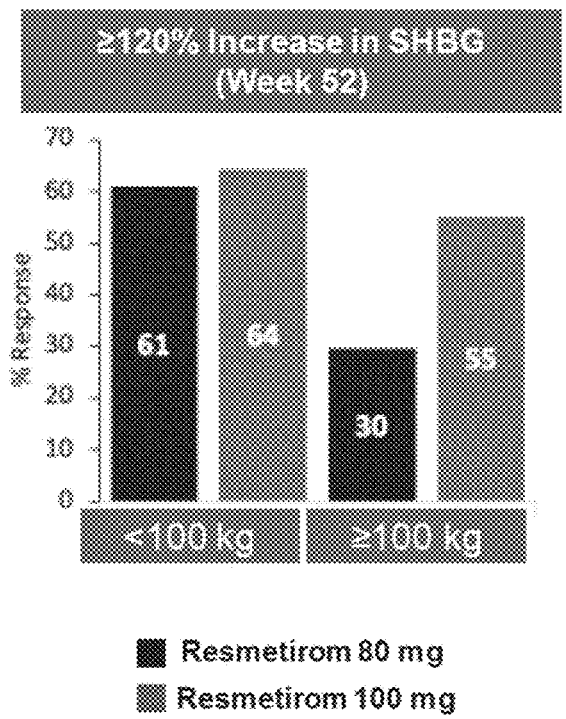
FIG. 24A is a graphical representation showing the percentage of patients that achieved ≥120% increase in SHBG at Week 52 in the resmetirom 80 mg and resmetirom 100 mg groups based on weight in Example 2.
Figure 24B:
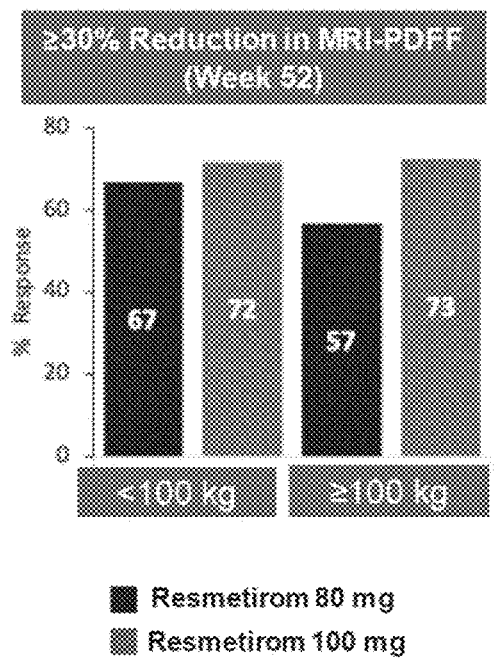
FIG. 24B is a graphical representation showing the percentage of patients that achieved ≥30% reduction in MRI-PDFF at Week 52 in the resmetirom 80 mg and resmetirom 100 mg groups based on weight in Example 2.

Pharmacokinetic modeling concluded that higher exposure to resmetirom was associated with higher hepatic target engagement as reflected by higher SHBG responses and higher MRI-PDFF reduction (FIGS. 24A and 24B). The only variable that determined exposure to resmetirom in the NASH population was body weight. More patients treated with resmetirom 100 mg when compared with resmetirom 80 mg achieved targets for SHBG and PDFF, and differences between doses occurred primarily in patients >100 kg.

Figure 25A:
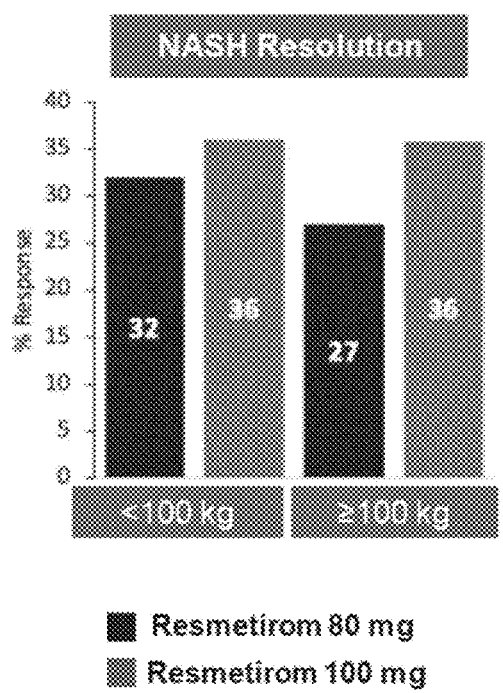
FIG. 25A is a graphical representation showing the percentage of patients that achieved NASH Resolution (ballooning score=0, inflammation score=0/1, and ≥2-point reduction in NAS with no worsening of fibrosis) in the resmetirom 80 mg and resmetirom 100 mg groups based on weight in Example 2.
Figure 25B:
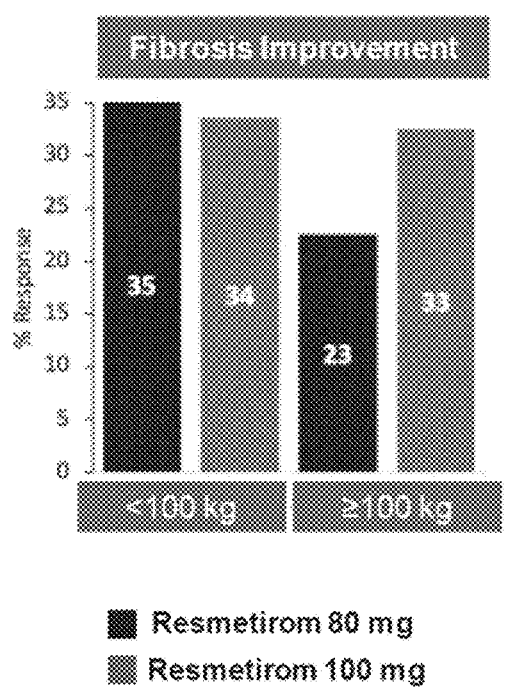
FIG. 25B is a graphical representation showing the percentage of patients that achieved Fibrosis Improvement (1-stage improvement in fibrosis with no worsening of NAS) in the resmetirom 80 mg and resmetirom 100 mg groups based on weight in Example 2.
Figure 26A:
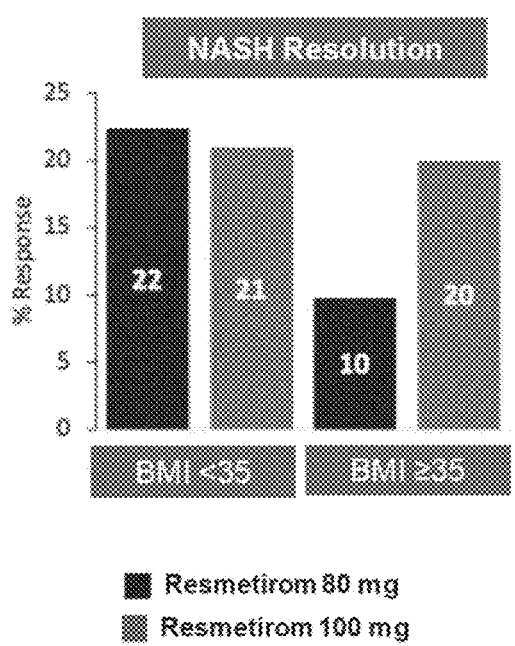
FIG. 26A is a graphical representation showing the percentage of patients that achieved NASH Resolution (ballooning score=0, inflammation score=0/1, and ≥2-point reduction in NAS with no worsening of fibrosis) in the resmetirom 80 mg and resmetirom 100 mg groups based on body mass index in Example 2.
Figure 26B:
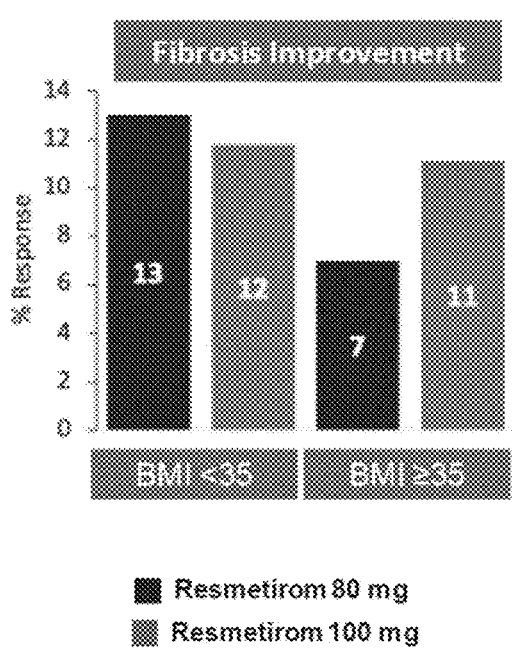
FIG. 26B is a graphical representation showing the percentage of patients that achieved Fibrosis Improvement (1-stage improvement in fibrosis with no worsening of NAS) in the resmetirom 80 mg and resmetirom 100 mg groups based on body mass index in Example 2.

Exposure modeling indicated that higher NASH and fibrosis responses on biopsy were associated with higher exposure to resmetirom. Study median body weight was 100 kg. In the population with both a baseline and Week 52 liver biopsy, equivalent biopsy responses were achieved in patients who were <100 kg at 80 mg and 100 mg (see FIGS. 25A and 25B). Lower responses were achieved at 80 mg in the ≥100 kg patients (FIGS. 25A and 25B). Study median BMI was 35 kg/m². Higher BMI patients maintained the biopsy response at 100 mg; patients with BMI≥35 had a lower response when randomized to 80 mg (FIGS. 26A and 26B).

Figure 27:
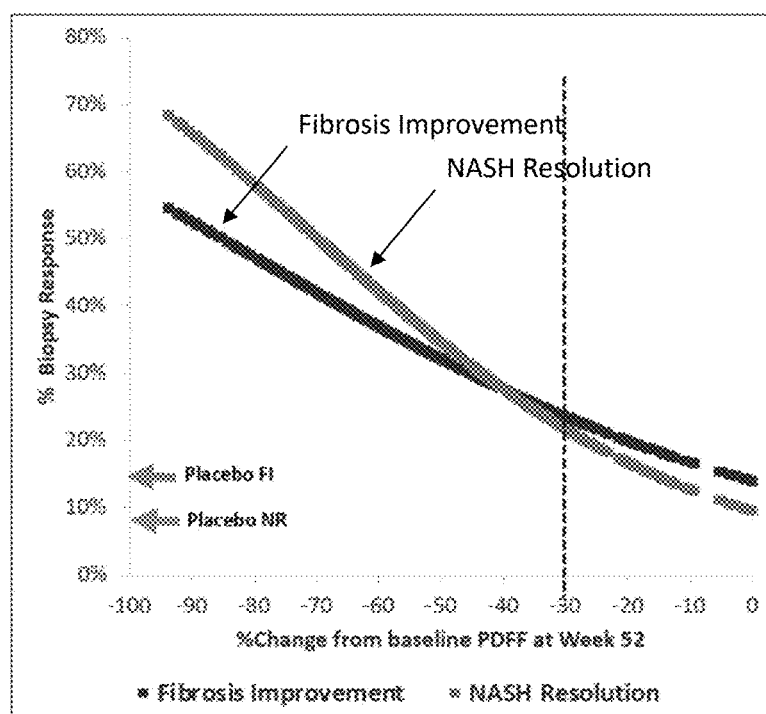
FIG. 27 is a graphical representation showing the percentage biopsy response for fibrosis improvement and NASH resolution in all resmetirom-treated patients (80 mg and 100 mg combined) and placebo patients based on the percentage change from baseline PDFF at Week 52 in Example 2. The graph shows that the greater the Week 52 PDFF reduction, the greater likelihood for fibrosis and NASH responses with resmetirom treatment.

The results show that the greater the week 52 PDFF reduction, the greater likelihood for fibrosis and NASH responses with resmetirom treatment (FIG. 27). PDFF reduction in resmetirom-treated patients was highly associated with both NASH resolution and fibrosis improvement. Placebo patients with more PDFF reduction had more NASH reduction but not fibrosis improvement. At least a 30% PDFF response was observed in 96% and 88% of resmetirom 100 mg responders for NASH resolution and fibrosis improvement, respectively. The percentage reduction in PDFF rather than resmetirom dose impacted the response on biopsy. The response on biopsy at resmetirom 80 mg and resmetirom 100 mg was equally correlated with the magnitude of PDFF response. Doses were combined in this predictive model.

Figure 28:
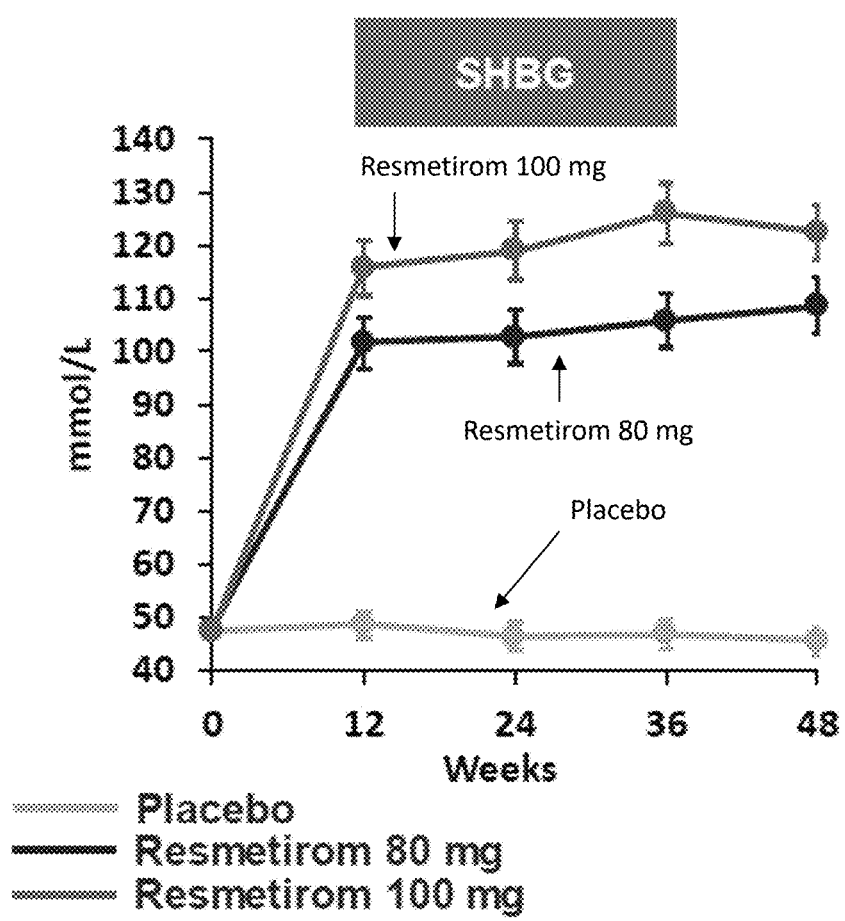
FIG. 28 is a graphical representation showing the change over time from baseline to 48 weeks in SHBG in the placebo, resmetirom 80 mg, and resmetirom 100 mg groups in the MAESTRO-NASH Week 52 primary analysis population in Example 2.
Figure 29A:
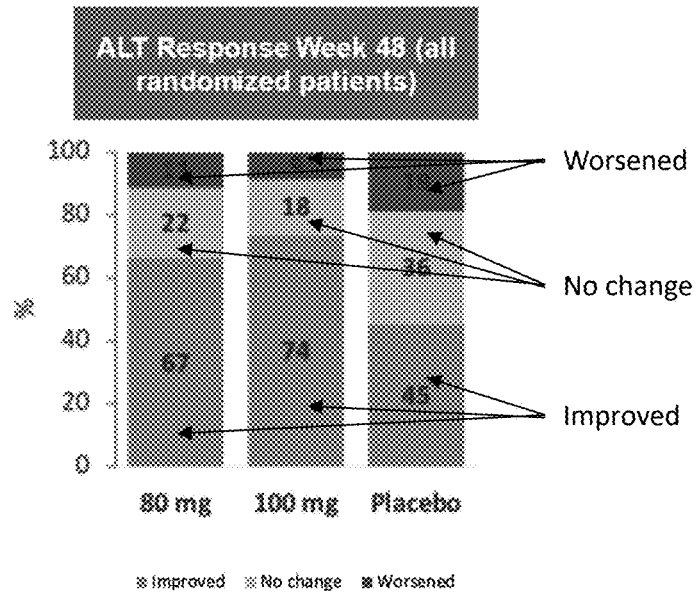
FIG. 29A is a graphical representation showing the ALT response at Week 48 in all randomized patients in the placebo, resmetirom 80 mg, and resmetirom 100 mg groups in the MAESTRO-NASH Week 52 primary analysis population in Example 2.
Figure 29B:
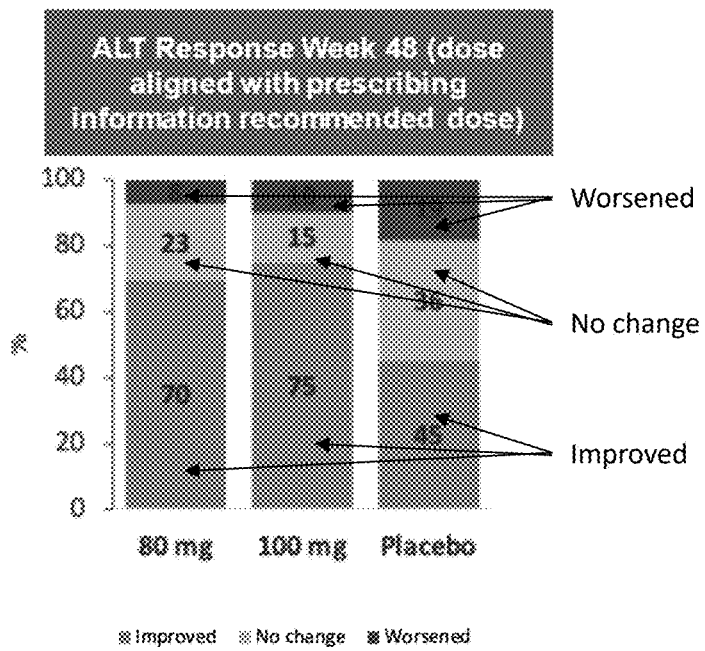
FIG. 29B is a graphical representation showing the ALT response at Week 48 where the dose aligned with prescribing information recommended dose for patients in the placebo, resmetirom 80 mg, and resmetirom 100 mg groups in the MAESTRO-NASH Week 52 primary analysis population in Example 2.
Figure 30A:
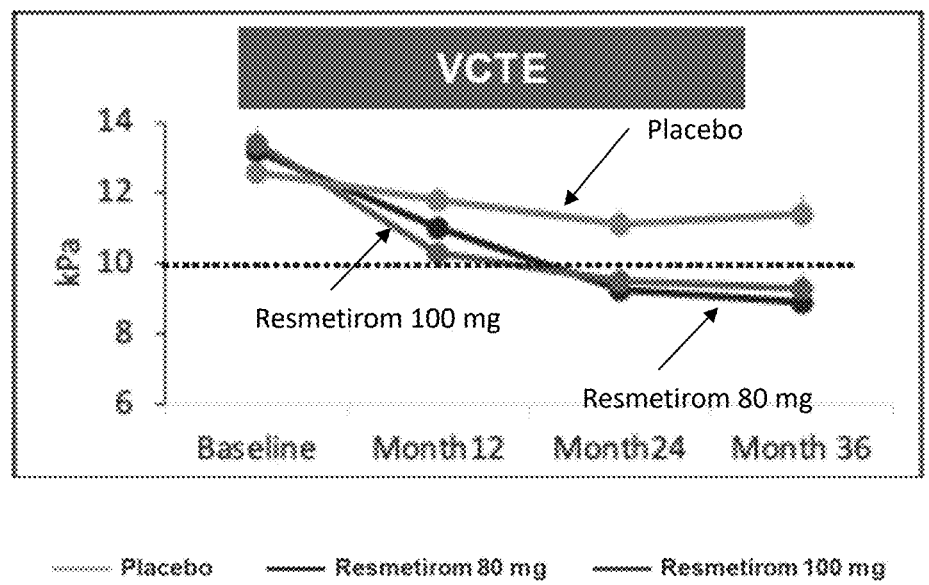
FIG. 30A is a graphical representation showing the change over time in VCTE from baseline to year 3 in patients in the placebo, resmetirom 80 mg, and resmetirom 100 mg group in Example 2.
Figure 30B:
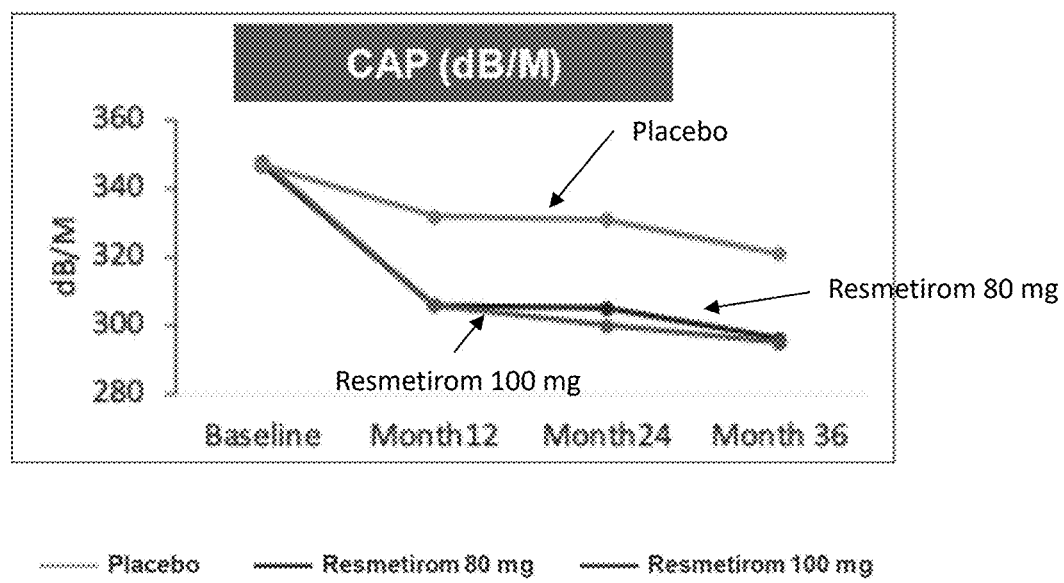
FIG. 30B is a graphical representation showing the change over time in CAP (dB/M) from baseline to year 3 in patients in the placebo, resmetirom 80 mg, and resmetirom 100 mg groups in Example 2.

Sensitive biomarkers SHBG, PDFF, and LDL/ApoB showed a persistent dose response over time with a difference between resmetirom 80 mg and resmetirom 100 mg (FIG. 28). Other tests like ALT showed an equally high response at both doses, irrespective of baseline body weight (FIGS. 29A and 29B). VCTE improved over time (1-3 years) relative to placebo in resmetirom-treated patients, both doses showing a similar durable response (FIG. 30A). New data indicates that less than 10 kPa correlates with less liver-related events. Garewh et al. (2024). CAP was stable over time, both doses showing a similar durable response (FIG. 30B). VCTE Responder analyses at 1-3 years in the MAESTRO-NASH population reflect improvement relative to placebo and <10% resmetirom-treated patients had worsening of VCTE (FIG. 31).

Pharmacokinetic modeling concluded that higher exposure to resmetirom was associated with higher hepatic target engagement as reflected by higher SHBG responses and higher MRI-PDFF reduction. The only variable that influenced exposure to resmetirom in the NASH population was body weight. Slightly lower rates of fibrosis improvement and NASH resolution on biopsy were observed in patients who were ≥100 kg or BMI≥35 in patients treated with resmetirom 80 mg versus resmetirom 100 mg. Other biomarkers such as ALT, FibroScan, CAP and VCTE showed similar improvements relative to placebo at resmetirom 80 mg and resmetirom 100 mg. Responses on FibroScan in resmetirom-treated patients were durable out to 3 years of treatment and showed improvement and less worsening than placebo.

Identification and Validation of Pre-Identified Morphological Baseline Features for Prediction of Fibrosis Progression in MAESTRO-NASH At Week 52, both primary endpoints were met at both clinical doses. Month 54 measured clinical outcomes including histologic conversion to cirrhosis. A second clinical outcomes study, MAESTRO-NASH-OUTCOMES (NCT05500222), studied approximately 700 well-compensated NASH cirrhosis patients.

Fibrosis stage predicts clinical outcomes in NASH/metabolic-associated steatohepatitis (MASH), with liver biopsies as the regulatory standard. Ordinal fibrosis staging on stained slides may limit the ability to visualize dynamic fibrosis features throughout the liver lobule. qFibrosis, an AI-driven fibrosis assessment methodology that utilizes laser driven (SHG) collagen detection on unstained biopsy slides, has identified 30 specific fibrotic features on NASH liver biopsies that may be predictive of liver-related clinical outcomes, progression to cirrhosis and decompensated cirrhosis based on the SteatoSITE population. Non-invasive measures such as baseline MRE or FibroScan VCTE, ELF, and other non-invasive fibrosis markers also predict progression to cirrhosis and decompensated cirrhosis.

SteatoSITE contains integrated clinical and pathological data from 940 cases across the NAFLD spectrum with outcome data from electronic health record and pathologist-assigned fibrosis stage and RNA on baseline biopsy. In the SteatoSITE liver biopsy cohort, the level of the baseline fibrosis feature #IntersectionPT, the number of intersections of all strings for portal tract fibrosis per unit tissue area, was validated as predictive of liver decompensation events.

Figure 32B:
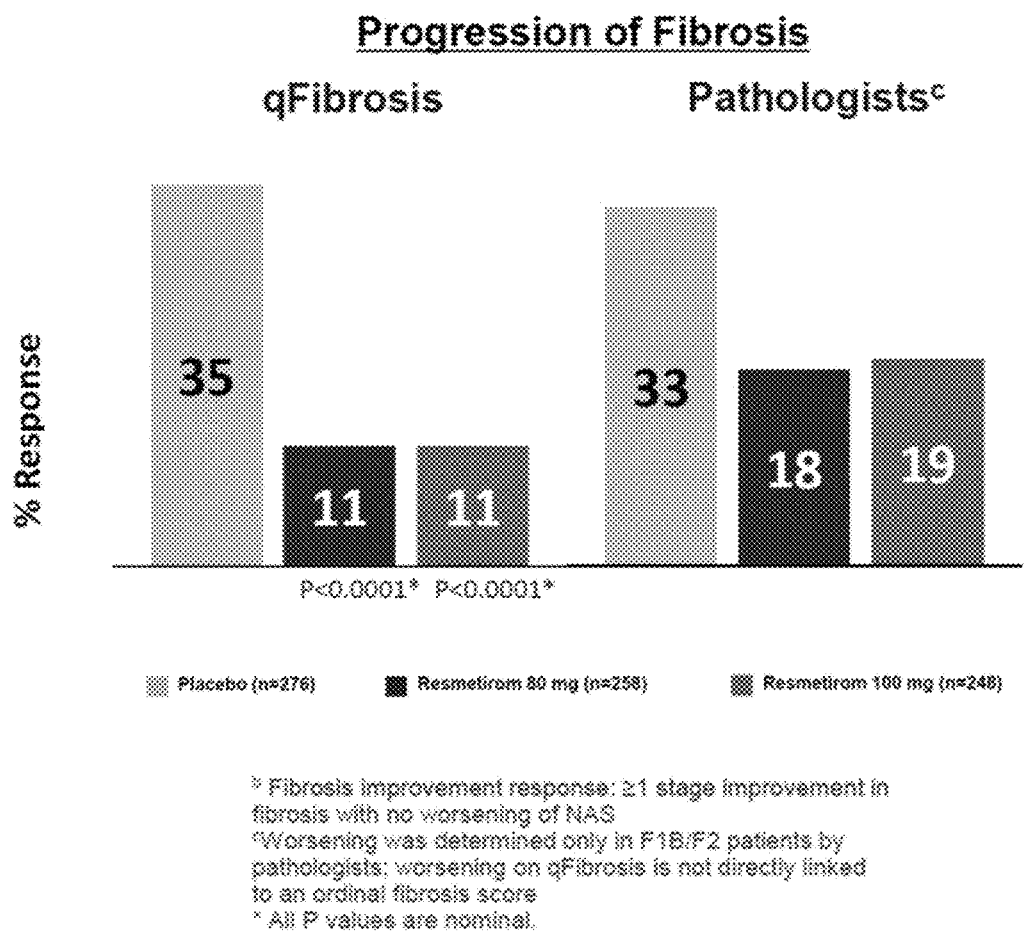
FIG. 32B is a graphical representation showing the percentage of patients in the placebo, resmetirom 80 mg, and resmetirom 100 mg groups that had progression of fibrosis as determined by qFibrosis and pathologists in Example 2.

Baseline biopsy RNA analyses and annotated patient timelines in high-risk fibrosis stages (F3 and F4) showed that low THR-β liver regulon activity identifies patients at higher risk for hepatic decompensation. F3 to F4 patients with low baseline THR-β activity in their liver had the highest chance of progression to decompensated cirrhosis. Kendall et al, Nature Medicine (2023). At Week 52 biopsy, total qFibrosis scores showed a highly significant improvement in fibrosis with resmetirom treatment and less progression of fibrosis as compared with placebo, similar to pathologist scoring (FIGS. 32A and 32B).

Figure 33A:
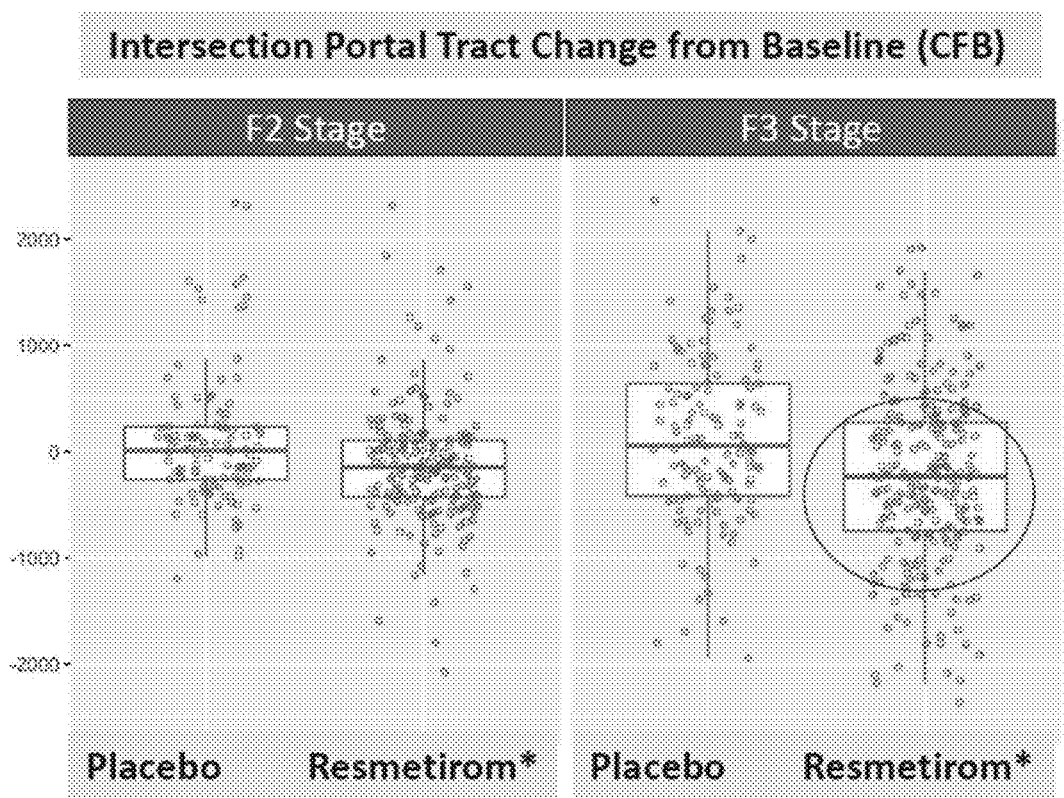
FIG. 33A is a graphical representation showing the intersection portal tract change from baseline in the placebo and resmetirom (80 mg and 100 mg combined) groups at the F2 and F3 stages in Example 2.
Figure 33B:
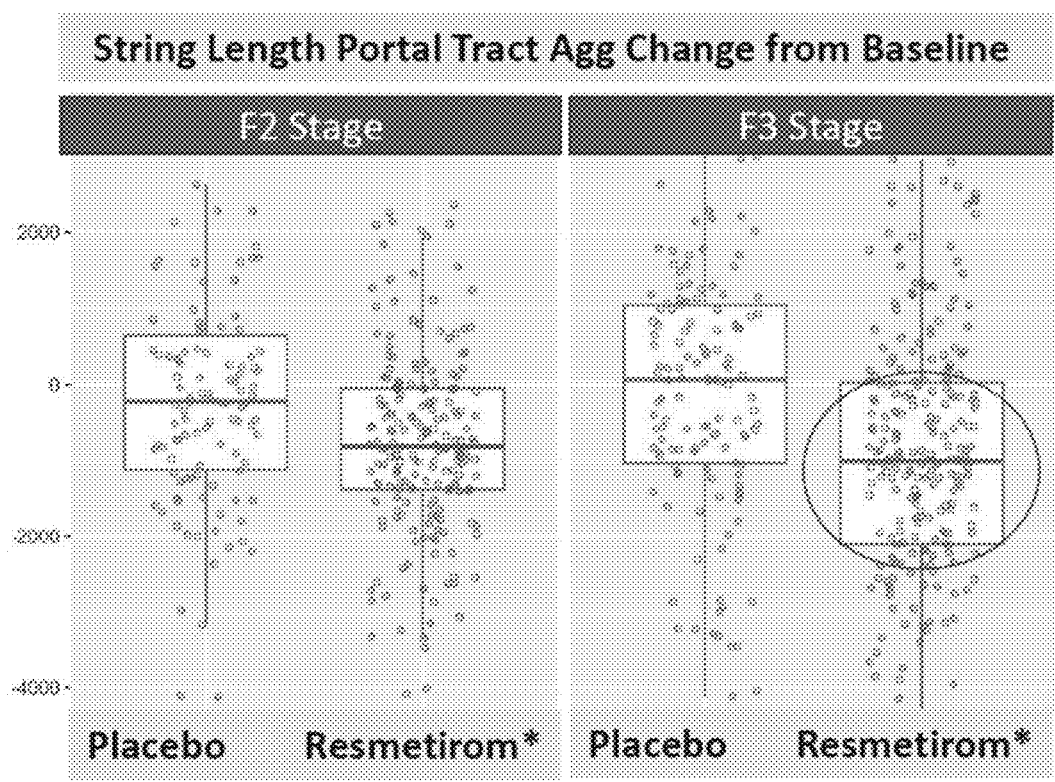
FIG. 33B is a graphical representation showing the string length portal tract change from baseline in the placebo and resmetirom (80 mg and 100 mg combined) groups at the F2 and F3 stages in Example 2.
Figure 34A:
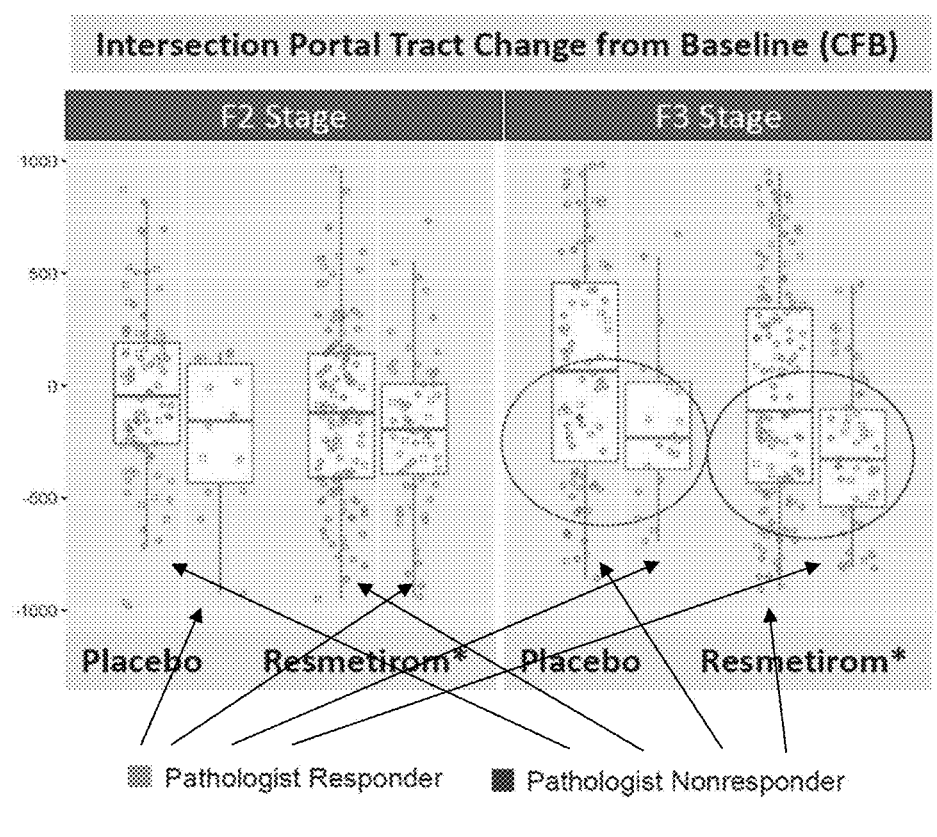
FIG. 34A is a graphical representation showing the intersection portal tract change from baseline in pathologist fibrosis responders and non-responders in the placebo and resmetirom (80 mg and 100 mg combined) groups at the F2 and F3 stages in Example 2.
Figure 34B:
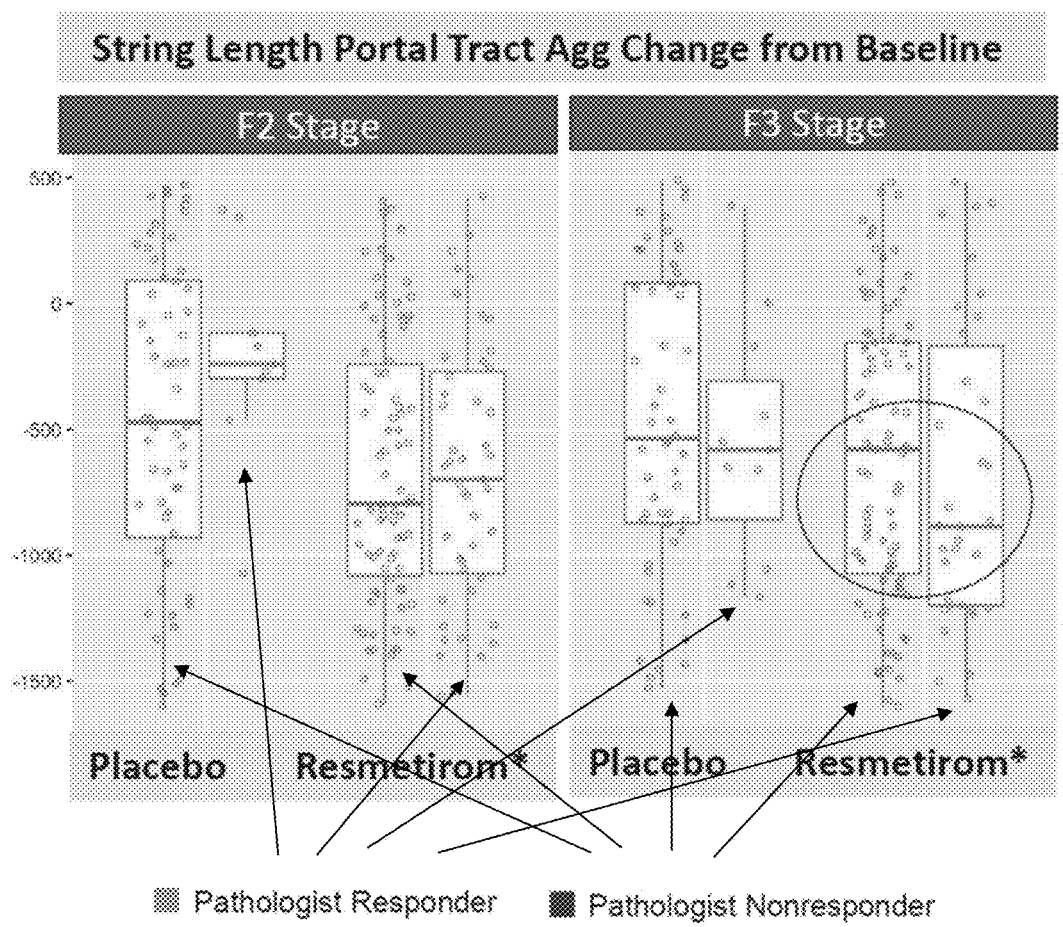
FIG. 34B is a graphical representation showing the string length portal tract change from baseline in pathologist fibrosis responders and non-responders in the placebo and resmetirom (80 mg and 100 mg combined) groups at the F2 and F3 stages in Example 2.
Figure 35A:
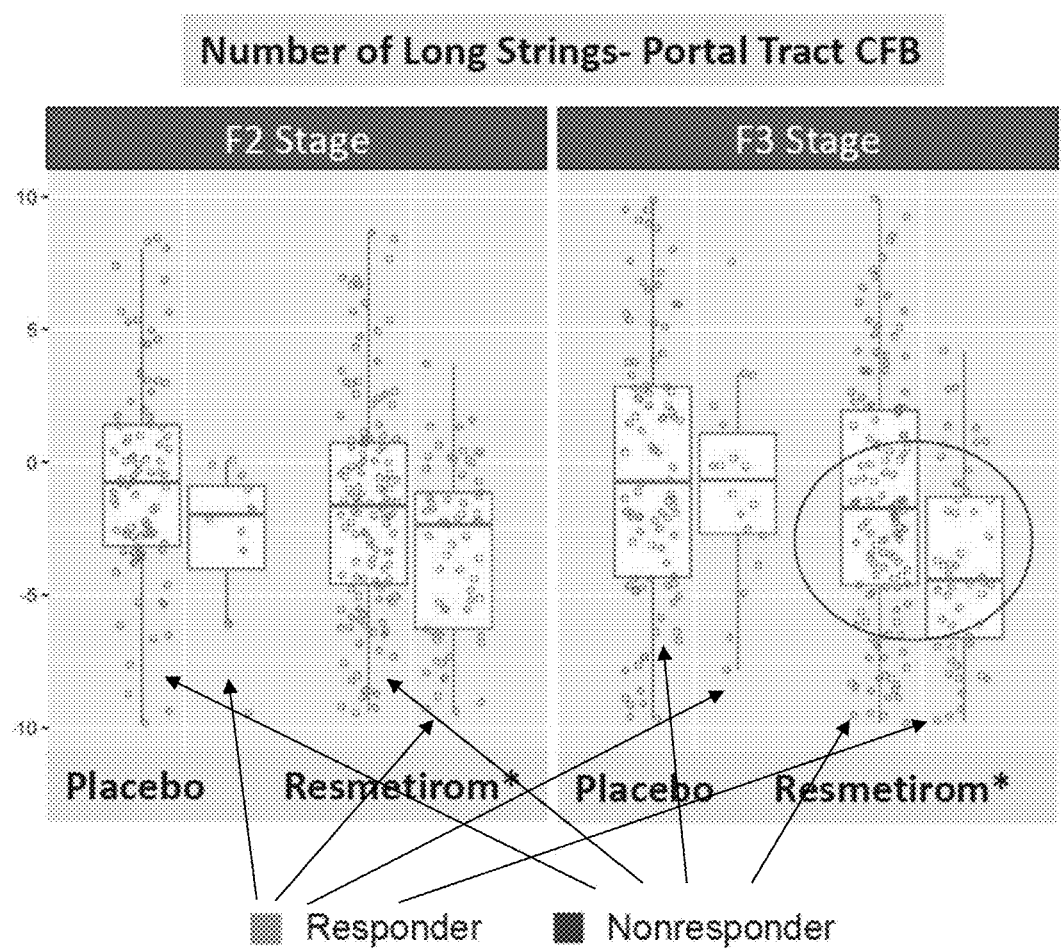
FIG. 35A is a graphical representation showing the change from baseline in the number of long strings-portal tract in responders and non-responders in the placebo and resmetirom (80 mg and 100 mg combined) groups at the F2 and F3 stages in Example 2.
Figure 35B:
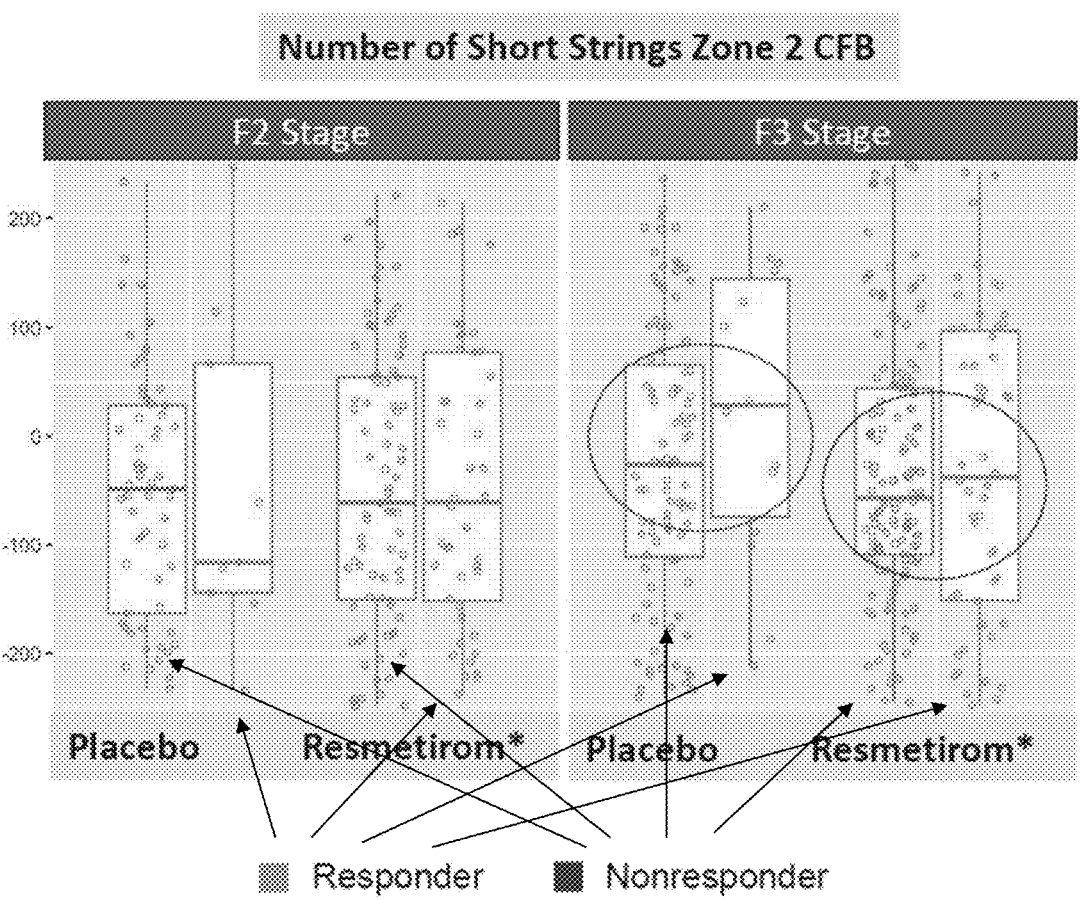
FIG. 35B is a graphical representation showing the change from baseline in the number of short strings zone 2 in responders and non-responders in the placebo and resmetirom (80 mg and 100 mg combined) groups at the F2 and F3 stages in Example 2.

Resmetirom Week 52 results showed reduction from baseline in the qFibrosis progression features compared to placebo (FIGS. 33A and 33B). Fibrosis responders as determined by pathologists had greater improvement in qFibrosis features compared with non-responders in each treatment group (FIGS. 34A and 34B). Placebo fibrosis responders were few in number and had similar improvements in some qFibrosis progression features (FIGS. 35A and 35B). Fibrosis biomarkers and imaging tests (MRE, FibroScan VCTE, AST, GGT) showed improvements that were correlated with reduction in qFibrosis progression features. Change in MRE showed the highest correlation with change in qFibrosis progression features. The most marked reductions in scores of qFibrosis progression features occurred in the resmetirom F3 population.

Baseline and Week 52 biopsies from MAESTRO-NASH were analyzed for 30 qFibrosis features identified by SteatoSITE that are associated with progression of NASH fibrosis to liver decompensation, and six features with the strongest correlations between baseline pathologist scoring and non-invasive tests were identified. MRE followed by FibroScan showed strong correlations with the six qFibrosis features at baseline. Resmetirom treatment relative to placebo, particularly in F3, reduced qFibrosis features associated with progression to decompensated cirrhosis. SteatoSITE demonstrated that the thyroid hormone receptor beta regulon activity in the liver is a critical suppressor of NASH fibrosis progression; qFibrosis features are associated with progression in the SteatoSITE Cohort. qFibrosis data provide support for resmetirom's potential in benefiting patients with NASH with advanced liver fibrosis by reversing fibrosis and preventing progression to more advanced liver disease.

Non-Invasive Predictive Markers of Resmetirom Biopsy Response

A total of 966 patients with biopsy-confirmed NASH were randomized 1:1:1 to resmetirom 80 mg, resmetirom 100 mg, or placebo administered once daily. Histologic endpoints were assessed after 52 weeks. Dual primary endpoints at Week 52 were achieved with both resmetirom 80 mg and 100 mg: NASH resolution with no worsening of fibrosis (NR) or ≥1-stage reduction in fibrosis with no worsening of NAS (FR). The non-invasive correlates of response in the MAESTRO-NASH trial are summarized below.

Adults with ≥3 metabolic risk factors, liver stiffness ≥8.5 kPa, hepatic fat ≥8%, biopsy-confirmed NASH with F1B-F3 fibrosis, and NAS≥4 were eligible to participate in MAESTRO-NASH. In this analysis, the relationship of changes in (1) FibroScan CAP, (2) FibroScan VCTE, and (3) alanine aminotransferase (ALT) to histological response (NR and/or FR) in the resmetirom 80 mg, resmetirom 100 mg, and placebo groups was assessed. The data used in these analyses were based on those 782 patients who had a paired biopsy at baseline and Week 52.

Figure 36:
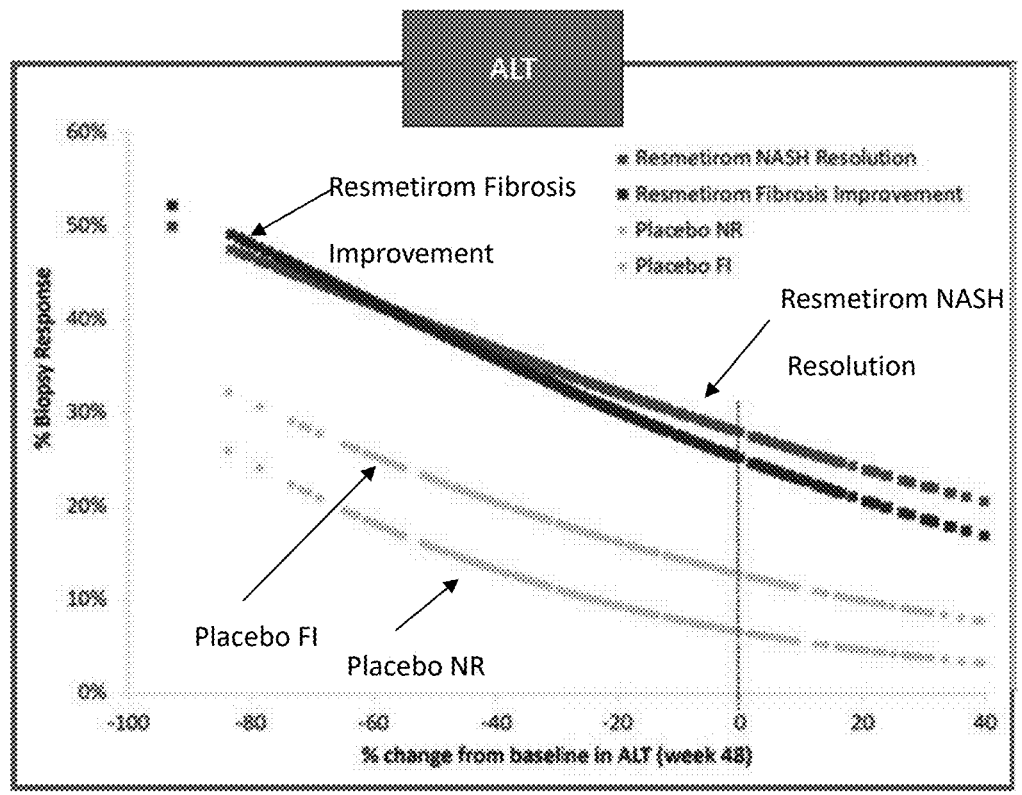
FIG. 36 is a graphical representation showing the percentage change from baseline in ALT at Week 48 compared to the percentage biopsy response in the patients who achieved resmetirom NASH resolution, resmetirom fibrosis improvement, placebo NASH resolution, and placebo fibrosis improvement in Example 2.
Figure 37:
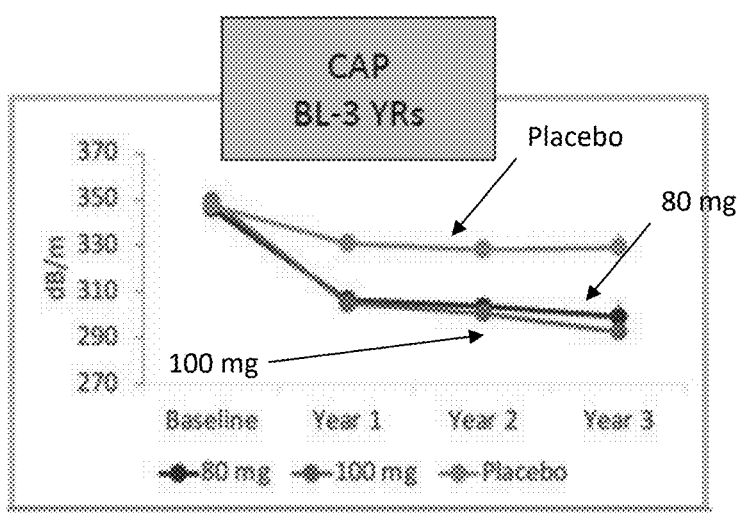
FIG. 37 is a graphical representation showing the CAP change over time from baseline to year 3 in patients in the placebo, resmetirom 80 mg, and resmetirom 100 mg groups in Example 2.
Figure 38:
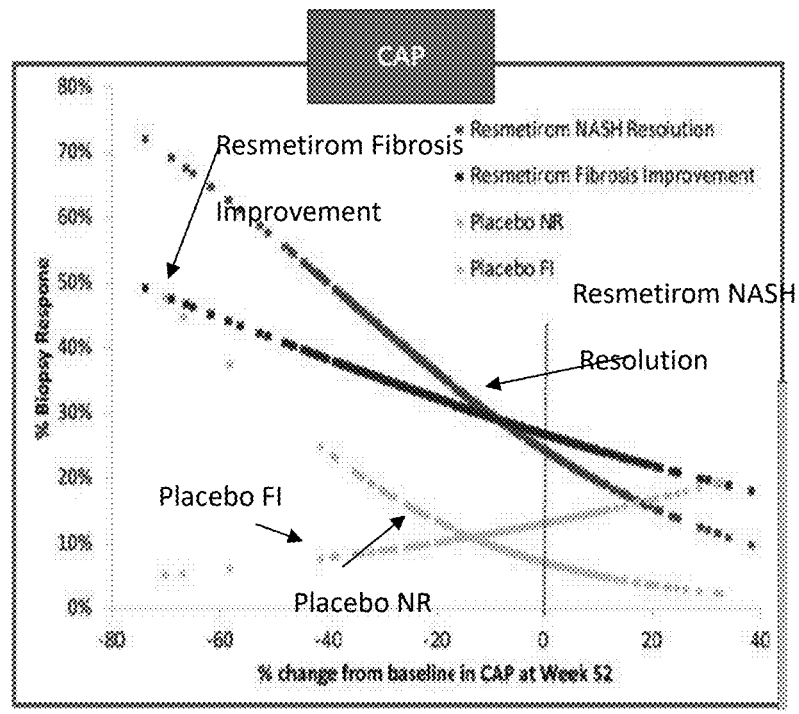
FIG. 38 is a graphical representation showing the percentage change from baseline in CAP at Week 52 compared to the percentage biopsy response in the patients who achieved resmetirom NASH resolution, resmetirom fibrosis improvement, placebo NASH resolution, and placebo fibrosis improvement in Example 2.

Both doses of resmetirom significantly reduced ALT approximately 30% relative to placebo (FIG. 36). In resmetirom-treated patients, higher percentage reductions in ALT were associated with slightly higher NASH resolution and fibrosis improvement on biopsy. For resmetirom-treated patients without a reduction in ALT or with worsening of ALT, the NASH resolution and fibrosis improvement responses were higher than the mean placebo biopsy responses. CAP improved with resmetirom treatment and improvement was stable over 3 years (FIG. 37). CAP improvement in individual resmetirom patients predicted both NASH resolution and fibrosis improvement responses; however, even no change in CAP predicted biopsy responses higher than the mean for placebo (FIG. 38). A CAP improvement in placebo patients did not predict a fibrosis improvement on biopsy.

Figure 39:
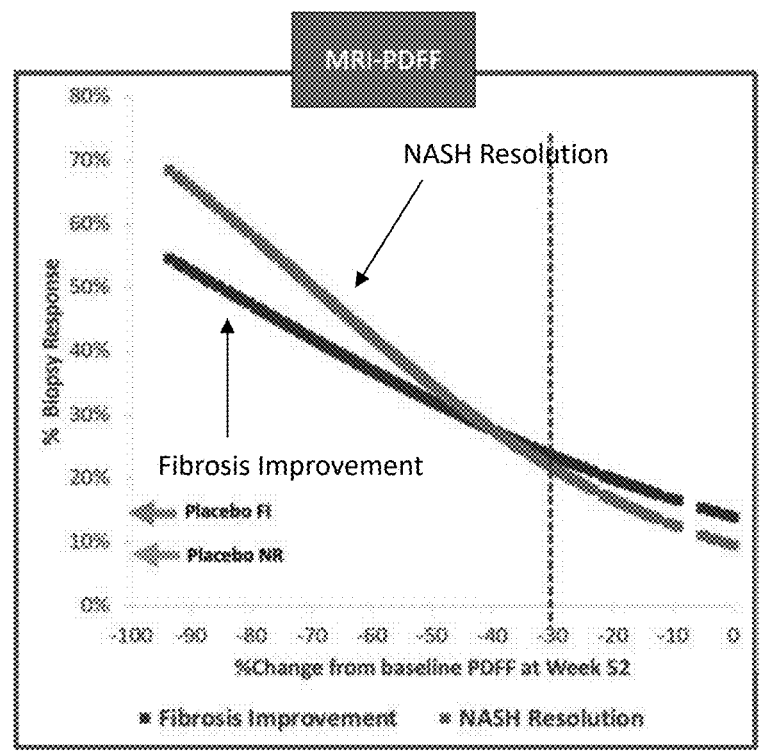
FIG. 39 is a graph showing the percentage change from baseline in PDFF at Week 52 compared to the percentage biopsy response in the patients who achieved resmetirom NASH resolution, resmetirom fibrosis improvement, placebo NASH resolution, and placebo fibrosis improvement in Example 2.
Figure 40:
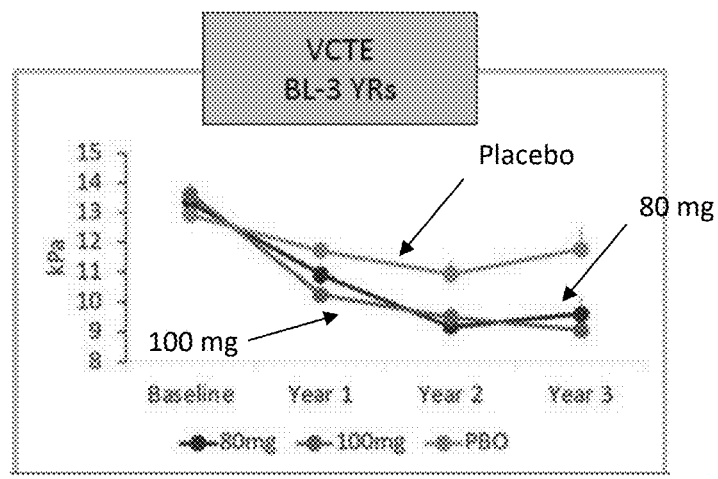
FIG. 40 is a graphical representation showing the VCTE change over time from baseline to year 3 in patients in the placebo, resmetirom 80 mg, and resmetirom 100 mg groups in Example 2.
Figure 41:
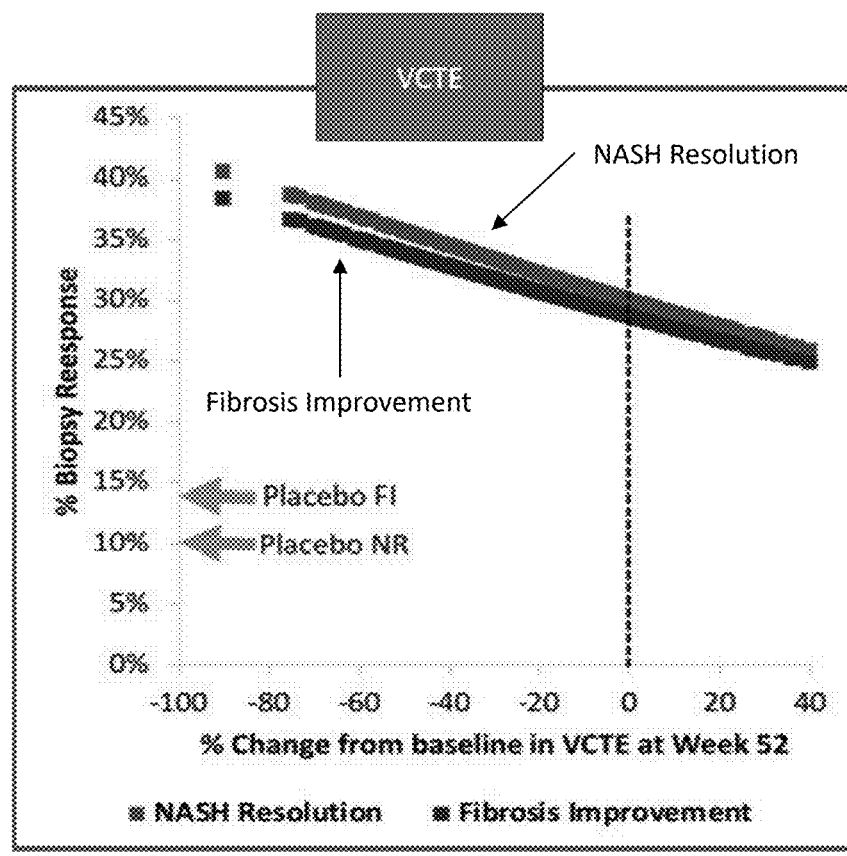
FIG. 41 is a graphical representation showing the percentage change from baseline in VCTE at Week 52 compared to the percentage biopsy response in the patients who achieved resmetirom NASH resolution, resmetirom fibrosis improvement, placebo NASH resolution, and placebo fibrosis improvement in Example 2.

PDFF reduction in resmetirom-treated patients was highly associated with both NASH resolution and fibrosis improvement (FIG. 39). Placebo patients with more PDFF reduction had more NASH reduction but not fibrosis improvement. At least a 30% PDFF response was observed in 96% and 88% of resmetirom 100 mg responders for NASH resolution and fibrosis improvement, respectively. Any PDFF response was associated with biopsy improvement higher than placebo. VCTE was improved over time (1-3 years) relative to placebo in resmetirom-treated patients (FIG. 40). There was a greater relative response at year 2 versus year 1. Resmetirom-treated patients, even those with no VCTE improvement, had higher NASH resolution and fibrosis improvement responses than the mean placebo response rates (FIG. 41). VCTE improvement at 1 year was not predictive of a placebo fibrosis improvement or NASH resolution response. Worsening of VCTE in placebo patients predicted a lower-than-average NASH resolution and fibrosis improvement.

Figure 42:
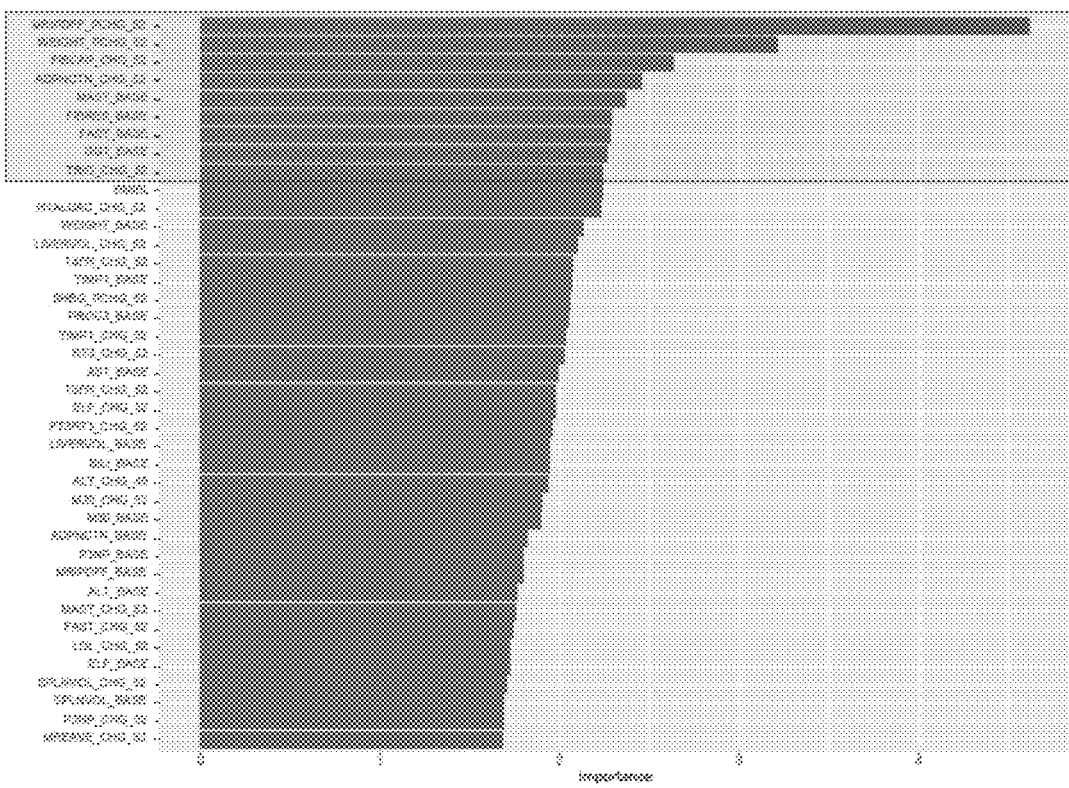
FIG. 42 is a graphical representation showing the importance of various response predictors of resmetirom NASH resolution response based on Week 52 data in Example 2.
Figure 43:
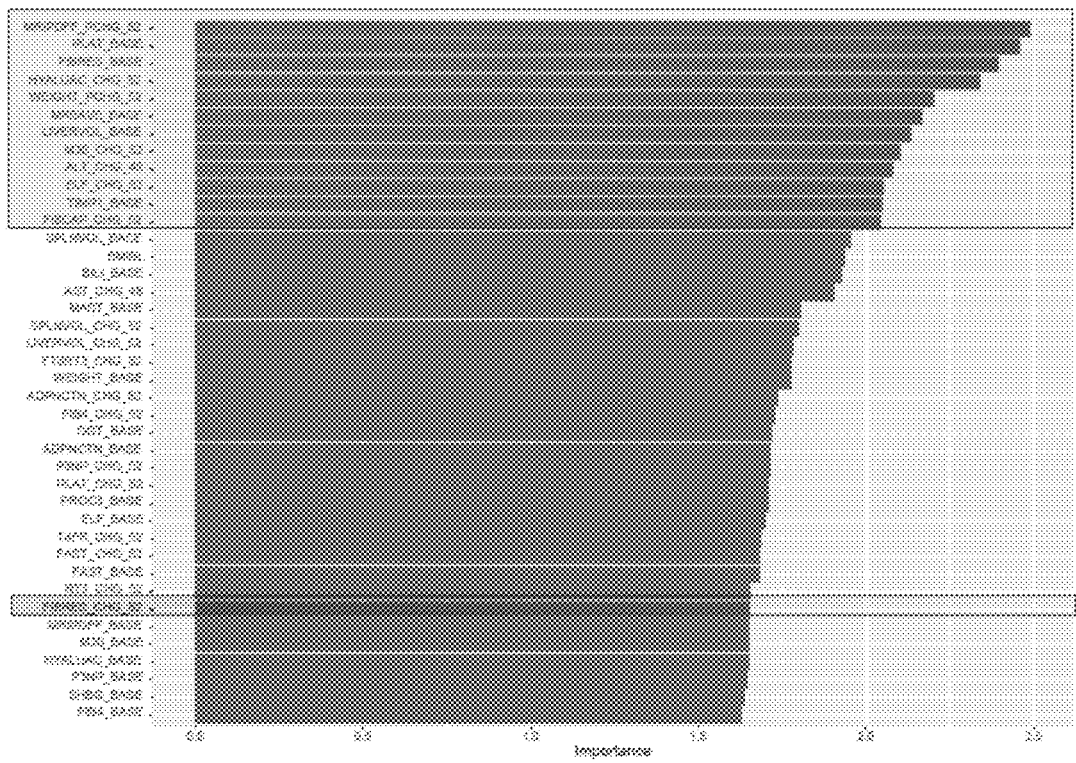
FIG. 43 is a graphical representation showing the importance of various predictors of resmetirom fibrosis improvement biopsy response based on Week 52 data in Example 2.

Data identifying important biomarkers/imaging that are associated with resmetirom response on NASH and fibrosis on serial biopsies at baseline and Week 52 was generated. Random Forest model was utilized to determine the biomarkers and imaging tests both at baseline and change from baseline that had the most important association with response on biopsy for NASH resolution and/or fibrosis improvement. The data was based on baseline characteristics and change from baseline of more than 40 variables: biomarkers, clinical features, and imaging. This analysis confirmed the importance of MRI-PDFF (FIGS. 42-43).

In conclusion, biomarkers and imaging tests from the MAESTRO-NASH and NAFLD-1 clinical trials can be used to generate predictive models of baseline fibrosis stage in patients with NASH. Biomarker and imaging tests were examined for association with resmetirom biopsy responses. The study confirmed the importance of MRI-PDFF for both NASH and fibrosis responses. It also identified changes in CAP, adiponectin and triglycerides as important factors for NASH response, and changes in M30 (CK18), CAP, ALT and ELF as important factors for fibrosis response. ALT, CAP, and VCTE were reduced by resmetirom relative to placebo. However, biopsy responses were not always associated with changes in these biomarkers. As confirmed by both logistic regression and random forest AI models, reduction in CAP showed a good relationship to biopsy response on fibrosis and NASH; reduction in ALT showed a relationship to fibrosis; and change in VCTE at Week 52 was not strongly associated with a fibrosis response on biopsy.

Resmetirom Treatment of a Subgroup of Patients with Possible METALD Enrolled in MAESTRO-NASH, a Phase 3 NASH/MASH Serial Liver Biopsy Study 966 patients with biopsy-confirmed NASH were randomized 1:1:1 to resmetirom 80 mg, resmetirom 100 mg, or placebo once daily. Dual primary endpoints at Week 52 were achieved with both resmetirom 80 mg and 100 mg: NASH resolution with no worsening of fibrosis (NR) or ≥1-stage improvement in fibrosis with no worsening of NAS (FI). The benefit of resmetirom in patients with and without indicators of increased alcohol consumption above protocol-allowed limits for NASH/MASH was assessed on biopsy endpoints and MRI-PDFF (liver fat reduction).

Analyses were performed on 782 patients who had both a baseline and Week 52 biopsy. Patients with a self-declared consumption of alcohol ≤2 drinks/day for men and ≤1.5 drinks/day for women were included as per usual MASH diagnostic recommendations. However, in attempt to objectify undisclosed moderate alcohol consumption above those limits, at baseline or during the trial, CDT measurements were performed longitudinally in all patients over 52 weeks. Post-randomization, a phosphatidylethanol (PEth) test was performed in patients tested for alcohol consumption based on increased liver enzymes ALT, AST and/or GGT (<2%). Those with increased PEth were included as MetALD. Patients with baseline or post-baseline CDT>2.5% (ULN 2.47) and/or a PEth>20 ng/mL (ULN 20 ng/mL) were assigned to a "possible MetALD" subgroup (possible increased alcohol consumption).

Of the 782 patients, 75 patients (9.6%) were included in the MetALD subgroup. Baseline characteristics that were different in the MetALD group included higher percentage male sex; slightly lower BMI; lower percentage type 2 diabetes; higher FIB-4, AST, GGT and CDT; slightly higher percentage with F3 fibrosis (Table 32). For the group of patients with low or no alcohol consumption, out of those treated with resmetirom 80 mg (n=224) and resmetirom 100 mg (n=228), 29.9% and 36% had NASH resolution; 29% and 33.3% had fibrosis improvement; and 59.2% and 71.2% showed a ≥30% reduction from baseline in MRI-PDFF, respectively (Table 33). For patients treated with placebo (n=255), the corresponding results were 10.3%, 13.7%, and 24.5% (Table 33). For the patients in the possible MetALD group, out of those treated with resmetirom 80 mg (n=34) and resmetirom 100 mg (n=20), 29% and 35% had NASH resolution; 35% and 30% had fibrosis improvement; and 88% and 81% showed a ≥30% reduction from baseline in MRI-PDFF, respectively (Table 33). For patients treated with placebo (n=21), the corresponding results were 10%, 19%, and 14% (Table 33).

In conclusion, a total of 75 (9.6%) of patients had possible MetALD during the first 52 weeks of MAESTRO-NASH. Baseline characteristics showed more males; higher mean AST, CDT, GGT, and FIB-4 score; and fewer patients with type 2 diabetes in the MetALD versus low alcohol group. Response rates to resmetirom in patients with suspected MetALD were similar to those without MetALD.

TABLE 32

| | N = 782 | |
|---|---|---|
| | MASH/NASH (low alcohol) n = 707 (90.4%) | MetALD (possible increased alcohol) n = 75 (96%) |
| Age, years | 60.1 (10.7) | 57.7 (10.5) |
| Males, % | 42 | 59 |
| Type 2 Diabetes, % | 67.9 | 50.7 |
| Carbohydrate Deficient Transferrin (CDT) % | 1.6 (0.3) | 2.2 (1.0) |
| Body Mass Index (BMI), kg/m$^2$ | 35.8 (6.6) | 33.0 (5.5) |
| FIB-4 Score | 1.37 (0.66) | 1.67 (0.69) |
| Aspartate aminotransferase (AST), U/L | 40.3 (22.9) | 45.6 (21.8) |
| Alanine transaminase (ALT), U/L | 55.5 (32.2) | 55.2 (24.8) |
| Gamma Glutamyl Transpeptidase (GGT), IU/L | 75.3 (85.6) | 117.9 (170.8) |
| Bilirubin, umol/L | 0.65 (0.29) | 0.69 (0.31) |
| Mean corpuscular volume (MCV), um$^3$ | 90.3 (5.6) | 92.3 (5.8) |
| F3 fibrosis, % | 62.5 | 66.7 |
| MRI-PDFF (%) | 17.4 (6.5) | 21.7 (7.4) |
| VCTE (mean kPa) | 13.2 (6.6) | 13.4 (6.7) |

[1]Met protocol defined alcohol requirements for NASH/MASH.
[2]Based on elevated CDT and/or PEth, alcohol intake possibly exceeding protocol allowance.
[3]NASH resolution with at least a 2-point reduction in NAS and no worsening of fibrosis stage.
[4]>1 stage fibrosis improvement with no worsening of NAS.

TABLE 33

| Subgroup | Endpoints | Resmetirom 80 mg (n = 224) | Resmetirom 100 mg (n = 228) | Placebo (n = 255) |
|---|---|---|---|---|
| MASH/NASH[1] (low alcohol) | NASH Resolution[3] | 67 (29.9%) | 82 (36%) | 23 (10.3%) |
| | Fibrosis Improvement[4] | 65 (29%) | 76 (33.3%) | 35 (13.7%) |
| | MRI-PDFF ≥30% reduction | 109/184 (59.2%) | 136/191 (71.2%) | 50/204 (24.5%) |

TABLE 33-continued

|  |  | Resmetirom 80 mg | Resmetirom 100 mg | Placebo |
| --- | --- | --- | --- | --- |
|  |  | (n = 34) | (n = 20) | (n = 21) |
| MetALD[2] (possibly increased alcohol) | NASH Resolution[3] | 10 (29%) | 7 (35%) | 2 (10%) |
|  | Fibrosis Improvement[4] | 12 (35%) | 6 (30%) | 4 (19%) |
|  | MRI-PDFF ≥30% reduction | 23/26 (88%) | 13/16 (81%) | 2/14 (14%) |

[1]Met protocol defined alcohol requirements for NASH/MASH.
[2]Based on elevated CDT and/or PEth, alcohol intake possibly exceeding protocol allowance.
[3]NASH resolution with at least a 2-point reduction in NAS and no worsening of fibrosis stage.
[4]≥1 stage fibrosis improvement with no worsening of NAS.

Analysis of Biomarkers PRO-C3 and ELF in Resmetirom-Treated Patients from the MAESTRO-NASH Trial, a 52-Week NASH/MASH Serial Liver Biopsy Study 966 patients with biopsy-confirmed NASH were randomized 1:1:1 to resmetirom 80 mg, resmetirom 100 mg, or placebo administered once daily. Dual primary endpoints at Week 52 were achieved with both resmetirom 80 mg and 100 mg: NASH resolution with no worsening of fibrosis (NR) or ≥1-stage improvement in fibrosis with no worsening of NAS (FI). The baseline and effect of resmetirom compared with placebo on fibrosis biomarkers PRO-C3 and P3NP/ELF were evaluated.

Pearson's correlation was used to examine the association between 2 PRO-C3 enzyme-linked immunosorbent assay (ELISA) assay methods (ELISA GEN1 and ELISA GEN2, NORDIC BIOSCIENCE) using PRO-C3 baseline data (N=919). The remainder of the analyses used the ELISA GEN2 assay. Mean SD or SE and median [Q1, Q3]were calculated to summarize PRO-C3 data. ANCOVA was used for comparisons between resmetirom 80 or 100 mg vs. placebo in PRO-C3 change from baseline at Week 52, while controlling for baseline PRO-C3 level. Mean difference with 95% CI and nominal P-values were obtained from the ANCOVA. Scatterplots and Spearman's correlations with 95% CIs were used to assess the associations between P3NP/ELF and PRO-C3 both at baseline and change from baseline at Week 52.

Figure 44:
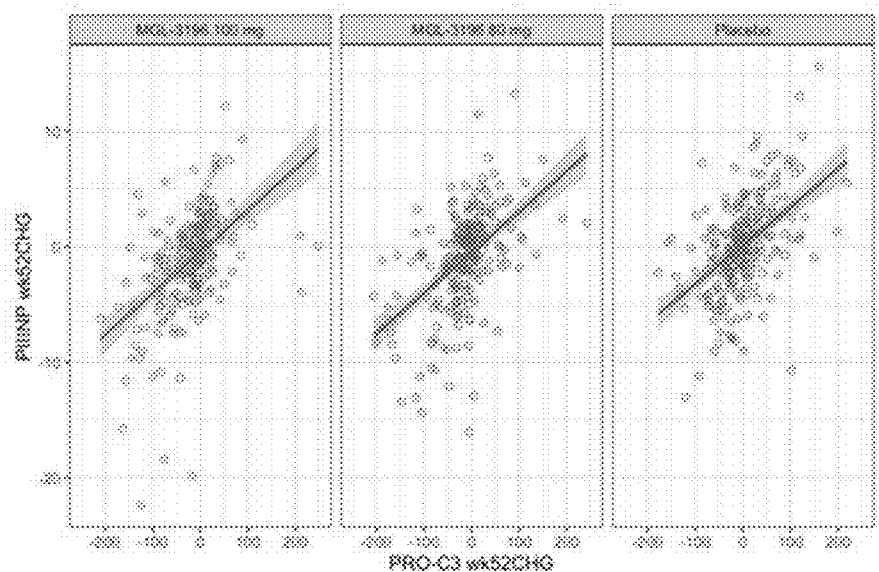
FIG. 44 is a graphical representation showing the P3NP change vs. the PRO-C3 change at Week 52 in patients in the placebo, resmetirom 80 mg, and resmetirom 100 mg groups in Example 2.

The two PRO-C3 assays ELISA GEN1 and ELISA GEN2 data were positively associated with a Pearson's correlation of 0.78 (P-value <0.0001). At baseline, PRO-C3 was mean (SD) 137 (71.7) ng/mL. At Week 52, PRO-C3 change from baseline for resmetirom 100 mg was −23.05 (4.76), resmetirom 80 mg was −17.93 (4.61), and placebo was −0.19 (4.07) (Table 34). The mean difference (95% CI) in PRO-C3 change from baseline at Week 52 was −16.9 (−27.0, −6.76; p=0.0011) between resmetirom 80 mg and placebo, and −22.1 (−32.3, −11.84; p<0.0001) between resmetirom 100 mg and placebo. Larger reductions in PRO-C3 mean (SD) on the resmetirom arms were observed in F3 patients. Resmetirom 80 mg reduced by −22.42 (6.38), resmetirom 100 mg reduced by −27.42 (6.72), and placebo reduced by −0.50 (5.46) (Table 37). Baseline P3NP and ELF were correlated with PRO-C3 (0.563 and 0.458, respectively). The change from baseline at Week 52 in P3NP was positively associated with change from baseline at Week 52 in PRO-C3 (0.557, 0.548 and 0.524 for resmetirom 100 mg, resmetirom 80 mg and placebo, respectively) (FIG. 44 and Table 38). A weaker positive correlation between the change from baseline at Week 52 for ELF and PRO-C3 (0.483, 0.484 and 0.487 for resmetirom 100 mg, resmetirom 80 mg and placebo, respectively) were also observed (FIG. 45 and Table 39).

In conclusion, two PRO-C3 assays (ELISA GEN1 and ELISA GEN2, NORDIC BIOSCIENCE) were correlated at baseline, indicating ELISA GEN2 assay was reasonable for measuring PRO-C3 levels. For PRO-C3 ELISA GEN2, drug effects were statistically significantly reduced at both doses of resmetirom vs. placebo. A greater magnitude of reduction with resmetirom was observed in F3 patients, who exhibited a higher baseline PRO-C3. ELF and PRO-C3 were less strongly correlated than P3NP and PRO-C3.

TABLE 34

Change from Baseline in PRO-C3 at Week 52 (Overall)

|  | Resmetirom 100 mg (n = 261) | Resmetirom 80 mg (n = 272) | Placebo (n = 283) |
| --- | --- | --- | --- |
| Baseline Mean (SD) | 138 (72.3) | 138 (73.5) | 136 (69.5) |
| Mean (Standard Error) | −23.05 (4.76) | −17.93 (4.61) | −0.19 (4.07) |
| Median (Q1, Q3) | −13.40 (−56.10, 10.20) | −11.95 (−41.78, 12.72) | −5.20 (−30.55, 29.30) |

TABLE 35

Change from Baseline in PRO-C3 at Week 52 (F1B patients only)

|  | Resmetirom 100 mg (n = 11) | Resmetirom 80 mg (n = 13) | Placebo (n = 18) |
| --- | --- | --- | --- |
| Baseline Mean (SD) | 94.8 (54.8) | 101 (32.3) | 114 (58.6) |
| Mean (Standard Error) | −7.20 (16.34) | −0.69 (8.58) | 21.33 (12.09) |
| Median (Q1, Q3) | 0.40 (−1.15, 18.60) | 4.30 (−21.90, 16.40) | 0.60 (−15.60, 61.72) |

TABLE 36

Change from Baseline in PRO-C3 at Week 52 (F2 patients only)

|  | Resmetirom 100 mg (n = 79) | Resmetirom 80 mg (n = 86) | Placebo (n = 93) |
| --- | --- | --- | --- |
| Baseline Mean (SD) | 116 (47.5) | 124 (56.8) | 122 (57.4) |
| Mean (Standard Error) | −15.79 (5.47) | −11.51 (6.75) | −3.78 (6.77) |
| Median (Q1, Q3) | −10.10 (−39.40, 11.25) | −13.65 (−34.55, 15.40) | −6.00 (−32.10, 18.70) |

TABLE 37

Change from Baseline in PRO-C3 at Week 52 (F3 patients only)

|  | Resmetirom 100 mg (n = 171) | Resmetirom 80 mg (n = 173) | Placebo (n = 172) |
| --- | --- | --- | --- |
| Baseline Mean (SD) | 150 (79.4) | 147 (80.9) | 146 (74.8) |
| Mean (Standard Error) | −27.42 (6.72) | −22.42 (6.38) | −0.50 (5.46) |
| Median (Q1, Q3) | −18.30 (−63.75, 8.45) | −11.90 (−43.70, 7.00) | −5.80 (−30.93, 29.95) |

TABLE 38

P3NP Correlation with PRO-C3

| Group | Spearman Correlation (95% CI) | Pearson's Correlation (95% CI) |
|---|---|---|
| Resmetirom 100 mg (N = 243) | 0.557 (0.454, 0.645) | 0.428 (0.320, 0.526) |
| Resmetirom 80 mg (N = 255) | 0.548 (0.445, 0.635) | 0.535 (0.442, 0.618) |
| Placebo (N = 260) | 0.524 (0.414, 0.624) | 0.538 (0.445, 0.619) |

TABLE 39

ELF Correlation with PRO-C3

| Group | Spearman Correlation (95% CI) | Pearson's Correlation (95% CI) |
|---|---|---|
| Resmetirom 100 mg (N = 256) | 0.483 (0.384, 0.575) | 0.346 (0.234, 0.450) |
| Resmetirom 80 mg (N = 265) | 0.484 (0.377, 0.583) | 0.453 (0.352, 0.544) |
| Placebo (N = 276) | 0.487 (0.388, 0.581) | 0.467 (0.369, 0.555) |

Any patents or publications mentioned in this specification are indicative of the levels of those skilled in the art to which the disclosure of the present invention pertains. These patents and publications are herein incorporated by reference for the indicated information to the same extent as if each individual publication was specifically and individually indicated to be incorporated by reference for such information. In case of conflict, the present specification, including definitions, will control.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A method of treating nonalcoholic steatohepatitis (NASH), comprising:
   determining a weight of an adult human subject in need thereof, and
   based on determination of the weight of the adult human subject in need thereof, administering to the adult human subject in need thereof a solid oral dosage form comprising:
   (i) resmetirom or a pharmaceutically acceptable salt thereof at a dosage of 100 mg per day, if the adult human subject in need thereof is determined to weigh 100 kg or more; or
   (ii) resmetirom or the pharmaceutically acceptable salt thereof at a dosage of 80 mg per day, if the adult human subject in need thereof is determined to weigh less than 100 kg.

2. The method according to claim 1, wherein the adult human subject in need thereof is determined to weigh 100 kg or more and is administered the solid oral dosage form comprising resmetirom or the pharmaceutically acceptable salt thereof at the dosage of 100 mg per day.

3. The method according to claim 1, wherein the adult human subject in need thereof is determined to weigh less than 100 kg and is administered the solid oral dosage form comprising resmetirom or the pharmaceutically acceptable salt thereof at the dosage of 80 mg per day.

4. The method according to claim 1, wherein the solid oral dosage form is a tablet.

5. The method according to claim 4, wherein the solid oral dosage form comprises resmetirom.

6. The method according to claim 2, wherein the solid oral dosage form is a tablet.

7. The method according to claim 6, wherein the solid oral dosage form comprises resmetirom.

8. The method according to claim 3, wherein the solid oral dosage form is a tablet.

9. The method according to claim 8, wherein the solid oral dosage form comprises resmetirom.

10. A method of improving liver fibrosis comprising:
    determining a weight of an adult human subject in need thereof; and
    based on determination of the weight of the adult human subject in need thereof, administering to the adult human subject in need thereof a solid oral dosage form comprising:
    (i) resmetirom or a pharmaceutically acceptable salt thereof at a dosage of 100 mg per day, if the adult human subject in need thereof is determined to weigh 100 kg or more; or
    (ii) resmetirom or the pharmaceutically acceptable salt thereof at a dosage of 80 mg per day, if the adult human subject in need thereof is determined to weigh less than 100 kg; and
    wherein the adult human subject in need thereof has nonalcoholic steatohepatitis (NASH) with moderate to advanced liver fibrosis consistent with stages F2 to F3.

11. The method according to claim 10, wherein the adult human subject in need thereof is determined to weigh 100 kg or more and is administered the solid oral dosage form comprising resmetirom or the pharmaceutically acceptable salt thereof at the dosage of 100 mg per day.

12. The method according to claim 10, wherein the adult human subject in need thereof is determined to weigh less than 100 kg and is administered the solid oral dosage form comprising resmetirom or the pharmaceutically acceptable salt thereof at the dosage of 80 mg per day.

13. The method according to claim 10, wherein the method is of improving the liver fibrosis by at least one stage in the adult human subject in need thereof.

14. The method according to claim 11, wherein the method is of improving the liver fibrosis by at least one stage in the adult human subject in need thereof.

15. The method according to claim 12, wherein the method is of improving the liver fibrosis by at least one stage in the adult human subject in need thereof.

16. The method according to claim 13, wherein the solid oral dosage form is a tablet.

17. The method according to claim 16, wherein the solid oral dosage form comprises resmetirom.

18. The method according to claim 14, wherein the solid oral dosage form is a tablet.

19. The method according to claim 18, wherein the solid oral dosage form comprises resmetirom.

20. The method according to claim 15, wherein the solid oral dosage form is a tablet.

21. The method according to claim 20, wherein the solid oral dosage form comprises resmetirom.

22. The method according to claim 13, wherein the adult human subject in need thereof has liver fibrosis characterized as fibrosis stage F3.

23. The method according to claim 14, wherein the adult human subject in need thereof has liver fibrosis characterized as fibrosis stage F3.

24. The method according to claim 15, wherein the adult human subject in need thereof has liver fibrosis characterized as fibrosis stage F3.

* * * * *